United States Patent
Spector

(10) Patent No.: US 9,706,935 B2
(45) Date of Patent: Jul. 18, 2017

(54) CATHETER SYSTEMS AND RELATED METHODS FOR MAPPING, MINIMIZING, AND TREATING CARDIAC FIBRILLATION

(71) Applicant: University of Vermont, Burlington, VT (US)

(72) Inventor: Peter S Spector, Burlington, VT (US)

(73) Assignee: University of Vermont, Burlington, VT (US)

(*) Notice: Subject to any disclaimer, the term of this patent is extended or adjusted under 35 U.S.C. 154(b) by 602 days.

(21) Appl. No.: 13/844,753

(22) Filed: Mar. 15, 2013

(65) Prior Publication Data

US 2014/0200430 A1 Jul. 17, 2014

Related U.S. Application Data

(60) Provisional application No. 61/753,387, filed on Jan. 16, 2013.

(51) Int. Cl.
*A61B 5/046* (2006.01)
*A61B 5/042* (2006.01)
(Continued)

(52) U.S. Cl.
CPC .......... *A61B 5/04014* (2013.01); *A61B 5/046* (2013.01); *A61B 5/04017* (2013.01);
(Continued)

(58) Field of Classification Search
CPC ............ A61B 5/04012; A61B 5/04014; A61B 5/0402; A61B 5/0408; A61B 5/042;
(Continued)

(56) References Cited

U.S. PATENT DOCUMENTS 5,222,501 A 6/1993 Ideker et al.
5,681,308 A * 10/1997 Edwards et al. ............... 606/41
(Continued)

FOREIGN PATENT DOCUMENTS

| EP | 1750215 A1 | 2/2007 |
|---|---|---|
| EP | 2540222 A2 | 1/2013 |
| WO | WO-9639929 A1 | 12/1996 |

OTHER PUBLICATIONS

Calkins, et al., "Treatment of Atrial Fibrillation with Antiarrhythmic Drugs or Radio Frequency Ablation: Two Systematic Literature Reviews and Meta-analyses" *Circ Arrhythmia Electrophysiol*, pp. 349-361 (2009) (41 pgs.).

(Continued)

*Primary Examiner* — Lee S Cohen
*Assistant Examiner* — Erin M Cardinal
(74) *Attorney, Agent, or Firm* — Wilmer Cutler Pickering Hale and Dorr LLP

(57) ABSTRACT

Catheters, systems, and related methods for optimized for mapping, minimizing, and treating cardiac fibrillation in a patient, including an array of at least one stacked electrode pair, each electrode pair including a first electrode and a second electrode, wherein each electrode pair is configured to be orthogonal to a surface of a cardiac tissue substrate, wherein each first electrode is in contact with the surface to record a first signal, and wherein each second electrode is separated from the first electrode by a distance which enables the second electrode to record a second signal, wherein the catheter is configured to obtain one or more measurements from at least a first signal and a second signal in response to electrical activity in the cardiac tissue substrate indicative of a number of electrical circuit cores and distribution of the electrical circuit cores for a duration across the cardiac tissue substrate.

21 Claims, 64 Drawing Sheets

(51) Int. Cl.
*A61B 5/04* (2006.01)
*A61B 18/14* (2006.01)
*A61B 34/20* (2016.01)
*A61B 17/00* (2006.01)

(52) U.S. Cl.
CPC ............ *A61B 5/0422* (2013.01); *A61B 18/14* (2013.01); *A61B 18/1492* (2013.01); *A61B 34/20* (2016.02); *A61B 2017/00053* (2013.01); *A61B 2034/2051* (2016.02); *A61B 2562/046* (2013.01)

(58) Field of Classification Search
CPC ... A61B 5/0422; A61B 5/04284; A61B 5/046; A61B 5/6852; A61B 5/6853; A61B 5/6858; A61B 5/6859; A61B 5/6869; A61B 2017/00053; A61B 2017/00044; A61B 2018/0022; A61B 2018/00226; A61B 2018/00351; A61B 2018/00357; A61B 2018/00375; A61B 18/14; A61B 19/50; A61B 2562/0209; A61B 2562/0214
USPC .................... 600/373, 374, 393, 509; 606/47
See application file for complete search history.

(56) References Cited

U.S. PATENT DOCUMENTS

| | | | |
|---|---|---|---|
| 5,683,424 A | 11/1997 | Brown et al. | |
| 5,748,491 A | 5/1998 | Allison et al. | |
| 5,857,977 A | 1/1999 | Caswell et al. | |
| 5,860,974 A | 1/1999 | Abele | |
| 6,023,638 A * | 2/2000 | Swanson | 600/510 |
| 6,086,581 A * | 7/2000 | Reynolds et al. | 606/41 |
| 6,978,168 B2 | 12/2005 | Beatty et al. | |
| 7,117,030 B2 * | 10/2006 | Berenfeld | A61B 5/046 128/920 |
| 7,505,810 B2 | 3/2009 | Harlev et al. | |
| 7,515,954 B2 | 4/2009 | Harlev et al. | |
| 7,957,792 B2 | 6/2011 | Harlev et al. | |
| 8,010,186 B1 | 8/2011 | Ryu | |
| 9,033,893 B2 | 5/2015 | Spector | |
| 9,254,093 B2 * | 2/2016 | Spector | A61B 5/04014 |
| 2007/0021679 A1 | 1/2007 | Narayan et al. | |
| 2007/0032826 A1 | 2/2007 | Schwartz | |
| 2007/0049816 A1 | 3/2007 | Damiano et al. | |
| 2007/0232949 A1 | 10/2007 | Saksena | |
| 2009/0204164 A1 * | 8/2009 | Efimov et al. | 607/17 |
| 2010/0094274 A1 | 4/2010 | Narayan et al. | |
| 2010/0130836 A1 | 5/2010 | Malchano et al. | |
| 2010/0137861 A1 | 6/2010 | Soroff et al. | |
| 2010/0305433 A1 | 12/2010 | Harlev et al. | |
| 2010/0312095 A1 | 12/2010 | Jenkins et al. | |
| 2011/0251505 A1 | 10/2011 | Narayan et al. | |
| 2013/0006131 A1 * | 1/2013 | Narayan et al. | 600/508 |
| 2013/0296959 A1 * | 11/2013 | Milbocker | 607/17 |
| 2014/0052013 A1 | 2/2014 | Narayan et al. | |
| 2014/0107453 A1 * | 4/2014 | Maskara | A61B 5/068 600/374 |
| 2014/0200429 A1 | 7/2014 | Spector et al. | |
| 2014/0243641 A1 * | 8/2014 | Boveja | A61B 6/463 600/374 |

OTHER PUBLICATIONS

Correa de Sa, et al., "Electrogram Fractionation: The Relationship Between Spatiotemporal Variation of Tissue Excitation and Electrode Spatial Resolution," *Circ Arrhythm Electrophysiol*, vol. 4, pp. 909-916 (2011).

International Search Report and Written Opinion Issued by the U.S. Patent and Trademark Office for International Application No. PCT/US2014/011866 mailed Jun. 17, 2014 (24 pgs.).

Matsuo, et al., "Clinical Predictors of Termination and Clinical Outcome of Catheter Ablation for Persistent Atrial Fibrillation," *J. of Am. College of Cardiology*, vol. 54(9), pp. 788-795 (Aug. 25, 2009).

Stinnett-Donnelly, et al., "Effects of Electrode Size and Spacing on the Resolution of Intracardiac Electrograms," *Coronary Artery Disease*, vol. 00, No. 00, pp. 1-7 (2011).

Spector et al., "Meta-Analysis of Ablation of Atrial Flutter and Supraventricular Tachycardia," *Am. J. Cardiol.*, vol. 104(5), pp. 671-677 (2009).

Spector, et al., "Ablation of Multi-Wavelet Re-entry: General Principles and In Silico Analyses," *Europace*, vol. 14, pp. v106-v111 (2012).

Dorostkar, P.C. et al., "Electroanatomical Mapping and Ablation of the Substrate Supporting Intraatrial Reentrant Tachycardia after Palliation for Complex Congenital Heart Disease", PACE, 21:1810-1819, Sep. 1998 (10 pages).

Kojodjojo, P. et. al., "Characterization of the Electroanatomical Substrate in Human Atrial Fibrillation: The Relationship between Changes in Atrial Volume, Refractoriness, Wavefront Propagation Velocities, and AF Burden", Journal of Cardiovascular Electrophysiology, 18(3):269-275, Mar. 2007 (7 pages).

European Extended Search Report issued in EP 14740326.5, dated Aug. 3, 2016 (13 pages).

* cited by examiner

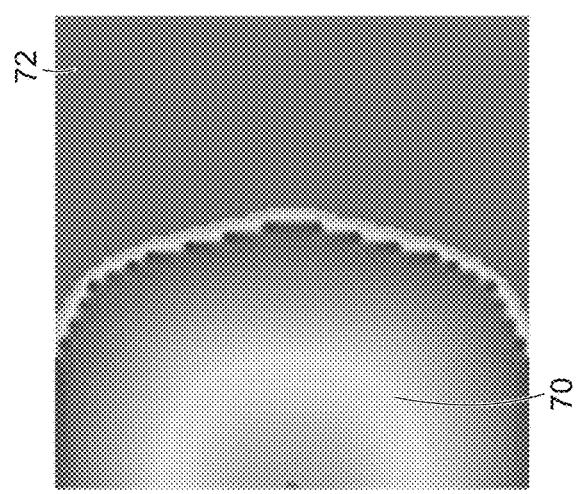
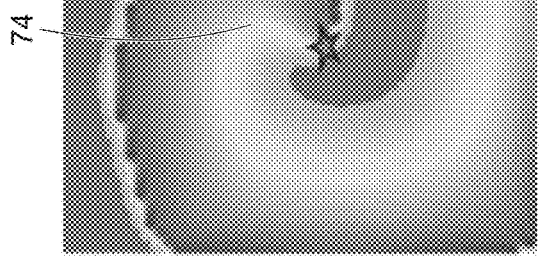
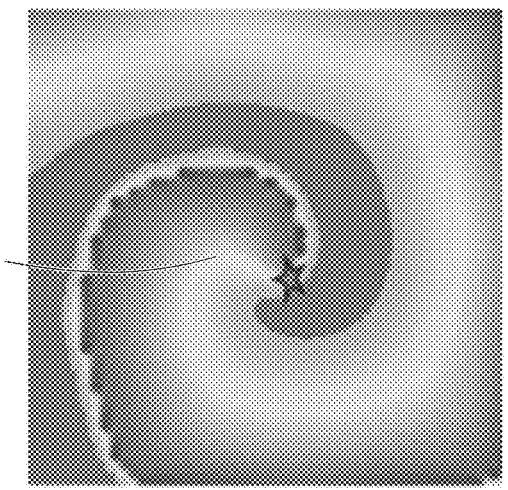
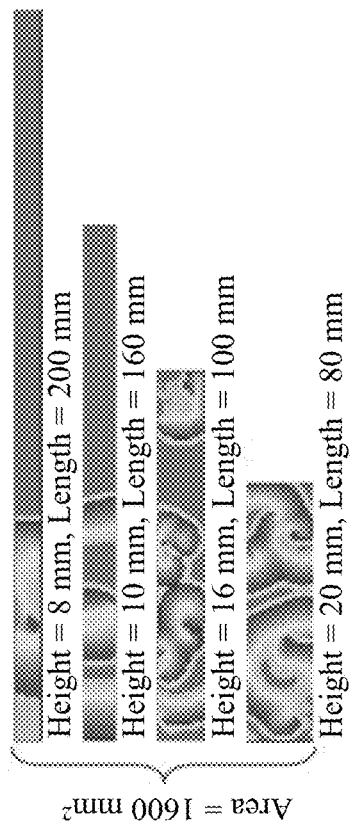

Temporal
Variation

Spatial
Variation

Spatiotemporal
Variation

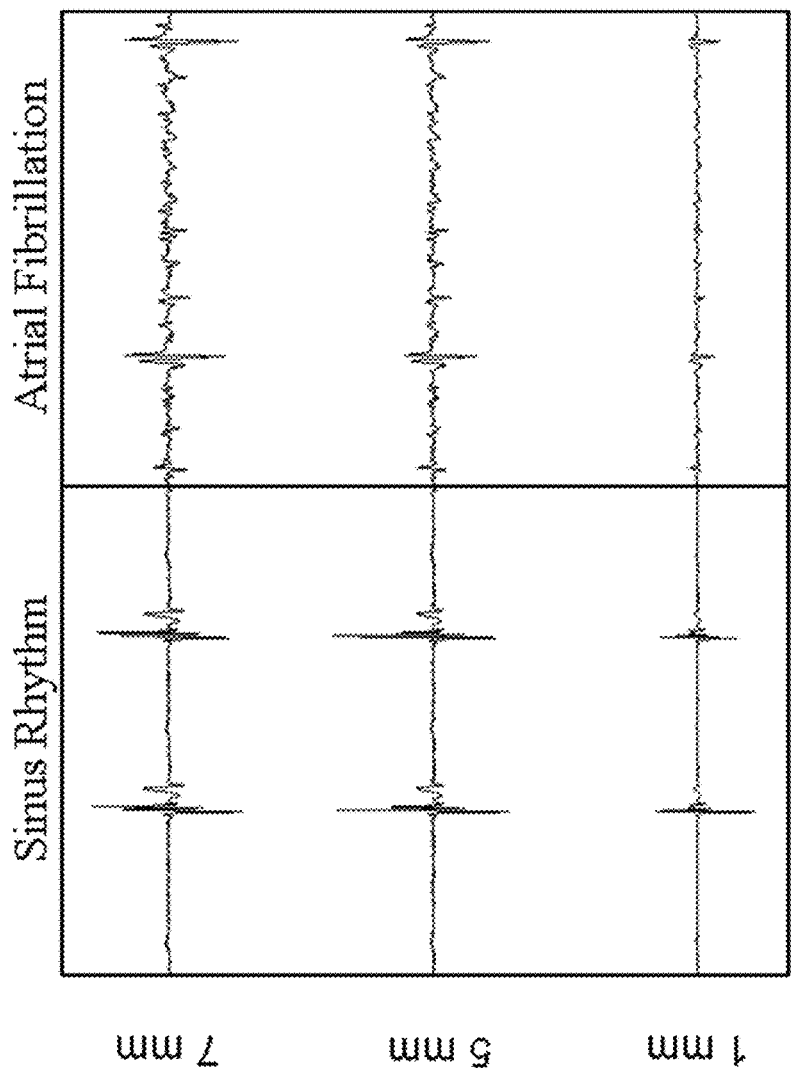
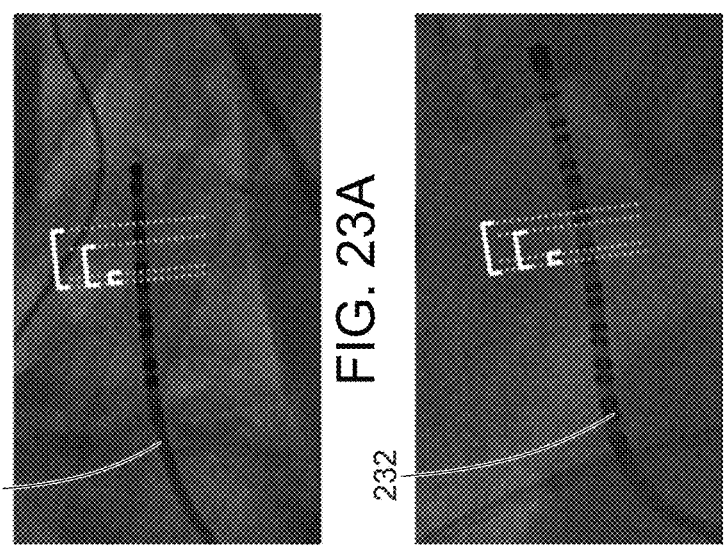
FIG. 23C
FIG. 23A
FIG. 23B

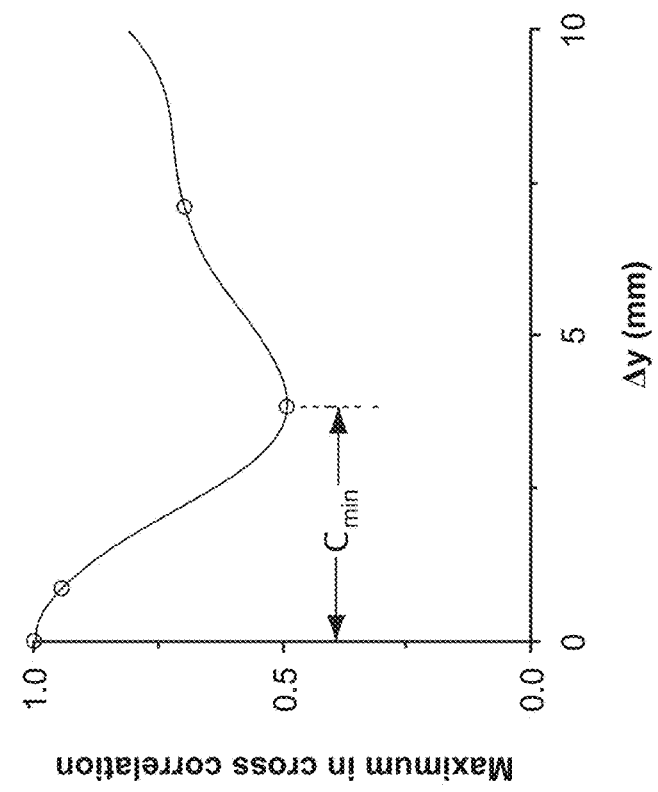
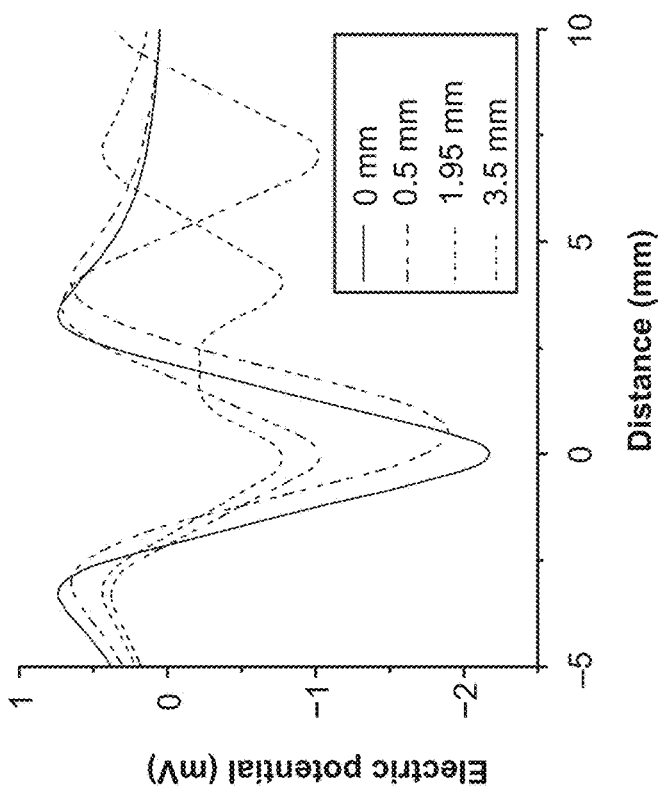
FIG. 27B
FIG. 27A

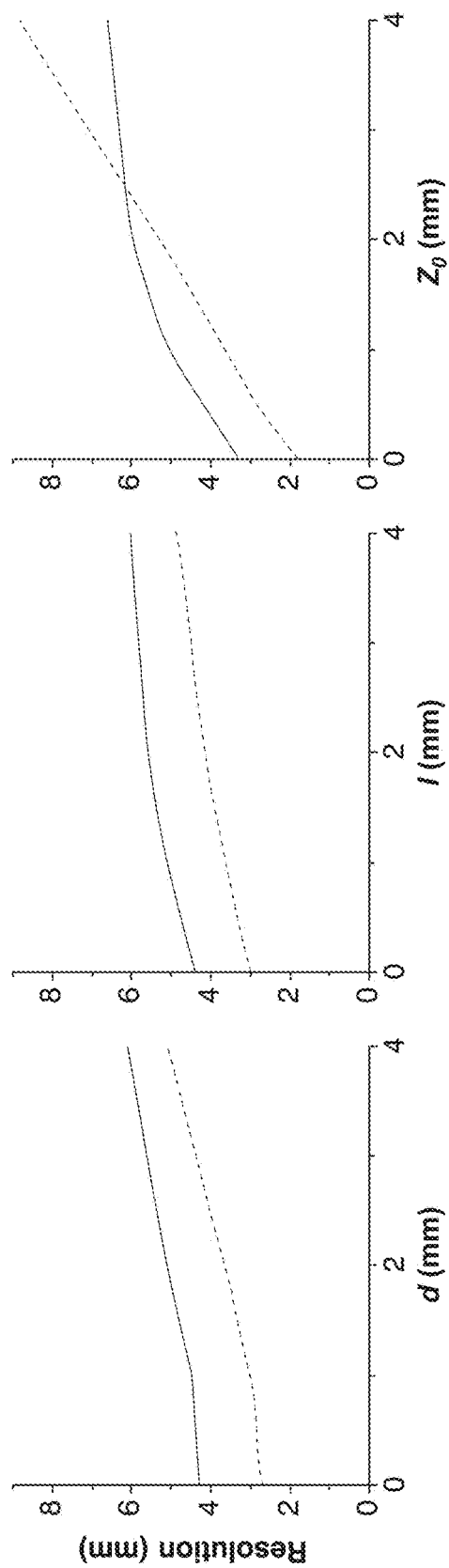

$I(x, y, h)$　　　$\Phi(x, y, h)$　　　$\hat{I}(x, y, h)$ $I(x, y, h)$  $\Phi(x, y, h)$  $\hat{I}(x, y, h)$
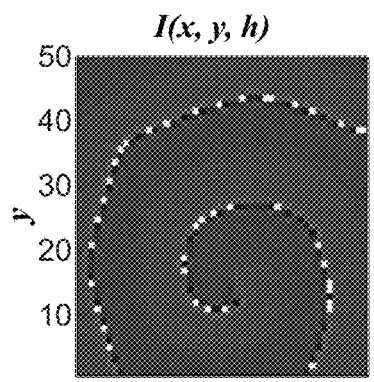 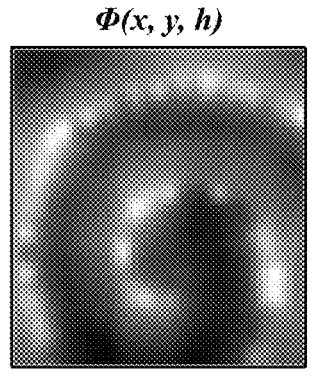 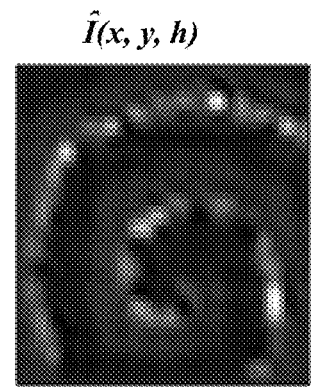
FIG. 47A  FIG. 47B  FIG. 47C
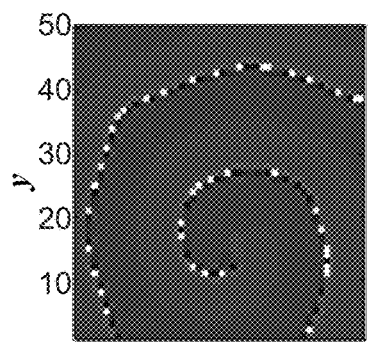 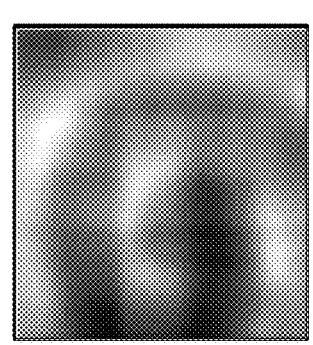 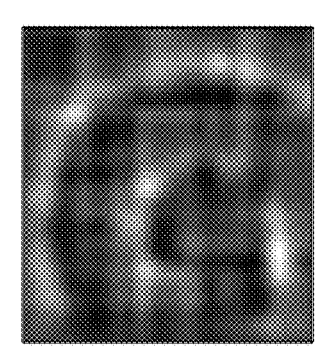
FIG. 47D  FIG. 47E  FIG. 47F
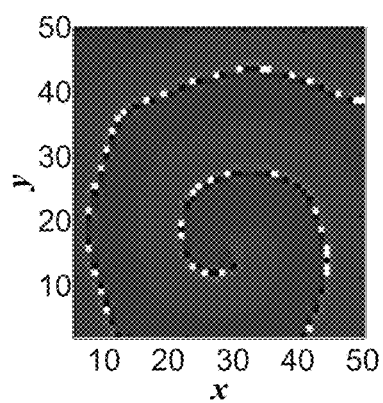 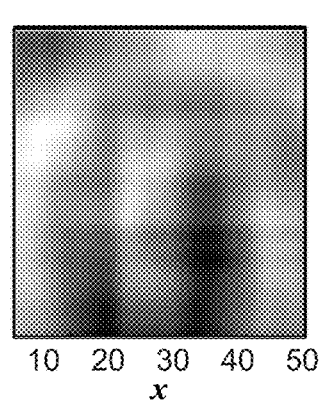 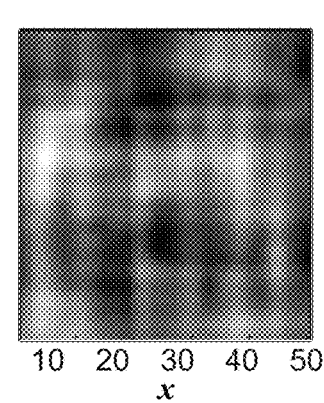
FIG. 47G  FIG. 47H  FIG. 47I

CATHETER SYSTEMS AND RELATED METHODS FOR MAPPING, MINIMIZING, AND TREATING CARDIAC FIBRILLATION

RELATED APPLICATIONS

This application claims priority to and incorporates by reference the entire contents of provisional application No. 61/753,387, filed on Jan. 16, 2013.

TECHNICAL FIELD

The present disclosure relates generally to methods and systems for detecting and treating cardiac fibrillation. More specifically, the present disclosure relates to physiologic, particularly electrophysiologic, methods and systems for preventing, treating, and at least minimizing if not terminating cardiac fibrillation by mapping cardiac fibrillation and optimizing the placement of ablation lesions.

BACKGROUND OF THE INVENTION

Atrial fibrillation, which accounts for almost one-third of all admissions to a hospital for a cardiac rhythm disturbance, is an uncontrolled twitching or quivering of muscle fibers (fibrils) resulting in an irregular and often rapid heart arrhythmia associated with increased mortality and risk of stroke and heart failure. See, e.g., Calkins et al., Treatment of Atrial Fibrillation with Anti-arrhythmic Drugs or Radio Frequency Ablation: Two Systematic Literature Reviews and Meta-analyses, 2(4) Circ. Arrhythmia Electrophysiol. 349-61 (2009). Atrial fibrillation may be paroxysmal or chronic, and the causes of atrial fibrillation episodes are varied and often unclear; however, atrial fibrillation manifests as a loss of electrical coordination in the top chambers of the heart. When fibrillation occurs in the lower chambers of the heart, it is called ventricular fibrillation. During ventricular fibrillation, blood is not pumped from the heart, and sudden cardiac death may result.

Existing treatments for cardiac fibrillation include medications and other interventions to try to restore and maintain normal organized electrical activity to the atria. When medications, which are effective only in a certain percentage of patients, fail to maintain normal electrical activity, clinicians may resort to incisions made during open heart surgery or minimally-invasive ablation procedures, whereby lines of non-conducting tissue are created across the cardiac tissue in an attempt to limit the patterns of electrical excitation to include only organized activity and not fibrillation. Id. at 355. If sufficient and well-placed, the non-conducting tissue (e.g., scar tissue) will interfere with and normalize the erratic electrical activity, ideally rendering the atria or ventricles incapable of supporting cardiac fibrillation.

Catheter ablation targeting isolation of the pulmonary veins has evolved over the past decade and has become the treatment of choice for drug-resistant paroxysmal atrial fibrillation. The use of ablation for treatment of persistent atrial fibrillation has been expanding, with more centers now offering the procedure.

Unfortunately, the success of current ablation techniques for treating cardiac fibrillation is less than desirable, for example, curing only about 70% of atrial fibrillation patients. Id. at 354. In contrast, ablation for treating heart arrhythmias other than fibrillation is successful in more than 95% of patients. Spector et al., Meta-Analysis of Ablation of Atrial Flutter and Supraventricular Tachycardia, 104(5) Am. J. Cardiol. 671, 674 (2009). One reason for this discrepancy in success rates is due to the complexity of identifying the ever-changing and self-perpetuating electrical activities occurring during cardiac fibrillation. Without the ability to accurately determine the source locations and mechanisms underlying cardiac fibrillation in an individual patient and develop a customized ablation strategy, clinicians must apply generalized strategies developed on the basis of cardiac fibrillation pathophysiologic principles identified in basic research and clinical studies from other patients. The goal of ablation is to alter atrial and/or ventricular physiology and, particularly, electrophysiology such that the chamber no longer supports fibrillation; it is insufficient to simply terminate a single episode. However, ablation lesions have the potential to cause additional harm to the patient (e.g., complications including steam pops and cardiac perforation, thrombus formation, pulmonary vein stenosis, and atrio-esophageal fistula) and to increase the patient's likelihood of developing abnormal heart rhythms (by introducing new abnormal electrical circuits that lead to further episodes of fibrillation).

In addition, existing catheters with their associated electrode configurations that are used to assist in preventing, treating, and at least minimizing if not terminating cardiac fibrillation have several shortcomings, including that the electrodes are too large, the inter-electrode spacing is too great, and the electrode configurations are not suitably orthogonal to the tissue surface. These catheters of the prior art tend to prompt time consuming methods since the catheter, and thus its electrodes, have to be moved to a relatively large number of locations in the heart cavity to acquire sufficient data. Additionally, moving the catheter to different locations so that the catheter's electrode(s) touch the endocardium is a cumbersome process that is technically challenging.

Further complicating the use of prior art contact-based catheters is the occurrence of unstable arrhythmia conditions. Particularly, ventricular tachyarrhythmias may compromise the heart's ability to circulate blood effectively. As a result, the patient cannot be maintained in fast tachyarrhythmia's for more than a few minutes, which significantly complicates the ability to acquire data during the arrhythmia. In addition, some arrhythmias are transient or nonperiodic in nature; therefore, contact-based catheters of the prior art are less suitable for mapping these arrhythmia's since the sequential contact-based methodology is predicated on the assumption that recorded signals are periodic in nature.

Thus, cardiac fibrillation patients would benefit from new methods and systems for the preventing, treating, and at least minimizing if not terminating cardiac fibrillation in the underlying "substrate" (i.e., the tissue on which abnormal electrical circuits of reentry are formed) responsible for the initiation and perpetuation of cardiac fibrillation. These methods and systems would help clinicians minimize or prevent further episodes and increase the success rate of non-invasive ablation treatments in cardiac fibrillation patients. There remains a need for patient-specific, map-guided ablation strategies that would minimize the total amount of ablation required to achieve the desired clinical benefit by identifying ablation targets and optimizing the most efficient means of eliminating the targets.

SUMMARY OF THE INVENTION

The methods and systems of the present invention are predicated on the recognition and modeling of the actual physiologic and, particularly, electrophysiologic principles underlying fibrillation. For instance, the prior ablation art fails to recognize the importance of and provide methods and systems for gauging a patient's fibrillogenicity, e.g., how conducive the atria are to supporting atrial fibrillation and how much ablation is required for successful treatment, detecting and mapping fibrillation, optimizing the distribution of ablation lesions for both effectiveness and efficiency, and guiding ablation based on quantitative feedback methods and systems. These methods and systems of the embodiments of the present invention are directed, therefore, to defining successful strategies, procedures, and clinical outcomes that are tailored for each patient with cardiac fibrillation.

In an embodiment, catheter optimized for mapping cardiac fibrillation in a patient, including an array of at least one stacked electrode pair, each electrode pair including a first electrode and a second electrode, wherein each electrode pair is configured to be orthogonal to a surface of a cardiac tissue substrate, wherein each first electrode is in contact with the surface to record a first signal, and wherein each second electrode is separated from the first electrode by a distance which enables the second electrode to record a second signal, wherein the catheter is configured to obtain one or more measurements from at least a first signal and a second signal in response to electrical activity in the cardiac tissue substrate indicative of a number of electrical circuit cores and distribution of the electrical circuit cores for a duration across the cardiac tissue substrate in the patient's heart.

In another embodiment, catheter optimized for assessing efficacy of an ablation procedure in a patient, comprising: an array of at least one stacked electrode pair, each electrode pair including a first electrode and a second electrode, wherein each electrode pair is configured to be orthogonal to a surface of a cardiac tissue substrate, wherein each first electrode is in contact with the surface to record a first signal, and wherein each second electrode is separated from the first electrode by a distance which enables the second electrode to record a second signal, wherein the catheter is configured to obtain one or more measurements from at least a first signal and a second signal in response to electrical activity in the cardiac tissue substrate indicative of a number of electrical circuit cores and distribution of the electrical circuit cores for a duration across the cardiac tissue substrate in the patient's heart.

The details of one or more embodiments of the present invention are set forth in the accompanying drawings and the description below. Other features, objects, and advantages of the present invention will be apparent from the description and drawings, and from the claims.

BRIEF DESCRIPTION OF THE DRAWINGS

FIGS. 7A-7C illustrate surface topology and reentry, in accordance with embodiments of the present invention;

FIG. 8 illustrates the impact of boundary-length-to-surface-area ratio on the duration of multi-wavelet reentry according to some embodiments of the present invention;

FIG. 10A illustrates homogenous tissue without a short wavelength patch, and FIG. 10B illustrates heterogeneous tissue with a wavelength patch, in accordance with embodiments of the present invention;

FIG. 15A illustrates relationship between mean surface ECG/EKG/AFCL a measurement from 10 and 30 CL, FIG. 15B illustrates relationship between surface ECG AFCL from 10 CL and AFCL using time frequency analysis, FIG. 15C illustrates the relationship between surface ECG AFCL from 10 CL and the LAA CL and FIG. 15D illustrates the relationship between ECG AFCL from 10 CL and RAA CL in accordance with embodiments of the present invention;

FIGS. 23A-23B are fluoroscopic images of a catheter in the coronary sinus, in accordance with embodiments of the present invention;

FIG. 23C is a set of electrograms simultaneously recorded during sinus rhythm and atrial fibrillation with varying inter-electrode spacing, in accordance with embodiments of the present invention;

FIG. 25A illustrates a comparison of predicted potential recorded by a unipolar electrode as a function of lateral distance from a dipole current source (solid line) and the potential measured experimentally in a saline bath (filled circles) and FIG. 25B illustrates a corresponding plot for bipolar recording, in accordance with embodiments of the resent invention;

FIG. 26A illustrates the potential due to a dipole current source recorded by a unipolar electrode as a function of lateral distance from the source, showing how resolution is quantified in terms of peak width at half maximum height and FIG. 26B illustrates the corresponding plot for a bipolar electrode, in accordance with embodiments of the present invention;

FIGS. 27A-27B are graphical plots of simulates bipolar electrograms, in accordance with embodiments of the present invention;

FIGS. 28A-28C graphically illustrate the resolution of a unipolar electrode recording of a dipole current source as assessed in terms of $C_{min}$ and $W_{1/2}$, In accordance with embodiments of the present invention;

FIGS. 47A-47I illustrate effects of electrode height on the resolution of a rotor showing the true current density, the observed signal. and the deconvolved signal at different heights, in accordance with embodiments of the present invention;

DETAILED DESCRIPTION

Figures 1A, 1B, 1C:
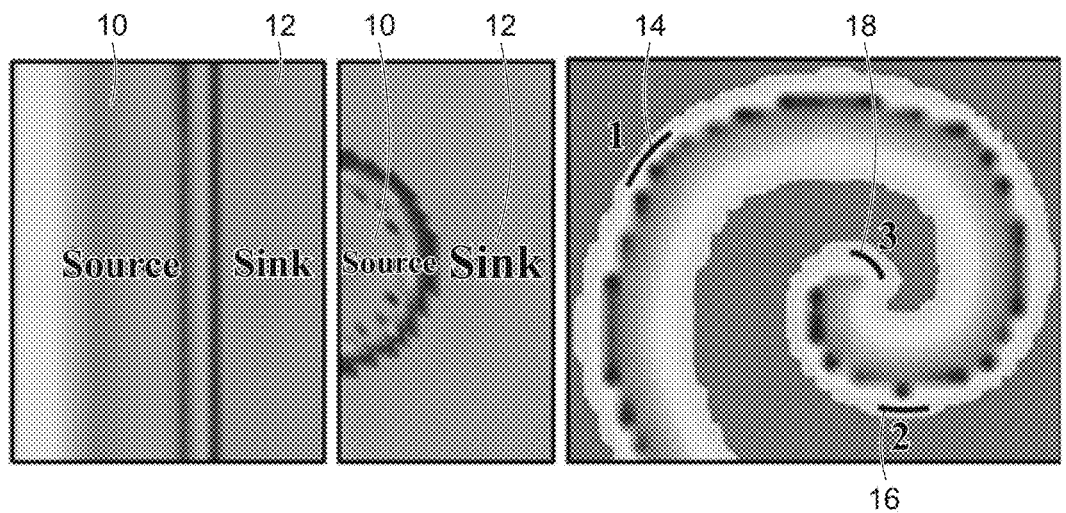
FIGS. 1A-1C illustrate the relationship between the source-sink ratio and wave curvature according to some embodiments of the present invention.

Embodiments of the present invention include new methods and systems for preventing, treating, and at least minimizing if not terminating cardiac fibrillation in the substrate responsible for initiation and perpetuation of fibrillation and for optimized treatments of that substrate, which are predicated on the recognition and modeling of the actual physiological information, including the electrophysiologic principles, underlying fibrillation. These methods and systems make it possible for a clinician to develop and implement patient-specific, tailored fibrillation treatment, minimization, and prevention strategies. More specifically, embodiments of the present invention allow a clinician to minimize or prevent further episodes and increase the success rate of ablation in fibrillation patients by preventing "reentry," which perpetuates fibrillation as described in greater detail below.

The methods and systems embodying the present invention are predicated on new recognitions that electrophysiological measurements, which will be discussed in detail, are clinically useful for defining successful strategies, procedures, and clinical outcomes that are tailored for each patient with cardiac fibrillation.

First, new methods and systems for predicting and mapping the density and distribution of the cores or centers of the reentrant circuits on the underlying tissue substrate are disclosed according to some embodiments of the present invention. Second, new methods and systems for optimizing (for efficacy and efficiency) the placement of ablation lesions to physically interrupt the circuits are disclosed according to some embodiments of the present invention. Third, these as well as other methods and systems for assessing fibrillogenicity to inform the extent of ablation required to reduce fibrillogenicity and prevent or at least minimize further fibrillation episodes are introduced according to some embodiments of the present invention. Fourth, new methods and systems for guiding treatment of fibrillation using quantitative feedback and determining when sufficient treatment has been provided are disclosed according to some embodiments of the present invention. Also disclosed are new catheter systems and methods for determining patient-specific and location-specific tissue spatiotemporal variations, mapping the density and distribution of circuit cores, and/or assessing the efficacy of a treatment procedure.

Although the embodiments of the present invention are described with respect to atrial fibrillation, the same methods and systems would apply to preventing, treating, and at least minimizing if not terminating ventricular fibrillation by mapping ventricular fibrillation and optimizing the placement of ablation lesions. Cardiac fibrillation, particularly atrial fibrillation, is a progressive disorder, wherein a heart's electrical properties become increasingly conducive to supporting fibrillation; hence episodes, once initiated, are progressively less likely to spontaneously terminate.

The outer wall of the human heart is composed of three layers. The outer layer is the epicardium, or visceral pericardium because it is also the inner wall of the pericardium. The middle layer is the myocardium, which is composed of cardiac muscle that contracts. The inner layer is the endocardium, which is in contact with the blood that the heart pumps. The endocardium merges with the endothelium of blood vessels and also covers heart valves.

The human heart has four chambers, two superior atria and two inferior ventricles. The pathway of blood through the human heart consists of a pulmonary circuit and a systemic circuit. Deoxygenated blood flows through the heart in one direction, entering through the superior vena cava into the right atrium. From the right atrium, blood is pumped through the tricuspid valve into the right ventricle before being pumped through the pulmonary valve to the pulmonary arteries into the lungs. Oxygenated blood returns from the lungs through the pulmonary veins to the left atrium. From the left atrium, blood is pumped through the mitral valve into the left ventricle before being pumped through the aortic valve to the aorta.

Cardiac Electrophysiology and Principles of Propagation

The study of clinical electrophysiology is essentially comprised of examining how electrical excitation develops and spreads through the millions of cells that constitute the heart. Human cardiac tissue constitutes a complex nonlinear dynamic system. Given the enormous number of cells in a human heart, this system is capable of generating a staggeringly large number of possible ways that the heart can behave, that is, potential activation patterns as excitation propagates through the tissue. Rhythms vary across a spectrum, from the organized and orderly behavior of sinus rhythm, with large coherent waves traversing across all cells and then extinguishing, to pathologic behaviors during which activation propagates in continuous loops, perpetually re-exciting the cardiac tissue (via reentry) in structurally defined circuits like the complex, dynamic and disorganized behavior of cardiac fibrillation. Despite these myriad possibilities, a basic understanding of the principles of propagation may be applied to predict how cardiac tissue will behave under varied circumstances and in response to various manipulations.

Cell Excitation and Impulse Propagation

A cell becomes excited when the voltage of its membrane rises above the activation threshold of its depolarizing currents (i.e., the sodium current (INa+) and calcium current (ICa++)). To reach activation threshold, the net trans-membrane current must be sufficient to discharge the membrane capacitance. The cell membrane separates charges across the space between its inner and outer surfaces, resulting in a voltage gradient. The size of the voltage gradient is determined by the number of charges and the distance by which they are separated.

The membrane capacity to hold charges on its surface, that is, the membrane capacitance, is determined by the surface area of a cell membrane and its thickness (i.e., the distance by which it separates charges). The force required to keep these charges from wandering away from a cell surface is generated by the electrical attraction to opposite charges on the other side of the membrane. The thinner the membrane, the closer the charges are to each other and the larger force they can exert to resist wandering off (i.e. the distance across the faces of a capacitor is inversely proportional to its capacitance).

As capacitance increases, the voltage change that results from the addition of a single charge to the cell membrane is reduced. An increase in capacitance means more charge is required per millivolt increase in membrane voltage. Because membrane thickness is the same in all cardiac cells, capacitance varies directly with cell size (i.e., surface area) and inversely with intercellular resistance (i.e., well-connected groups of cells act much like one large cell). Consequently, larger cells or well-connected groups of cells are more difficult to excite than smaller or poorly connected groups of cells since more current is required to reach activation threshold.

Cardiac cell membranes can simultaneously accommodate inward and outward currents (via separate ion channels/exchangers/pumps). Membrane depolarization is determined not by inward current alone, but rather by net inward current. If both inward and outward currents exist, the amount of depolarization (or repolarization) is determined by the balance of these currents. In their resting state, the majority of open channels in typical atrial and ventricular cells are potassium (K+) channels. This is why the resting membrane potential is nearly equal to the "reversal potential" for K+. As current enters a cell (e.g., via gap junctions from a neighboring cell), its membrane will begin to depolarize. This depolarization reduces the force preventing K+ from traveling down its concentration gradient. K+ flows out of the cell once this concentration gradient force exceeds the voltage gradient counter-force so that the outside of the cell is less positive than the inside of the cell. This, in turn, results in membrane repolarization. Therefore, in order for inward current to result in depolarization, the magnitude of the inward current must be greater than the magnitude of the outward current that it "unleashes." This resistance to membrane depolarization associated with outward K+ current is amounts to "voltage clamping" (i.e., keeping voltage fixed). A K+ channel open at rest is the inward rectifier. Cardiac cells that have a large number of inward rectifier channels have a resting membrane potential close to the K+ reversal potential, and a higher capacitance via the depolarization-resistant voltage clamping action of its inward rectifier channels.

Source-Sink Relationships

Propagation refers not simply to cell excitation but specifically to excitation that results from depolarizing current spreading from one cell to its neighbors. Electrical propagation may be described in terms of a source of depolarizing current and a sink of tissue that is to be depolarized. A source of current from excited cells flows into a sink of unexcited cells and provides a current to depolarize the unexcited cells to activation threshold.

A source is analogous to a bucket filled with electrical current, and a sink is analogous to a separate bucket into which the source current is "poured." When the "level" of source current in the sink bucket reaches a threshold for activation, the sink bucket is excited and fills completely with current from its own ion channels. The sink bucket itself then becomes part of the source current. With respect to the sink bucket, the net depolarizing current is the inward/upward current as limited by the "leak" current or outward/downward current, which is analogous to a leak in the bottom of the sink bucket. Using this bucket analogy, the amount of current poured into the sink, in excess of that required to reach activation threshold, is the safety factor, which is the amount by which source current may be reduced while maintaining successful propagation.

The increased capacitance of multiple sink cells connected via gap junctions is analogous to two or more sink buckets connected at their bases by tubes. The intercellular resistance of the tubes (i.e., gap junctions) influences the distribution of current poured into the first sink-bucket. With high intercellular resistance in the tube between a first and second bucket, the majority of the current poured into the first bucket will contribute to raising the voltage level of that bucket, with only a small trickle of current flowing into the second bucket. As intercellular resistance is reduced, the rate of voltage change in the first and second buckets progressively equalizes. With sufficiently low intercellular resistance, the sink effectively doubles in size (and the amount of depolarization of each membrane is reduced by half). Therefore, sink size increases as the intercellular resistance decreases and the number of electrically connected sink cells increases.

All else being equal, the source-sink ratio is determined by the number of source cells and the number of sink cells to which they are connected. If the source amplitude is held constant while sink size is increased, the source-sink ratio is reduced. For example, when multiple sink cells are connected via gap junctions, source current is effectively diluted, reducing the source sink ratio. Outward currents competing with the source current also increase the sink size. As the source-sink ratio decreases, the rate of propagation (i.e., conduction velocity) also decreases because it takes longer for each cell to reach activation threshold.

In the case of a sufficiently low source-sink ratio (i.e., a source-sink mismatch), the safety factor may diminish to less than zero, excitation may fail, and propagation may cease. The physical arrangement of cells in a tissue influences this balance. For example, a structurally determined source-sink mismatch occurs when propagation proceeds from a narrower bundle of fibers to a broader band of tissue. The narrower bundle of fibers provides a smaller source than the sink of the broader band of tissue to which it is connected. In this case the source-sink ratio is asymmetric. However, if propagation proceeds in the opposite direction (i.e., from the broader band of tissue into the narrower bundle of fibers), the source is larger than the sink, excitation succeeds, and propagation continues. Therefore, this tissue structure may result in a uni-directional conduction block and is a potential mechanism for concealed accessory pathways, as described further below.

The physical dimensions of wavefront also influence the source-sink ratio. For example, source and sink are not balanced in a curved wavefront. In a convex wavefront the source is smaller than the sink; therefore, convex wavefronts conduct current more slowly than flat or concave wave-fronts. Thus the rate and reliability of excitation is proportional to wavefront curvature: as curvature increases, conduction velocity decreases until critical threshold resulting in propagation failure. This is the basis of fibrillation.

FIGS. 1A-1C illustrate the relationship between the source-sink ratio and wave curvature according to some aspects of the current invention. In FIG. 1A, a flat wavefront maintain a balance between source 10 and sink 12, while in FIG. 1B, a convex wavefront have a smaller source 10 and a larger sink 12. FIG. 1C illustrates a spiral wavefront with a curved leading edge, in which the curvature is progressively greater towards the spiral center. As curvature increases, conduction velocity decreases. Thus, the spiral wavefront in FIG. 1C has less curvature but faster conduction at location 14 than at location 16, where the wavefront has less curvature but faster conduction than at location 18. At the inner most center or core of the wavefront, the source is too small to excite the adjacent sink and, due to the source-sink mismatch, propagation fails, resulting in a core of unexcited and/or unexcitable tissue around which rotation occurs.

Reentry

While several mechanisms may contribute to cardiac fibrillation, by far the most conspicuous culprit in fibrillation is reentry. The fundamental characteristic of reentry is that ongoing electrical activity results from continuous propagation, as opposed to repeated de novo focal impulse formation. The general concept of reentry is straight-forward: waves of activation propagate in a closed loop returning to re-excite the cells within the reentry circuit. Because of the heart's refractory properties, a wave of excitation cannot simply reverse directions; reentry requires separate paths for conduction away from and back towards each site in the circuit.

The details of circuit formation can be quite varied and in some cases quite complex. In the simplest case, a circuit is structurally defined in that physically separated conduction paths link to form a closed loop (resulting in, e.g., atrial flutter). Circuits can also be composed of paths that are separated due to functional cell-cell dissociation (e.g., rotors, to be described further below). In all cases reentry requires: (1) a closed loop of excitable tissue; (2) a conduction block around the circuit in one direction with successful conduction in the opposite direction; and (3) a conduction time around the circuit that is longer than the refractory period of any component of the circuit.

Topologically, a region of tissue substrate may be described as a finite two-dimensional sheet of excitable cells. The edges of the sheet form a boundary, resulting in a bounded plane. If a wave of excitation traverses the plane, it will extinguish at its edges. However, if a disconnected region of unexcited and/or unexcitable cells within the plane, a closed loop may exist with the potential to support reentry provided the other criteria for reentry are met. Topologically, this region of disconnection is an inner boundary, and the result is an interrupted, bounded plane regardless of whether the disconnection is due to physical factors (e.g., scar tissue, no gap junctions, and/or a hole formed by a vessel or valve) or functional factors (e.g., source-sink mismatch and/or refractory conduction block).

Figures 2A, 2B:
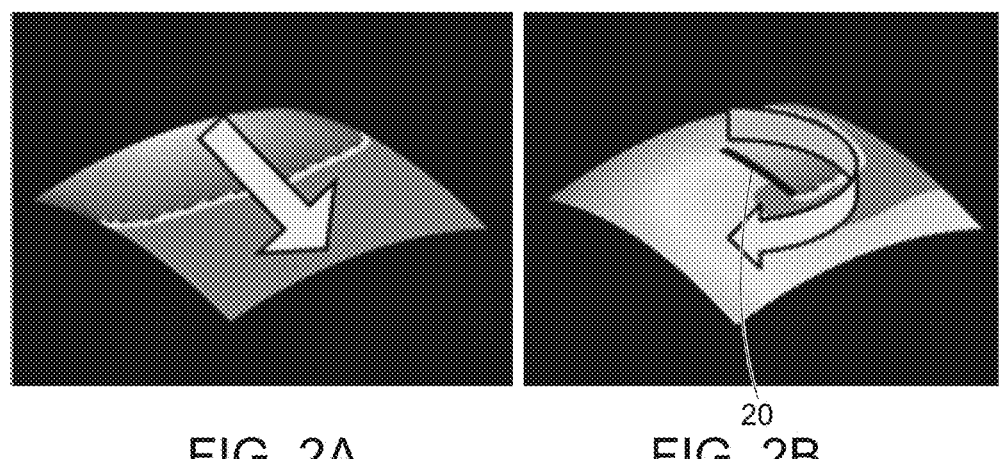
FIGS. 2A-2B illustrate reentry circuits using a topological perspective of the tissue substrate, in accordance with embodiments of the present invention.

FIGS. 2A-2B illustrate reentry circuits using a topological perspective of the tissue substrate in accordance with some aspects of the present invention. In FIG. 2A, an uninterrupted, bounded plane of tissue substrate cannot support reentry. However, in FIG. 2B, the addition of a inner, disconnected region of unexcited and/or unexcitable cells 20 transforms the tissue substrate into an interrupted, bounded plane and a potential circuit for reentry.

One benefit of a topological approach is the generalizability with which it applies to the full range of possible circuits for reentry. Despite a myriad of potential constituents, all reentrant circuits may be modelled as interrupted, bounded planes. Another benefit of a topologic approach is the unification it confers on all treatments for reentry: circuit transection by any means results in termination. Topologically, all circuit transections constitute transformation back to an uninterrupted, bounded plane.

Reentry may be prevented in two ways: (1) increasing the tissue excitation wavelength; and (2) physically interrupting the circuits of reentry by, for example, introducing an electrical boundary (e.g., scar tissue formed following an ablation lesion). The embodiments of the present disclosure provides methods and systems for effectively and efficiently preventing reentry by the latter method of physically interrupting the circuits and, consequently, reducing the ability of a heart to perpetuate fibrillation.

A reentrant circuit may be transected physically, as with catheter ablation, or functionally, as with antiarrhythmic medications (which may, e.g., reduce tissue excitability and/or extend the refractory period). Either way, a circuit transection results when a continuous line of unexcited and/or unexcitable cells is created from a tissue edge to an inner boundary, and the interrupted, bounded plane is transformed into an uninterrupted, bounded plane.

Figure 3A:
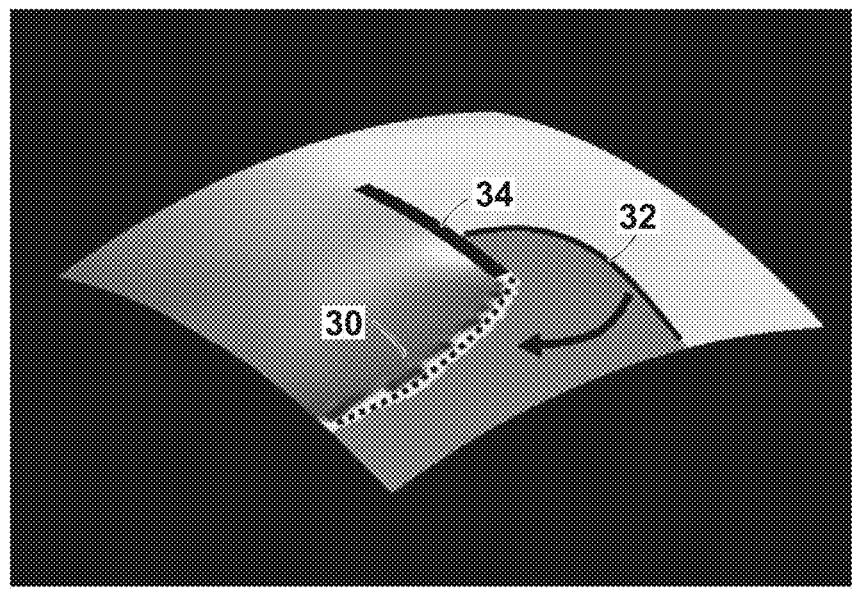
FIGS. 3A-3B illustrate how the minimum path of a curling wavefront is limited by tissue excitation wavelength, in accordance with embodiments of the present invention.
Figure 3B:
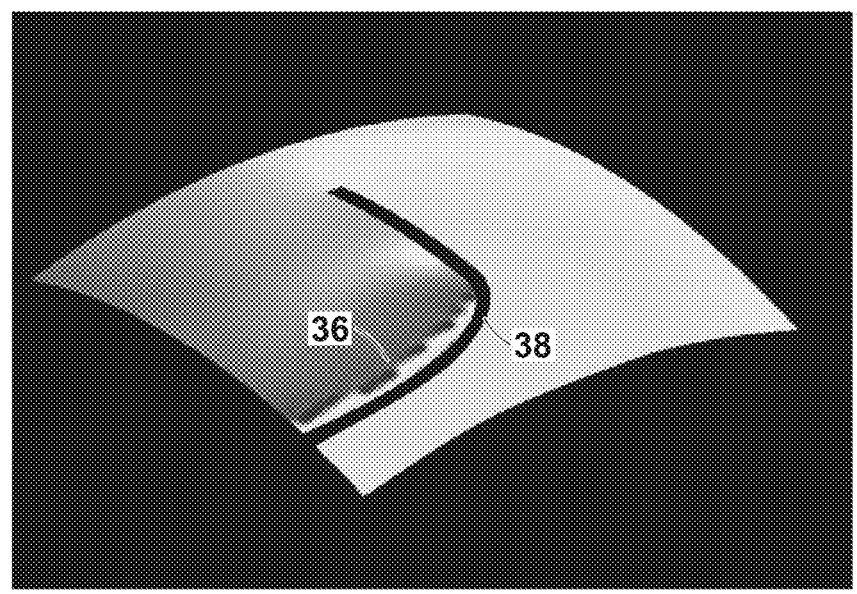

FIGS. 3A-3B illustrate circuit transection due to refractory prolongation. In FIG. 3A, if the trailing edge of refractory tissue 32 is extended in the direction of the arrow to meet the leading edge of excitation 30, such that the entire leading edge encounters unexcitable tissue ("head meets tail") then, in FIG. 3B, the propagation ends where the unexcitable tissue begins 36 and a line of conduction block 38 transects the circuit from inner to outer boundary.

Complex Reentrant Circuits: Rotors and Multi-Wavelet Reentry

The self-perpetuating reentry properties of fibrillation are in part the result of cyclone-like rotating spiral waves of tissue excitation ("rotors"). A rotor is an example of a functional reentrant circuit that is created when source-sink relationships at the end of an electrical wave create a core of unexcited and/or unexcitable tissue (i.e., a rotor core) around which rotation occurs. Activation waves propagate radially from the rotor core, producing a spiral wave that appears as rotation due to the radial propagation with progressive phase shift.

Rotors can occur even in homogeneous and fully excitable tissue in which, based on the timing and distribution of excitation, groups of cells in separate phases of refractoriness create separate paths which link to form a circuit. The simplest rotors have spatially-fixed cores, whereas more complex rotors have cores that are more diffuse and meander throughout the tissue. At the highest end of the spectrum, rotors encountering spatially-varying levels of refractoriness divide to form distinct daughter waves, resulting in multi-wavelet reentry.

As described above wave curvature influences source-sink balance. A rotor has a curved leading edge, in which curvature is progressively greater towards its spiral center of rotation. As curvature increases, conduction velocity decreases. At the spiral center the curvature is large enough to reduce the safety factor to less than zero, and propagation fails due to source-sink mismatch, creating a core of unexcited and/or unexcitable tissue (i.e., a sink) around which rotation occurs.

If the wavelength at the inner most part of a rotor is shorter than the path length around the sink, its unexcited and/or unexcitable core is circular and/or a point. If the wavelength is longer than the path length, then the rotor may move laterally along its own refractory tail until it encounters excitable tissue at which point it can turn, thus producing an elongated core. If conduction velocity around its core is uniform, a rotor will remain fixed in space. Alternatively, if conduction velocity is greater in one part of rotation than another, the a rotor and its core will meander along the tissue substrate.

If the edge of this spiral wave encounters unexcitable tissue it will "break," and if the newly created wave-ends begin rotation, "daughter-waves" are formed. In the most complex iterations, reentry may comprise multiple meandering and dividing spiral waves, some with wave lifespans lasting for less than a single rotation.

Terminating and Preventing Reentrant Rhythms

The mechanism of reentry provides insight into the strategies that will result in its termination: If reentry requires closed circuits then prevention, minimization, and/or termination requires transection of these circuits. Transection can be achieved in several different ways. In the case of fixed anatomic circuits, the circuit simply be physically transected with, for example, a linear ablation lesion.

Another approach to transection is to prolong the tissue activation wavelength by increasing refractory period sufficiently that wavelength exceeds path-length (i.e., "head meets tail"), and the circuit is transected by a line of functional block. Increasing conduction velocity sufficiently would ultimately have the same effect but is not practical therapeutically, in part, because conduction velocity itself is proarrhythmic and antiarrhythmic agents are limited by the degree to which they decrease conduction velocity.

The antiarrhythmic approach to treating multi-wavelet reentry in atrial fibrillation may include: decreasing excitation (thereby increasing the minimum sustainable curvature, increasing core size, meander and core collision probability) or increasing action potential duration and thereby wavelength (again increasing the probability of core collision/annihilation). However, as atrial fibrillation progresses, electrical remodeling of the atria render it progressively more conducive to perpetuation of reentry such that the antiarrhythmic dose required to sufficiently prolong action potential duration in the atria can result in proarrhythmia in the ventricles.

Ablation for Reentrant Rhythms

It is relatively straight forward to see how ablation can be used to transect a spatially fixed circuit but less clear how delivery of stationary ablation lesions can reliably transect moving functional circuits. Circuits are spontaneously transected when their core collides with the tissue edge (annulus) or with a line of conduction block that is contiguous with the tissue edge.

Figure 4A:
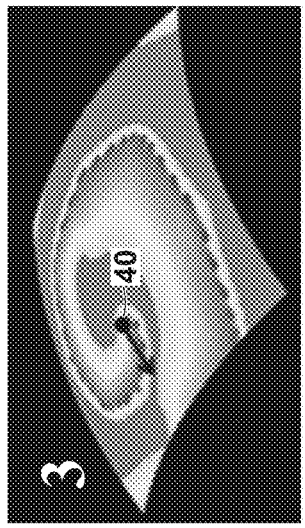
FIGS. 4A-4F illustrate rotor termination resulting from circuit transection via core collision with a tissue boundary according to some embodiments of the present invention.
Figure 4B:
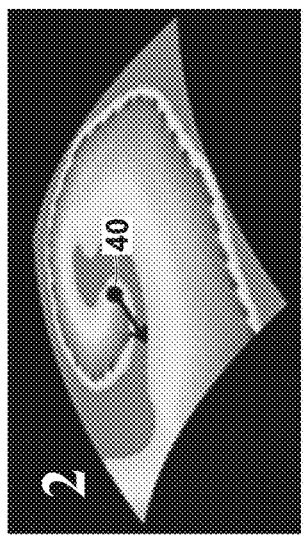
Figure 4C:
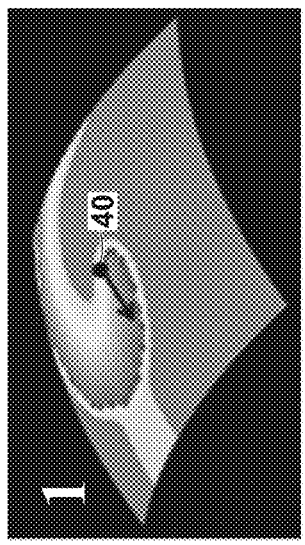
Figure 4D:
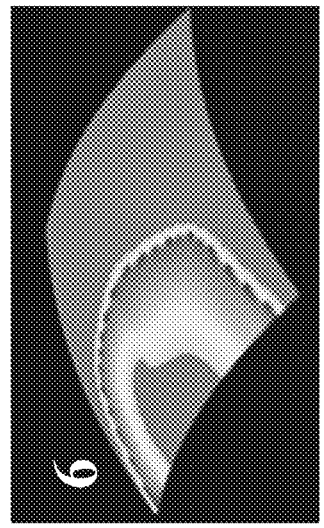
Figure 4E:
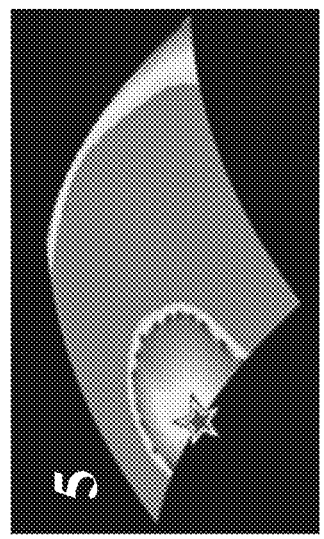
Figure 4F:
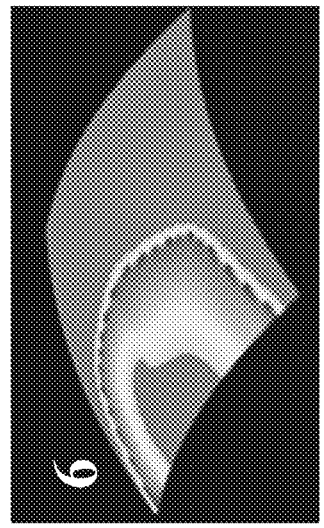

FIGS. 4A-4F illustrate rotor termination resulting from circuit transection via core collision with a tissue boundary according to some aspects of the present invention. The rotor core 40 moves closer to the tissue edge with each rotation 1-4, shown in FIGS. 4A-4D respectively. Upon collision of the core 40 with the tissue edge, as shown in FIG. 4E, the circuit is transected and reentry is terminated as shown in FIG. 4F.

Based upon this premise it is not surprising that the probability that multi-wavelet reentry will perpetuate is inversely proportional to the probability of such collisions. As tissue area is increased (while keeping tissue boundary fixed), the probability of core/boundary collision is reduced and perpetuation probability enhanced. If the area over which waves meander is reduced or the number of waves is increased, the probability that all waves will collide/annihilate is increased. Thus, atrial remodeling promotes fibrillation by decreasing the boundary-length-to-surface-area ratio (chamber dilation (surface area) is greater than annular dilation (boundary length)) and by decreasing wavelength (conduction velocity is decreased and action potential duration is decreased). The circuit transection/collision-probability perspective on atrial fibrillation perpetuation suggests the means to reduce atrial fibrillogenicity (tendency to maintain fibrillation). The boundary-length-to-surface-area ratio can be increased by adding linear ablation lesions. In order to transect a rotor circuit, an ablation line must extend from the tissue edge to the rotor core. Focal ablation at the center of a rotor simply converts the functional block at its core into structural block; ablation transforms spiral wave reentry into fixed anatomic reentry.

Figure 5A:
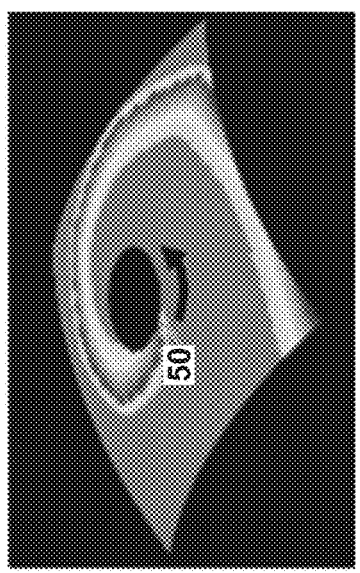
FIGS. 5A-5C illustrates the rotor ablation requirement of a linear lesion from the rotor core to the tissue edge, in accordance with some embodiments of the present invention.
Figure 5B:
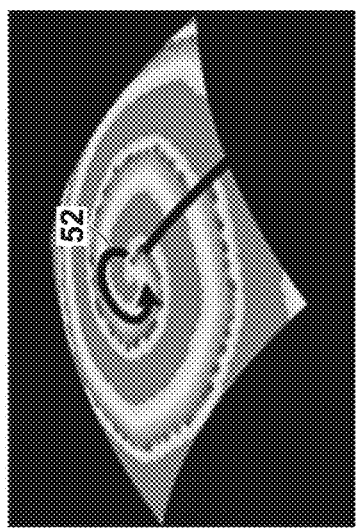
Figure 5C:
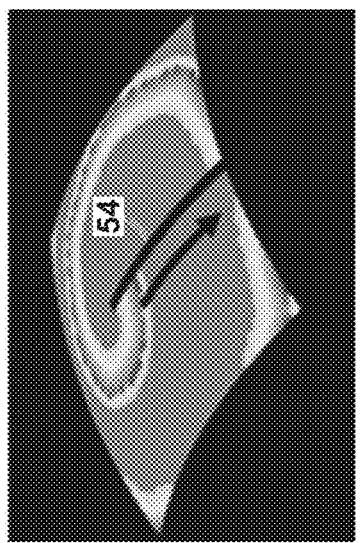

FIGS. 5A-5C illustrates the rotor ablation requirement of a linear lesion from the rotor core to the tissue edge in accordance with some aspects of the present invention. In FIG. 5A, focal ablation 50 at a rotor core converts a functional circuit (i.e., spiral wave) into a structural circuit but does not eliminate reentry. FIG. 5B illustrates how reentry continues if a linear lesion does not extend to the rotor core 52 (similar to a cavo-tricuspid isthmus ablation line that fails to extend all the way to the Eustachian ridge). In FIG. 5C, an ablation line 54 from the rotor core to the tissue edge transects the reentry circuit. Instead of circulating around its core the wave end travels along the ablation line 54 and ultimately terminates at the tissue edge.

Reentrant electrical rhythms persist by repeatedly looping back to re-excite or activate tissue in a cycle of perpetual propagation rather than by periodic de novo impulse formation. Due to its refractory properties, cardiac tissue activation cannot simply reverse directions. Instead, reentry rhythms or circuits require separate paths for departure from and return to each site, analogous to an electrical circuit.

The components of these reentrant circuits can vary, the anatomic and physiologic constituents falling along a continuum from lower to higher spatiotemporal complexity. At the lower end of the spectrum, the circuits are composed of permanent anatomically-defined structures such as a region of scar tissue; however, circuit components may also be functional (i.e., resulting from emergent physiologic changes) and therefore transient, such as occurs when electrical dissociation between adjacent fibers allows formation of separate conduction paths.

Figure 6A:
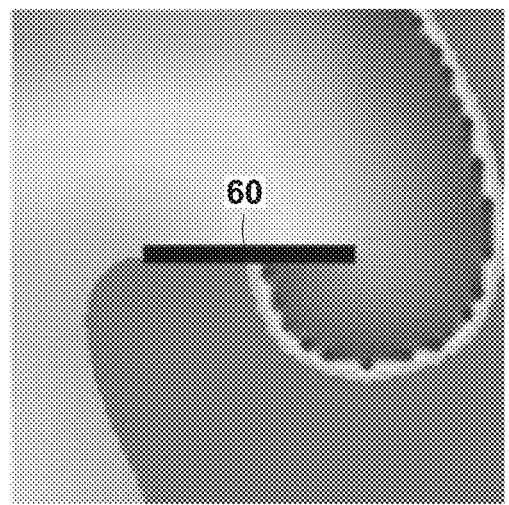
FIGS. 6A-6C are simulated patterns of cardiac tissue activity produced by a computational model, in accordance with embodiments of the present invention.
Figure 6B:
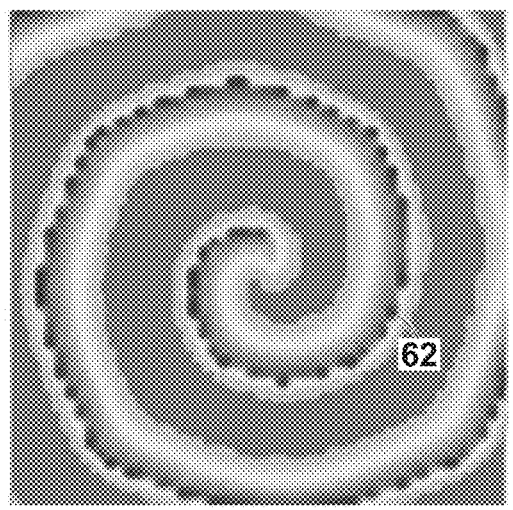
Figure 6C:
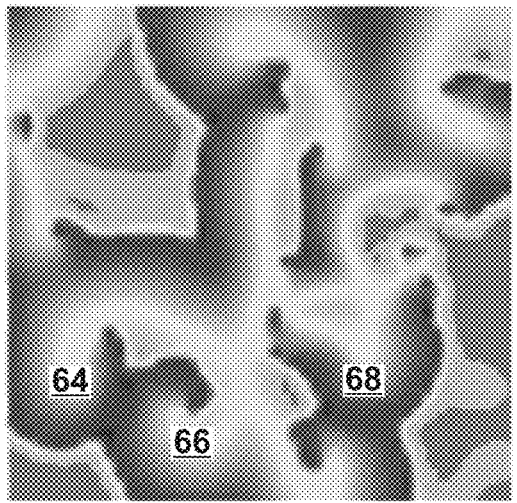

FIGS. 6A-6C illustrates these concepts using simulated patterns of cardiac tissue activity produced by a computational model. The reentrant circuits illustrated in FIGS. 6A-6C are of increasing complexity. FIG. 6A illustrates spiral waves of a simple reentrant circuit around a structural inner-boundary region of non-conducting tissue 60 (i.e., a simple rotor with a spatially-fixed core of, e.g., scar tissue). FIG. 6B illustrates spiral waves of a more complex reentrant circuit 62 that is free to travel the tissue (i.e., a rotor with a functionally-formed core). Spiral waves are an example of functional reentrant substrate created when source-sink relationships at the spiral center create a core of unexcited and/or unexcitable tissue around which rotation occurs. This can occur even in homogeneous and fully excitable tissue in which, based on the timing and distribution of excitation, groups of cells in separate phases of refractoriness create the separate paths which link to form a circuit. The simplest spiral-waves have spatially fixed cores as in FIG. 6A, whereas more complex examples have cores that meander throughout the tissue as in FIG. 6B. At the most complex end of the reentry spectrum, spiral-waves encountering spatially varying refractoriness can divide to form distinct daughter-waves, resulting in multi-wavelet reentry. FIG. 6C illustrates multi-wavelet reentry with, for example, daughterwaves 64, 66, and 68 (i.e., multiple rotors dividing to form daughter waves).

A rotor terminates when: (1) the rotor core (i.e., the center of the wave's rotation) collides with an electrical boundary in the atria, which physically interrupts the circuit of reentry; or (2) the tissue excitation wavelength is increased beyond the length of the circuit of reentry, thus physiologically interrupting the circuit of reentry (i.e., the circuit "interrupts itself" as the leading edge of tissue excitation collides with the trailing edge of refractory tissue). FIGS. 3A and 3B illustrate how the minimum path of a rotor is limited by tissue excitation wavelength in accordance with some aspects of the present invention. In FIG. 3A, the leading edge 401 of the tissue excitation wave does not overlap the trailing edge 402 of refractory tissue so the reentrant circuit is not interrupted. However, in FIG. 3B, the wavelength of the tissue excitation wave exceeds the length of the circuit of reentry: the leading edge 403 of the tissue excitation wave meets the trailing edge 404 of refractory tissue. When the rotor encounters the unexcitable refractory tissue 404, its path—and its circuit of reentry—is interrupted. When all circuits of reentry have been interrupted, when all rotors have been terminated, the fibrillation episode itself terminates.

Because reentrant circuits may be defined topologically, the cardiac tissue substrate, for example, the left atrium, may be viewed as a bounded and interrupted plane, which is capable of forming a reentrant circuit. In the left atrium, the annulus forms the edge or "outer" boundary of the plane, while the pulmonary veins form holes or discontinuities interrupting the plane. A discontinuity is any place within the tissue across which current does not flow.

A discontinuity may be structural and/or functional. As a result of tissue refractory properties (or source-sink mismatch), a structurally uninterrupted plane may nonetheless be capable of forming a reentrant circuit around a functional inner discontinuity, such as a physiologic conduction block. Thus, a heart may be described based upon its physical topology (defined by the geometrical structure of the tissue) and based upon its functional topology (defined by the physiologically possible paths of tissue activation).

Topologically, two surfaces are considered homomorphic (i.e., the same) if one surface can be transformed into the other surface by stretching, but not by cutting or pasting. All bounded surfaces with an inner-discontinuity may be considered homomorphic and functionally identical. Likewise, all bounded surfaces with an inner discontinuity may be considered homomorphic and functionally identical. From this perspective, a bounded surface with no inner discontinuity and a bounded surface with a discontinuity that is connected to a boundary (i.e., a tissue edge) are the same despite being of different shapes because one surface can be merely stretched to become the other surface. As a result of tissue refractory properties a structurally uninterrupted plane may nonetheless be capable of forming a circuit (around an inner-discontinuity to physiological conduction block). One can describe a physical topology (defined by the tissue structural geometry) and a functional topology (defined by the physiologically possible paths of activation).

Reentry requires a complete electrical circuit; disruption causes propagation to cease. If its circuit is disrupted, reentry is terminated, whether by prolongation of the tissue excitation wavelength beyond the circuit length or by physical interruption. As such, termination of fibrillation requires "breaking" each reentrant circuit. Topologically, this equates to converting a tissue substrate from a bounded and interrupted plane (capable of reentry) to a bounded but uninterrupted plane. As discussed above, a bounded but uninterrupted plane is functionally identical to a bounded plane in which the interruption is connected to the boundary. Thus, by connecting any discontinuities in a tissue substrate with a tissue edge, the tissue substrate may become functionally identical to a bounded but uninterrupted surface and less or no longer capable of supporting reentry. Thus, by connecting any discontinuities in a tissue substrate with a tissue edge, the tissue substrate may become functionally identical to a bounded but interrupted surface and less or no longer capable of supporting reentry.

FIGS. 7A-7C illustrate surface topology and reentry in accordance with some aspects of the present invention. More specifically, FIG. 7A illustrates a single wave 70 in an uninterrupted plane 72 with an outer boundary; FIG. 7B illustrates an interrupted place with a disconnected inner-boundary 74; and FIG. 7C illustrates a plane several time-steps after an ablation lesion 76 has connected the inner-boundary (e.g., the wave tip) to the tissue edge, thus eliminating the inner boundary. From a topological perspective, despite their differences in shape, a surface like the plane in FIG. 7A with no innerdiscontinuity and a surface like the plane in FIG. 7C with a discontinuity that is connected to the tissue edge are equivalent. That is, FIGS. 7A and 7C are homomorphic.

As with any reentrant rhythm, termination of multi-wavelet reentry requires circuit disruption. Unfortunately, the circuits involved in multi-wavelet reentry are spatially complex and temporally varying, so actually achieving circuit disruption is a pragmatic challenge. Nevertheless, the topologic perspective on reentry provides a conceptual framework for deciding where ablation lesions should be placed so as to yield the greatest likelihood of terminating multi-wavelet reentry. The goal of ablation is to reconfigure the tissue's topology (structural and functional) into that of an uninterrupted plane.

The simplest situation is presented by a fixed spiral-wave. The leading edge of excitation in spiral-wave reentry is curved, and curvature increases progressively until source-sink relationships at the spiral centre result in propagation failure. As shown in FIG. 7B, the point of propagation failure at the wave tip forms the inner-edge of the spiral-wave around which rotation occurs. As shown in FIG. 7C, circuit disruption requires a lesion to span from the tissue edge to the innerdiscontinuity at the wave tip.

The situation becomes more complicated with a meandering spiral-wave, as it is difficult to determine where a fixed lesion can be placed that is guaranteed to transect the reentrant circuit. Movement of the spiral-core provides a means to overcome this pragmatic hurdle; spiral meander can result in collision of the wave tip with a boundary. In fact, the probability of termination (tip/boundary collision) increases as the ratio of total boundary length to tissue area increases. Linear ablation lesions that are contiguous with the tissue edge can increase the boundary length area ratio and thereby increase the probability of termination. Note that such lesions do not change the topology of the atrial tissue; it remains an uninterrupted plane, but with a boundary that becomes progressively long and tortuous as the number of lesions increases. As tissue regions with shorter wavelength are more likely to contain spiral-waves, linear lesions in these areas are more likely to cross a tip-trajectory and cause spiral-wave termination. The crucial point remains, however, that all lesions must be placed such that the topology of the atrial tissue remains that of an uninterrupted plane.

These topological principles of and mechanisms underlying reentry provide a conceptual framework for optimizing an ablation lesion distribution that effectively and efficiently prevents, minimizes, and/or terminates reentry of progressively greater complexity. Using this framework, a computational model of cardiac excitation was developed to generate reentrant rhythms with emergent behavior including formation of stable and meandering spiral waves as well as multi-wavelet reentry. To test the impact of linear ablation (lines of electrically inert cells) on propagation during multiwavelet reentry, the model required a sufficiently small computational burden such that multiple simulations of extended periods of excitation could be run in a manageable amount of time.

Cells were arranged in a two-dimensional grid, each cell connected to its four neighbours (up, down, left, and right) via electrically resistive pathways. Each cell had an intrinsic current trajectory (Im—equivalent to net transmembrane current) that followed a prescribed profile when the cell became excited. Excitation was elicited either when the current arriving from the four neighbouring cells accumulated sufficiently to raise the cell voltage (Vm—equivalent to transmembrane voltage) above a specified threshold or when the cell received sufficient external stimulation (pacing). Once excited, a cell remained refractory (i.e. non-excitable) until Vm repolarized to the excitation threshold. The duration of a cell's refractory period was thus determined by the duration of its action potential. Following the absolute refractory period, there was a period of relative refractoriness during which excitation can occur but with decreased upstroke velocity. Each cell's intrinsic action potential morphology (voltage vs. time) was modulated by its prior diastolic interval and lowest achieved voltage at the time of its depolarization. This modulation conferred restitution upon upstroke velocity and action potential duration. Tissue heterogeneity was represented by an action potential duration that varies randomly about a set mean, which itself could also vary across the tissue.

This computational model did not include all the known biophysical details of individual cardiac cells. Nevertheless, it did incorporate the key behavioural features of individual cells that are required to reproduce realistic global conduction behaviour. This behaviour included source-sink relationships with wave curvature-dependent conduction velocity and safety factor, and the potential for excitable but unexcited cells to exist at the core of a spiral-wave. The computational model thus combined the computational expediency of cellular automata with the realism of much more complicated models that include processes at the level of the ion channel.

The voltage matrices from each time-step of the cardiac model simulations were saved. Each voltage map was converted into a phase map by performing a Hilbert transform to generate an orthogonal phase-shifted signal from the original signal at each coordinate of the tissue space-time plot (x, y, t). From the original and phase-shifted signals, the phase at each coordinate at each time-step was calculated.

The location of the leading edge of each excitation wave was determined for each time-step of the simulation (based on the coordinates at which each cell first crossed the threshold for excitation). Phase singularities were identified, and phase singularity sites were considered to represent a spiral wave tip if (1) all phases surrounded the singularity in sequence (from $-\Pi$ to $\Pi$) and (2) the phase singularity was located at the end of a leading edge of activation. Space-time plots of the phase singularities were created to delineate wave-tip trajectory. The total number of spiral-wave tips (measured during each time-step over the sampling interval) divided by the space-time volume was defined as the spiral-wave-tip density. Spiral waves were initiated by rapid pacing from two sites in close proximity with an offset in the timing of impulse delivery. Spiral waves were spatially stable in the setting of homogeneous tissue (all cells identical) with a shorter wavelength than circuit length. As action potential duration was increased (wavelength circuit length), the spiral waves began to meander. Multi-wavelet reentry resulted when action potential duration was randomized across the tissue. A region with higher spiral-wave density resulted when a patch of tissue with shorter mean action potential duration was created.

Consistent with the topological view of ablation strategies, lesions placed at the center of spiral waves simply converted a functional discontinuity into a structural discontinuity, but did not result in termination of reentry. Termination required placement of a lesion spanning from the tissue edge to the wave tip. Even a single excitable cell between the lesion and wave tip was sufficient for spiral-wave perpetuation. However, lesions needed only connect the tissue edge to the outermost extent of the wave tip-trajectory. Meandering spiral waves terminated when their wave tips collided with a lesion.

To study the ablation of meandering spiral waves and multi-wavelet reentry, cellular action potential duration was randomly varied about a mean value (75±25 ms) in a set of simulations to produce a random spatial distribution of refractoriness. Using this approach, varied patterns of multi-wavelet reentry were initiated by varying the distribution of action potential duration. To test the hypothesis that mobile spiral-waves and multi-wavelet reentry are terminated through probabilistic collisions with the tissue boundary, the duration of multi-wavelet reentry as a function of the boundary-length-to-surface-area ratio was examined. In rectangular sections of tissue, width and height (and thus boundary length) were varied while surface area remained fixed. The average duration of multi-wavelet reentry increased progressively as the boundary-length-to-surface-area ratio was decreased (average duration $2.2\pm1.7\times10^3$ time-steps at a ratio of 0.26; average duration $4.0\pm2.1\times10^6$ time-steps at a ratio of 0.125; simulations at the lowest ratio were truncated at $5.0\times10^6$ time-steps; only 2 of 10 simulations terminated within this time frame).

FIG. 8 illustrates the impact of boundary-length-to-surface-area ratio on the duration multi-wavelet reentry according to some aspects of the present invention. Keeping tissue area fixed (at 1,600 mm$^2$) the length and height were varied such that boundary-length-to-surface-area ratio decreased from top to bottom: 0.26, 0.2125, 0.145, and 0.125, respectively.

Figure 9A:
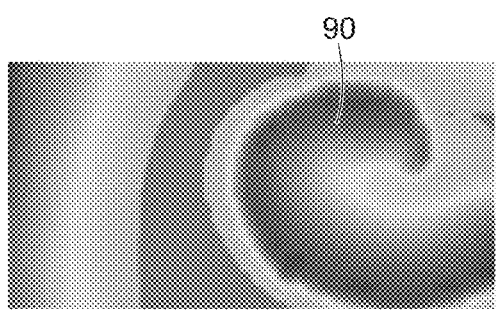
FIGS. 9A-9D illustrate how ablation lines increase the boundary-length-to-surface-area ratio and decrease the duration of multi-wavelet reentry, in accordance with embodiments of the present invention.
Figure 9B:
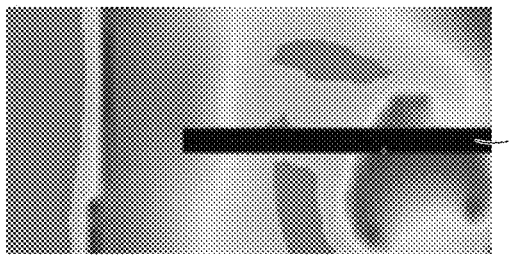
Figure 9C:
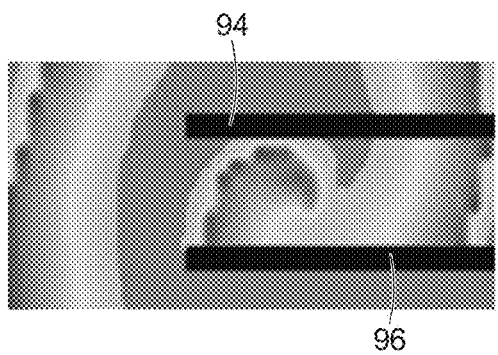
Figure 9D:
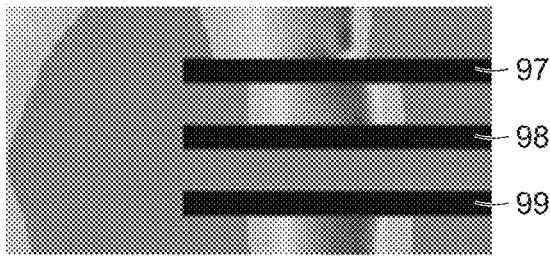

In a related set of experiments, the effects of linear ablation on the average duration of multi-wavelet reentry were tested. Tissue area was 800 mm$^2$ and baseline boundary-length-to-surface-area ratio was 0.15 prior to simulated ablation. As ablation lines were added to the tissue, the average time to termination of multi-wavelet reentry progressively decreased. FIGS. 9A-9C illustrate how ablation lines increase the boundary-length-to-surface-area ratio and decrease the duration of multi-wavelet reentry in accordance with some aspects of the present invention. In FIG. 9A, zero ablation lines produced termination of multi-wavelet reentry 90 in $2.2 \pm 2.9 \times 10^5$ time-steps; in FIG. 9B, one ablation line 92 produced termination of multi-wavelet reentry in $4.2 \pm 8.5 \times 10^4$ time-steps; in FIG. 9C, two ablation lines 94 and 96 produced termination of multi-wavelet reentry in $1.6 \pm 2.5 \times 10^3$ time-steps; in FIG. 9D, three ablation lines produced termination of multi-wavelet reentry in $575 \pm 67$ time-steps.

Finally, the effects of heterogeneous tissue properties on the effectiveness of ablation lesions were tested. When the central area of the tissue had shorter average action potential duration ($90 \pm 15$ ms) than the surrounding regions ($115 \pm 10$ ms), spiral waves meandered and were preferentially located within the central short refractory period zone. The mean spiral-wave-tip density (measured as the number of cores per space-time volume) was significantly higher in the central shorter action potential duration zone ($4.73 \pm 0.71$ cores/mm$^2$ ms) compated to the surrounding tissue ($2.95 \pm 0.18$ cores/mm$^2$ ms), $P<0.001$. In tissue without a central short action potential duration zone, there was no significant difference in spiral-wave-tip density between the central zone and the periphery ($1.58 \pm 0.65$ vs. $1.57 \pm 0.52$ cores/mm$^2$ ms, $P=0.963$).

The regional efficacy of ablation for termination of multi-wavelet reentry was assessed by delivering ablation lesions either to the central zone (high spiral-wave density) or the surrounding tissue (low spiral-wave density). In both cases, the total boundary-length-to-surface-area ratio was kept fixed (0.13) by varying only the location but not length or number of ablation lines. One hundred percent of episodes terminated when lesions were delivered inside the central zone, compared with 76% termination following ablation outside the central zone (n=25). The average time to termination was shorter when lesions were placed within the central zone ($1.0 \pm 1.2 \times 10^4$ time-steps) compared with lesions placed only in the surrounding tissue ($7.5 \pm 8.2 \times 10^4$ time-steps), $P=0.0005$. Conversely, when the tissue periphery had shorter average action potential duration ($90 \pm 15$ ms vs. $115 \pm 10$ ms), spiral-wave-tip density was higher within that area ($4.05 \pm 0.64$ cores/mm$^2$ ms) compared with the central longer action potential duration zone ($3.29 \pm 0.52$ cores/mm$^2$ ms), $P<0.001$. Ablation resulted in termination of multi-wavelet reentry in 80% of simulations (whether lesions were placed in the central zone (n=25) or in the periphery (n=25)). The average time to termination was shorter when lesions were placed in the peripheral high spiral-wave-tip density zone ($1.7 \pm 2.8 \times 10^4$) compared with the central low spiral-wave-tip density zone ($4.9 \pm 3.7 \times 10^4$ time-steps, $P=0.009$).

The framework presented here offers a perspective for understanding treatment of multi-wavelet reentry—when it succeeds and when it fails. Anti-arrhythmic medications alter atrial functional topology and ablation alters atrial structural topology. The requirements for rendering atrial functional topology incapable of supporting reentry are prescribed by the framework of circuit interruption/inner-boundary elimination. The pragmatic realization of this goal in the complex functional and structural architecture of the atria is a tremendous challenge.

In multi-wavelet reentry spirals terminate when all spiral-cores collide with an outer boundary. The probability of collision, and therefore termination, is increased as the ratio of total boundary length to area is increased. The addition of linear ablations (contiguous with the tissue edge) can substantially increase the probability of termination. Ablation lines are most likely to result in termination of multi-wavelet reentry when delivered to areas of high spiral-wave density. Interestingly, the addition of linear scar resulted in increased dispersion of refractoriness (through reduced electrotonic interactions, data not shown). Although this alone enhances the propensity for reentry, because scars were contiguous with an outer boundary they did not provide a circuit and hence were not arrhythmogenic.

The key question, then, is where to place additional lesions in order to optimally treat the significant of patients not responsive to current strategies. This topological framework guides us in answering this question, the goal being to distribute linear lesions that provide the greatest likelihood of producing wave extinction while at the same time minimizing total lesion length.

The framework also helps to shed light on some controversial aspects of atrial fibrillation ablation. For example, there are numerous reports of improved outcome with addition (or sole use) of focal ablation that targets complex fractionated atrial electrograms. On the basis of the findings in this study, one would predict that focal ablation would create new potential reentrant circuits (unless lesions are continued to an atrial boundary).

Ultimately, it is desirable to apply this topological analysis to individual patients to prospectively identify those requiring additional ablation lesions and to design optimal ablation strategies that are patient specific. This has not been possible prior to the present invention and its embodiments.

Mass Hypothesis of Cardiac Fibrillation

The propensity of a tissue to maintain fibrillation is proportional to its area. However, total surface area is not the only determinant of fibrillogenicity. Fibrillation terminates more quickly in long, skinny strips of tissue compared with square tissue of the same total area. It was this observation that led to the recognition that cardiac fibrillation is a reentrant rhythm requiring a minimum radius within which to turn around. Using this approach, atrial fibrillation should not be maintained if the tissue substrate is divided into segments too small to allow a reentrant circuit. Using computer modeling studies, this approach was expanded based on the recognition that multi-wavelet reentry terminates when rotor cores collide with a tissue outer boundary and that collision is more likely as the ratio of tissue boundary to tissue area is increased (e.g., through addition of linear ablation lesions contiguous with the tissue edge). It was further recognized that when the distribution of rotor cores is concentrated in certain regions (based upon tissue physiology and architecture), the probability of collision is greatest when ablation lines are placed in the regions with higher rotor density.

Evolutionary Hypothesis of Ablation Lesion Placement

In a study, a Covariance Matrix Adaptation Evolutionary Strategy ("CMA-ES") was used to "evolve" an optimized distribution (location, orientation, and length) ablation lesions for preventing, minimizing, and or terminating cardiac fibrillation. Optimization or fitness feedback was based upon the extent to which these proposed ablation lesions decreased the ability of the cardiac tissue substrate to induce and sustain multi-wavelet reentry. The characteristics of the evolving ablation lesion sets were assessed with regard to their adherence to the principles outlined by the conceptual strategy, specifically: (1) the percent of lines that are contiguous with the tissue's outer boundary; and (2) the total contiguous tissue area (i.e., the amount of tissue not electrically isolated (quarantined) by enclosing ablation lesions).

In order to test whether the CMA-ES would identify the strategy of concentrating ablation lines in regions of higher circuit density, ablation lines were evolved under at least one of two conditions: (1) "homogeneous" simulated tissue in which circuits were uniformly distributed (i.e., the control condition); and (2) "heterogeneous" simulated tissue containing a patch of tissue with a higher concentration of circuits then the remainder of the tissue.

A computational model was used to generate simulated two-dimensional tissue sheets, comprised of an array of (e.g., 60×60) "cells." Each cell represents a large number of myocytes. The intercellular resistance was uniform in each direction and throughout the tissue (unless otherwise stated). The action potential duration (and refractory period) of each cell varied randomly throughout the tissue with a mean of 100±25 ms. The cells properties included restitution; action potential duration was rate-dependent (varying as a function of preceding diastolic interval). In homogeneous tissue the distribution of baseline action potential duration (prior to the effects of restitution) was randomly selected producing a relatively uniform concentration of circuits across the tissue when following induction of multi-wavelet reentry was induced. In heterogeneous tissue the action potential duration of cells within a patch of tissue (20×20 cells located along the middle third of the tissue border) was set to vary about a mean of 50±25 ms. The inter-cellular resistance within this patch was increased by 140% relative to the tissue outside the patch. In each case (homogeneous and heterogeneous) 10 separate replicates of macroscopically similar tissues were generated which had unique (random) distributions of action potential duration (using the same mean and standard deviation).

Figure 10A:
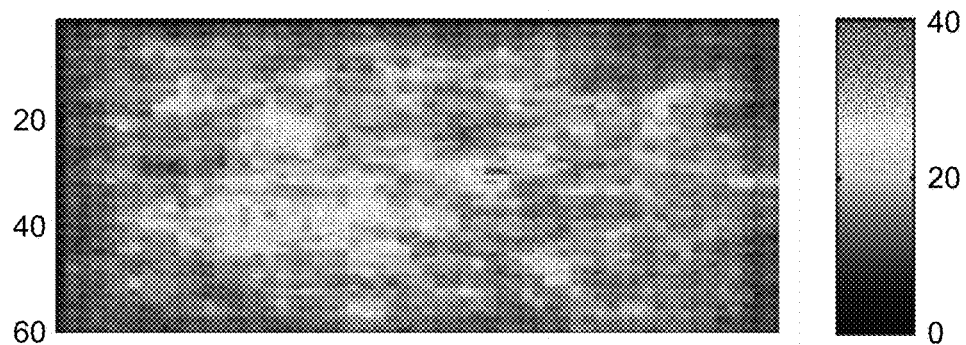
FIGS. 10A-10B illustrate the circuit density maps, particularly
Figure 10B:
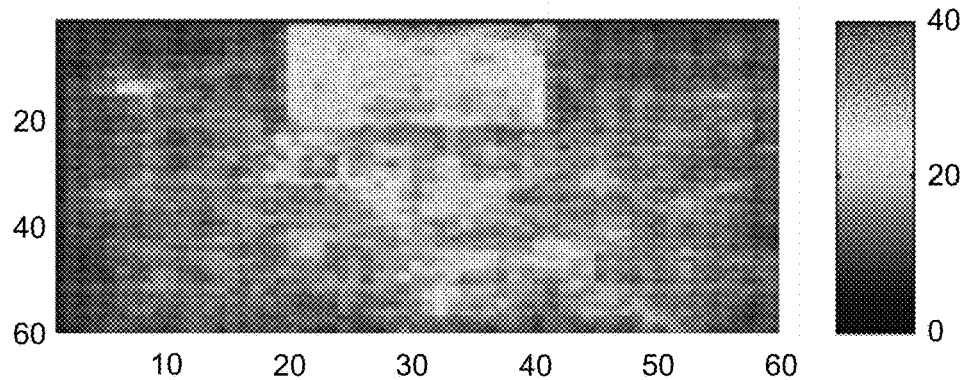

FIGS. 10A-10B illustrate the circuit density across simulated tissue in accordance with some aspects of the invention. In FIG. 10A, the distribution is homogenous; however, in FIG. 10B, the distribution is heterogeneous.

Multi-wavelet reentry was generated using cross field stimulation. In the baseline state the duration of induced multi-wavelet reentry is assessed, if termination occurred within the 2.5 second simulation the tissue is was rejected and a new tissue generated. This process was repeated until 10 acceptable test tissues were generated.

Circuits were identified by first converting the space-time plots of tissue voltage to phase maps using a Hilbert transform. Phase singularities were identified as sites at which (1) all phases meet at a single point and (2) phases are arranged in sequence from −Π to Π. In order to eliminate false positive phase singularities (those not identifying a rotor core), the leading edge of each wave was delineated (based upon initiation of AP upstroke). Phase singularities that were not located at the end of a wave-front were eliminated.

Evolutionary algorithms are biologically inspired solution-space search methods. In general such algorithms involve: (1) randomly creating a population of candidate solutions; (2) assessing the fitness of these solutions relative to a fitness function or criterion; (3) selecting at least one of fittest solutions; and (4) creating a new generation of candidate solutions through some process of varying the prior generation's selected solution(s). These steps are iterated resulting in progressive optimization of the solutions' fitness. CMA-ES is one of many different types of evolutionary algorithms that may be appropriate for lesion optimization. CMA-ES is designed to optimize real valued functions of real-valued vectors. For example one might seek a real-valued vector z that minimizes y in the fitness function $f$.

$$f(z1, z2, \ldots, zn) = y \quad (1)$$

The fitness function may be non-differentiable, non-linear and non-convex; CMA-ES treats the function as a black box. In our case z corresponds to a set of ablation lines and $f$ is a fitness function designed to optimize the ability of those lines to terminate and preclude multi-wavelet reentry.

CMA-ES works by naturally following the contours of a co-evolving estimate of the surrounding fitness landscape in seeking to improve a single current solution estimate. Rather than maintaining a fixed population size as in many evolutionary algorithms, CMA-ES starts by assuming a multivariate normal distribution around a single randomly selected solution vector m with covariance C, which is initially assumed to be a diagonal matrix (i.e., uncorrelated variables in solution space) with a pre-defined global standard deviation σ. It then proceeds to co-evolve improved estimates of the solution (new mean m) and an improved estimate of the covariance matrix C of the variables in surrounding solution space, as follows.

For every generation: (1) a population cloud of λ potential solutions is generated according to the current estimate of the multivariate normal distribution described by C around the solution vector m; (2) this population is then truncated to the best μ solutions, where μ is typically on the order of one half λ; (3) a fitness-weighted average of the remaining μ solutions becomes the new m, thus reducing the population to only one candidate solution; and (4) the covariance matrix C is updated using local fitness landscape information based on the generational change in m (a rank 1 update), the most recent t samples of the solution space in the vicinity of m (a rank μ update), and the length of evolution path of successive estimates of m. As the search nears an optimum, the variance estimates approach zero and CMA-ES converges. Multiple random restarts of CMA-ES can be used to avoid getting stuck in local optima. To apply CMA-ES one must define an encoding for the solutions and a function to measure fitness.

The encoding defines how a real vector z maps to a solution, in this case a set of six ablation lines. Ablation lines are represented by a vector of 24 real numbers bounded from [−1; 1]:

$$z = [x1, y1, x2, y2, \ldots, x12, y12] \quad (2)$$

The successive pairs of values are interpreted as (x, y) Cartesian coordinates. Each coordinate pair defines the endpoints of a single straight ablation line, so there are six lines for each ablation set. Any cell i that falls underneath an ablation line is set to "dead" (unexcitable) and has an infinite resistance with its neighbors. All potential solutions (m and the clouds of λ potential solutions created each generation) are of this form.

The initial ablation sets were explicitly biased to discourage connections of ablation lines to an exterior boundary, in order to see if such connections would reliably evolve. All values in the initial vector m that encodes ablation sets are drawn from a uniform distribution [−0.4, 0.4]. The initial standard deviation σ is 0.2, hence the initial covariance matrix estimate is:

$$C = \begin{bmatrix} \sigma^2 & 0 & 0 \\ 0 & \ddots & 0 \\ 0 & 0 & \sigma^2 \end{bmatrix} \quad (3)$$

or $\alpha^2 I$. These parameters ensure that 95% of the ablation lines in the initial population are within the range of [−0.8, 0.8], thus they tend not to connect to an exterior boundary.

Tissue activation frequency, FR, is defined as the mean activation frequency of all the cells:

$$FR = \frac{1}{TN}\sum_{i=1}^{N} s_i \tag{4}$$

where $s_i$ is the number of activations of the ith cell, N is the total number of cells, and T is the number of seconds the tissue is simulated (2.5). The units of FR are activations per second. An FR of 1 means cells on average are activated once per second.

Our CMA-ES minimizes the fitness function:

$$f(x) = F \tag{5}$$

$$= \frac{1}{10}\sum_{j=1}^{N} FR_j$$

where F is the mean activation frequency FR of ten training tissues. Two constraints are imposed on the ablation sets: (1) the total number of ablated cells cannot exceed 20% of the tissue; and (2) no more than 18% of the tissue can be quarantined. Any ablation set that violates these constraints is eliminated and replaced until an ablation set that satisfies the constraints is produced.

Population sizes of $\lambda=15$ and $\mu=7$ were selected based on the genome size of 24. The CMA-ES was run for 200 generations (before which the rate of fitness improvement had diminished). For each evolutionary run, fitness was evaluated on ten randomly generated training tissues of a given type (homogeneous or heterogeneous) exhibiting MWR, and the resulting fitness's were averaged. By testing on 10 different tissues with varied distribution of similar electrophysiologic parameters the evolved solutions were general to a "type" of tissue rather than a specific individual tissue.

Each lesion set was assigned characteristics, including percent of lesions contiguous with an outer boundary, percent quarantine, and boundary-length-to-surface-area ratio. The proportion of ablated cells that connect to a tissue boundary was defined as pC. If all ablated cells ultimately connect to a boundary, pC=1. If the ablated cells form an island never connecting to an edge, pC=0.

If ablation lines enclose a region of the tissue the enclosed cells become electrically isolated from the remainder of the tissue, effectively reducing the tissue area. The proportion of cells isolated by ablation is defined as pQ. If a tissue were ablated with a line extending from the top center of the tissue to the bottom center then pQ would equal 0.5.

Let pA be the proportion of cells that are ablated. The length of the exterior boundary L is the total number of ablated cells connected to the exterior boundary (N pA pC) plus the exterior boundary (B) (which is 240=60×4 for a 60×60 tissue bounded on its four sides). The contiguous electrically excitable tissue area A is the total number of cells N minus the ablated cells, pA, and the quarantined cells, pQ. To test the hypothesis that the probability of multi-wavelet termination is directly proportional to the exterior boundary length and inversely proportional to the tissue surface area, the following ratio was calculated:

$$\frac{L}{A} = \frac{N \cdot pA \cdot pC + B}{N(1 - pA - pC)} \tag{6}$$

To determine the contribution of boundary continuity to the fitness of each final evolved set of ablation lines we retested their fitness after disconnecting them from the tissue edge. The last two ablation lesions (points) connecting the line to the tissue boundary are "un-ablated" so that no ablation lines connect to the exterior boundary and pC=0.

Two sets of experiments were run with ten independent evolutions each. In the first, ablation lesion sets were evolved on homogeneous tissues. In the second, ablation lesion sets were evolved on tissue containing a patch of cells with shorter wave length (refractory period×conduction velocity) due to reduced action potential duration and increased intercellular resistance. In the latter heterogeneous tissues, we confirmed that there was increased circuit density in the short wave-length patch.

Figure 11:
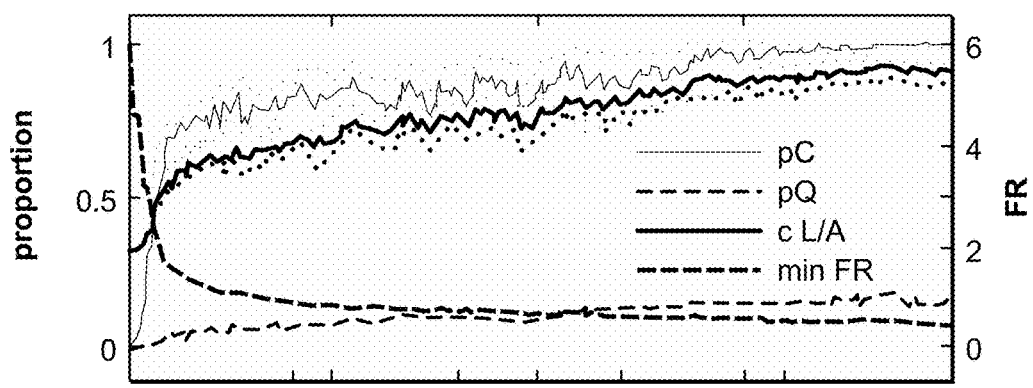
FIG. 11 illustrates graphically ablation lesion characteristics and fitness of tissue with homogeneous circuit density, in accordance with embodiments of the present invention.

In the first set of experiments, the following were examined: (1) the proportion of ablation lines contiguous with the exterior boundary pC; (2) the amount of quarantined tissue pQ; (3) the length to area ratio L/A (i.e., the total exterior boundary length, including ablation lines divided by the contiguous tissue area excluding quarantined tissue); and (4) the fitness FR. The results (mean±standard error of the mean (SEM)) are presented in FIG. 11, which is a plot of ablation lesion characteristics and fitness in tissue with homogeneous circuit density in accordance with some aspects of the present invention. Fitness improves as lesions evolve (0.93±0.12 to 0.07±0.01 p<0.001). The percentage of ablation points contiguous with the exterior boundary steadily increases (0.01±0.02 to 0.99±0.02, p<0.001). The total lesion length also increases to the maximum allowable of 18% (0.00±0.00 to 0.15±0.03, p<0.001). The proportion of quarantined tissue also increases. The net result is an increase in the boundary-length-to-surface-area ratio (0.07±0.00 to 0.20±0.01, p<0.001).

As the total length of ablation lines contiguous with the exterior boundary (L) decreases, hat ablation set was expected to be less likely to terminate multi-wavelet reentry. To test this hypothesis, in each of the best evolved ablation sets, the last two ablation points connecting a line to the tissue edge were "unablated" and fitness retested. Ten new test tissues (that were not used during training) exhibiting MWR were generated to re-evaluate each modified ablation set. Prior to modifying the ablation sets, the average pC=0.99±0.02, the average L/A=0.20±0.01, and the average fitness FR=0.90±0.03 (mean±standard error). Following ablation modification (disconnection from outer boundaries), the average pC=0±0, the average L/A=0.08±0.001, and the average pT=0.23±0.04.

Figure 12A:
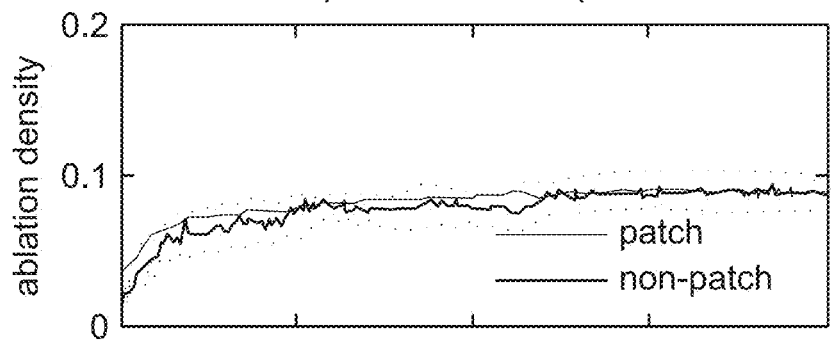
FIGS. 12A-12B illustrate graphically the relationship of ablation density versus circuit density, in accordance with embodiments of the present invention.
Figure 12B:
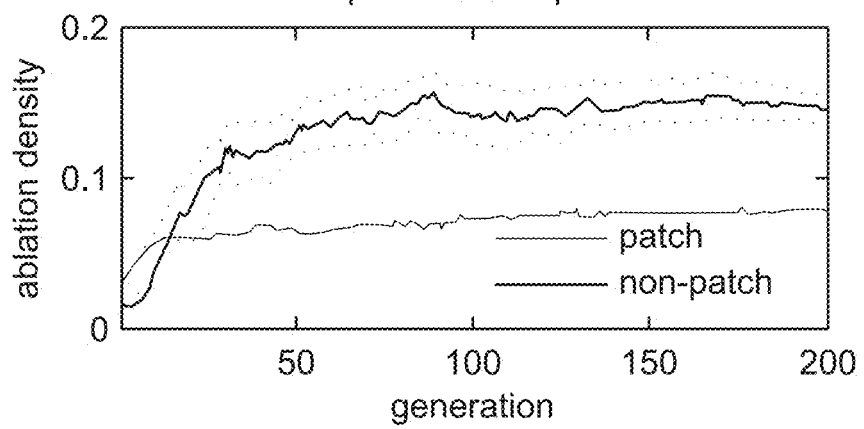

In a second set of experiments, the ablation sets that evolved in heterogeneous tissue (with a high circuit density patch) were examined. The density of ablation lesions in the top middle portion of the tissue (high circuit density patch) were compared with that in the remainder of the tissue. Ablation density was higher in the patch than in the remainder of the tissue (0.08±0.01 vs 0.15±0.01, p<0.001). FIG. 12A is a plot of ablation density versus circuit density for tissue without a high circuit density patch, in accordance with some aspects of the present invention. In contrast, the ablation density was the same in and outside of the top middle portion of the tissue in the homogeneous tissue experiments. FIG. 12B is a plot of ablation density versus circuit density for tissue with a high circuit density patch, in accordance with some aspects of the present invention. Ablation density is markedly increased in the high circuit density region.

Based upon an explanatory model for propagation through excitable tissue, multi-wavelet reentry necessitates complete circuits for its perpetuation. This implies the strategy for its ablation: interrupt these circuits causing termination. Interruption requires complete circuit transection thus the first tenet of the conceptually-guided strategy: lines must be contiguous with the tissue's exterior boundary and extend to the circuit-core. To corroborate this principle using the CMA-ES a first generation of ablation lines was created that were not contiguous with an outer boundary so that if the evolved ablation strategies had a greater percentage of lines connected to the outer boundary than would result from random mutation, fitness pressure for such connection must be at work. Starting from an initial generation in which virtually none of the lines were contiguous with the tissue's outer boundary (by design), by the end of evolution nearly 100% of lines were connected.

To confirm that it was continuity with the boundary that conferred increased fitness, the ends of each ablation line were eliminated at their point of contact with the boundary. In each case the fitness decreased when lines were disconnected from the outer boundary.

If collision is fundamental to efficacy then lines in areas with higher circuit density, where collision is more likely, should be more effective than those in areas with lower density. To test whether fitness pressure would drive ablation lines toward areas of high circuit density solutions were evolved on tissue with a patch of increased circuit density. In each evolution performed on heterogeneous tissue, ablation lines were concentrated within the high circuit-density patch. In contrast, the density of ablation lines in the same tissue region was not increased when evolved on homogeneous tissue.

The current results help to validate the fundamental principles that underlie the conceptually-guided strategy. The two approaches to searching the solution space of the ablation problem (evolutionary algorithmic and conceptually-guided) are fundamentally different and non-derivative. The fact that in each case the lesion sets adhere to the same principles (due to fitness pressure on the one hand and by mechanistically-inspired design on the other) supports the importance of these tenets. This is critical because an evolutionary approach does not apply in human hearts (only a single lesion set may be delivered). The key characteristic of the conceptually-guided approach is that it effectively allows for a priori efficacy evaluation (through mental modeling) so when ablation lesions are delivered they have already been "tested".

In modern science there has been a growing appreciation of the existence and nature of complex systems. Such systems, comprised of multiple parts interacting in non-linear fashion, are capable of extremely complex behaviors. The heart is such a system. It has a very simple job description: it must pump blood. The achievement of this task, however, is tremendously complex requiring the coordinated activity of billions of ion channels in millions of cells interacting electrically and mechanically in an elegant symphony, and without the benefit of a conductor. When functioning normally the heart sustains life, when sufficiently deranged it precludes it.

In the context of multi-wavelet reentry, ablation amounts to manipulating the structure of a complex non-linear system so as to constrain its behavior. Even if we limit allowable manipulations to the placement of ablation lines, the number of possible solutions is vast and exhaustive search is intractable.

Measurements Indicative of the Fibrillogenicity of a Cardiac Tissue Substrate

Fibrillogenicity is a measure of how conducive a patient's heart is to supporting fibrillation. A fibrillogenicity assessment allows a clinician to estimate the amount of ablation (e.g., the total length of ablation lesions) that will be required to treat and minimize fibrillation in a particular patient.

The relationship between a patient's fibrillogenicity and physiologic factors may be represented as, for example:

$$FB \propto \frac{A}{L} \qquad (7)$$

where FB is fibrillogenicity, A is the surface area of the tissue substrate, and L is the boundary length of the substrate. As shown in the equation above, fibrillogenicity may be considered proportional to the ratio of surface area to boundary length of the tissue substrate.

Fibrillogenicity also may be considered inversely proportional to the tissue excitation wavelength $\lambda$:

$$FB \propto \frac{1}{\lambda} \qquad (8)$$

As discussed above, a reentrant circuit will be interrupted if the tissue excitation wavelength exceeds the circuit length. The tissue excitation wavelength is the distance from the leading edge of a tissue excitation wavefront to its trailing edge of unexcitable refractory tissue. As tissue excitation wavelength increases, fewer reentrant circuits can be supported per unit area of tissue substrate. Thus, fibrillogenicity may be considered proportional to the number of reentrant circuits the tissue is capable of supporting per unit area.

Ideally, an assessment of a patient's fibrillogenicity should take into account measurements (even if only indirect indications are available) of the substrate surface area (e.g., the patient's atrial surface area), the total boundary length of the substrate (e.g., the patient's atrial boundary length), and the minimum substrate area required to support one reentrant circuit.

Minimum Circuit Area

The minimum substrate area required to support one reentrant circuit informs the extent of electrical derangement in the tissue. The measure of the area of tissue required to support an individual rotor is the minimum circuit area. As the minimum circuit area decreases, the tissue substrate as a whole becomes capable of supporting more rotors, and the probability that all circuits will be interrupted simultaneously and fibrillation will terminate. Thus, fibrillogenicity increases as the minimum circuit area decreases.

However, the determinants of minimum circuit area are multifactorial and many of the factors are emergent (i.e., the result of interactions between cell physiology, tissue anatomy, and the evolving circumstances of global and local activation states). While the minimum circuit area cannot be measured directly, the minimum circuit area is related, at least in part, to the tissue excitation wavelength.

Tissue excitation wavelength is not a single static parameter of tissue but a product of the conduction velocity of a wave and the refractory period (i.e., the amount of time required to recover excitability following excitation) of the tissue through which the wave is traveling. Both of these factors depend upon spatiotemporal context. For example, the refractory period of cardiac tissue varies with the frequency at which a given heart cell is excited. A given heart cell is excited at frequencies that tend to range from 4 to 15 Hz, particularly 5 to 10 Hz. Meanwhile, the conduction velocity of a wave is influenced by wave shape: curved waves (e.g., rotors) conduct more slowly than flat waves. Hence, tissue excitation wavelength—and thus minimum circuit area—may vary over time and across the heart, even in an individual patient.

Electrocardiography ("ECG/EKG") may be used to gather measurements indicative of tissue excitation wavelength and thus minimum circuit area by recording the electrical activity of a patient's heart at the body surface. An electrocardiograms (also a "ECG/EKG") translates the electrical deflections or changes in the electrical potential produced by the contractions of a heart into graphical waveforms. During an atrial fibrillation episode, for example, the ECG/EKG may show fibrillatory waves ("F-waves"), which are small, irregular, rapid deflections. The wavelength of F-waves in a patient may be considered proportional to, and thus indicative of, tissue activation wavelength and minimum circuit area. As described above, these measurements correlate with a patient's fibrillogenicity and, consequently, may be incorporated into the estimation of how much ablation is needed and/or whether an ablation procedure is complete.

Boundary-Length-to-Surface-Area Ratio

Fibrillogenicity is also modulated by the total boundary length of the tissue substrate, which, for an atrium, is the sum of the circumferences of the atrial boundaries and orifices (e.g., the superior vena cava, inferior vena cava, atrioventricular tricuspid valve, atrioventricular mitral valve, and orifices of the pulmonary veins). As described above, reentrant circuits terminate upon complete interruption. A complete interruption requires the absence of a continuous path of excitable tissue at any point in the reentrant circuit. A moving circuit may cause its own interruption when its core collides with a physical boundary. Thus, the core of a moving circuit may interrupt the circuit itself by meandering into a tissue boundary or orifice In the context of moving circuits, the probability of such a collision increases with the total length of any boundaries. Therefore, total boundary length may be considered inversely proportional to fibrillogenicity.

Figures 63A, 63B:
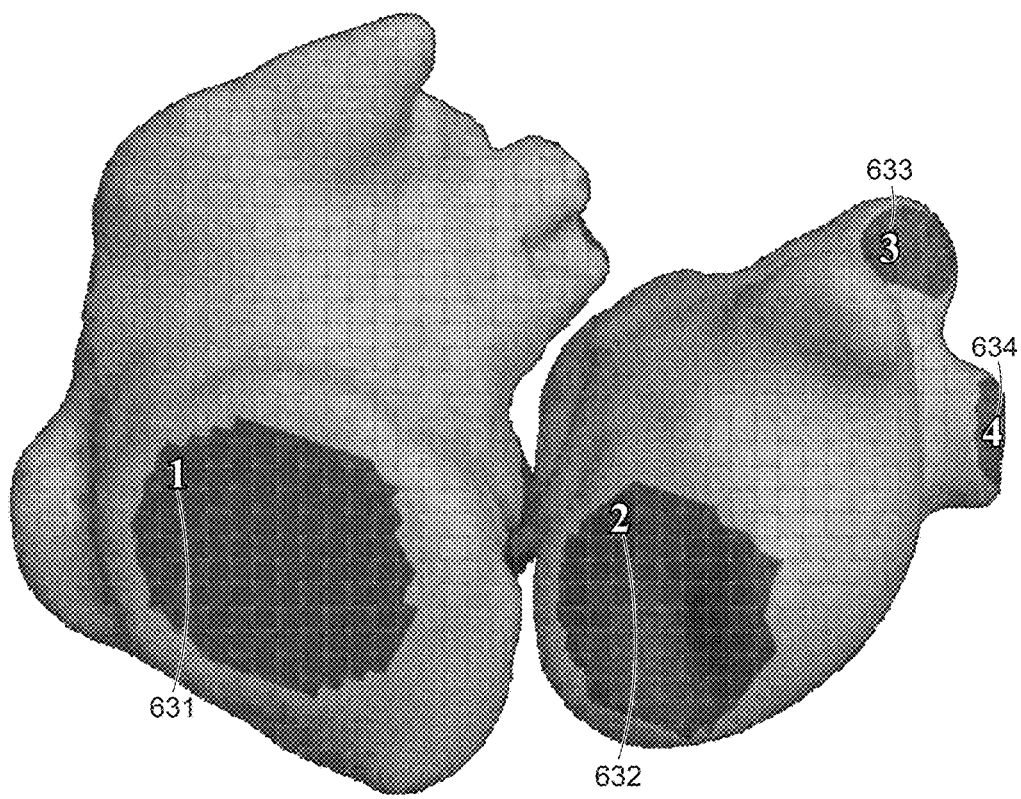
FIGS. 63A-63B are computer axial tomography scans of a human heart, in accordance with embodiments of the present invention.

FIG. 63A-63B are computer axial tomography scans of a human heart. FIG. 63A is a right atrium with boundary/orifice 631. FIG. 63B is a left atrium having three boundaries/orifices 632, 633, and 634. To calculate the total boundary length of the tissue substrate, add the sum of the circumferences of the atrial boundaries and orifices shown in FIGS. 63A and 63B. The total surface area is calculated by removing the area of the boundaries/orifices from the surface area of the tissue substrate.

Meanwhile, as the surface area of a tissue substrate (e.g., the atrial surface area) increases, a moving circuit may have more space to meander without its core colliding with a boundary and interrupting the circuit itself. The probability of a such a collision decreases with an increase in total surface area. Therefore, total surface area may be considered directly proportional to fibrillogenicity.

Given these multiple relationships, the probability of collision may be increased by extending the electrical boundaries of tissue substrate by the interventional placement of ablation lesions connected to existing boundaries (e.g., anatomic boundaries and/or previously created ablation lesions). From another perspective, lesions may be placed to decrease surface area, thus increasing the probability of collision. Therefore, boundary-length-to-surface-area may indicate (at least in part) an amount or length of boundaries (i.e., lesions) to be added and/or an amount of surface area to be removed, such that the final boundary-length-to-surface-area ratio favors collision and termination of fibrillation.

The boundary lengths and surface areas of the heart may be mapped onto and measured from, for example, a cardiac magnetic resonance imaging (MRI) scan, computed tomography (CT) scan, rotational angiogram, three-dimensional ultrasound image, three-dimensional electro-anatomic map, and/or other medical representation. Once the surface of a tissue substrate (e.g., an atrium) is scanned and reconstructed as one or more representations (e.g., two-dimensional images or three-dimensional models) via one of these imaging modalities, the one or more representations may be used to measure and/or compute boundary lengths, the surface areas, and/or boundary-length-to-surface-area ratios.

Like the minimum circuit area, the boundary-length-to-surface-area ratio provides a more complete indication of the tissue fibrillogenicity and informs the extent of ablation required to reduce fibrillogenicity and minimize or prevent further fibrillation. As described below, this information—combined with the density and distribution of circuit cores—may be used to assess and even quantify fibrillogenicity in accordance with some embodiments of the present invention.

Figure 13:
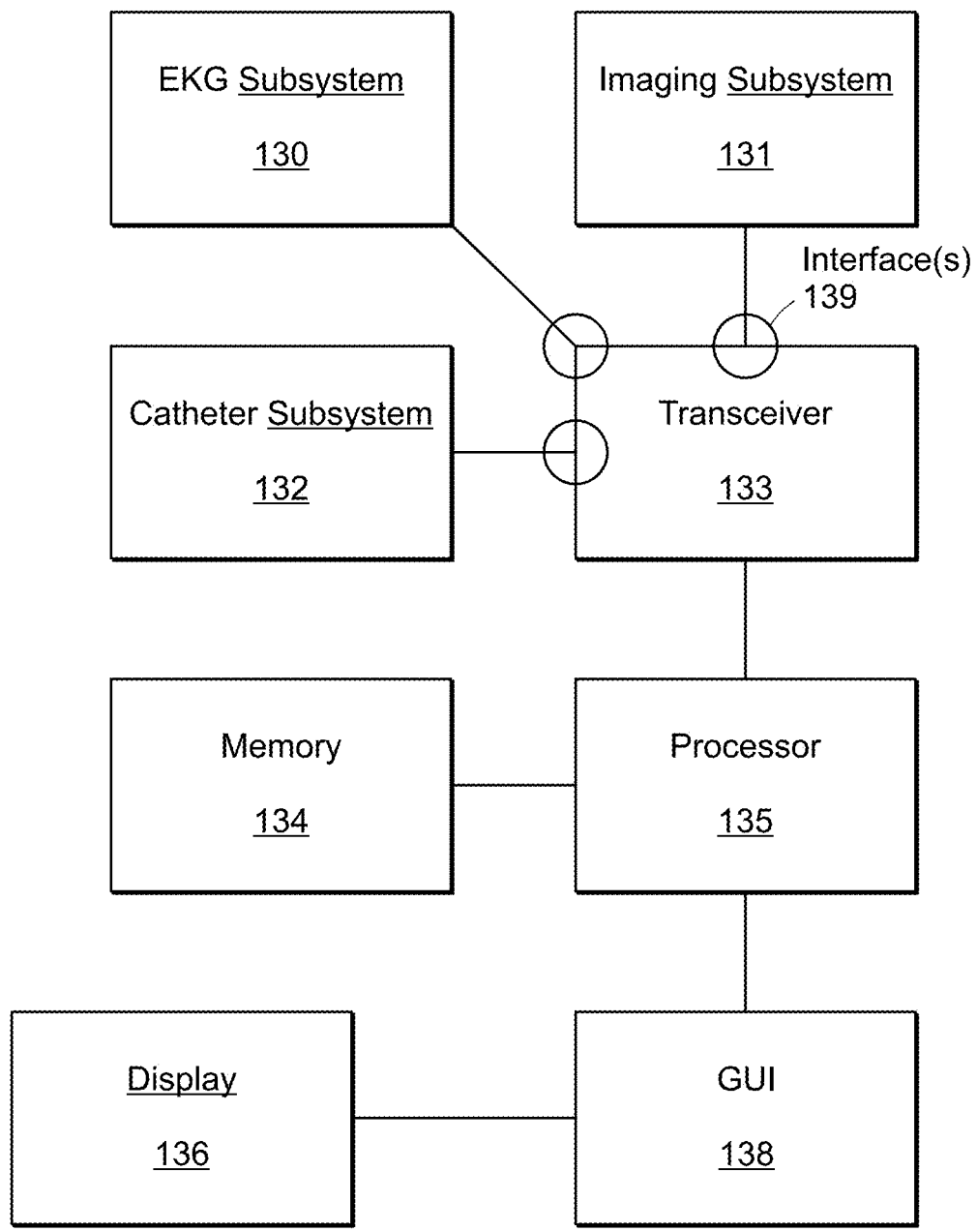
FIG. 13 is a system component block diagram, in accordance with embodiments of the present invention.

FIG. 13 is a system component block diagram in accordance with certain embodiments of a system for making measurements indicative of fibrillogenicity in a patient. The system may include an ECG/EKG subsystem 501 for collecting measurements indicative of tissue activation wavelength (and minimum circuit area) and/or an imaging subsystem 502 for acquiring or collecting measurements indicative of a tissue substrate's total boundary length, total surface area, and/or boundary-length-to-surface-area ratio. The system may also include, but is not limited to, a catheter subsystem 503, a processing unit 504, a memory 505, a transceiver 506 including one or more interfaces 507, a graphical user interface ("GUI") 508, and/or a display 509 (each described in detail below).

The ECG/EKG subsystem 501 may be used to measure the heart's electrical activity (e.g., F-waves) as recorded at the body surface. These measurements correlate with the fibrillogenicity and, consequently, may be incorporated into the calculus for estimation of how much ablation needs to be performed (and, as described below, whether or not an ablation procedure is complete). The ECG/EKG subsystem 501 may include a separate display and/or share a display 509 with other components of the system shown in FIG. 13. The ECG/EKG subsystem 501 and its components may be operated manually and/or automatically.

The imaging subsystem 502 may include any means by which a medical representation (e.g., a two-dimensional image or three-dimensional model) of a tissue substrate is acquired and/or generated, allowing the measurement of, for example, an atrium's surface area along with the veins and valves (i.e., boundaries) that interrupt its surface. Suitable imaging modalities include, but are not limited to, MRI, CT, rotational angiography, three-dimensional ultrasound, and/or three-dimensional electro-anatomic mapping. Some imaging modalities may require the injection of one or more contrast agents. The imaging subsystem 502 may include a separate display and/or share a display 509 with other components of the system shown in FIG. 5. The imaging subsystem 502 and its components may be operated manually and/or automatically.

A electrophysiological study was undertaken to investigate which clinical variables, including a noninvasive measurement of cycle length from a surface ECG/EKG, are predictive of a successful procedural and medium-term clinical outcome using a sequential catheter ablation approach in patients with persistent cardiac fibrillation. Ninety patients, who underwent first-time radiofrequency catheter ablation for long-lasting persistent cardiac fibrillation, were included in the study. Long-lasting persistent cardiac fibrillation was defined as continuous cardiac fibrillation lasting longer than one month and resistant to either electrical or pharmacological cardioversion.

Figure 14:
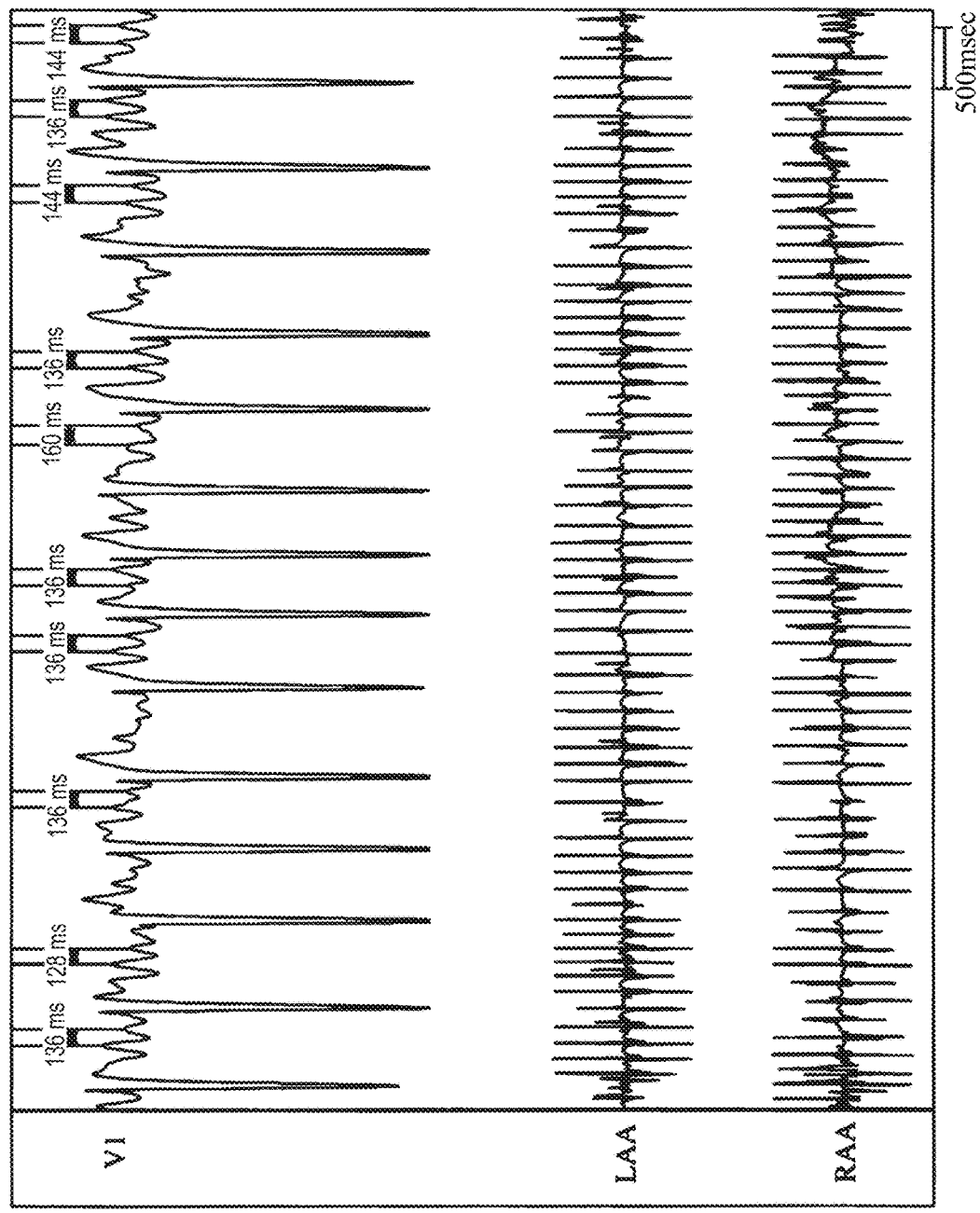
FIG. 14 is a plot of simultaneous measurements of the atrial fibrillatory cycle length from surface ECG/EKG and the left and right atrial appendages according to some embodiments of the present invention.

Surface ECG/EKG and endocardial electrograms were continuously monitored during the ablation procedure and recorded for off-line analysis. The surface ECG/EKG cycle length was compared with the endocardial cycle length obtained simultaneously from the intracardiac recordings at both the left atrial appendage and the right atrial appendage before ablation. In all patients, the surface ECG/EKG cycle length was manually measured from 10 unambiguous fibrillatory waves on lead $V_1$ (minimal voltage>0.01 mV) that were not fused with QRST segments at a paper speed of 50 mm/s and a gain setting of 20, 40, or 80 mm/mV. FIG. 14 is a plot of simultaneous measurements of the atrial fibrillatory cycle length from surface ECG/EKG and the left and right atrial appendages according to some aspects of the present invention. Seiichiro Matsuo et al., "Clinical Predictors of Termination and Clinical Outcome of Catheter Ablation for Persistent Atrial Fibrillation," 54:9 *J. of Am. College of Cardiology* 788-95 (2009). In FIG. 14, the cycle lengths from surface ECG/EKG, left atrial appendage ("LAA"), and right atrial appendage ("RAA") were 139 ms, 144 ms, and 145 ms, respectively. Id.

In the first 30 patients, intraobserver and interobserver error of the surface ECG/EKG cycle length from 10 cycle lengths was assessed. The surface ECG/EKG cycle length from 10 cycle lengths was measured on two different days and using two independent experts, respectively. The mean surface ECG/EKG cycle length from 10 cycle lengths was compared with that from 30 cycle lengths (manually measured) and with the mean cycle length using automated time frequency analysis of 60 s of simultaneous surface ECG/EKG recording. Digital measurement of fibrillatory rates using time frequency analysis was disqualified because of poor signal quality in 4 patients.

In all patients, sequential stepwise ablation was performed, involving pulmonary vein isolation, electrogram-based ablation, and linear ablation. Ablation around the pulmonary veins was performed with the aid of a Lasso catheter. The end point of this step was the elimination or dissociation of the pulmonary vein potentials as determined by a Lasso catheter in all veins. Isolation of the pulmonary veins was confirmed after restoration of sinus rhythm. After this, electrogram-based ablation was performed at sites in the left atrium showing any of the following electrogram features: continuous electrical activity, complex rapid and fractionated electrograms, and a gradient of activation (a temporal gradient of at least 70 ms between the distal and proximal bipoles on the roving distal ablation electrode, potentially representing a local circuit). Linear ablation in the left atrium was performed if atrial fibrillation persisted after electrogram-based ablation. A roof line was performed joining the right and left superior pulmonary veins, and if atrial fibrillation continued, a mitral isthmus line from the mitral annulus to the left inferior pulmonary vein was performed. After restoration of sinus rhythm, assessment of conduction block across the lines was performed in all patients with supplementary ablation, if necessary, to achieve block. A cavotricuspid isthmus line was performed in all patients with an end point of bidirectional block.

The procedural end point was termination of longlasting persistent atrial fibrillation by catheter ablation, either by conversion directly to sinus rhythm or via one or more atrial tachycardias, which were subsequently mapped and ablated. When atrial fibrillation was not terminated by ablation, it was terminated by electrical cardioversion. After cardioversion, if necessary, supplemental radiofrequency energy was delivered to establish pulmonary vein isolation and conduction block of any linear lesion. Clinical outcome of long-lasting persistent atrial fibrillation ablation. Success was defined as maintenance of sinus rhythm without antiarrhythmic drug treatment more than 12 months after the final procedure. Failure was defined as documented recurrence of atrial fibrillation or atrial tachycardia lasting for more than 3 min.

Patients were hospitalized for between 3 and 5 days post-procedure and seen at 1, 3, 6, and 12 months for clinical interview, echocardiography, and 24-hour ambulatory monitoring in addition to routine follow-up by the referring cardiologist. One year from the last procedure, patients were seen every 6 months by their referring cardiologist. All patients underwent 24-hour Holter monitoring within the last 3 months of follow-up. Antiarrhythmic medication was continued for 1 to 3 months after the index procedure, and anticoagulation treatment was continued for at least 6 months. A repeat ablation procedure was undertaken in the event of a recurrence of atrial fibrillation or atrial tachycardia lasting more than 3 min.

Linear regression analysis was used to test the association between the surface ECG/EKG cycle length from 10 cycle lengths and 30 cycle lengths, time frequency analysis of a 60-s sample window, LAA cycle length, RAA cycle length, and procedure time. A Bland-Altman plot was generated to examine the precision between the RAA cycle length and the surface ECG/EKG cycle length from 10 cycle lengths, 30 cycle lengths, and time frequency analysis. To evaluate intraobserver and interobserver variability, the Pearson correlation coefficient (r) was calculated for the surface ECG/EKG cycle length from 10 cycle lengths. Continuous variables are expressed as mean±standard deviation or median with interquartile range where indicated. Statistical significance was assessed using the unpaired Student t test or Mann-Whitney U test if necessary. Categorical variables, expressed as numbers or percentages, were analyzed using the chi-square test or Fisher exact test. To analyze independent predictive factors of termination of atrial fibrillation during ablation and independent factors of clinical success, univariate factors presenting p<0.1 were analyzed using logistic regression (multivariate analysis). The receiver-operator characteristic curve was determined to evaluate the performance of the best independent predictor of atrial fibrillation termination by catheter ablation. The optimal cutoff point was chosen as the combination with the highest sensitivity and specificity. All tests were 2-tailed, and p<0.05 was considered significant. Cumulative event rates (recurrence of arrhythmia) were calculated according to the Kaplan-Meier method.

Figure 15A:
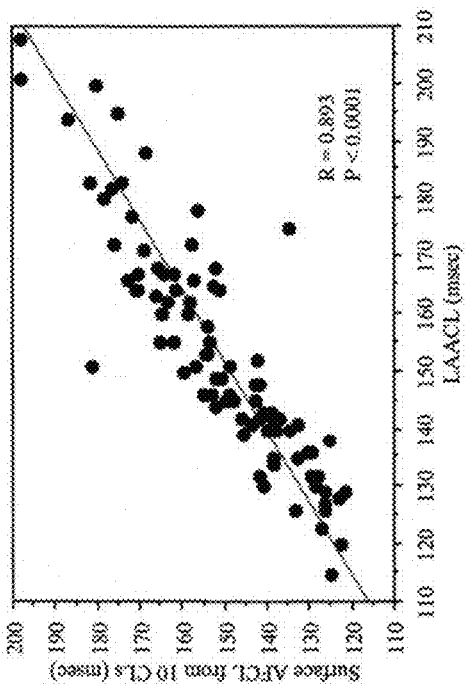
FIGS. 15A-15D illustrate graphically atrial fibrillation cycle length (AFCL) correlation, particularly.
Figure 15C:
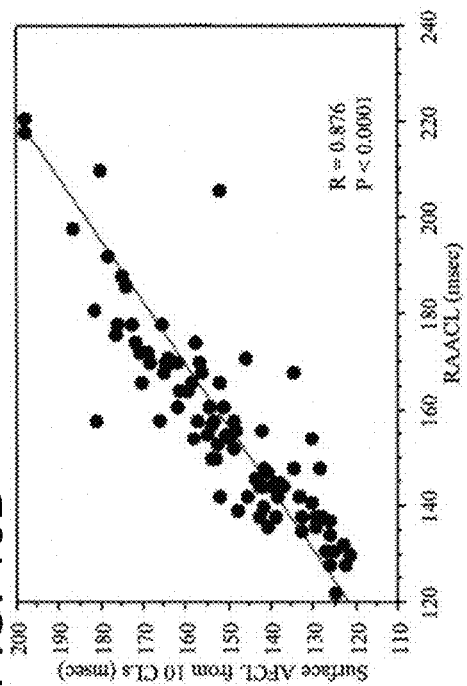
Figure 15B:
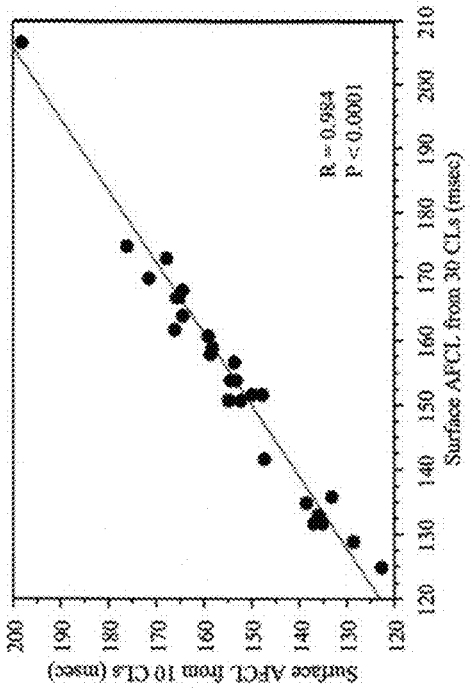

Intraobserver and interobserver correlations were high in the measurement of the cycle length from the surface ECG/EKG using 10 cycle lengths (R=0.97 and R=0.98, respectively). In the first 30 patients, surface ECG/EKG cycle length was calculated using manual measurement of 10 and 30 cycle lengths and the use of time frequency analysis of a 60-second simultaneous recording window. FIG. 15A is a plot showing the relationship between mean surface ECG/EKG atrial fibrillation cycle length measurement from 10 and 30 cycle lengths. Id. FIG. 15B is a plot showing the relationship between surface ECG/EKG cycle length from 10 cycle lengths and atrial fibrillation cycle length using time frequency analysis. Id. There was a strong correlation between the cycle length from the surface ECG/EKG measured with 10 and 30 cycle lengths (R=0.984, p<0.0001), plotted in FIG. 15A, and between the surface ECG/EKG cycle length calculated manually using 10 cycle lengths and digital measurement using time frequency analysis (R=0.941, p<0.0001), plotted in FIG. 15B. Id.

Figure 15D:
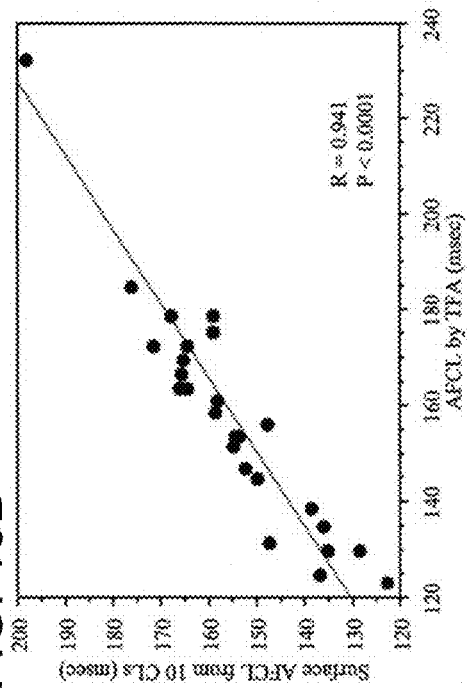

The mean surface ECG/EKG cycle length from 10 cycle lengths and LAA and RAA cycle length of the total population were 150±19 ms, 153±20 ms, and 157±20 ms, respectively. The mean surface ECG/EKG cycle length was longer in patients taking amiodarone (163±18 ms vs. 146±16 ms, p<0.0001). The mean differences between the surface ECG/EKG cycle length from 10 cycle lengths and the endocardial cycle length in the LAA and RAA were 7±6 ms and 8±8 ms, respectively. FIG. 15C is a plot showing the relationship between surface ECG/EKG atrial fibrillation cycle length from 10 cycle lengths and the LAA cycle lengths. Id. FIG. 15D is a plot showing the relationship between surface ECG/EKG atrial fibrillation cycle length from 10 cycle lengths and the RAA cycle length. Id. The surface ECG/EKG cycle length from 10 cycle lengths was strongly correlated with both the LAA cycle lengths (R=0.893, p<0.0001), plotted in FIG. 15C, and the RAA cycle lengths (R=0.876, p<0.0001), plotted in FIG. 15D. Id.

Figure 16A:
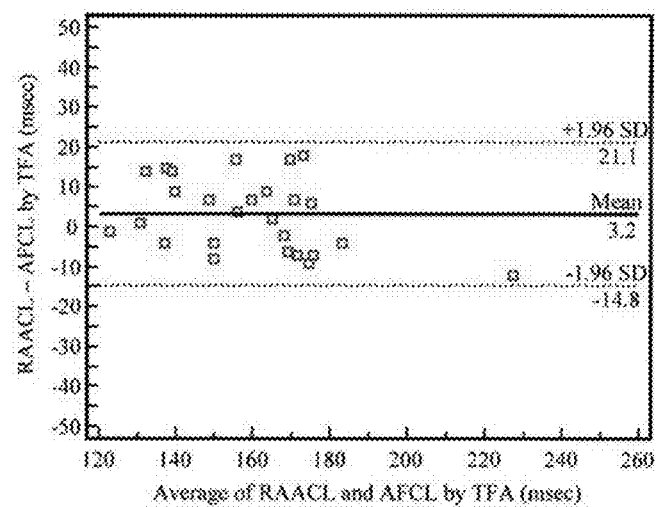
FIGS. 16A-16C are Bland-Altman plots illustrating relationship between the RAA cycle length and the cycle lengths from time frequency analysis and surface ECG/EKG, in accordance with embodiments of the present invention.
Figure 16B:
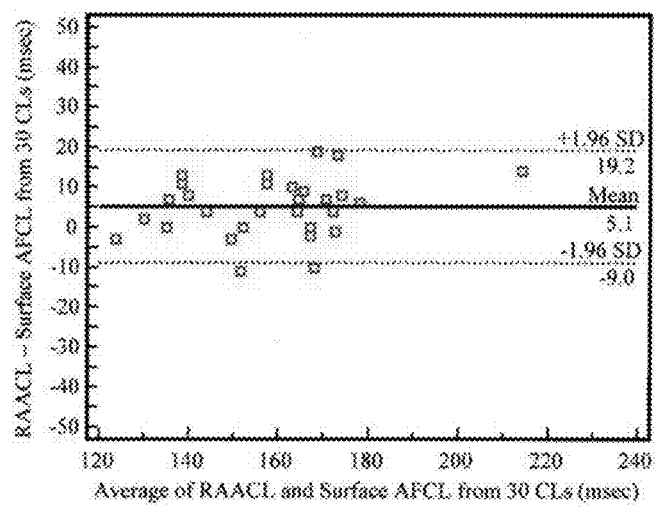
Figure 16C:
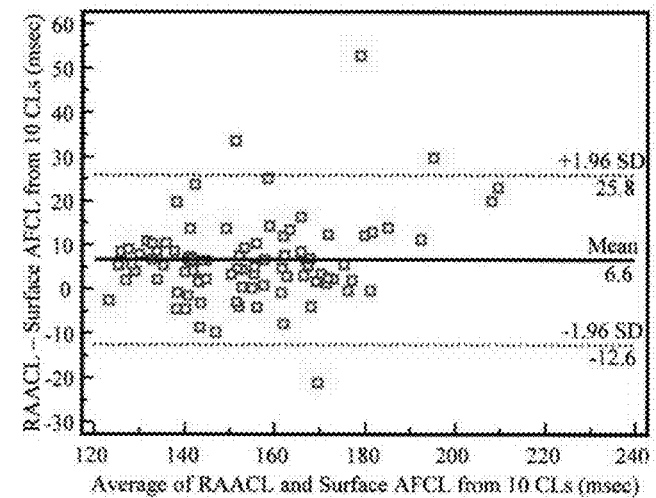

FIGS. 16A-16C are Bland-Altman plots in accordance with some aspects of the study and the present invention. Id. The plot in FIG. 16A shows good agreement between the RAA cycle lengths versus the cycle length from time frequency analysis. Id. The plot in FIG. 16B shows good agreement between the RAA cycle lengths versus the manual measurement surface ECG/EKG cycle length from 30 cycle lengths. Id. The plot in FIG. 16C shows good agreement between the RAA cycle lengths versus the manual measurement surface ECG/EKG cycle length from 10 cycle lengths. Id.

Long-lasting persistent atrial fibrillation was terminated by ablation in 76 of 90 patients (84%), with a mean procedure time of 245±70 min. Pre-procedural clinical variables were compared in patients in whom atrial fibrillation was terminated by ablation versus in those who were not. Compared with patients in whom atrial fibrillation was not terminated, patients with atrial fibrillation termination had a significantly shorter duration of continuous atrial fibrillation (22±24 months vs. 60±44 months, p<0.0001), a longer surface ECG/EKG cycle length (154±17 ms vs. 132±10 ms, p<0.0001), and a smaller left atrium dimension (47±7 mm vs. 54±11 mm, p<0.01).

Using multivariate analysis, the surface ECG/EKG cycle length was the only independent predictor of atrial fibrillation termination by catheter ablation (p<0.005). There was a trend toward duration of continuous atrial fibrillation predicting atrial fibrillation termination (p<0.08), but left atrium dimension was not an independent predictor.

Figure 17:
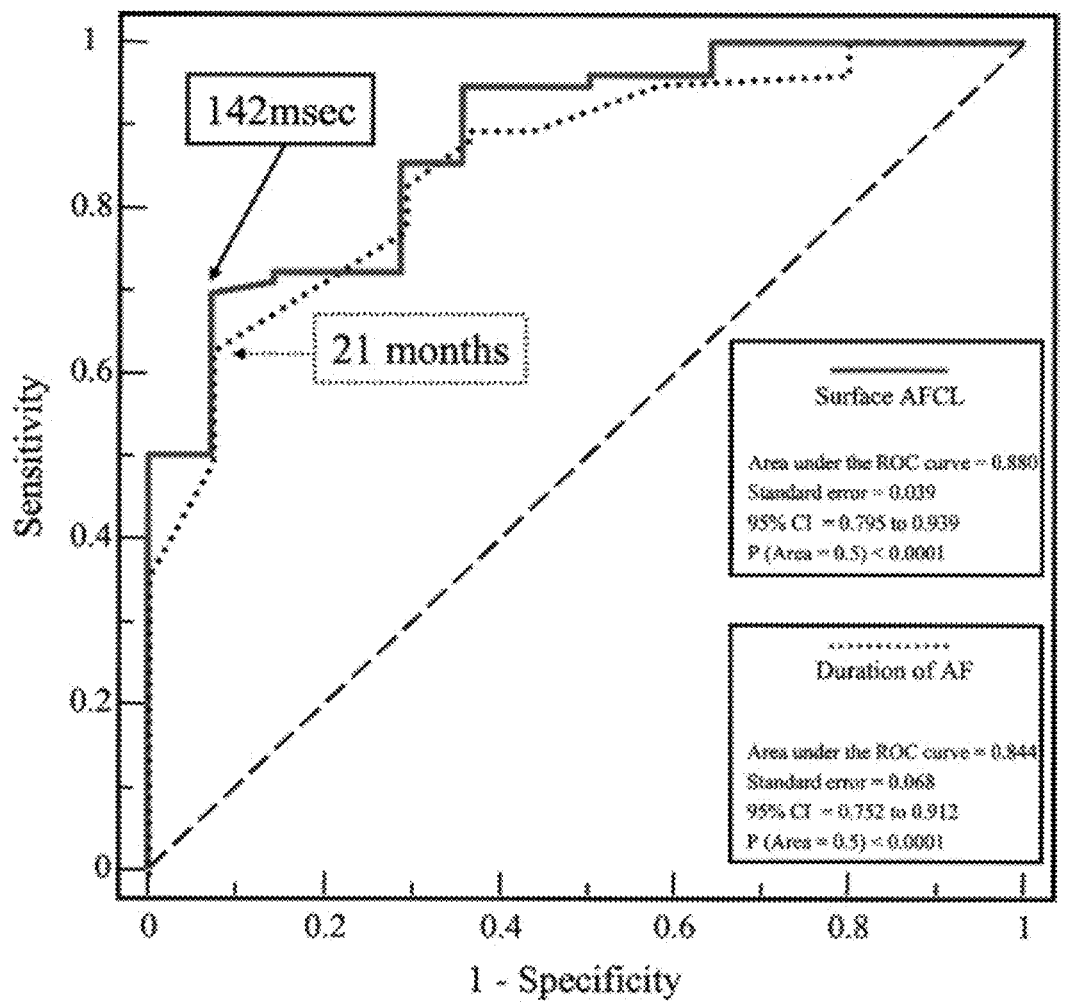
FIG. 17 is a plot of the receiver-operator characteristic curve for the surface ECG/EKG cycle length, in accordance with embodiments of the present invention.

FIG. 17 is a plot showing the receiver-operator characteristic curve for the surface ECG/EKG cycle length as a predictor of termination of long-lasting persistent atrial fibrillation in accordance with some aspects of the invention. Id. The area under the receiver-operator characteristic curve of 0.880 (95% confidence interval: 0.795 to 0.939, p<0.0001). As shown in FIG. 17, a cutoff point of 142 ms of the cycle length had a specificity of 92.9% and a sensitivity of 69.7% in predicting procedural termination of persistent atrial fibrillation. Id. The positive and negative predictive value of the cycle length 142 ms were 98.1% and 36.1%, respectively, for procedural termination of persistent atrial fibrillation. There was an inverse relationship between procedural time and the surface ECG/EKG cycle length (R=0.55, p<0.0001). For the association between the duration of continuous atrial fibrillation and procedural termination, the area under the receiver-operator characteristic curve was calculated to be 0.844 (95% confidence interval: 0.752 to 0.912, p<0.0001). As shown in FIG. 17, the optimal cutoff point for the duration of continuous atrial fibrillation was 21 months for atrial fibrillation termination (specificity 92.9%, sensitivity 61.8%). Id. The combined cutoff using a surface ECG/EKG cycle length >142 ms and a duration of continuous atrial fibrillation <21 months had 100.0% specificity in predicting procedural termination of persistent atrial fibrillation (sensitivity 39.5%, positive predictive value 100.0%, negative predictive value 23.3%).

After the final procedure, 84% (76 of 90) of patients were in sinus rhythm without antiarrhythmic drug treatment during follow-up of 18 6 months (median 18 months, interquartile range 12 to 24 months). There was no difference in total number of procedures between patients with and without recurrence (1.8±0.8 vs. 1.9±0.9, p=NS). The duration of continuous atrial fibrillation (57±54 months vs. 23±21 months, p<0.0001) and the surface ECG/EKG cycle length were longer (154±18 ms vs. 136±11 ms, p<0.001) in patients with recurrence of arrhythmia than in those who maintained sinus rhythm without antiarrhythmic drugs. The dimension of the left atrium was smaller (48±8 mm vs. 53±8 mm, p<0.05) in patients with a successful medium-term outcome. There was a trend toward lower left recurrence after the final ablation (53±10% vs. 60±14%, p<0.08).

Figure 18A:
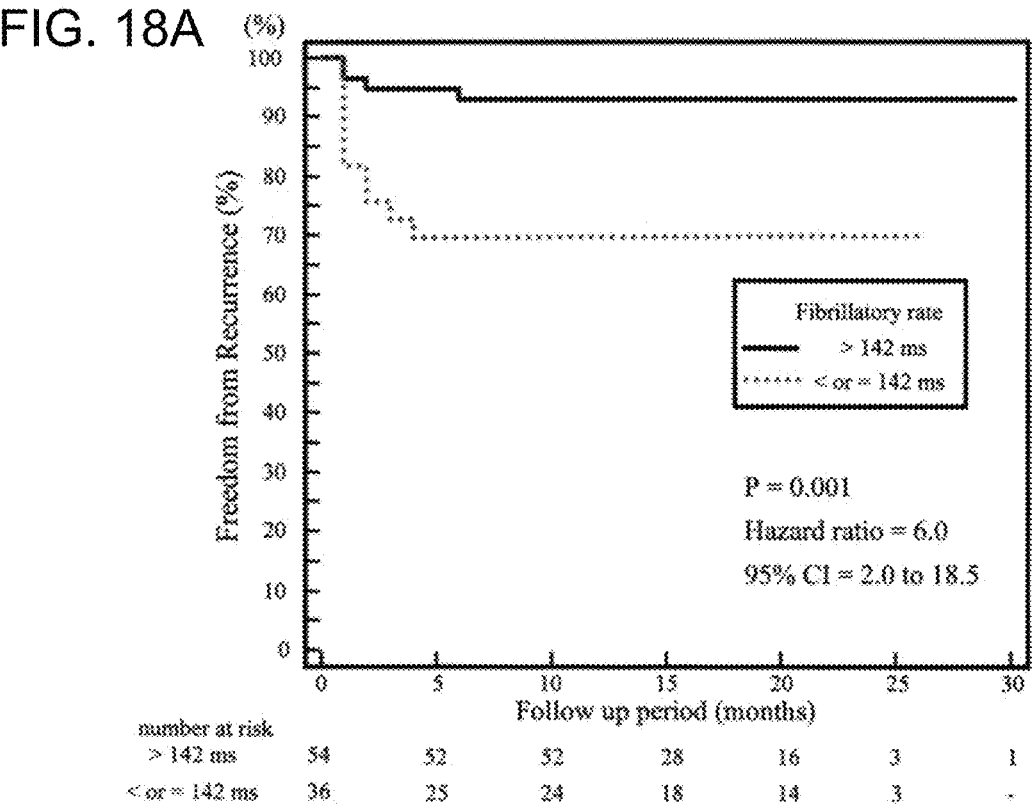
FIGS. 18A-18B are plots of Kaplan-Meier curve analyses of the incidence of recurrent arrhythmia following ablation procedure, in accordance with embodiments of the present invention.
Figure 18B:
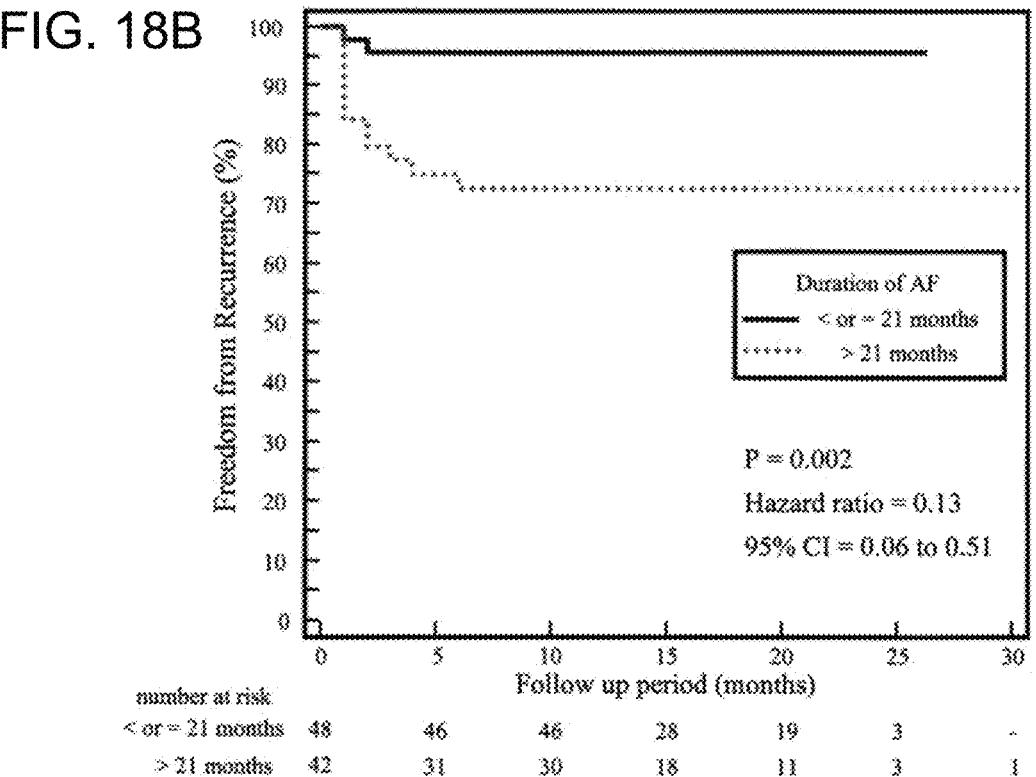

FIGS. 18A-18B are plots of Kaplan-Meier curve analyses in accordance with some aspects of the invention. Id. The plot in FIG. 18A shows a Kaplan-Meier curve analysis of the incidence of recurrent arrhythmia after the last procedure in patients with or without the cycle length from surface ECG/EKG>142 ms. Id. The plot in FIG. 18A shows a Kaplan-Meier curve analysis of the incidence of recurrent arrhythmia after the last procedure in patients with or without the duration of persistent atrial fibrillation >21 months. Id. In multivariate analysis, the surface ECG/EKG cycle length and the duration of continuous atrial fibrillation independently predicted clinical outcome of persistent atrial fibrillation ablation (p<0.01 and p<0.05, respectively). Patients with a surface ECG/EKG cycle length <142 ms had a significantly higher rate of recurrent arrhythmia (p=0.001, hazard ratio: 6.0, 95% CI: 2.0 to 18.5), as shown in FIG. 18A. Additionally, arrhythmia recurrence after the final ablation was frequently observed in patients with duration of continuous atrial fibrillation >21 months compared with those with persistent atrial fibrillation lasting <21 months (p=0.002, hazard ratio: 0.13, 95% CI: 0.06 to 0.51), as shown in FIG. 18B. Id.

Recurrence of arrhythmia after the index procedure was observed in 69% (62 of 90) of patients. Recurrence of atrial fibrillation after the index procedure was observed more frequently in patients with clinical failure compared with those with clinical success (93% [13 of 14] vs. 4% [3 of 76], p 0.0001). In the remaining patients with recurrent arrhythmia, atrial tachycardia was observed and was terminated during the repeat ablation procedure. Additionally, procedural atrial fibrillation termination during the index procedure was associated with clinical success (92% [70 of 76] vs. 43% [6 of 14], p<0.0001).

Multivariate analysis showed that the surface ECG/EKG cycle length independently predicts procedural termination using the sequential stepwise approach. Furthermore, patients with a longer surface ECG/EKG cycle length and a shorter duration of continuous atrial fibrillation have a better outcome of catheter ablation. Validation of cycle length from surface ECG/EKG. The surface ECG/EKG cycle length manually assessed from 10 cycle lengths correlated well with the cycle length recorded by intracardiac catheters in the LAA and RAA, and using time frequency analysis showed that cycle length can reliably be assessed from lead V1 on the surface ECG/EKG.

The procedural end point in this study was termination of persistent atrial fibrillation, and this was achieved in the majority of patients. This study shows that a longer surface ECG/EKG cycle length, a shorter duration of continuous atrial fibrillation, and a smaller left atrium dimension are predictive of procedural atrial fibrillation termination. A shorter surface ECG/EKG cycle length was associated with longer procedural times, suggesting that the results are not caused by operator bias, but by an increased complexity of atrial fibrillation. Although cycle length measured from the LAA is correlated with procedural outcome, cycle length calculated from the surface ECG/EKG is noninvasive and can be performed at the initial consultation. The study also showed that a cycle length 142 ms predicts the outcome of catheter ablation, indicating that surface ECG/EKG cycle length is a powerful predictor of clinical outcome. The durations of continuous atrial fibrillation and left atrium dimensions are predictive of maintenance of sinus rhythm after DC cardioversion.

In the study, the surface ECG/EKG cycle length was measured using a computer-based system that allows modification of gain and sweep speed. It is sometimes difficult to assess the cycle length on the surface ECG/EKG using conventional settings, and therefore multiple settings may be used to get unequivocal fibrillatory waves on the surface ECG/EKG. There were only 2 patients in whom the cycle length was unable to be calculated from the surface ECG/EKG, and the findings are only relevant when the cycle length can be calculated. The study was focused on identifying clinical factors that can be assessed before ablation; however, other potential predictors for atrial fibrillation recurrence after ablation, for example, intraoperative parameters including, but not limited to, procedural termination of long-lasting persistent atrial fibrillation.

Most importantly, the study confirmed that long-lasting persistent atrial fibrillation can be terminated and potentially cured by catheter ablation. The surface ECG/EKG cycle length independently predicts procedural termination of persistent atrial fibrillation, and both the surface ECG/EKG cycle length and the duration of continuous atrial fibrillation are predictive of clinical outcome. The measurement of the surface ECG/EKG cycle length and the duration of continuous atrial fibrillation could help with patient selection for catheter ablation of long-lasting persistent atrial fibrillation.

Cardiac Fibrillation Detection and Mapping

Fibrillation detection and mapping is aimed at identifying the density and distribution of reentrant circuit cores that are responsible for the perpetuation of fibrillation. For the reasons described in greater detail below, electrogram signal frequency may indicate tissue activation frequency (provided the electrogram recording is of adequate spatial resolution), which is indicative of circuit core density and distribution. Thus, a patient-specific map of a tissue substrate indicating appropriately acquired electrogram frequencies informs the optimal placement of ablation lesions to treat fibrillation.

Circuit Core Density and Distribution

The goal of ablation should be the interruption of all reentrant circuits. A circuit core meandering on the tissue surface is interrupted if it collides with an electrical boundary. As discussed above, one or more ablation lesions may be created to increase the boundary-length-to-surface-area ratio and, generically, the probability of collision. The one or more ablation lesions should be placed contiguous with existing tissue boundaries to prevent or at least minimize the formation of a new circuit of reentry.

Importantly, not all ablation lesions increase the probability of collision equally. The creation of new boundaries at tissue sites with high circuit core density results in a higher probability of collision than the creation of new boundaries at tissue sites with low circuit core density. Therefore, it remains important to identify indicators of the number of circuit cores in a given area of tissue substrate (i.e., the circuit core density) and the arrangement of circuit cores across the tissue substrate (i.e., the circuit core distribution). Applied assessment of circuit core density and distribution enhances the efficiency of an ablation treatment by maximizing the effectiveness of new boundaries while minimizing the extent of harmful lesions.

Tissue Activation Frequency

One challenge to detecting and mapping fibrillation is the ability to identify circuit core density; however, circuit core density correlates with tissue activation frequency. Tissue activation frequency is the frequency of the variation of tissue current, which rises and falls as tissue is excited. Tissue activation frequency may indicate a circuit core and a surrounding area of tissue in 1-to-1 conduction continuity with that circuit.

To have 1-to-1 conduction continuity, a surrounding area of tissue undergoes excitation whenever a heart cell at one tissue site is excited or activated (e.g., by a reentrant circuit). Two tissue sites do not have 1-to-1 conduction continuity if some degree of conduction block prevents an excitation from traveling from one tissue site to the other. All heart cells in a reentrant circuit path must have 1-to-1 conduction continuity; otherwise, the circuit will be interrupted, and the rotor extinguished. Alternatively, a patient may develop multi-wavelet reentry (i.e., wave break and new wave formation) if 1-to-1 conduction continuity does not exist across the tissue. Because tissue activation frequency identifies surrounding tissue with 1-to-1 conduction continuity in addition to the actual tissue site of the circuit core, detection and mapping of tissue activation frequencies alone may not always accurately indicate circuit core density and distribution (i.e., tissue activation frequency is overinclusive). However, even so, knowledge of tissue activation frequencies may be applied to enhance the effectiveness and efficiency of ablation treatments.

Consider that tissue activation frequencies may vary over time as well as across the surface of a tissue substrate. For example, rotors and the refractoriness of a tissue area may shift (due, e.g., to autonomic tone), resulting in new conduction blocks and changing tissue activation frequencies across the tissue substrate.

Even though the actual tissue site of a circuit core and its 1-to-1 conduction continuity area may have the same tissue activation frequency for a short time period (e.g., a few seconds), shifts in rotors and the refractoriness of tissue areas over longer periods of time exhibit a tendency for tissue activation frequencies to be higher at actual tissue sites of circuit cores than in transient 1-to-1 conduction continuity areas.

Electrogram Signal Frequency

Another challenge to detecting and mapping fibrillation is measuring tissue activation frequency, which cannot be done directly. Thus, instead of tissue activation frequency, measurements of electrogram signal frequency are used to indicate circuit core density and distribution. Electrogram signal frequency is the frequency of the variation of the net electric field potential at a recording electrode, as opposed to the frequency of the variation of tissue current.

An electrode is an electrical conductor. In accordance with some embodiments of the present invention, one or more electrodes are designed to be positioned in a patient's heart. The types of electrodes used in some embodiments of the present invention may be microelectrodes and may include, but are not limited to, solid conductors, such as discs and needles. In accordance with further embodiments of the present invention, the one or more electrodes are deployed in proximity to cardiac tissue using one or more catheters, which may be inserted via thoracotomy at the time of surgery, percutaneously, and/or transvenously. Catheters and electrode configurations according to some embodiments of the present invention are discussed in detail below.

An electric field potential recorded by an electrode is the electric potential energy o at the electrode location. The net electric field potential recorded by an electrode is the sum of electric potentials from different sources at the electrode location. With the uncommon exception of a single current source (as opposed to multiple spatially distributed current sources), a complex relationship exists between the net electric field potential at a tissue site and the possible current source distributions that produced that net electric field potential. While a net electric field potential at any tissue site surrounded by multiple spatially distributed current sources can be uniquely determined, the actual current source distribution that generated the net electric field potential at a recording electrode cannot be uniquely determined. Thus, the use of electrogram recordings to reconstruct tissue electrical events (e.g., local tissue activation frequency) may not always provide an accurate prediction of circuit core density and distribution. However, an electrogram signal frequency map of a tissue substrate that identifies changes in electrogram signal frequency may be optimized to enhance the effectiveness and efficiency of ablation treatments as described below in accordance with some embodiments of the present invention.

Electrode Spatial Resolution and Determination of Tissue Spatiotemporal Variation Fractionated electrograms may be used as targets for ablation in atrial and ventricular arrhythmias. Fractionation has been demonstrated to result when there is repetitive or asynchronous activation of separate groups of cells within the recording region of a mapping electrode.

In a study of temporal variation (i.e., spatially coordinated changes in the frequency of activation) and spatiotemporal variability (i.e., asymmetrical excitation of various tissue sites in time), tissue activation patterns with increasing spatiotemporal variation were generated using a computer model. Virtual electrograms were calculated from electrodes with decreasing resolution. Then, electrogram fractionation was quantified. In addition, unipolar electrograms were recorded during atrial fibrillation in 20 patients undergoing ablation. The unipolar electrograms were used to construct bipolar electrograms with increasing inter-electrode spacing and quantified fractionation. During modeling of spatiotemporal variation, fractionation varied directly with electrode length, diameter, height, and inter-electrode spacing. When resolution was held constant, fractionation increased with increasing spatiotemporal variation. In the absence of spatial variation, fractionation was independent of resolution and proportional to excitation frequency. In patients with atrial fibrillation, fractionation increased as inter-electrode spacing increased.

A model was developed for distinguishing the roles of spatial and temporal electric variation and electrode resolution in producing electrogram fractionation. Spatial resolution affects fractionation attributable to spatiotemporal variation but not temporal variation alone. Electrogram fractionation was directly proportional to spatiotemporal variation and inversely proportional to spatial resolution. Spatial resolution limits the ability to distinguish highfrequency excitation from overcounting. In patients with atrial fibrillation, complex fractionated atrial electrogram detection varies with spatial resolution. Electrode resolution must therefore be considered when interpreting and comparing studies of fractionation. Fractionated electrograms have attracted the attention of clinical electrophysiologists in the setting of mapping reentrant rhythms (eg, ventricular and atrial tachycardia) and more recently mapping of atrial fibrillation. Fractionation in these settings is felt to identify substrate relevant to the arrhythmia circuitry. Although fractionation can identify a critical isthmus in scar-based reentrant ventricular tachycardia circuits, the use of fractionated electrograms to guide atrial fibrillation ablation has had conflicting results.

Although there is no uniformly accepted definition, the term "complex fractionated atrial electrograms" has been used to describe electrograms with low amplitude and high-frequency deflections. Electrograms measure the changing potential field at the site of a recording electrode. Any pattern of tissue activation within the recording region of an electrode that results in alternation between increasing and decreasing potential will produce electrogram fractionation. Several disparate tissue activation patterns have been shown to result in electrogram fractionation, including meandering rotors, wave collision, discontinuous conduction, and longitudinal dissociation. Because of their non-unique relationship (activation and electrogram), one cannot unambiguously determine a specific tissue activation pattern based solely on the observation of fractionation. Because fractionation results from tissue dyssynchrony within the electrode recording region, it follows that the area of tissue that contributes to the electrogram will influence fractionation. Spatial resolution refers to the area of tissue that contributes to the electrogram. Because tissue currents create a potential field that spreads infinitely through space, the "area that contributes to the electrogram" is in fact infinite.

However, because potential decreases with distance from a current source, the effective area that contributes to an electrogram is small and varies with electrode size (length and diameter), configuration (unipolar versus bipolar), height above the tissue, and inter-electrode spacing. In a series of studies using a computer model of excitable tissue and electrogram recordings from patients with atrial fibrillation, the components that produce electrogram fractionation were defined.

Activation was examined in a two-dimensional sheet of electrically excitable tissue using a computer model. The surrounding potential field produced by tissue excitation was calculated. The model was used to independently vary the temporal and spatiotemporal complexity of tissue excitation.

By recording from virtual electrodes of varied size, configuration, and height, the impact of spatial resolution on fractionation was quantified.

The model was a monodomain cellular automaton, in which the cells are arranged in a two-dimensional grid with each cell connected to its four neighbors (up, down, left, and right). Cell voltage changes in response to an action potential, external stimulation, or intercellular current flow. The membrane voltage of a cell corresponds to its level of electrical depolarization. The resting state of a cell corresponds to quiescence. As a cell gathers current, membrane voltage depolarizes; when membrane voltage exceeds voltage threshold, an action potential is initiated. Action potential upstroke velocity and action potential duration are rate- and voltage-dependent. Cells connect to their immediate neighbors through electrically resistive pathways. The vertical and horizontal resistive constants are Rv and Rh, respectively. Cells exchange current with their neighbors according to first-order kinetics, whereby the voltage of a quiescent cell (j, k) at time t is affected by that of its neighbors according to the following equation:

$$\frac{dV(j,k,t)}{dt} = \frac{1}{R_h}[V(j-1,k,t)+V(j+1,k,t)-2V(j,k,t)] + \frac{1}{R_v}[V(j,k-1,t)+V(j,k+1,t)-2V(j,k,t)] \quad (9)$$

At each time step in the simulation, all cells have their values of membrane voltage updated according to the following equation:

$$V(j,k,t) = V(j,k,t-1) + \frac{dV(j,k,t)}{dt}\delta t + V_{intrinsic} \quad (10)$$

where t is the time step size. A cell may be defined as scar, in which case it is permanently quiescent and electrically isolated from its neighbors.

In a flat square sheet of tissue 1 cell thick (1010 mm) without anisotropy, temporal variation was introduced by modulating excitation frequency. Activation wavefronts propagate through the homogeneous tissue at constant conduction velocity. Spatial variation was created by adding parallel lines of scar alternately extending to the top or bottom edge of the tissue. Spatiotemporal variation was then introduced by stimulating in the upper left corner; activation waves proceed through the tissue with a "zig-zag" pattern. Two components of tissue activation complexity could then be independently manipulated: (1) temporal variation can be modulated by changing activation frequency; and (2) spatiotemporal complexity can be increased by increasing the number of parallel lines of scar, that is, increasing the number of separate tissue bundles through which excitation spreads.

Figure 19A:
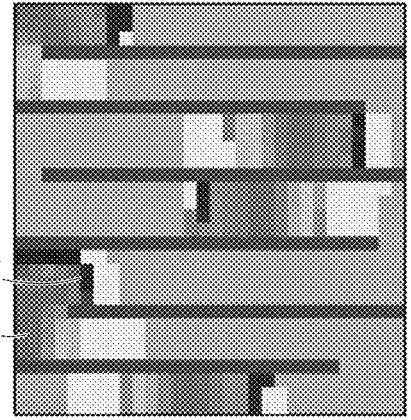
FIGS. 19A-19F illustrate temporal, spatial, and spatiotemporal variation of tissue excitation, in accordance with embodiments of the present invention.
Figure 19B:
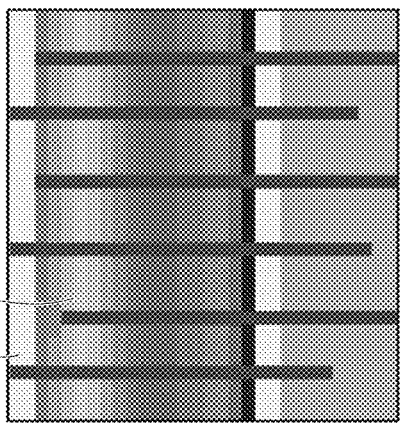
Figure 19C:
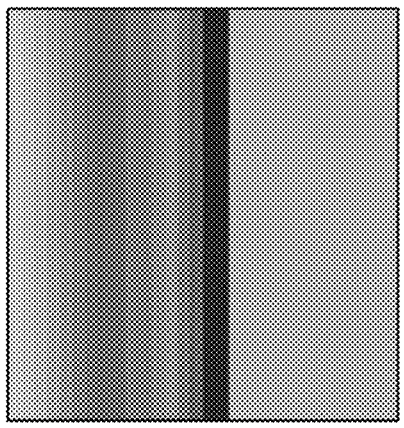

FIGS. 19A-19F illustrate temporal, spatial, and spatiotemporal variation of tissue excitation in accordance with some aspects of present invention. FIGS. 19A-19C illustrate tissue voltage distribution (single time step; 1010 mm). FIG. 19A illustrates temporal variation, in which stimulation of the top row of cells (cycle length 150 ms) produced sequential planar waves of excitation. FIG. 19B illustrates spatial variation. Although tissue is divided by multiple alternating linear scars 190 and 192, activation proceeds from top to bottom in parallel (secondary to simultaneous stimulation of the top row of cells). FIG. 19C illustrates spatiotemporal variation. Stimulation from the top left corner of the tissue results in sequential excitation of vertical channels between linear scars 194 and 196, producing "zig-zag" activation waves every 150 ms.

Figure 19D:
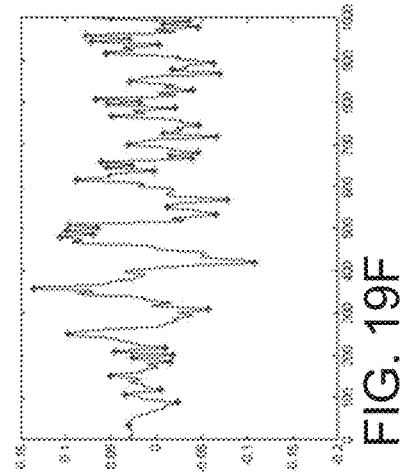
Figure 19E:
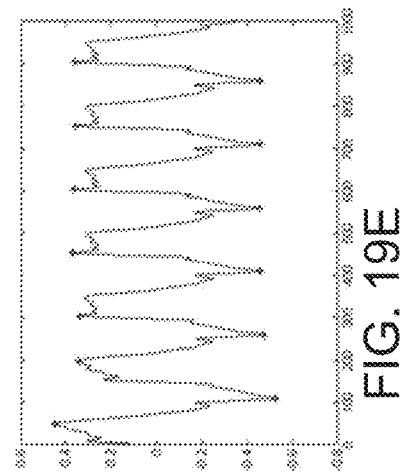
Figure 19F:
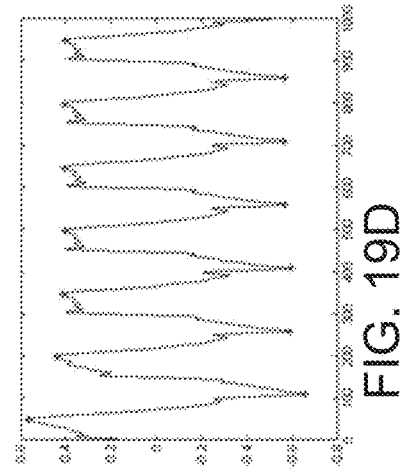

FIGS. 19D-19F are corresponding virtual unipolar electrograms (electrode diameter 1 mm, height 0.5 mm, length 6 mm, and horizontal orientation) in accordance with aspects of the present invention. Note that even with linear scars, if activation occurs simultaneously in all bundles, the electrogram is very similar to that seen with in tissue without scars. To visualize this, compare FIGS. 19D and 19E. The contributions of each bundle to the potential field occur simultaneously and are hence superimposed in the electrogram (no fractionation).

The potential Φ(m, n, t) was calculated that would be recorded by an electrode placed at a height h above a site in the tissue plane (m, n) at each time (t). In the context of the monodomain approximation used, each cell in the tissue makes a contribution to the electrogram that is proportional to the cell's transmembrane current and inversely proportional to its linear distance from the electrode. The transmembrane current at a particular cell was defined as the time derivative of voltage (V), approximated as the difference in V between successive time steps:

$$\Phi(m,n,t) = \sum_{j=1}^{n}\sum_{k=1}^{n}\frac{V(j,k,t)-V(j,k,t-1)}{\sqrt{(j-m)^2+(k-n)^2+h^2}} \quad (11)$$

where j and k are position indices in the x and y directions.

Figure 20:
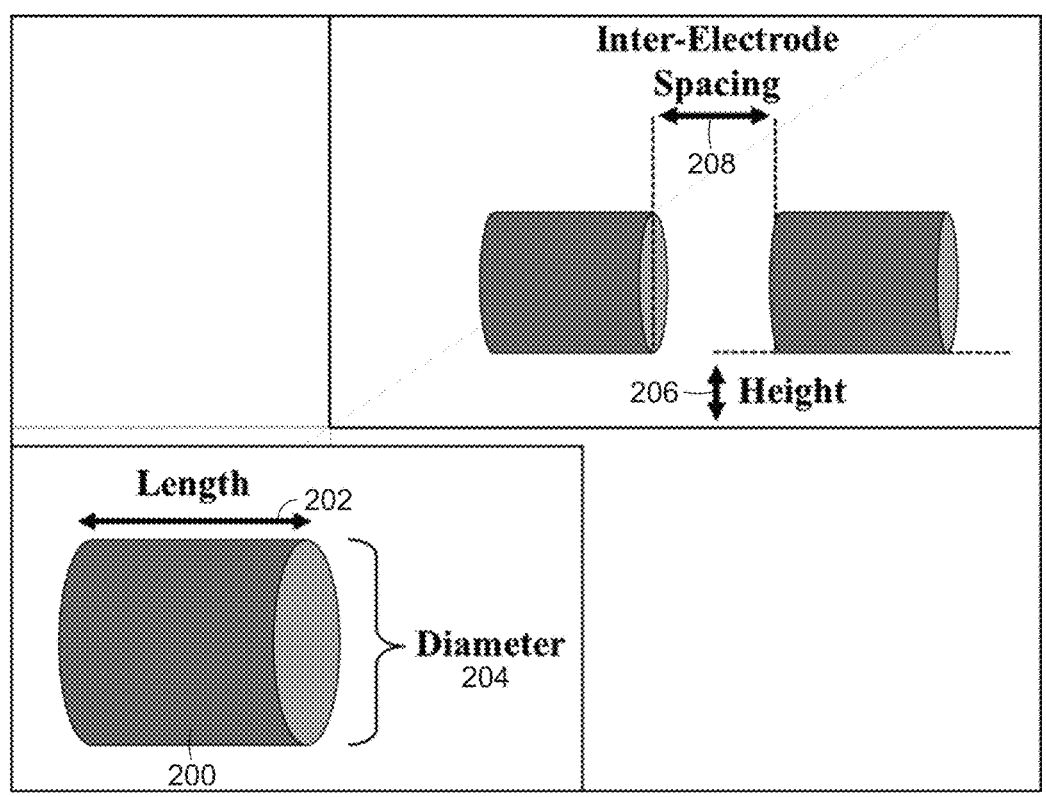
FIG. 20 illustrates electrode geometry, spacing, and position, in accordance with embodiments of the present invention.

FIG. 20 illustrates electrode geometry, spacing, and position according to some aspects of the study and the present invention. In the study, three-dimensional cylindrical electrodes 200 with varied length 202, diameter 204, and height 206 were modeled. The electrodes were modeled as hollow cylinders divided into a finite element mesh with elements evenly distributed about the circumference and along the length 202 of the electrode. The number of elements varied depending on electrode geometry so no element area was 1 mm². The electric potential contribution from each cell was calculated at the center of each element. The potential recorded by the entire unipolar electrode was then calculated as the sum of each element potential multiplied by the element area and divided by the total surface area of the electrode.

The bipolar electrogram was obtained simply as the difference in the potentials recorded by the two unipolar electrodes. Height 206 was measured from the tissue to the electrode's bottom edge and, for bipolar recording, interelectrode spacing 208 was measured between edges. Electrodes were positioned over the center of the tissue (perpendicular to lines of scar—unipolar; parallel to lines of scar—bipolar recordings). Electrode spatial resolution varies inversely with electrode surface area (length and diameter), height above tissue, and inter-electrode spacing (for bipolar recordings).

The cellular automaton model evolved through discrete time steps; as a result, electrogram amplitude fluctuated from time step to time step. The electrogram signal was therefore processed with a smoothing function to reduce this artifact. The number of turning points was quantified as the number of peaks and troughs with a 10% tolerance.

Two 60-second unipolar recordings were obtained during atrial fibrillation from the coronary sinus of 20 patients presenting for atrial fibrillation ablation. Unipolar electrograms (indifferent electrode in the inferior vena cava (length=diameter=2 mm; available from Bard Electrophysiology (Billerica, Mass.)) were recorded with either a 20-pole (1-mm electrodes, 1-3-1-mm spacing; 10 patients) or a 10-pole (2-mm electrodes, 2-5-2-mm spacing; 10 patients) catheter (available from Biosense Webster (Diamond Bar, Calif.)). Signals (sampled at 1 kHz, filtered 30-250 Hz) were exported for offline analysis. From these we constructed bipolar electrograms with increasing inter-electrode spacing (electrodes 1-2, 1-3, and 1-4). Bipolar signals were analyzed using standard algorithms for average interpotential interval (AIPI) and interval confidence level (ICL). The voltage window for ICL was 0.05 to 0.2 mV; the upper limit of 0.2 mV was selected as an average of values used by different groups. The amplitude of electromagnetic noise in each signal was measured in 10 patients (during sinus rhythm).

A mixed effects linear model was used for the analysis of the experimental data for studying fractionation as a function of inter-electrode spacing. Data for each catheter type and each outcome (ICL and AIPI) were analyzed separately. Subjects within a catheter type were treated as random effects, thereby inducing a compound-symmetrical correlation structure among within subject measurements. Measurements between subjects were independent. inter-electrode spacing and time of measurement were treated as fixed effects with time of measurement nested within subject. Analysis was done using PROC MIXED in SAS, Version 9.3.

Figures 21A, 21B:
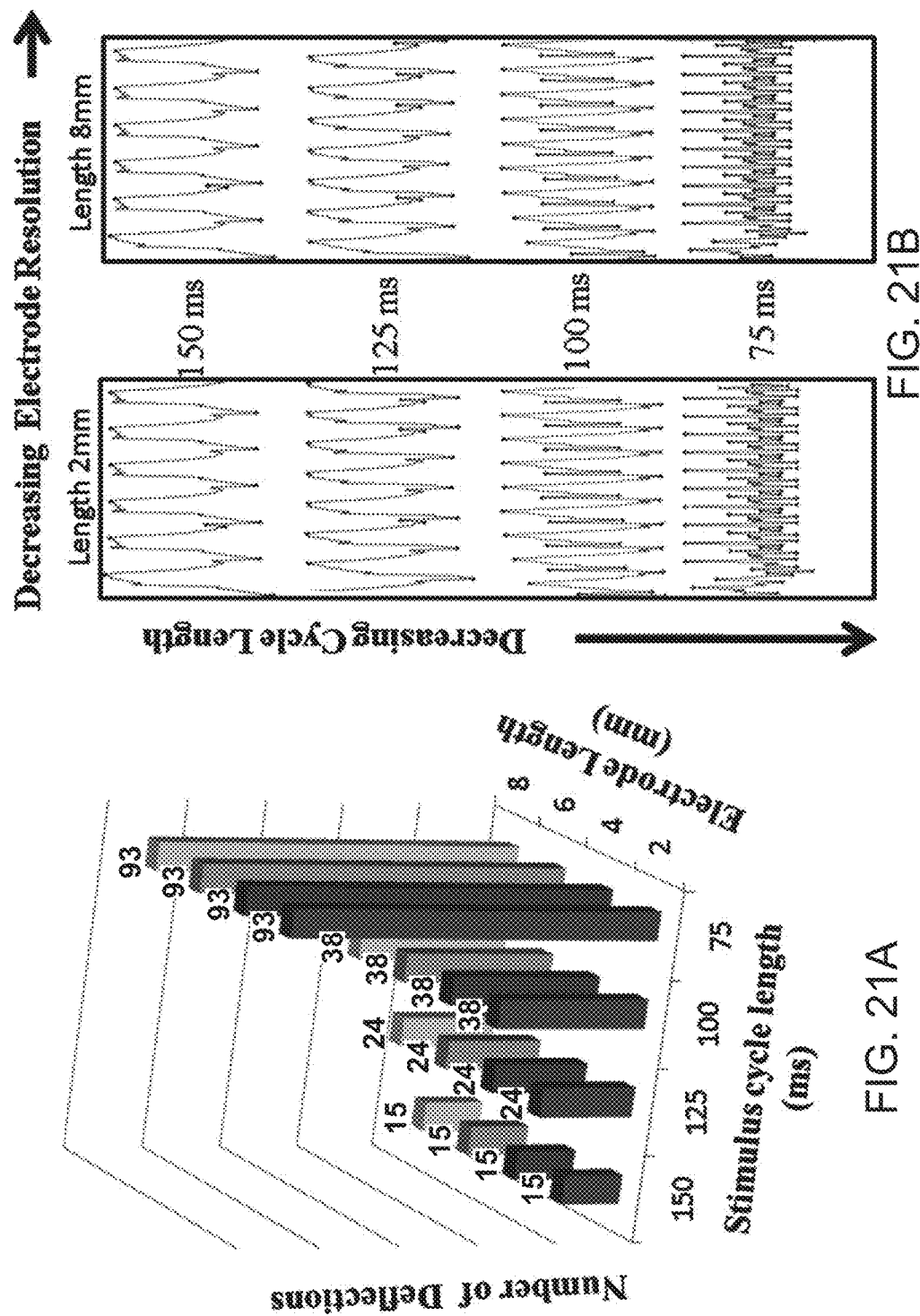
FIG. 21A is a graph illustrating fractionation as a function of temporal variation by the number of deflections versus stimulus cycle length, in accordance with embodiments of the present invention.
FIG. 21B is a series of virtual unipolar electrograms from tissue excited at decreasing cycle lengths, in accordance with embodiments of the present invention.

Results showed that fractionation is a function of temporal variation. In a series of simulations tissue (without linear scars) was stimulated at progressively shorter cycle lengths (150, 125, 100, and 75 ms). Virtual electrograms were recorded using unipolar electrodes (6-mm length, 1-mm diameter, and 0.5-mm height). Fractionation was directly proportional to tissue frequency; 15, 24, 38, and 93 deflections at cycle lengths of 150, 125, 100, and 75 ms, respectively. FIG. 21A is a graph illustrating fractionation as a function temporal variation by the number of deflections versus stimulus cycle length according to some aspects of the study and the present invention. The underlying data corresponds to electrode length 2, 4, 6, and 8 mm (with fixed diameter 1 mm, height 0.5 mm). FIG. 21B is a series of virtual unipolar electrograms from tissue excited at decreasing cycle lengths: cycle length 150 ms (top) to 75 ms (bottom), recorded with a unipolar electrode of 2 mm (left) and 8 mm (right) in length. The number of deflections is independent of electrode size.

Results showed the impact of electrode spatial resolution in tissue with temporal variation on fractionation. With temporal variation alone, fractionation was independent of electrode spatial resolution, as shown in FIGS. 21A-21B, in accordance with some embodiments of the present invention. In tissue without scars stimulated at 150-ms cycle length, the number of deflections in the unipolar electrogram was independent of electrode length, diameter, or height (15 deflections for electrode length 2, 4, 6, and 8 mm; diameter 1, 2, 3, and 4 mm; height 0.5, 1, 2, and 3 mm). Bipolar recordings (1-mm length and diameter, 0.5-mm height) had 27 deflections regardless of inter-electrode spacing (1, 3, 5, and 7 mm).

Results showed that fractionation is a function spatiotemporal variation. To create spatiotemporal variation, tissue was stimulated at a fixed cycle length of 150 ms from the upper left corner resulting in a "zig-zag" activation pattern. When electrode spatial resolution was kept constant, fractionation was directly proportional to the number of linear scars (i.e., spatiotemporal complexity); the number of deflections was 19, 26, 45, and 52 for tissue with 1, 2, 4, and 6 lines of scar, respectively (unipolar 6-mm length, 1-mm diameter, and 0.5-mm height). With bipolar recordings (1-mm length and diameter, 0.5-mm height, and 5-mm inter-electrode spacing), there were 24, 25, 29, and 32 deflections for tissue with 1, 2, 4, and 6 lines of scar, respectively.

Figure 22B:
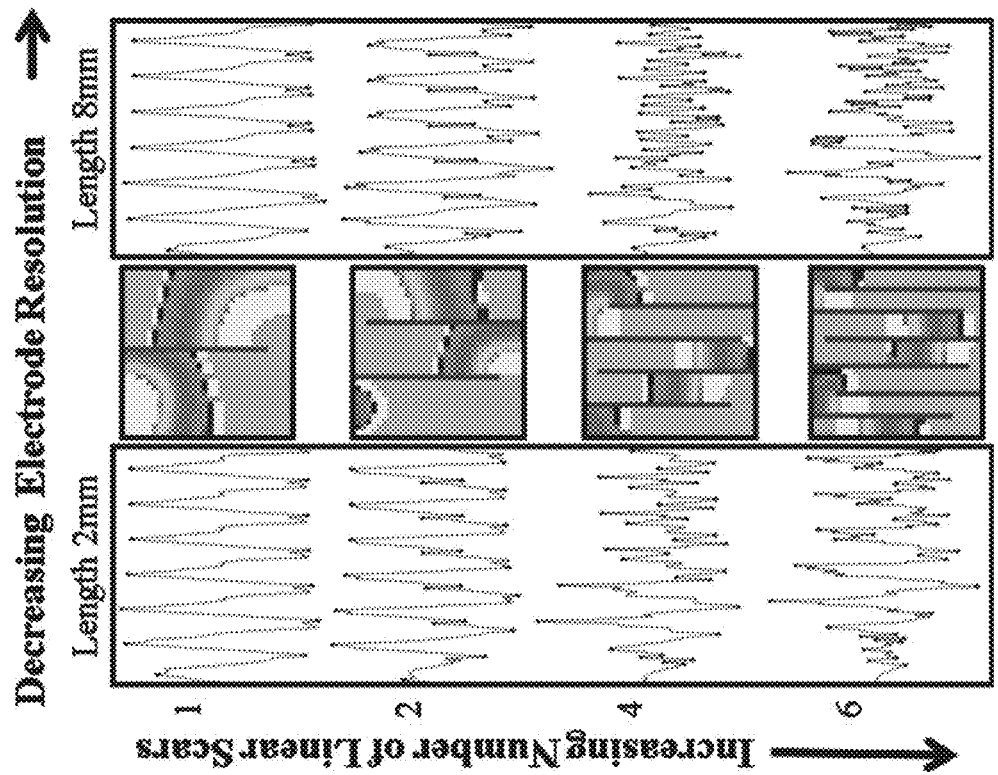
FIG. 22B is a series of virtual unipolar electrograms from tissue excited with increasing spatiotemporal variation, in accordance with embodiments of the present invention.
Figure 22A:
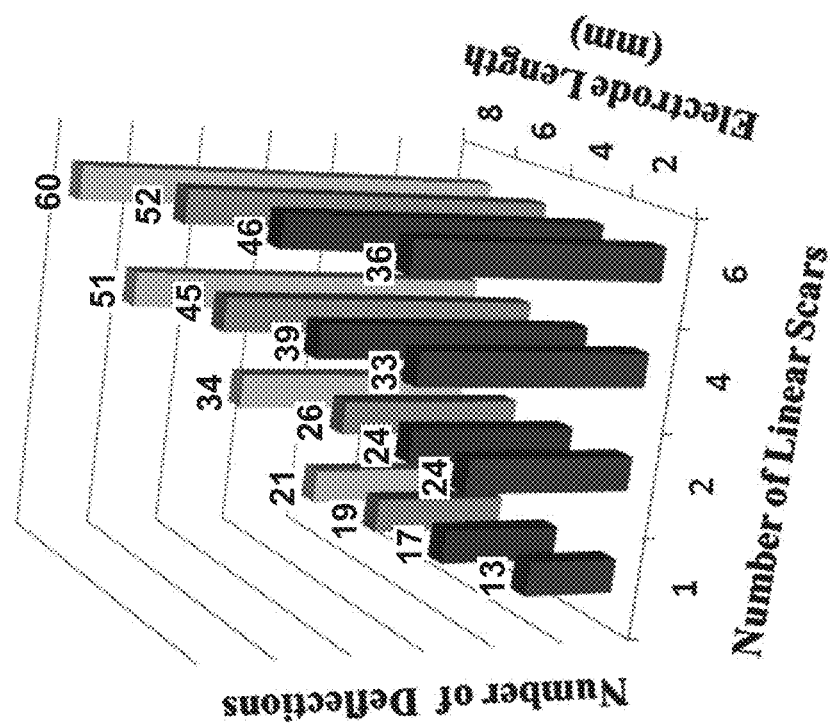
FIG. 22A is a graph of the number of deflections in unipolar recordings as a function of spatiotemporal variation and electrode resolution, in accordance with embodiments of the present invention.

FIG. 22A is a graph of number of deflections in unipolar recordings as a function of spatiotemporal variation (number of scars) and electrode resolution (length; diameter 1 mm, height 0.5 mm). FIG. 22B is a series of virtual electrograms from tissue stimulated every 150 ms with increasing spatiotemporal variation (1 scar [top] to 6 scars [bottom]) recorded with a unipolar electrode (length 2 mm [left] and 8 mm [right]). The number of deflections increases with decreased electrode resolution (and the effect is more prominent as the number of scars increases).

Results showed the impact of electrode spatial resolution in tissue with spatiotemporal variation on fractionation. In the setting of spatiotemporal variation (cycle length 150 ms, varied number of scars), the number of turning points increased in proportion to unipolar length (diameter 1 mm and height 0.5 mm) and number of linear scars. In tissue with 6 lines of scar, the number of deflections was proportional to electrode diameter: 52, 66, 74, and 76 deflections for electrodes of 1-, 2-, 3-, and 4-mm diameter, respectively (length 6 mm and height 1 mm). With constant electrode size (length 6 mm and diameter 1 mm), the number of deflections was directly proportional to electrode height: 52, 68, 76, and 84 deflections at heights of 0.5, 1, 2, and 3 mm above the tissue, respectively. Fractionation also increased with increasing inter-electrode spacing: 22, 24, 32, and 33 deflections for inter-electrode spacing 1, 3, 5, and 7 mm, respectively (1-mm length and diameter, 0.5-mm height).

Qualitatively the effect of inter-electrode spacing on spatial resolution (in sinus rhythm) and fractionation (during atrial fibrillation) is easily appreciated. FIG. 23A is a fluoroscopic image of 10-pole catheter 230 in the coronary sinus (electrode length 2 mm, inter-electrode spacing 2-5-2 mm). Brackets indicate inter-electrode spacings used for reconstruction of bipolar recordings. FIG. 23B is afluoroscopic image of 20-pole catheter 232 (electrode length 1 mm, inter-electrode spacing 1-3-1 mm). FIG. 23C is a set of simultaneous electrogram recordings during sinus rhythm and atrial fibrillation with inter-electrode spacing of 1, 5, and 7 mm. There is a minor increase in baseline noise as inter-electrode spacing increases (sinus rhythm) and increased fractionation with increased inter-electrode spacing (atrial fibrillation).

To quantify the effects of spatial resolution on complex fractionated atrial electrogram, we measured ICL and AIPI as a function of inter-electrode spacing during atrial fibrillation. Fractionation increased with increasing inter-electrode spacing. Average values (and SEs) were as follows: ICL 10-pole catheter: 5.2±1.0, 8.7±1.0, and 9.5±1.0 for 2, 9, and 13 mm inter-electrode spacing, respectively ($P<0.001$, 2 versus 9 and 2 versus 13 mm); 20-pole catheter: AIPI confidence level 6.8±1.0, 9.9±1.0, and 10.3±1.0 for 1, 5, and 7 mm inter-electrode spacing, respectively ($P<0.001$, 1 versus 5 mm and 1 versus 7 mm). AIPI decreased with increased inter-electrode spacing—10-pole catheter: 207±19, 116±19, and 106±19 for 2, 9, and 13 mm inter-electrode spacing, respectively ($P<0.001$, 2 versus 9 mm and 2 versus 13 mm); AIPI 20-pole catheter: 144±13, 99±13, and 92±13 ($P<0.001$, 1 versus 5 mm and 1 versus 7 mm). As inter-electrode spacing increases, electrodes record signals from locations that are progressively farther apart and are therefore exposed to different electromagnetic noise. Bipolar recordings reflect only the difference between the signals recorded at each electrode; therefore, as the difference in noise recorded at each electrode becomes greater, the amplitude of noise in the bipolar signal becomes larger. As a result one can expect that noise is progressively increased as inter-electrode spacing increases. Noise was measured as a function of inter-electrode spacing; the mean amplitude of noise increased with inter-electrode spacing but remained 0.05 mV (maximum 0.028 0.01 mV).

The fact that electrodes measure electric potential rather than tissue current density creates a possible source of ambiguity in the interpretation of electrograms. Because currents generate a potential field that spreads through space (with amplitude that decreases with distance), potential recordings at any site reflect contributions from current sources at multiple sites. This capacity for "far-field" recording has the result that electrogram deflections occur with variation of current density over an area larger than the physical dimensions of the electrode. Electrogram fractionation is generally defined as low-amplitude, high-frequency deflections. As the number of sites contributing to an electrode's potential increases, the number of deflections will increase so long as these sites are excited asynchronously. When sites are excited simultaneously, their impact on the electrogram amplitude is additive but fractionation does not result.

In the study, a simple model was used to independently control each of the components that contribute to fractionation: tissue spatiotemporal variation, tissue temporal variation, and electrode spatial resolution. The following observations were made: (1) fractionation is not observed with spatial variation alone; secondary to temporal superposition, the contributions from spatially disparate currents to the potential recorded at any electrode location sum to alter amplitude without producing fractionation; (2) fractionation is observed with temporal variation, which is independent of electrode spatial resolution; and (3) fractionation is observed with spatiotemporal variation and in this case is dependent on electrode spatial resolution. Consequently, spatial resolution determines the limit of the ability to distinguish temporal from spatiotemporal variation; that is, increased frequency as a result of overcounting.

Electrogram fractionation results from the interaction of 3 components: tissue temporal variation, tissue spatiotemporal variation, and electrode spatial resolution. In the absence of tissue spatiotemporal variation (ie, temporal variation alone), fractionation is independent of electrode spatial resolution. In a computer model of electrically excitable tissue with spatiotemporal variation and in patients with atrial fibrillation, fractionation increased with decreasing electrode spatial resolution. Electrograms measure the average potential field at the surface of an electrode over time. As a consequence, multiple different patterns of tissue activation can generate similar electrograms. Analysis of a single fractionated electrogram does not permit differentiation of temporal versus spatiotemporal tissue variation; therefore, one cannot distinguish highfrequency excitation from overcounting. Electrode spatial resolution must be considered when comparing studies of fractionation.

In another study, a computational model of an electrode situated above a sheet of excitable tissue, validated against experimental measurements in vitro, was used to determine how spatial resolution is affected by electrode diameter, electrode length, inter-electrode distance (in the case of bipolar recordings), and height of the electrode above a dipole current source, and how spatial resolution could be varied over clinically relevant ranges.

Mapping during atrial fibrillation frequently reveals fractionated electrograms that confound identification of local activation time and therefore preclude activation mapping. Optimizing electrode configuration and placement to minimize the area of tissue seen by the electrode is thus crucial to accurate activation mapping of atrial activity, which in turn may facilitate successful ablation of atrial fibrillation.

Figure 24:
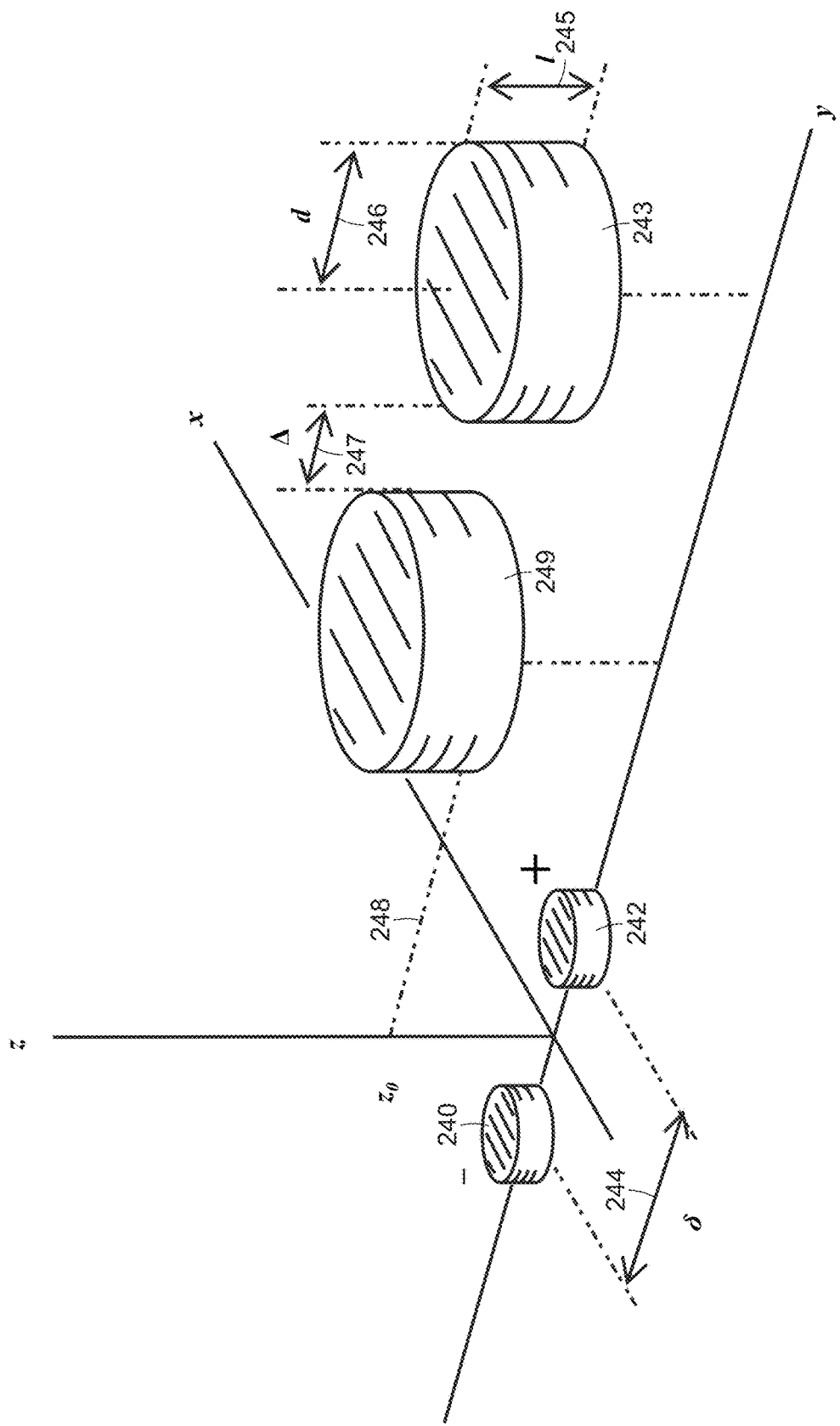
FIG. 24 is a schematic of a dipole current source located at $\pm\delta/2$ about the origin and a bipolar pair of electrodes of diameter d and height l separated by $\Delta$ and located at height $z_0$ along the y-axis, in accordance with embodiments of the present invention.

Using a custom software (MATLAB®, available from The Mathworks Inc., (Natick, Mass.)), the potential field surrounding a dipole current source was modeled to represent the basic unit of electric potential generation from heart tissue, namely, a flow of current from the interior of a cell to the extracellular space as the cell depolarizes and an equal and opposite currently flow nearby as adjacent cells repolarize. The potentials were calculated as would be recorded by electrodes of various diameters d and lengths l placed relative to this dipole source at various positions along the y-axis and at various heights $z_0$ when the positive and negative current sources were placed at $y=\pm\delta/2$. The electrodes for bipolar electrode recordings, were separated by a nearest surface distance of $\Delta$. FIG. 24 is a schematic of a dipole current source located at $\pm\delta/2$ about the origin and a bipolar pair of electrodes of diameter d and height l separated by $\Delta$ and located at height $z_0$ along the y-axis.

Arbitrary units were assigned to $\delta=0.25$ mm and $\rho=1$. The electrodes were modeled as hollow cylinders divided into a finite element mesh with 30 elements evenly distributed about the circumference and 15 elements along the length for a total of 450 elements of equal area. The electric potential produced by the dipole source was calculated at the center of each element. The potential recorded by the entire unipolar electrode was then calculated as the sum of each element potential multiplied by the element area and divided by the total surface area of the electrode. The bipolar electrogram was obtained simply as the difference in the potentials recorded by two unipolar electrodes.

An in-vitro apparatus was created for confirming that commonly used clinical intracardiac electrodes do, in fact, record potentials as our model predicts. A Plexiglas chamber was filled with 0.9% saline. Two 0.3-mm wide copper wires with flat ends were fixed 0.5-mm apart (center to center) into the bath (the x-y plane shown in FIG. 24) with only their tips exposed to the bath interior. Biphasic square wave impulses (2.4 mV, 10-ms pulse width) were delivered to the electrodes to simulate a dipole source in the heart tissue. Recording electrodes (both unipolar and bipolar) were also placed in the saline bath and positioned with a micromanipulator attached to a machined aluminum base under the bath. The electrode positions could be adjusted with a resolution of ±0.1 mm over 10 cm.

Unipolar electrode recordings were taken with standard catheters (available from Biosense Webster Inc. (Diamond Bar, Calif., USA)) having electrode tips of width 2.333 mm and lengths of 1, 4, and 8 mm. Bipolar recordings were taken between the tip electrodes on two standard catheters (Biosense Webster Inc.) having a variety of inter-electrode spacing (1, 2, 3, 4 mm). The recording electrodes were oriented to be perpendicular to the bath floor at a height of 1 mm, as diagrammed in FIG. 24.

The electrograms from the recording electrodes were sampled at 1 kHz and filtered from 0.5 to 250 Hz (available from Bard EP (Lowell, Mass.)). Ten recordings were taken using each electrode configuration at 10 positions along the y-axis at intervals of 0.2 mm. The entire set of recordings was repeated five times, with the order of catheter positions reversed (and electrodes polished) between runs to minimize effects due to electroplating of the cathode. Signals were exported and analyzed offline with the use of MATLAB®-based software.

Figure 25A:
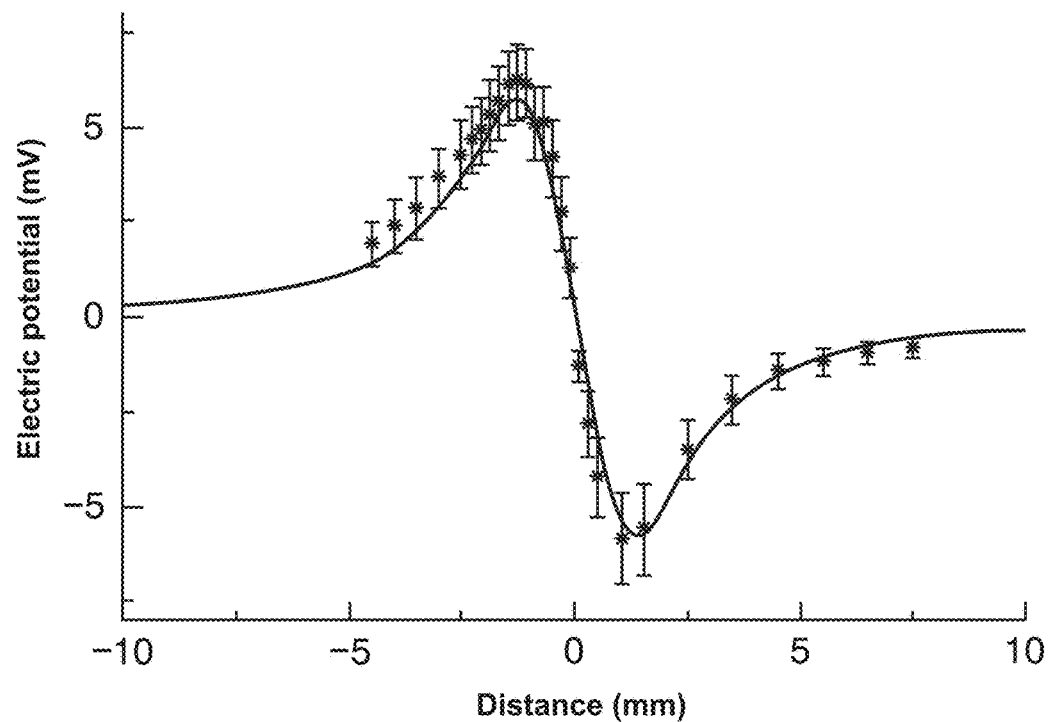
FIGS. 25A-25B are graphical plots where
Figure 25B:
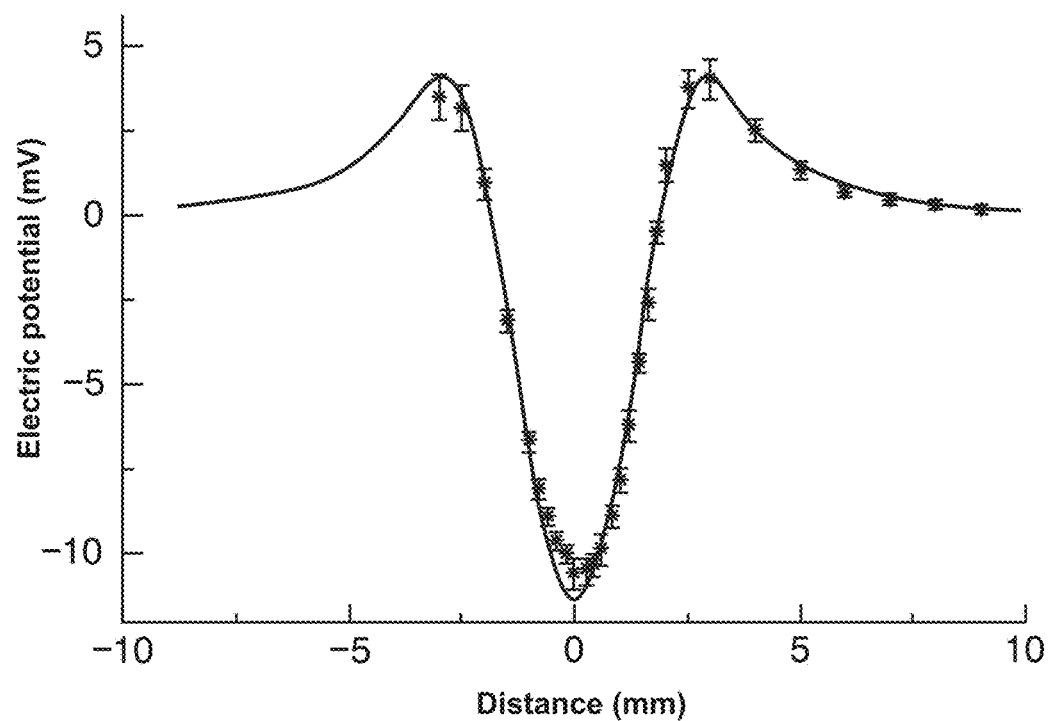

FIGS. 25A-25B are unipolar and bipolar space domain electrograms calculated with the computational model and measured in the physical in-vitro model. Unipolar electrodes with tips having lengths of 1, 4, and 8 mm (2.33-mm diameter) were examined, and correlation coefficients were found of 0.99, 0.99, and 0.97, respectively, between the computed and measured electrograms. Bipolar recordings with inter-electrode spacings of 1, 2, 3, and 4 mm (2.33-mm tip diameter) were examined, and correlation coefficients of 0.99 were found in all cases.

Figure 26A:
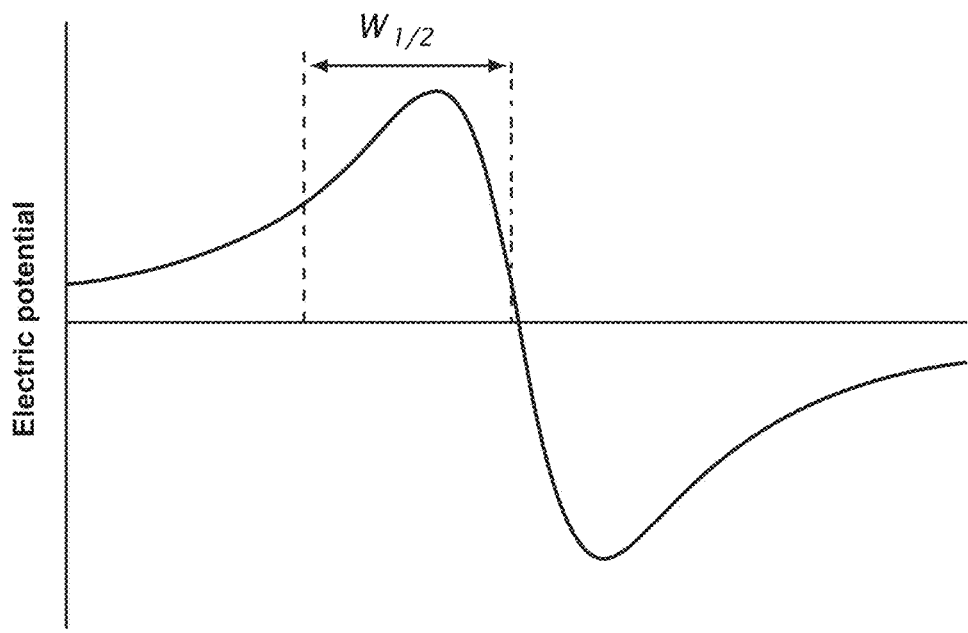
FIGS. 26A-26B are graphical plots where
Figure 26B:
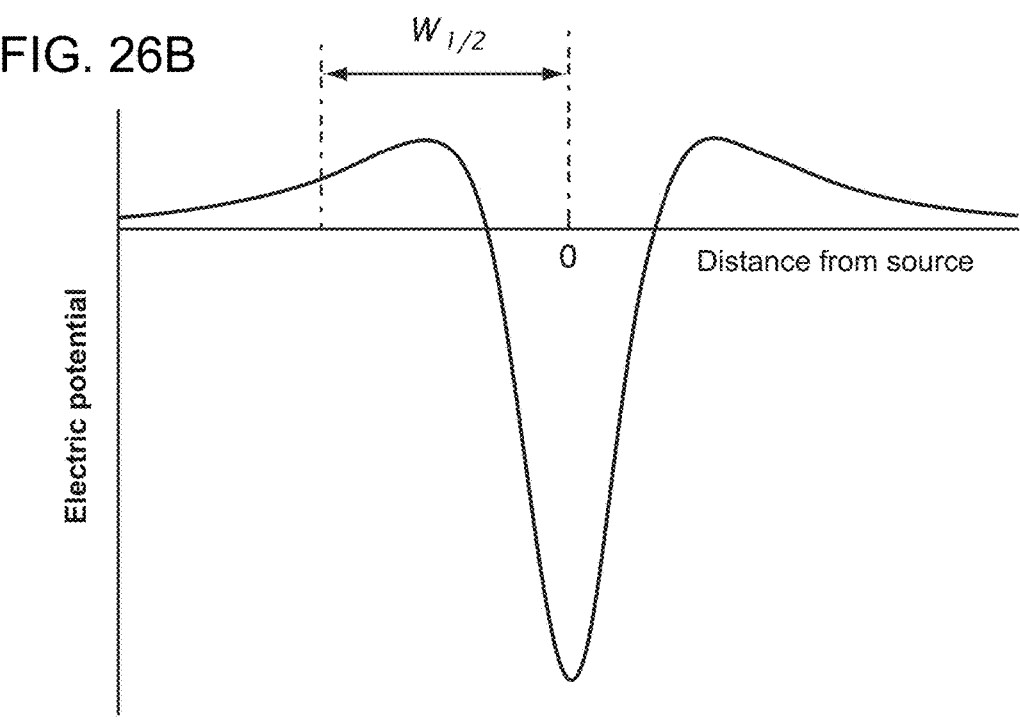
Figure 29A:
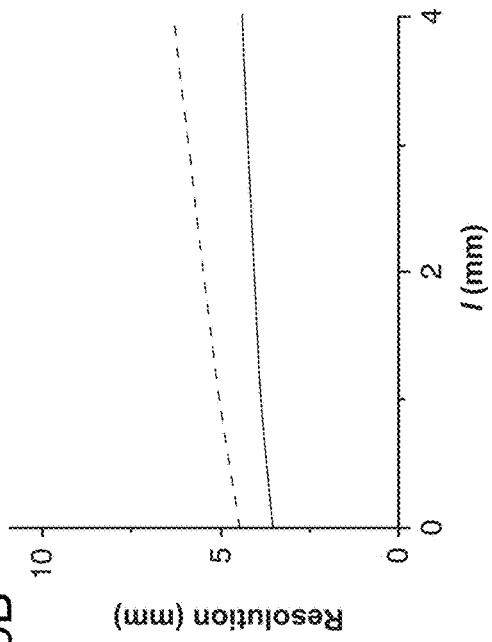
FIGS. 29A-29D are graphical plots illustrating resolution of a bipolar electrode recording of a dipole current source, as assessed in terms of $C_{min}$ and $W_{1/2}$, in accordance with embodiments of the present invention.
Figure 29B:
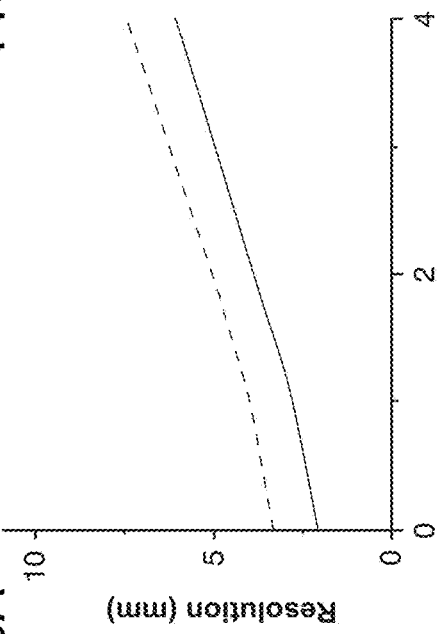
Figure 29C:
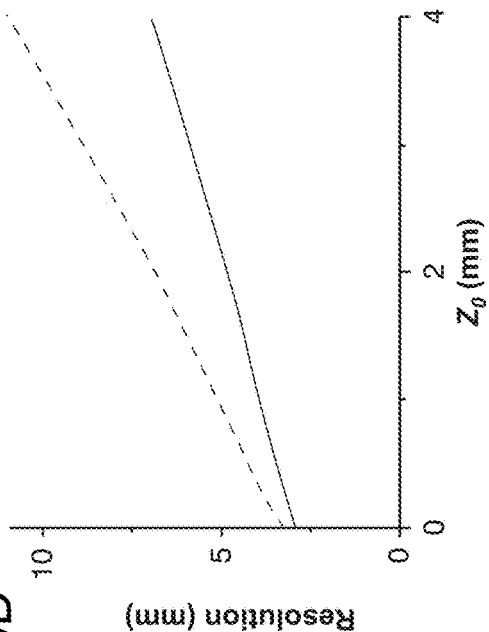
Figure 29D:
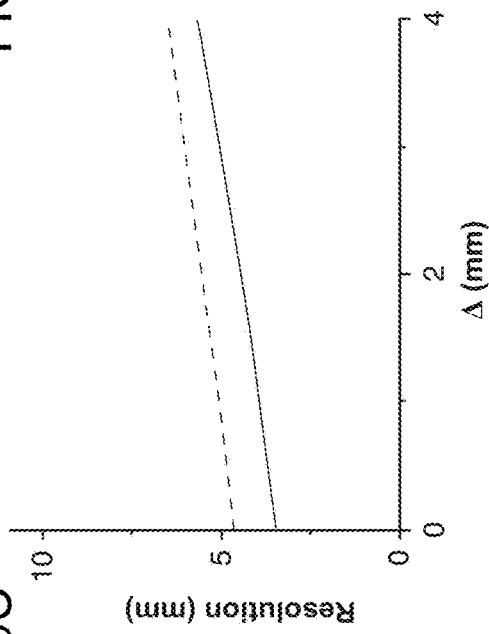

Two measures of spatial resolution were used. The first is the conventional distance to half amplitude used to quantify the spread of many measurement functions. The space domain electrograms for unipolar and bipolar electrodes have more than a single peak, as shown in FIGS. 25A-25B, but the distance to half amplitude concept still usefully applies. Thus, the resolution provided by a unipolar recording of a dipole source was equated to the lateral distance from the dipole center to the point of half maximal amplitude, defined as $W_{1/2}$, which for bipolar recordings was taken as the distance from its center to the point of half maximum positive deflection. FIG. 26A is a plot of the potential due to a dipole current source recorded by a unipolar electrode as a function of lateral distance from the source, showing how resolution is quantified in terms of peak width at half maximum height $W_{1/2}$. FIG. 26B is the corresponding plot for a bipolar electrode.

Due to concern that the two and three peaks, respectively, of the unipolar and bipolar point-source electrograms might make the resolution of multiple sources more complicated than if they had only single peaks, a second measure of spatial resolution was designed to detect the minimal resolvable separation between two dipole sources. Considering resolution in the y direction, $\Phi_0(y,z_0)$ was defined as the electrogram measured when the dipole sources are separated by a distance of zero (i.e. equivalent to a single dipole source), and $\Phi_{\Delta y}(y,z_0)$ was defined as the electrogram measured when the sources are separated by some finite distance $\Delta y$.

When $\Delta y$ is small compared with d, $\Phi_0(y,z_0)$ and $\Phi_{\Delta y}(y,z_0)$ are similar. Consequently, their cross correlation achieves a maximum value close to 1, becoming precisely 1 in the limit as $\Delta y$ approaches zero. When $\Delta y$ is sufficiently large, $\Phi_{\Delta y}(y,z_0)$ assumes the appearance of two distinct dipole electrograms located at well separated positions, so the cross correlation between $\Phi_0(y,z_0)$ and $\Phi_{\Delta y}(y,z_0)$ again achieves a relatively high maximum value. At intermediate separations, $\Phi_{\Delta y}(y,z_0)$ consists of two partially overlapping dipole electrograms and thus has a complex morphology that bears little resemblance to that of a single dipole. In this case, the cross correlation between $\Phi_0(y,z_0)$ and $\Phi_{\Delta y}(y,z_0)$ has a relatively low maximum value because the two signals are dissimilar in shape. Thus, the nominal measure of resolution was selected to be the value of $\Delta y$ for which the maximum in the cross correlation between $\Phi_0(y,z_0)$ and $\Phi_{\Delta y}(y,z_0)$ achieves its minimum value. This is defined as $C_{min}$.

FIG. 27A is a plot of superimposed simulated bipolar electrograms (d=2 mm, l=z=$\Delta$=1 mm) produced by two dipole sources with $\Delta y$=0, 0.5, 2.95, and 3.5 mm (as indicated in the legend). FIG. 27B is a plot of the maximum on the cross correlation between the bipolar electrogram with $\Delta y$=0 and the electrogram with $\Delta y$ as indicated on the horizontal axis. Open circles correspond to the four electrograms shown in FIG. 27A. This relationship has a maximum for $\Delta y$=0 mm and a minimum for $\Delta y$=3.9 mm=$C_{min}$.

FIGS. 28A-28C are plots illustrating how the two measures of spatial resolution, $W_{1/2}$ (dotted lines) and $C_{min}$ (dashed lines), vary as functions of electrode dimensions when the potential from a dipole current source is recorded by a unipolar electrode. The nominal baseline values for the various quantities in question were set as d=2 mm, l=1 mm, and $z_{0=1}$ mm, and each quantity was varied in turn while the others remained fixed. Not surprisingly, the two measures of resolution are not precisely equal. Nevertheless, they are clearly comparable and exhibit similar trends, both showing that resolution worsens progressively as d, l, and $z_0$ increase. It is also clear that resolution depends most strongly on z. FIGS. 28A-28C: Resolution of a unipolar electrode recording of a dipole current source as assessed in terms of Cmin (solid lines) and W½ (dashed lines). The three plots show dependence of resolution on electrode diameter (d), length (l), and height above the tissue (z0). Although each of these quantities was varied, the remaining quantities were held fixed at d=2 mm, l=1 mm, and z0=1 mm. FIG. 29A-29D are corresponding plots for bipolar electrode recordings, including showing the effects of changing the distance D between the two electrodes of a bipolar pair (FIG. 1). In deciding what conditions correspond to the highest electrogram accuracy that is currently achievable, the fact that the myocardial tissue is covered with a layer of endothelial cells that adds to the distance between the active tissue and the closet approach of an electrode tip. Thus, even when an electrode is placed right against the tissue surface, a nominal best case scenario would place it an average of approximately 1 mm from the active tissue. Currently, the smallest clinically available electrodes have diameter and length both of 1 mm. Setting these conditions in our computational model (i.e. z0=d=l=1 mm), resolution values were obtained for a unipolar recording of Cmin=4.5 mm and W½=3.0 mm. For a bipolar recording (imposing the additional condition that D=1 mm), Cmin=2.8 and W½=4.0 mm were obtained. Reducing d to the relatively negligible value of 0.001 mm while keeping the remaining parameters unchanged, reduced W½ and Cmin by factors of between 2 and 4. Conversely, reducing l to 0.001 mm, reduced W½ and Cmin by factors of between 1.6 and 2.9. Thus, by reducing an electrode to a single point one would improve resolution over that currently achievable by the product of these two effects, or roughly one order of magnitude.

Identification of atrial activation patterns depends crucially on the ability to create spatially accurate maps of atrial electrical activity. The fact that this activity is often complex and nonperiodic would make mapping a significant challenge even if the entire activity pattern could be visualized perfectly. In reality, the practicing cardiac electrophysiologist must make do with nothing more than a series of electrograms from a small number of electrodes placed on the atrial endocardium. The challenge of mapping is further compounded because these electrograms are distance-weighted averages of the activity from an extended region of heart tissue in the vicinity of each electrode. In particular, when different patches of tissue each provide out of phase contributions to the potential measured by a single electrode, the result is a fractionated electrogram. Consequently, it is most desirable to obtain electrograms of the highest achievable spatial resolution. Resolution of a bipolar electrode recording of a dipole current source as assessed in terms of Cmin (solid lines) and W½ (dashed lines). The four plots show dependence of resolution on electrode diameter (d), length (l), separation (D), and height above the tissue (z0). Although each of these quantities was varied, the remaining quantities were held fixed at d=2 mm, l=1 mm, D=1 mm, and z0=1 mm. Here, two different measures of resolution (FIGS. 26A-26B) were used to investigate how spatial resolution is affected by the dimensions and configuration of both unipolar (FIGS. 28A-28C) FIGS. 29A-29D: Resolution of a bipolar electrode recording of a dipole current source as assessed in terms of Cmin (solid lines) and W½ (dashed lines). The four plots show dependence of resolution on electrode diameter (d), length (l), separation (D), and height above the tissue (z0). Although each of these quantities was varied, the remaining quantities were held fixed at d=2 mm, l=1 mm, D=1 mm, and z0=1 mm. and bipolar (FIGS. 29A-29D) electrograms. The resolution degrades progressively and substantially as electrode width, height, separation (in the case of bipolar), and distance from the tissue are increased. Changes in electrode height had the greatest impact on spatial resolution, however, implying that the most important aspect of electrode design is not related to the electrode itself, but rather to the physical proximity of the electrode to the tissue. There are two principle ways in which the spatial resolution of intracardiac electrode recordings can be diminished: the amount of tissue that is 'near field' [i.e. immediately beneath the electrode(s)]can be increased, and/or the ratio of near-field to far-field tissue can be diminished. An increased electrode diameter results in an effective increase of the electrode's footprint over the myocardial surface, thereby increasing the amount of tissue contributing to the near-field signal. In contrast, an increased electrode height results in greater attenuation of near-field signal relative to far-field signal, resulting in a diminished ability to discriminate between the two. An increased electrode length has a similar effect because it also increases the average height of the electrode above the tissue surface. These various effects are experienced by both unipolar and bipolar electrodes (FIGS. 28A-28C and 29A-29D), although to a lesser extent by bipolar because taking the difference between two nearby potentials effectively cancels the common far-field components while spatially differentiating the near-field signal. The theory of intracardiac electrode measurement performance has been known for many years. For example, in 1951 Schaefer et al. [10] outlined the mathematical relationship describing how unipolar and bipolar electrograms are affected by the distance between a dipole source and the recording electrode(s), and observed that bipolar electrodes reduced far-field 'contamination' and that this effect was increased as inter-electrode spacing was decreased. Later in the same decade, Durrer et al. [11] investigated methods for measuring electrical activation in the canine left ventricle and made the qualitative observation that only with bipolar recordings 'y Can the influence of activity in distant parts of the heart be excluded'. They also described unipolar and bipolar electrogram morphologies corresponding closely to those simulated in the present study (FIGS. 25A-25B), and noted that increasing the spacing between bipolar electrodes caused the electrogram morphology to change in the same way as our model simulations predict (FIGS. 27A-27B). Similar investigations have been undertaken more recently by other investigators [12,13] and corroborate our findings with respect to unipolar and bipolar electrogram morphologic features. The notion that various electrode characteristics should affect spatial resolution is also not new. For example, Kimber et al. assessed the ability of unipolar and bipolar recordings to accurately determine local activation time in 'ambiguous' or fractionated signals from ventricular tachycardia mapping studies and found that bipolar recordings were better able to determine local activation time. Nevertheless, to our knowledge, there has been no formal study quantifying how electrode characteristics affect the spatial resolution of intracardiac electrograms, despite the important implications for clinical electrophysiology. The foundation of activation mapping is identification of local activation time, which is dependent on spatial resolution [14]. During organized rhythms, the resolution provided by currently available electrodes is adequate for accurately identifying local activation times. However, this is not always the case for atrial fibrillation in which tissue activation can have high spatiotemporal complexity, changing rapidly with time [15]. This would lead to meaningless maps if local activation time is sampled sequentially with a single mapping electrode. It would thus appear that accurate mapping of atrial fibrillation will require the use of electrode arrays to provide beat-to-beat activation at multiple sites simultaneously. This raises questions as to the ideal size and spacing of electrodes in the array. Our results indicate that with the smallest electrodes currently available, one cannot expect a resolution of better than about 5 mm (FIGS. 28A-28C and 29A-29D), therefore spacing the electrodes any closer than this is unlikely to confer added benefit unless methods of digital signal processing such as deconvolution can be used to further enhance resolution.

A computational model was created and validated for evaluating the impact of electrode size, shape, inter-electrode spacing, and height above the tissue on spatial resolution. Two independent metrics were used to quantify spatial resolution, both indicating that spatial resolution becomes degraded roughly in proportion to the above four factors. Electrode height above the tissue has the greatest effect on spatial resolution, so electrode tissue contact is the most important factor impacting resolution. Finally, these calculations suggest that even if electrodes could be constructed to have negligible dimensions compared with those in use today would increase resolution by at most about one order of magnitude. Increases in all these quantities caused progressive degradation in two independent measures of spatial resolution, with the strongest effect being due to changes in height above the tissue.

The accuracy of any electrogram signal frequency analysis is a function of the ratio between electrode spatial resolution and tissue spatiotemporal variation. The voltage (i.e., the electric potential difference) of an electrogram rises and falls with the net electric field potential at the recording electrode, and the electrogram signal frequency is simply a measure of the frequency of those variations in voltage. Any factor that influences the voltage will also influence the electrogram signal frequency. Because the magnitude of an electric field potential decreases with radial distance from its current source, the net electric field potential at a recording electrode will be dominated by nearby current sources. Effectively, only a limited region of tissue in the vicinity of a recording electrode substantively contributes to the net electric field potential recorded by that electrode. The spatial extent of such an electrode recording region is the spatial resolution of that electrode.

Meanwhile, spatiotemporal variation (caused by, for example, heart cells whose excitations are dissociated and hence out of phase from each other) between current sources within an electrode recording region may produce a deflection in the electrogram recording. A deflection results in an electrogram signal frequency that is higher than the tissue activation frequency of any individual cell within the electrode recording region. Thus, an attempt to determine the maximum tissue activation frequency of individual cells may be inaccurate in the presence of spatiotemporal variation within the electrode recording region.

The accuracy with which an electrogram signal frequency indicates the tissue activation frequency of individual cells within the recording region is a function of the ratio between the spatial resolution of the recording electrode and the spatiotemporal variation of the tissue. Once the electrode recording region is limited to only cells that are synchronously excited, the electrogram signal frequency becomes the same as the tissue activation frequency in the recording region. This "threshold" spatial resolution and/or higher spatial resolutions accurately reflect tissue activation frequency without over-counting. Therefore, the correlation between electrogram signal frequency and tissue activation frequency (and thus circuit density and distribution) increases as the spatial resolution of the recording electrode increases (i.e., includes fewer cells that are dssynchronously activated); and the optimal spatial resolution is close to the threshold where dssynchronously activated cells are eliminated.

The threshold spatial resolution is different for each patient (and at different locations in each patient's heart). In accordance with some embodiments of the present invention, the threshold spatial resolution may be found by iteratively employing recording electrodes with higher spatial resolutions until dssynchronously activated cells are eliminated from the recording region. As spatial resolution is increased, electrogram signal frequency will change if dyssynchrony remains within the recording region. The spatial resolution at which electrogram signal frequency no longer changes (with improved spatial resolution) may be considered an accuracy-promoting spatial resolution threshold for a particular recording region.

FIG. 13 is a system component diagram in accordance with some embodiments of a system for identifying an optimal spatial resolution for local tissue with spatiotemporal variation. The system may include, but is not limited to, an imaging subsystem 131 (described above) and/or a catheter subsystem 132. The system may also include a processing unit 135, a memory 134, a transceiver 133 including one or more interfaces 139, a GUI 138, and/or a display 136 (each described in detail below).

The catheter subsystem 132 includes one or more catheters according to some embodiments of the present invention. In some embodiments, the catheter subsystem 132 also may include, but is not limited to, one or more puncture or surgical devices for accessing a patient's vasculature and/or heart, one or more sheaths with one or more valves for preventing flowback, a saline solution for flushing components of the subsystem, one or more guidewires for positioning the one or more catheters, and/or one or more contrast agents (used in combination with an appropriate imaging subsystem 131) for viewing the tissue during use. The catheter subsystem 132 may include a separate display and/or share a display 136 with other components of the system shown in FIG. 13. The catheter subsystem 132 and its components may be operated manually and/or automatically.

According to some embodiments of the present invention, the catheter subsystem 132 also may include, but is not limited to, one or more electrode localization technologies, such as triangulation-based localization, radio-frequency-based localization (e.g., the CARTO™ XP System, which is available from Biosense Webster® (Diamond Bar, Calif.)), and/or impedance-based localization (e.g., the EnSite NavX™ Navigation & Visualization Technology, which is available from St. Jude Medical (St. Paul, Minn.)).

Figure 30:
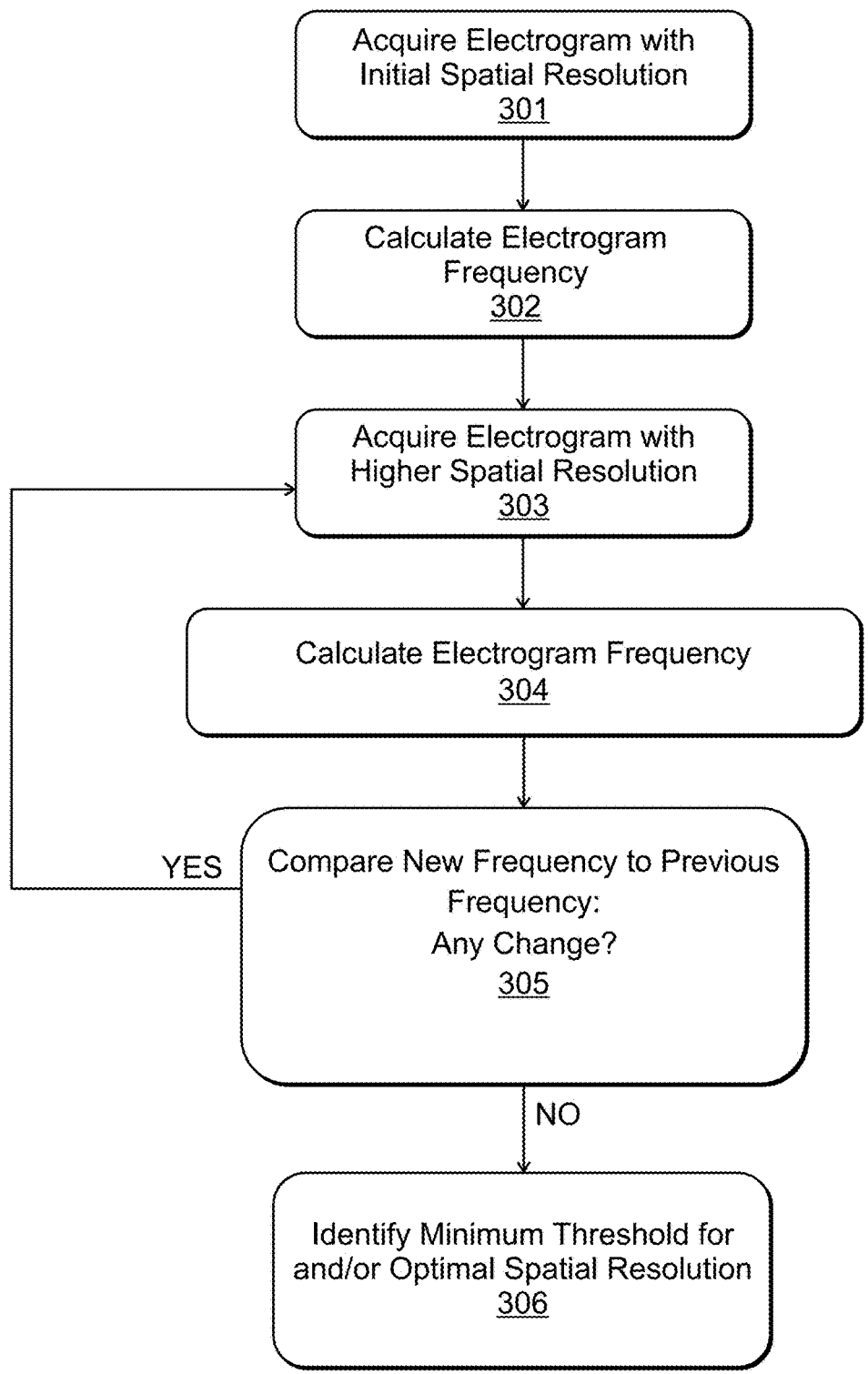
FIG. 30 is a process flowchart for identifying an optimal spatial resolution for local tissue with spatiotemporal variation, in accordance with embodiments of the present invention.

FIG. 30 is a process flowchart for identifying an optimal spatial resolution for local tissue with spatiotemporal variation in accordance with some embodiments of the present invention. In step 301, an electrogram recording is acquired for a particular tissue location using an electrode with an initial spatial resolution. In step 302, the frequency of the electrogram signal is calculated and stored. In step 303, another electrogram recording is acquired using an electrode with a spatial resolution that is higher than that of the previous electrode. In step 304, the frequency of the electrogram signal is calculated and, in step 305, compared to the frequency of the previous electrogram signal. If the frequency has changed, the process returns to step 303 using an electrode with a spatial resolution that is even higher yet. In some embodiments, the frequency must change substantially to return to step 303; while in other embodiments, any change in the frequency requires returning to step 303. If the frequency has not changed, the spatial resolution is identified in step 306 as a minimum threshold for and/or optimal spatial resolution. In some embodiments, the frequency must not change at all to identify the optimal spatial resolution; while in other embodiments, a small change in the frequency is not considered in identifying the optimal spatial resolution.

Spatial resolution is influenced by electrode location, size, and configuration. More specifically, spatial resolution can be improved by the following: (1) moving the electrode closer in proximity to the tissue surface (i.e., the current source); (2) reducing the size of the electrode itself; and (3) using a bipolar electrode configuration (or another means of producing spatial differentiation). The electrode configuration is not limited to only two electrodes, but may include more than two electrodes, and the differences between the electric field potentials may still be calculated.

The distance between an electrode and the tissue as well as the size of an electrode matter because an electrode is an electrical conductor that cannot support a voltage gradient. Instead, an electrode records the average of all electric potentials on its surface. Thus, spatial resolution will be reduced to the extent that positioning and/or an increase in electrode size results in an increase in the average height of an electrode above the tissue. Likewise, spatial resolution will be reduced to the extent that an increase in electrode size results in an electrode covering a larger region of tissue. Again, because an electrode recording is an average of all electric potentials, a larger electrode "footprint" eliminates the ability to distinguish between the contributions to the field potential of individual heart cells within that footprint.

Figure 31B:
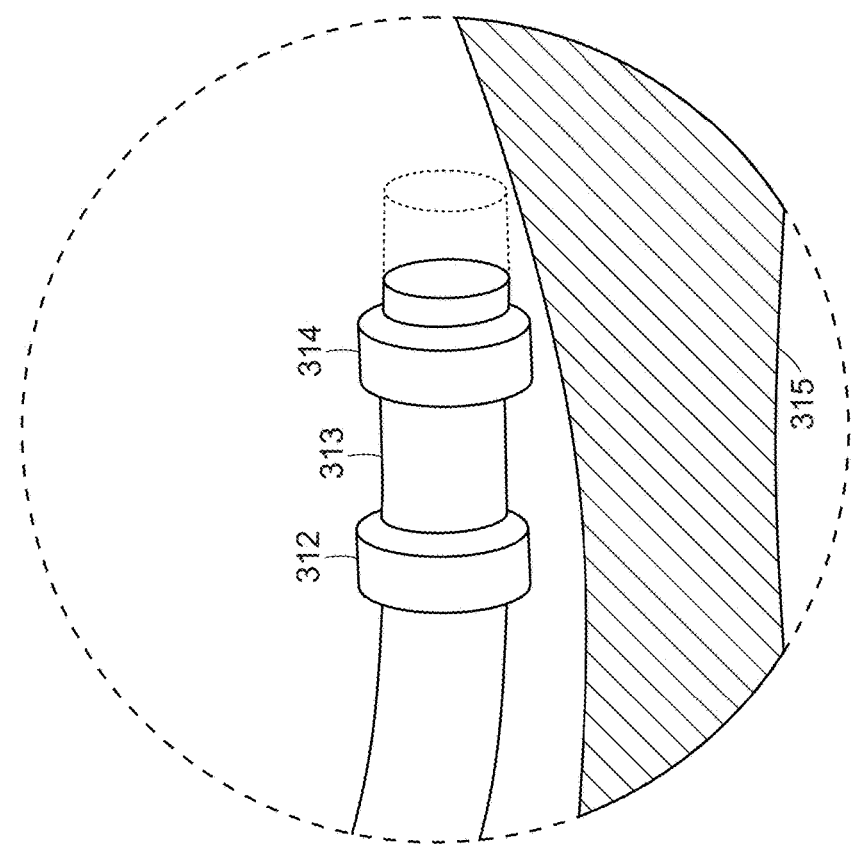
FIGS. 31A-31B illustrate a catheter with a contact bipolar electrode configuration, in accordance with embodiments of the present invention.
Figure 31A:
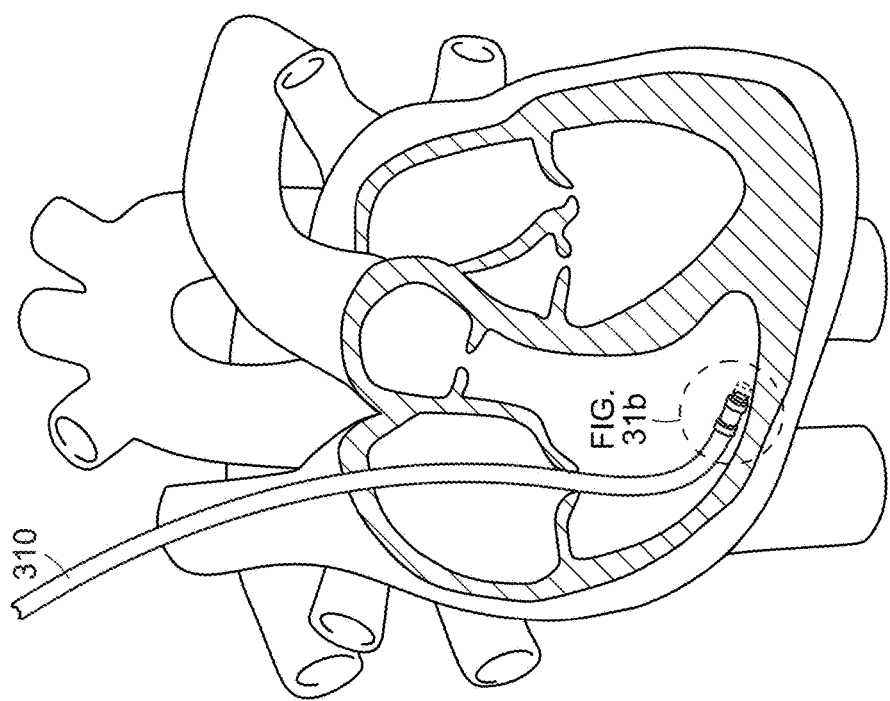

Practically, all electrode recordings are bipolar; but by convention, an electrode configuration is "unipolar" when only one of two electrodes—the "index" electrode—is close enough to the tissue to record a signal, while the second electrode—the "indifferent" electrode—is far enough from the tissue that it does not record a signal and/or cannot be in contact with the tissue. On the other end of the spectrum, when both electrodes may be in contact with the tissue to record a signal, an electrode configuration is "contact bipolar." FIGS. 31A and 31B illustrates an example of a contact bipolar electrode configuration. Catheter 313 has two electrodes 314, both of which are close enough to tissue surface 315 to record a signal.

As an electric field potential spreads outward from a current source, its magnitude diminishes with the radial distance r from the source at a rate of about $1/r^2$ for unipolar electrogram recordings. For bipolar electrogram recordings, the magnitude of an electric field potential diminishes more rapidly, at a rate of about $1/r^3$. The difference between the electric potentials as recorded by two bipolar electrodes may be represented by:

$$\delta\psi \propto \frac{1}{r^3} - \frac{1}{(r+d)^3} \quad (12)$$

where Ψ is the electric field potential and d is the distance between the two bipolar electrodes. Both the magnitude of the electric field potential at each electrode and the difference between the two recordings decrease as the distance to the current source increases. Thus, when using a bipolar configuration, the potential difference becomes negligible for potential current sources that are far from the two electrodes relative to the distance between those electrodes. Spatial resolution is higher if sources far from the recording site are not contributing substantively to the electrogram. Hence, bipolar electrogram recordings possess better spatial resolution than unipolar electrogram recordings.

OCU Electrode Configuration

For most current electrophysiological procedures, intracardiac electrodes are used to measure electrical activity within the heart. There are generally two electrode types: unipolar and bipolar electrodes. Unipolar electrodes are the simplest configuration, with one recording electrode within the heart and another at a relatively long distance away. Unipolar electrodes are adequate but have a tendency to include far field electrical activity in the recorded signal which can result in a fractionated electrogram. This is a particularly relevant when trying to map complex arrhythmias (e.g. cardiac fibrillation) and accurately identifying local activation time. Bipole electrode configurations ameliorate this problem by placing both electrodes within the heart at a relatively narrow distance apart. Since both electrodes "see" approximately the same far field electrical activity and the recorded potential is the difference of the two the resultant electrogram includes little far field signal.

There are, however, at least two limitations of bipole electrodes. First, the recorded electrical potential of bipole electrodes vary with their orientation relative to the direction of a passing wavefront. Second, because bipole electrodes have both electrodes on the heart surface, there is potential inclusion of distinctly different electrical activity from each electrode. In view of these limitations, it was hypothesized that bipolar electrodes oriented perpendicular to the tissue plane (orthogonal close unipolar (OCU)) retain the superior near/far-field discrimination of common bipolar electrode recordings with the directional independence and smaller footprint of unipolar recordings. A series of in silico and in vivo experiments were performed to test the potential utility of this hypothesis.

Electrical excitation was modeled as a static dipole with 0.5 mm spacing. The direction of the dipole moment is parallel to "wave direction." Electrodes were modeled as cylinders with the same dimensions as those used in the in vivo experiments (1-mm length, 2-mm diameter, 4-mm spacing).

Figure 32:
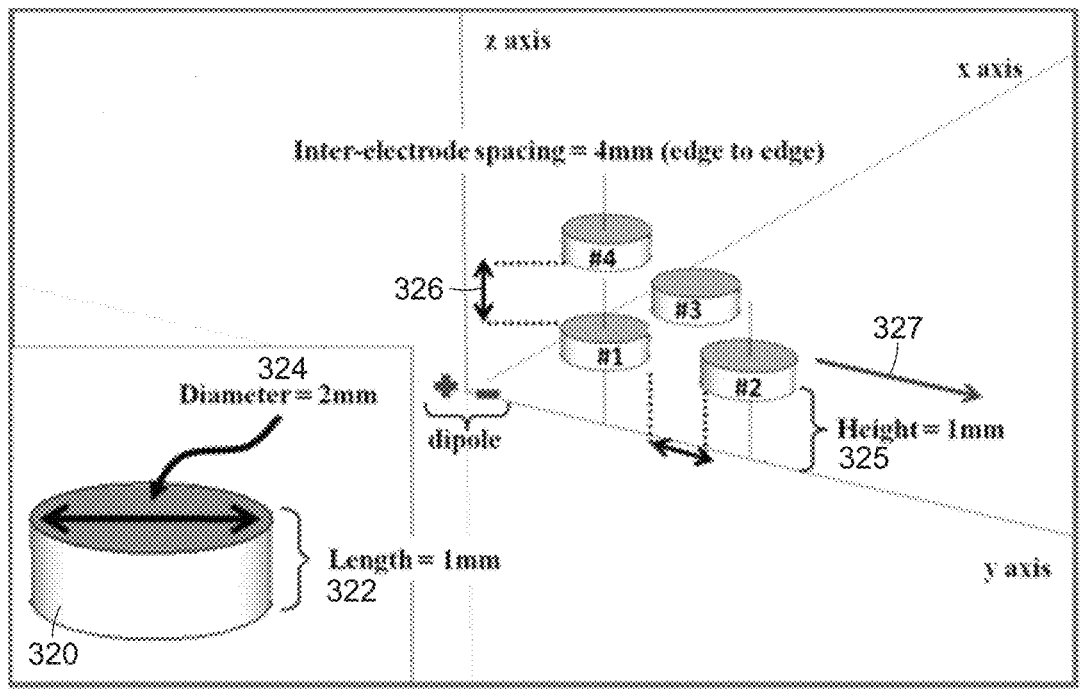
FIG. 32 illustrates the orientation of electrodes relative to an electric dipole, in accordance with embodiments of the present invention.

FIG. 32 illustrates the collection of electrograms in accordance with some aspects of the study. Electrograms were recorded in a plane of a height (1 mm) above the dipole moment using electrodes 320 with length (1 mm) diameter 324 (2 mm). To assess the effect of wavefront direction, electrode bipoles with inter-electrode distance 236 were oriented parallel, perpendicular, and orthogonal to the dipole moment. Measurements were made with the electrode bipoles directly over the dipole, and at increments (0.1 mm) up to a determined distance (10 mm) from the dipole in direction 327.

Figure 33:
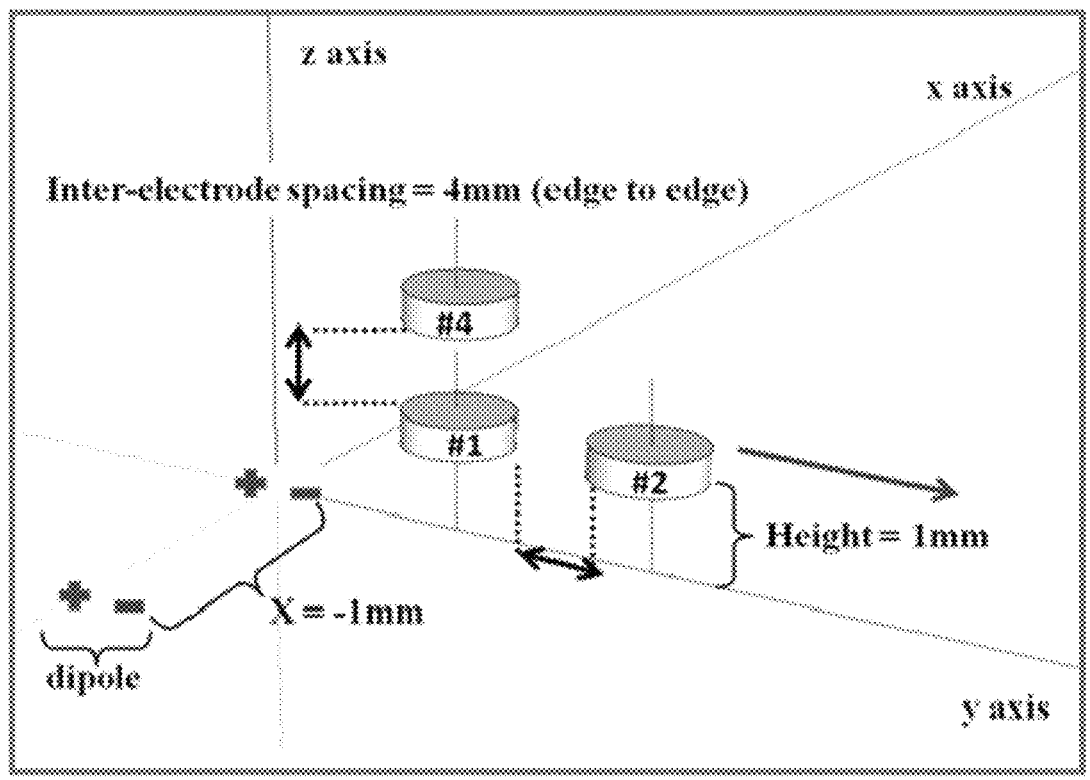
FIG. 33 illustrates the orientation of electrodes relative to near and far field charges, in accordance with embodiments of the present invention.

FIG. 33 illustrates the collection of electrograms in accordance with some aspects of the study. Near field dipole is at the origin, and far field dipole 1 mm along the x axis. Electrical potential is measured as the electrodes move along the y axis. Common bipolar and OCU electrograms were recorded from two dipoles to assess near- and far-field discrimination. A first dipole was the near field signal, and a second dipole was the far field signal. Measurements were made with the electrode bipoles directly over the first dipole, and at increments (0.1 mm) up to a determined distance (10 mm) from the second dipole in direction 327.

Electrical potentials were plotted as a function of distance from the dipole (spatial electrograms). Comparisons were made between specific electrode configurations at maximum electrical potential (difference between maximum peak and trough). The ratio of the far field maximal amplitude to the near field maximal amplitude was calculated for OCU and bipolar configurations. The difference in maximal amplitude between OCU recordings and bipolar recordings in parallel and perpendicular orientations relative to the DP.

To apply the electrode model to moving charges, a cellular automaton model was used to create a two-dimensional plane of tissue (60×60 cells). A standard action potential duration (action potential duration=80) and resistance (R=13) was used. Two layers of evenly spaced electrodes with standard electrode dimensions (1-mm length and 2-mm diameter) were positioned in an array (10×10 electrodes) over the tissue surface. The electrode array was used to record electrograms in bipolar, OCU, and unipolar orientations. The mean dominant frequency of the recorded electrograms from the different array types was compared with the mean dominant frequency of the tissue directly underneath the electrodes.

Electrogram recordings with standard catheters (2 mm electrode tip) were made in 5 swine hearts. Recordings were made with a Bard recording system. Catheters were held in place by a spacer that allowed simultaneous recordings of CBP and OCU electrograms with a fixed inter-electrode spacing of 4 mm.

To assess near and far-field discrimination simultaneous CBP and OCU electrograms were measured along the mitral annulus over the right atrium. The CBP electrodes were oriented parallel to the annulus.

To assess the effect of wavefront direction, simultaneous CBP and OCU electrograms were recorded over the right ventricle. Wavefront direction was estimated by rotating the electrodes and spacer and finding the relative minimal amplitude of a CBP recording; simultaneous recordings were made at that position.

Electrograms were analyzed offline. MATLAB®-based software was used to measure the amplitude of electrical signals. Groups of values were compared with a Student's t-test.

Figure 34:
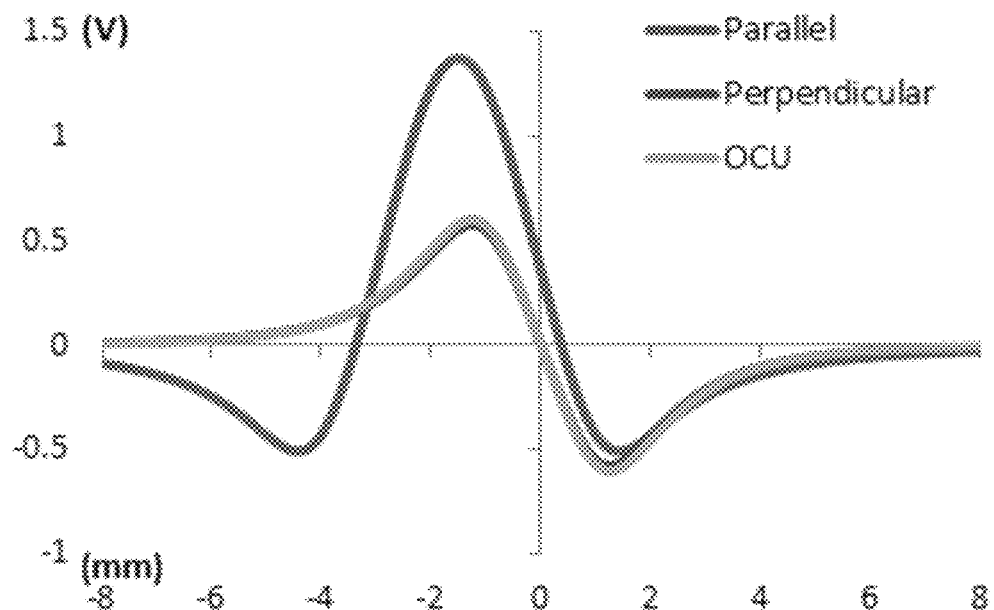
FIG. 34 graphically illustrates near fields spatial electrograms from a model, in accordance with embodiments of the present invention.

In the in silico model there was a 0.72 mV difference in electrical potential between CBP recordings in the parallel and perpendicular position. Parallel to the direction of the wavefront, the recorded potential was 1.88 mV. Perpendicular to the direction of the wavefront, the recorded potential was 1.15 mV. With the OCU configuration the recorded potential was 1.20 mV. The computer model used yields the same absolute values in multiple runs, and thus, does not define statistical measures of variance with its use. FIG. 34 graphically illustrates near fields spatial electrograms from a model, in accordance with embodiments of the present invention.

In swine hearts there was an average 5.5+/−2.9 mV (mean±SD) difference in electrical potential between CBP recordings in the parallel and perpendicular position. Parallel to the direction of the wavefront, the average recorded potential was 9.1+/−3.1 mV. Perpendicular to the direction of the wavefront, the average recorded potential was 3.6+/−0.7 mV. With the OCU configuration the average recorded potential was 4.0+/−0.7 mV, n=5.

Figure 35:
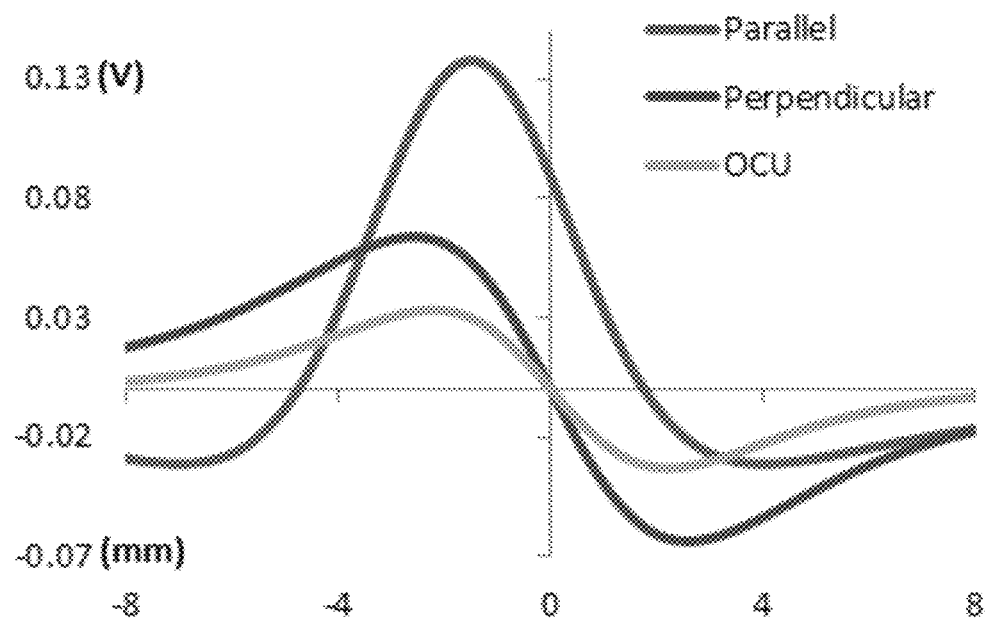
FIG. 35 graphically illustrates far field spatial electrograms from a model, in accordance with embodiments of the present invention.
Figure 36:
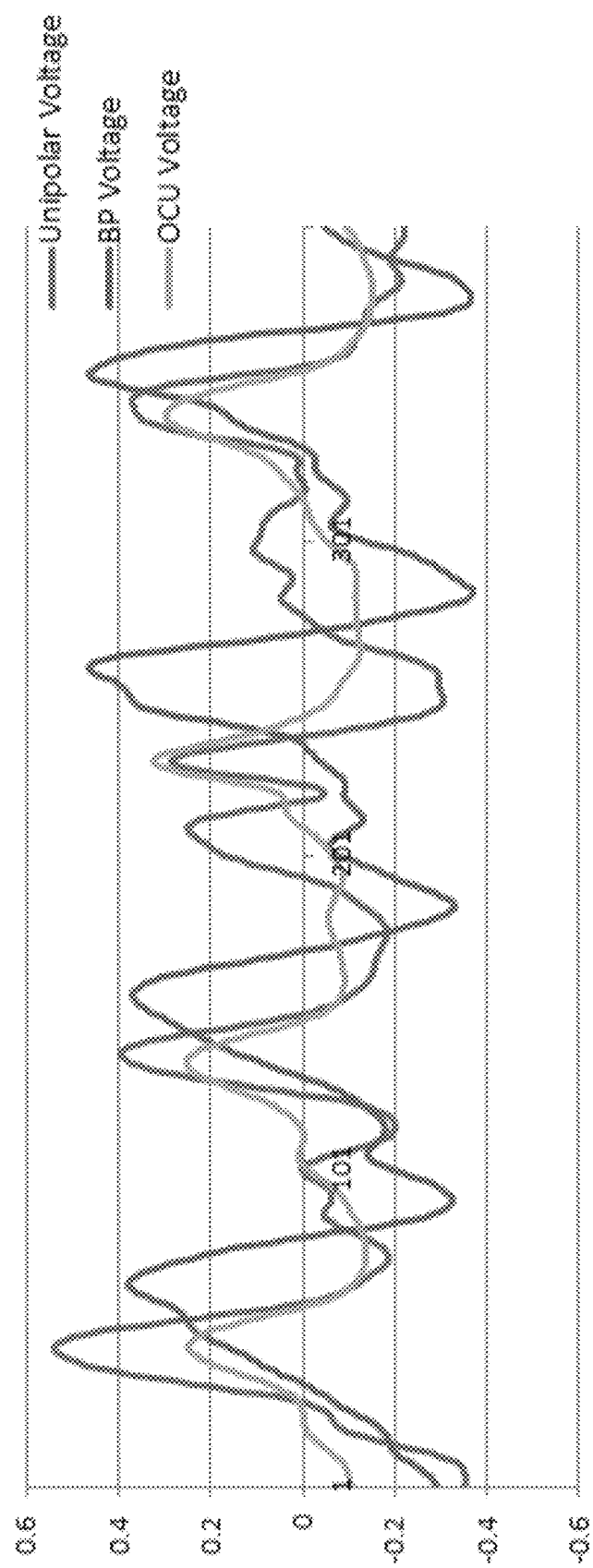
FIG. 36 illustrates graphically electrical potential recordings at a single electrode, in a model, in accordance with embodiments of the present invention.
Figure 37:
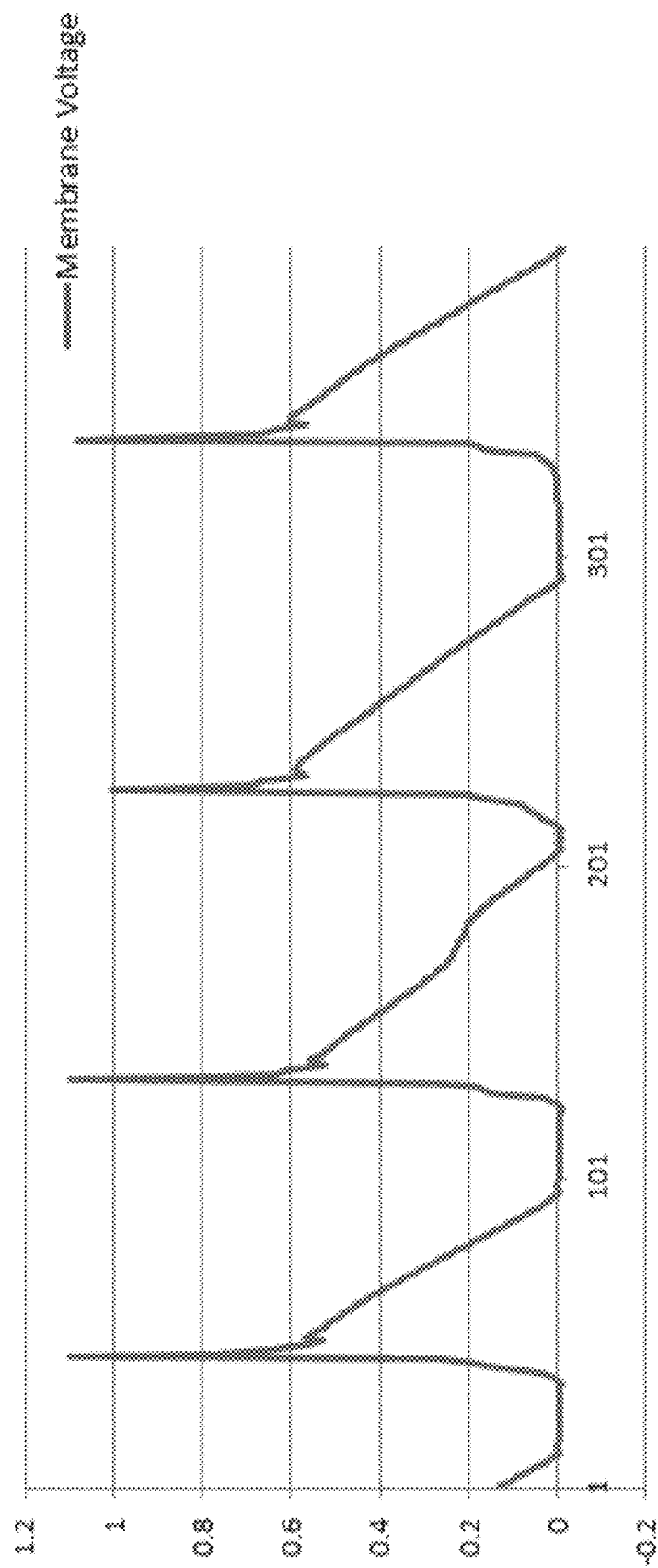
FIG. 37 graphically illustrates membrane voltage underneath a single electrode, in a model, in accordance with embodiments of the present invention.

In the in silico model average V/A ratio for the CBP configuration was 0.09. In the in silico model average V/A ratio for the OCU configuration was 0.05. FIG. 35 graphically illustrates far field spatial electrograms from a model, in accordance with embodiments of the present invention. FIG. 36 illustrates graphically electrical potential recordings at a single electrode, in a model, in accordance with embodiments of the present invention. FIG. 37 graphically illustrates membrane voltage underneath a single electrode, in a model, in accordance with embodiments of the present invention;

There is a 55.5% reduction in the V/A ratio in the OCU configuration compared to the CBP configuration. In swine hearts the average ratio of ventricular to atrial signal (V/A ratio) for CBP recordings along the mitral annulus was 0.15+/−0.04, n=5. The average V/A ratio for OCU recordings was 0.08+/−0.10. There is a 53.3% reduction in the V/A ratio in the OCU configuration compared to the CBP configuration.

In the FEM model with moving charges the average tissue DF was 10.43+/−1.44 Hz. The average UNI electrode array recording DF was 9.53+/−0.94 Hz. The average BP electrode array recording DF was 10.84+/−1.45 Hz. The average OCU electrode array recording DF was 10.33+/−1.36 Hz.

An electrode type (OCU) that ameliorates these limitations was conceptualized with an understating of the physical limitations of current electrode designs. In a computer model with static charges, OCU is superior to CBP electrodes in resolving near and far field electrical activity (55% decrease in the ratio of far and near-field signals), and OCU is independent of wavefront direction. In more clinical relevant conditions, multi-wavelet reentry was created in a cellular automaton. Here arrays of OCU electrodes demonstrated improved ability to identify tissue frequency than either unipolar or bipolar electrodes. Results from our animal study correlate with our results found in both of our computer models.

OCU electrodes appeared to be superior in part because of the smaller effective electrode footprint compared with that of conventional electrodes. This may explain partially the improved tissue accuracy of the OCU electrode arrays. With complex moving wavefronts, the CBP electrodes can be influenced by independent electrical events that can lead to erroneous estimates of the frequency of repetitive wavefronts within the tissue as a function of time.

OCU electrodes are superior compared with that of CBP electrodes with respect to the ability to resolve near and far field activity. Geometry and relationship of the electrodes to the near and far field sources provide for the improved electrodes. These results are consistent with this in both the FEM model and our animal preparations.

The clinical implications of OCU electrodes are promising. For mapping complex arrhythmias and atrial fibrillation in particular arrays of OCU electrodes with the spatial resolution and spatial sampling required to more accurately discern tissue electrical activity may lead to more effective ablation procedures. A benefit of such arrays is that they can maintain the OCU electrodes orthogonality relative to the tissue surface, a key determinant of their effectiveness. OCU electrodes may also bear fruit in other fields that require sensors for electromagnetic fields.

Thus, OCU electrogram recordings are superior to CBP recordings in differentiating near field from far field activity (~50% decrease in the ratio of far and near-field signals) and retaining the wavefront independence of UP electrodes. Furthermore, OCU recordings are more accurate than those obtained with conventional electrodes in delineating tissue frequency. It appears likely that deployed in arrays of electrodes, OCU electrodes will yield electrogram recordings that may be particularly helpful in mapping complex arrhythmias and lead to more effective ablation procedures.

TABLE 1

| | | Directional dependence | | | | Far/near field discrimination V/A ratio | |
|---|---|---|---|---|---|---|---|
| | | Orientation | | | | Orientation | |
| | | Parallel | Perpendicular | Difference | | Parallel | OCU |
| Model: | CBP | 1.88 mV | 1.15 mV | 0.72 mV (p = NA) | Model | 0.09 | 0.05 |
| | OCU | 1.20 mV | | NA | | p = NA | |
| In vivo: | CBP | 9.1 ± 3.1 mV | 3.6 ± 0.7 mV | 5.5 ± 2.9 mV (p < 0.001) | In vivo | 0.15 ± 0.04 | 0.08 ± 0.10 |
| | OCU | 4.0 ± 0.7 mV | | NA | | p < 0.001 | |

In Table 1: V = ventricular, A = atrial dimension; NA = not applicable; significance was defined as p ≤ 0.001.

In accordance with some embodiments of the present invention, one or more electrodes are put in proximity to the cardiac tissue surface using one or more catheters. Existing catheters and electrode configurations used to assist in diagnosis and treatment of fibrillation have several shortcomings for these purposes, including: (1) the inter-electrode spacing is too great; (2) the electrodes are too large; and (3) the electrode configurations are not suitably orthogonal to the tissue surface.

Figure 38B:
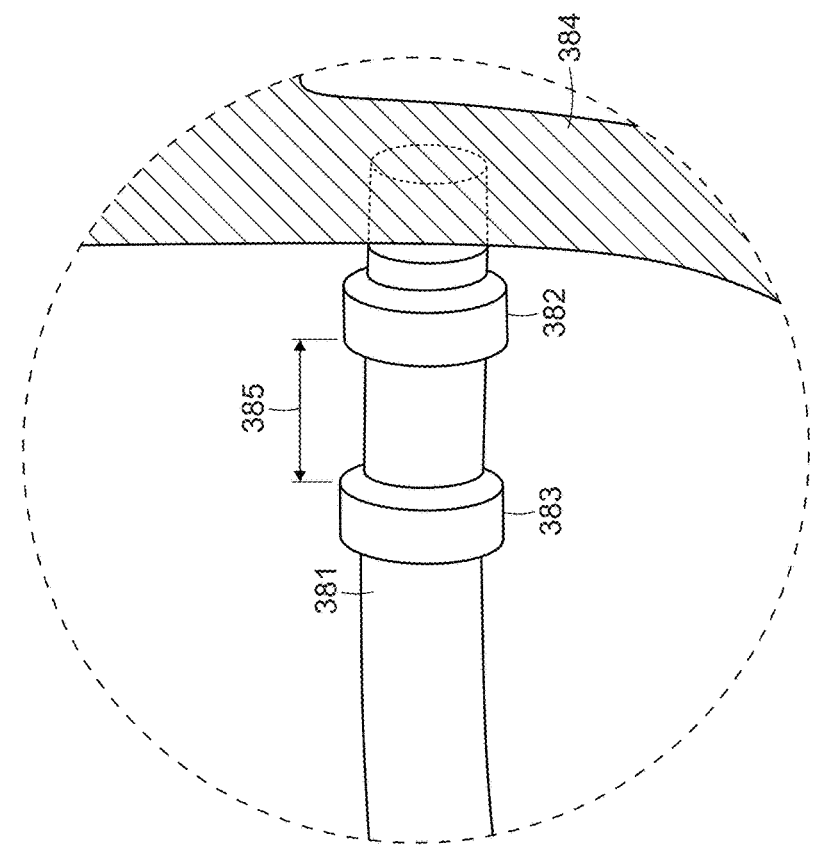
FIGS. 38A-38B illustrate a catheter with an orthogonal, close, unipolar ("OCU") electrode configuration, in accordance with embodiments of the present invention.
Figure 38A:
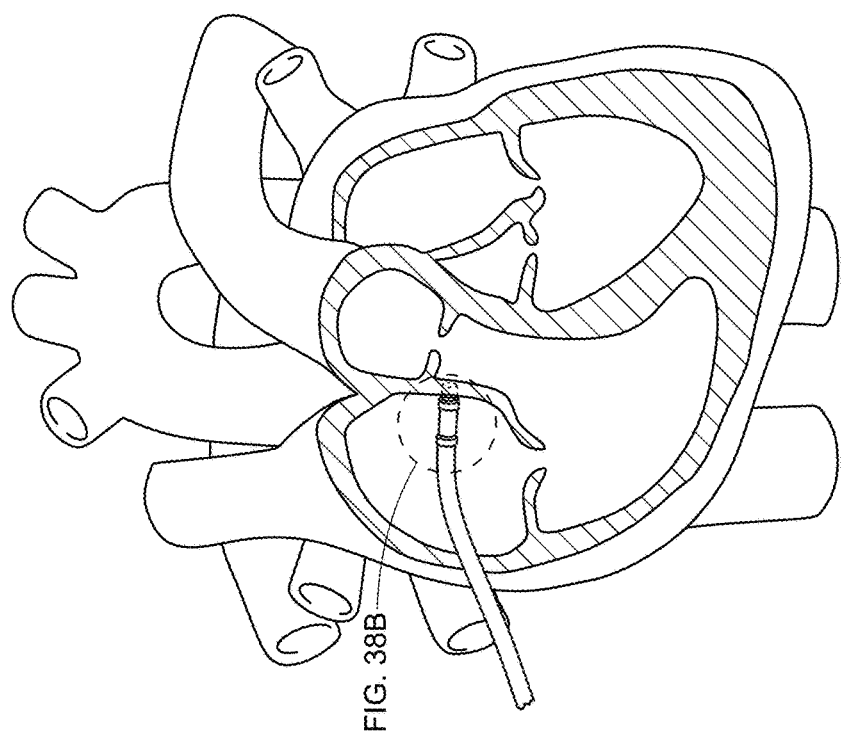

In a preferred embodiment, as diagrammed in FIGS. 38A and 38B, a pair of electrodes on catheter 801 are configured to be: (1) "orthogonal"; (2) "close"; and (3) "unipolar" (i.e., an "OCU" electrode configuration).

Figure 39:
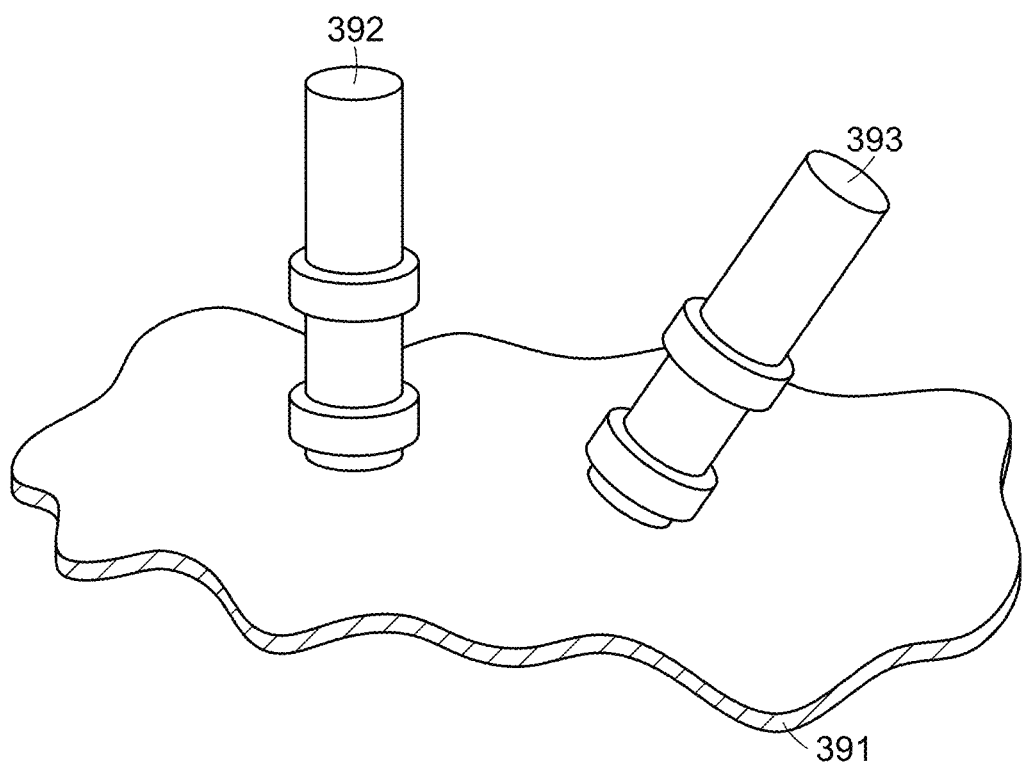
FIG. 39 illustrates the difference between a first catheter with an inter-electrode axis orthogonal to a tissue surface and a second catheter with an inter-electrode axis that is not orthogonal to the tissue surface, in accordance with embodiments of the present invention.

First, according to some embodiments, the inter-electrode axis from index electrode 382 to indifferent electrode 383 is "orthogonal" to the tissue surface 384. Existing catheters and electrode configurations are not designed to be suitably orthogonal to the tissue surface. Even though existing catheters have been called "orthogonal" (e.g., the "Orthogonal Fixed" and "Orthogonal Deflectable" catheters available from Biosense Webster® (Diamond Bar, Calif.)), a need has remained for catheters with electrodes configured to be orthogonal (normal) to the surface of tissue (i.e., in accordance with some embodiments of the present invention) as opposed to orthogonal to biological structures (e.g., fibers) on a surface for direction independent recordings. FIG. 39 illustrates the difference between two curvilinear catheters in contact with tissue surface 391, where catheter 392 has a pair of electrodes with an inter-electrode axis orthogonal to the surface 391, and catheter 393 has a pair of electrodes with an inter-electrode axis that is not orthogonal to the surface 391.

Second, according to some embodiments and as shown in FIGS. 38A and 38B, the inter-electrode distance 385 (i.e., the distance between the pair of electrodes) is "close." For example, the inter-electrode distance 385 may be within an order of magnitude of the electrode size (i.e., from approximately 0.1 mm to 3.0 mm). For example, the inter-electrode distance 385 may vary from approximately 0.01 mm to 30.0 mm. Preferably, the inter-electrode distance 385 is between approximately 0.1 mm and 1 mm so that the indifferent electrode is "close" enough to the tissue surface to detect a signal. Thus, the proximity of the indifferent electrode to the tissue surface may be determined by the thickness of the index electrode 382 and the inter-electrode distance 385.

Third, according to some embodiments, the electrode pair is "unipolar" because only the index electrode 382 may be in contact with the tissue. This unipolar electrode configuration has at least two advantages over a contact bipolar electrode configuration, in which both electrodes may be in contact with the tissue. The first advantage is that the unipolar electrode configuration retains all of the spatial resolution benefits of the contact bipolar configuration, but with the additional spatial resolution enhancement conferred by a smaller footprint (i.e., only half of the electrodes may be in contact with the tissue surface). The second advantage is that the unipolar electrode configuration can retain the inter-electrode difference 385 independent from the direction of a tissue activation wavefront. Contact bipolar electrogram amplitude depends upon the direction of tissue activation. When an activation wavefront is parallel to the inter-electrode axis, the potential difference between bipolar electrodes is maximum, and the resulting electrogram has maximum amplitude. However, when an activation wavefront is perpendicular to the inter-electrode axis, the potential difference between bipolar electrodes is zero, and the resulting electrogram has zero amplitude. Furthermore, as the angle of incidence of a tissue activation wavefront varies relative to the inter-electrode axis of a contact bipolar electrode configuration, fractionation may be produced in the resulting electrogram. Fractionation may also influence the electrogram frequency, thus affecting accuracy in the assessment of tissue activation frequency. Therefore, the unipolar electrode configuration can retain the inter-electrode difference 385 independent from the direction of a tissue activation wavefront and is immune to fractionation in response to changing wave-front direction.

Figure 40:
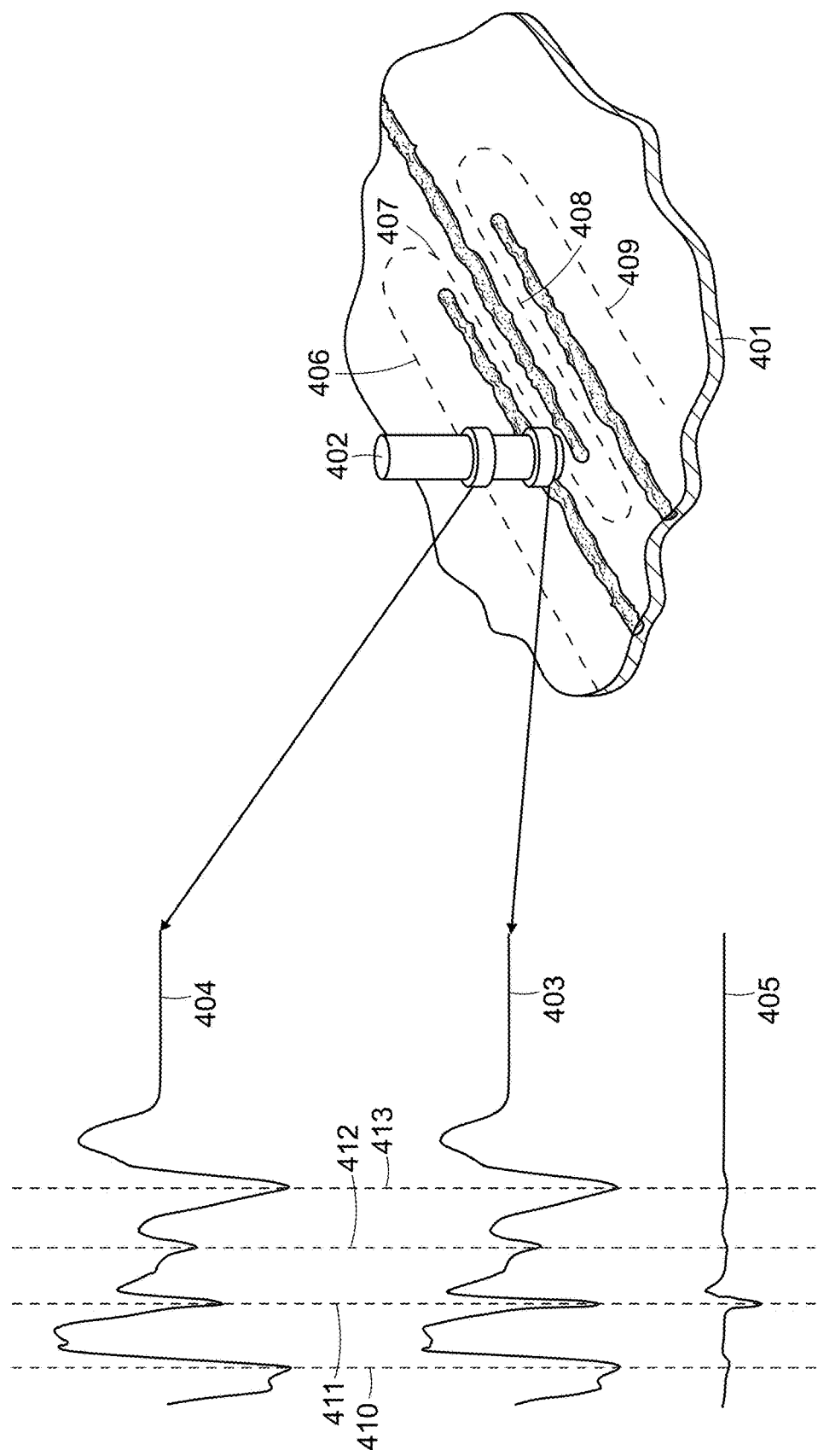
FIG. 40 illustrates an example of improved spatial resolution obtained by use of an OCU electrode configuration, in accordance with embodiments of the present invention.

FIG. 40 illustrates an example of improved spatial resolution obtained by use of an OCU electrode configuration in accordance with some embodiments of the present invention. The tissue substrate surface 401 is assessed by a catheter with one pair of recording electrodes in an OCU electrode configuration 402. The index electrode records electrogram signal 403, and the indifferent electrode records electrogram signal 404. The resulting OCU electrogram signal 405 is calculated by subtracting the indifferent electrogram 404 from the index electrogram 403.

In the example shown in FIG. 40, the tissue substrate surface 401 contains three linear non-conducting scars (resulting, e.g., from ablation lesions). The scars separate the tissue surface 401 into four conducting channels 406-409. The index electrode of the catheter is in close proximity to and/or touching the tissue surface 401 directly above the second conducting channel 407. As indicated by the dashed arrows, the path of tissue activation within the vicinity of the recording electrodes is serpentine. The index electrode and indifferent electrode electrogram signals 403-404 exhibit large deflections at times 410-413 as the tissue activation wavefront moves through the conducting channels 406-409. However, the OCU electrogram signal x05 exhibits very small deflections at times 410 and 412-413 as the tissue activation wavefront moves through the conducting channels 406 and 408-409 not directly beneath the catheter, and a much larger deflection at time 411 as the tissue activation wavefront moves through the local conducting channel 407 directly beneath the catheter. Also, while each cell in the tissue surface 401 was activated only once, the index electrode and indifferent electrode electrograms 403-404 feature four deflections, indicating that a measurement of the frequency content of either electrogram would be higher than the true tissue activation frequency content of tissue surface 401. Meanwhile, the frequency content of the OCU electrogram 405 is a more likely indicator of the true tissue activation frequency.

Multi-Electrode Arrays

Atrial fibrillation is widely treated by catheter ablation, and is curative in about 75% of patients. The remaining patients in whom atrial fibrillation persists would benefit from improved activation mapping methods to resolve the complex dynamic patterns of tissue activation that typify recalcitrant atrial fibrillation. Tissue activation patterns and their corresponding electric potential maps were simulated using a computational model of cardiac electrophysiology, and sampled the maps over a grid of locations to generate a mapping data set. Following cubic spline interpolation and an edge-extension and windowing method the data was deconvolved and compared the results to the model current density fields. Deconvolution can lead to improved resolution for arrays of 10×10 electrodes or more that are placed within a few mm of the atrial surface when the activation patterns include 3-4 features that span the recording area.

Atrial fibrillation is commonly treated with the use of catheter ablation whereby lines of non-conducting tissue are created across the atria in an attempt to limit the patterns of electrical excitation to include only organized activity and not fibrillation. This procedure has been found to have relatively high overall success rates, even though multiple procedures are often required. In about 25% of cases, however, current approaches to catheter ablation fail to eliminate this arrhythmia. These recalcitrant cases of atrial fibrillation generally involve advanced disease of the atrial myocardium with extensive tissue remodeling. Knowing how to treat these difficult cases with the administration of additional or alternative ablation lesions would be enormously facilitated by accurate mapping of the electrical activity over the atrial surface. Currently, clinical mapping entails the use of a single roving electrode that is used to build up an isochronal map of tissue activation times relative to a fixed reference point. Unfortunately, this proves inadequate in atrial fibrillation because the activation sequence involved is perpetually changing in random ways; sequential mapping yields ambiguous results in these situations. Thus, the only way to elucidate the atrial activation pattern in atrial fibrillation is to measure electrical activity simultaneously at multiple locations.

An intra-cardiac electrode measures an electric potential that is generated by the combined electrical activities of each cell in the heart, the contribution from each cell being weighted in proportion to the cell's current density and in inverse proportion to the linear distance of the cell to the electrode. The recorded potential field is thus a blurred version of the tissue current density field, the latter being the desired reflection of tissue activation. This blurring process can be approximated as a convolution of the current density field with a point spread function that depends on the height of the electrode above the tissue.

Figure 69A:
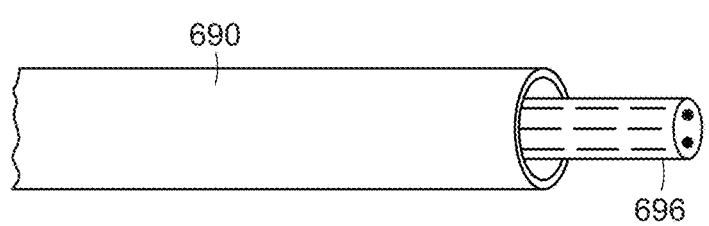
Figure 69B:
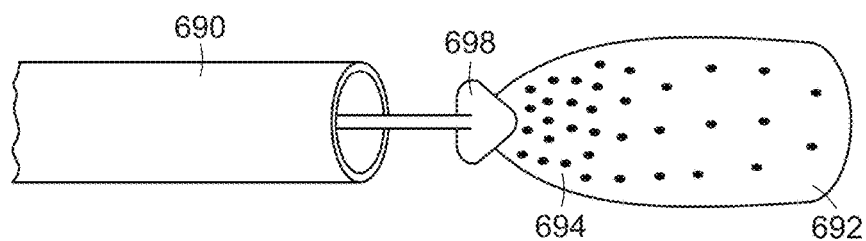

A catheter design, such as illustrated in FIGS. 68, 69A-69B, and 70, that facilitates the arrangement of electrodes such that they are aligned normal to the tissue surface is described. In one possible embodiment a soft flexible planar material is used. This is constructed such that while fully deployed (advanced out of a long sheath the end of which is placed in the mapped chamber of the heart) the material is unfurled into a relatively flat surface 692, as shown in FIG. 69B. The material is flexible enough that it can deform to the shape of the local tissue surface. Small, paired electrodes (see above) are placed directly opposite each other on both sides of the surface. In this configuration when the catheter surface is in contact with the tissue these electrode pairs are orthogonal to the tissue. The end of the flat portion of the catheter is smoothly tapered so that it can be pulled back into the long sheath and as it enters the sheath it furls to conform to the cylindrical shape 696 of the inside of the sheath.

The junction of the flat portion of the catheter (tip) with the catheter shaft is flexible enough that as the shaft is deflected forcing it to approach a position in which the shaft is normal to the tissue surface, the flat portion bends relative to the shaft and is pushed into an orientation co-planar with the tissue surface.

In another embodiment, the catheter tip (flat portion) catheter shaft junction acts like a hinge such that any pressure of the shaft towards the surface naturally places the tip into a co-planar orientation relative to the tissue surface.

Figure 70:
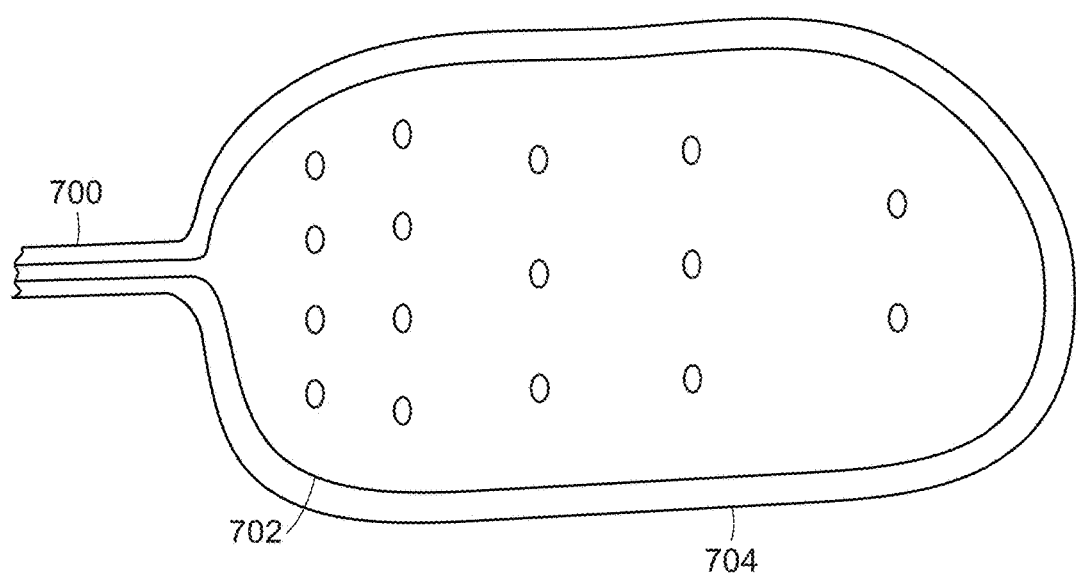

When mapping the heart's electrical activity one sometimes desires multisite-simultaneous information broadly distributed and at other times one desires more detailed information from a smaller region. It is common that these needs are sequential; first one makes a general assessment of activation over a large area with low density of data points 680, based upon this data one identifies a sub-region (of the larger recording area) in which a higher density of data 682, 694 is required. In one embodiment, a catheter design in which the flat two-dimensional surface of the catheter tip is made from a distensible material. Thus when distended the surface area is larger than when the surface is not distended. Electrode pairs distributed as above (in pairs on opposite sides of the tip surface) will be distributed over a smaller or larger area depending upon the amount of distension of the tip allowing for higher or lower density of recording sites. In either case the distance between the electrodes on the bottom and top surface of the tip (the OCU pairs) remains fixed; as such this design allows for each recording site to have high (and unchanging) spatial resolution even as recording site density is varied. Distention of the surface could be achieved with a loop of wire 702 (possibly constructed of nitinol) that when advanced out of the catheter shaft increases the circumference of the tip surface. In another possible embodiment, as shown in FIG. 70, the tip can be constructed of an inflatable balloon, but with the balloon constructed such that it doesn't inflate in a spherical shape rather it inflates in a flat plate-like shape 704.

Variable recording site density can be achieved through the use of a catheter design in which electrodes on the two-dimensional array (described above) are not evenly distributed but rather are concentrated with high density in one part of the catheter tip and lower density at other locations on the catheter tip. In this way using a single catheter and without need for changing the catheter size or shape one can focus density in one region while simultaneously having a broad view of other areas. Much like the increased density of rods and cones in the Fovea of the retina.

Deconvolution

Numerical deconvolution of the measured potential field would thus seem to be a promising approach to extracting additional spatial information about patterns of tissue activation from multi-electrode recordings. However, even if such electrode arrays reach a high degree of sophistication, the potential success of deconvolution for improving map resolution is subject to a number of practical constraints. First, only a finite number of electrodes can be placed simultaneously inside the heart, so the potential maps that they provide will inevitably be coarsely sampled versions of the desired continuous potential field. If the sparseness is not too great, and a suitable interpolation scheme is used to approximate the missing data, then deconvolution may still lead to improved maps as has been shown previously. There is a second constraint, however, that is potentially more problematic. It is very likely that high-density electrode arrays will be able to cover only a modest region of the atrial surface, thereby sampling a truncated version of the complete atrial activation pattern at any instant. Deconvolution of a truncated map leads to the phenomenon known as leakage, which can be ameliorated to a certain degree by either windowing or by artificially extending the edges of the sampled map.

Understanding how sparseness and incompleteness affect the ability of deconvolution to reconstruct a tissue current density field from of sampled potential field is important for optimizing the design of future electrode arrays. Accordingly, this was the goal of the present study.

Atrial tissue is considered to be two-dimensional, as would be the case if one were mapping over a limited region and tissue thickness can be neglected. The electric potential, $\Phi$, recorded by a point electrode located above the tissue consists of a contribution from the membrane current density in each cell in the tissue weighted inversely by its linear distance to the electrode. Consequently, the transformation between the tissue membrane current density field and the potential field at height h can be described by the following integral equation:

$$\Phi(x, y, h) = \frac{\rho_e}{4\pi} \int_{-\infty}^{\infty} \int_{-\infty}^{\infty} \frac{I_m(w, z)}{\sqrt{(x-w)^2 + (y-z)^2 + h^2}} dw dz \quad (13)$$

where $I_m(x, y)$ is the membrane current density field, $\rho e$ is the specific resistivity of the medium between the tissue and the electrode (assumed to be blood), and w and z are dummy variables of integration representing the tissue spatial coordinates x and y. In other words, $\Phi(x, y, h)$ is the convolution of $I_m(x, y)$ with the point spread function $$f(x,y,h)=[x^2+y^2+h^2]^{-1/2} \qquad (14)$$

The problem addressed here is how to estimate Im(x, y) from an incomplete and coarsely sampled version of Φ(x, y, h).

Figure 41C:
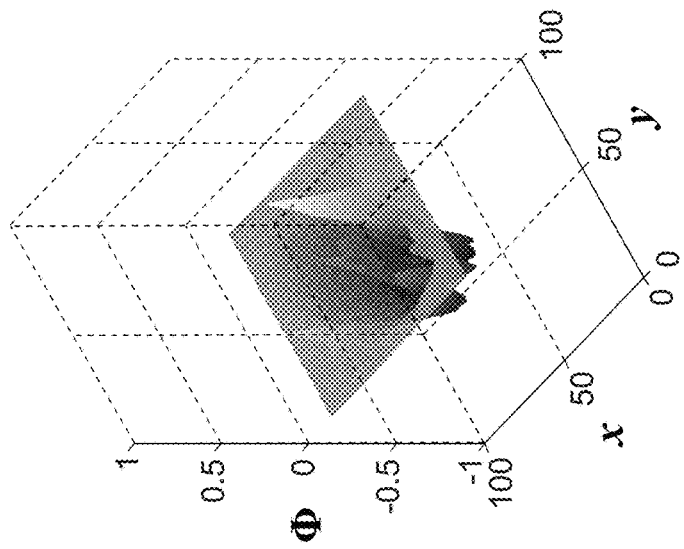
FIGS. 41A-41C illustrates the edge extension and windowing process applied to an exemplary transformation between the tissue membrane current density field and the potential field at height, in accordance with embodiments of the present invention.
Figure 41B:
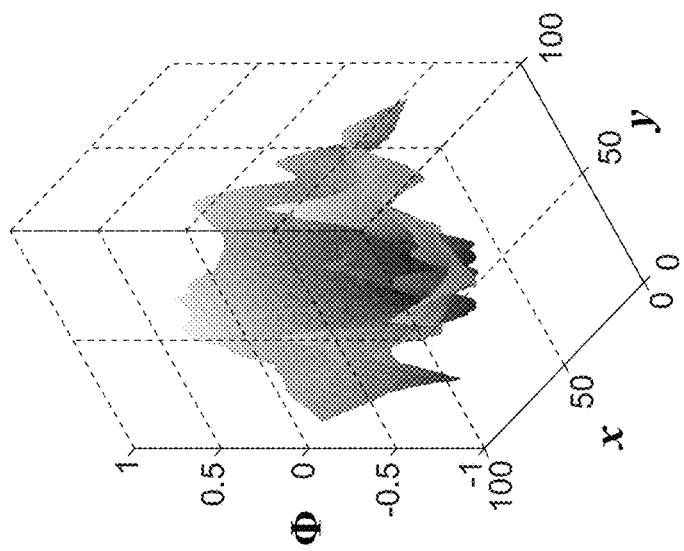
Figure 41A:
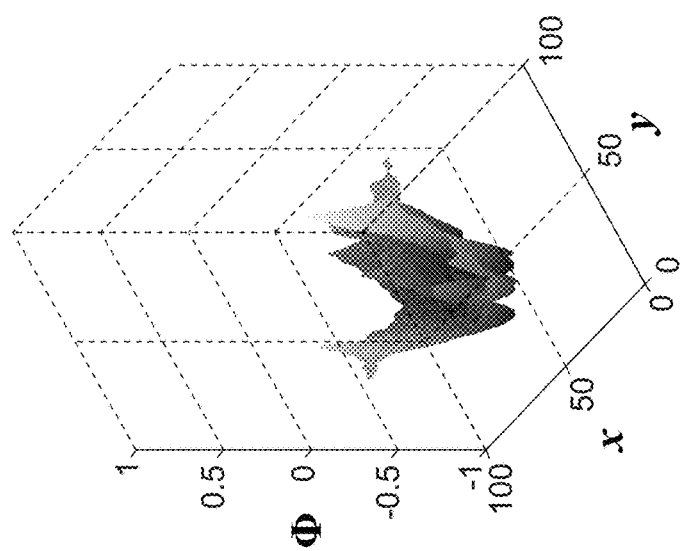

Two-dimensional maps of Im(x, y) and Φ(x, y, h) were generated, representative of those likely to be encountered during atrial fibrillation using a computational model of cardiac excitation. This model is a hybrid between a physics-based and a rule-based model is shown in FIG. 41A. Example of a truncated version of Φ(x, y, h) produced by the computational model of atrial excitation following sampling over a n×n grid and cubic spline interpolation between the samples. As shown in FIG. 41B, an extended version of the map in FIG. 41A with spatial derivative matching at the boundaries of the original grid. FIG. 41C is the result of multiplying the map in FIG. 41B by the window described herein. The map in FIG. 41C is denoted Φ (x, y, h) to be able to recapitulate the key dynamic features of the aberrant excitation encountered in atrial fibrillation, including meandering rotors and multi-wavelet reentry. The model consists of a sheet of square cells, each of which represents a small patch of cardiac myocytes. These model cells exhibit time-varying voltages according to the particular equations and rules that govern their behavior. The time-derivative of the voltage of a cell located at position (x, y) is taken to be Im(x, y), which then allows Φ(x, y, h) to be calculated according to Eq. 1. The dimensions of x, y and h are expressed in units of the edge length of a cell, which is nominally 1 mm.

The intra-atrial potentials are measured by a square array of electrodes. This is simulated by sampling Φ(x, y, h) at n×n equally spaced grid points, and then use two-dimensional cubic spline interpolation between the sampled points to create an estimate of the complete potential field over the region encompassed by the electrode array. Varying the value of n thus allows us to experiment with different spatial densities of electrodes. The electrodes themselves are assumed to have negligible extent. To simulate the effect of finite coverage of an electrode array over the atrial tissue, the n×n samples of Φ(x, y, h) are selected from a square subset of the simulated tissue. Then the edges of the data array are extended by adding synthetic samples around the boundaries of the electrode positions in such a way as to bring the spatially extended grid of sampled values smoothly down to zero. Simply adding extra data samples outside the original set does not guarantee, however, that the transition between the original data and the extra samples will be smooth, something that is desirable when performing deconvolution in the Fourier domain in order to avoid the introduction of spurious high frequencies in the deconvolved map. Therefore smoothness is ensured as follows. First the continuous function obtained by cubic spline interpolation of the original n×n data points are continued analytically past the boundaries of the grid to a distance of one quarter the nominal width of the point spread function. This width is defined as the horizontal distance from the peak of the point spread function to its value at 10% of peak. This extended Φ(x, y, h) is then multiplied by a window comprised of a central square section of unity height with a border consisting of a cosine bell so that it proceeds smoothly down to zero at its edges. The dimensions of the central section are the same as those of the original array of data samples less one quarter of the nominal width of the point spread function. FIGS. 41A-41C illustrate the edge extension and windowing process applied to an example Φ(x, y, h=2 mm) with n=20, yielding an approximation to the true potential field that we denote Φ(x, y, h).

Deconvolution is performed in the spatial frequency domain by dividing the fast Fourier transform of Φ(x, y, h) by the fast Fourier transform of f(x, y, h). To prevent amplification of noise arising from numerical errors (and in real applications, also from measurement error), theory of the Wiener filter is invoked by replacing simple division in the Fourier domain by $$\hat{I}(x, y) = \mathfrak{I}^{-1}\left\{\frac{\hat{\Phi}(u, v, h)}{f(u, v, h) + c}\right\} \qquad (15)$$

where Î(x, y) is an estimate of I (x, y), $\mathfrak{I}^{-1}$ denotes the inverse Fourier transform of the bracketed quantity, and Φ (u,v,h) and f(u, v, h) are the Fourier transforms of Φ (x, y,h) and f(x, y, h), respectively. The constant c in Eq. 2 has the effect of adding a small delta function to the point spread function. This serves to prevent division by something close to zero at those frequencies where the power in f(u, v, h) is zero, or very close to zero, and the power in Φ(x, y,h) is finite. In the present study, c=1 is set to suppress the effects of noise without having a noticeable effect on the structures of interest in the deconvolved maps.

Figure 42C:
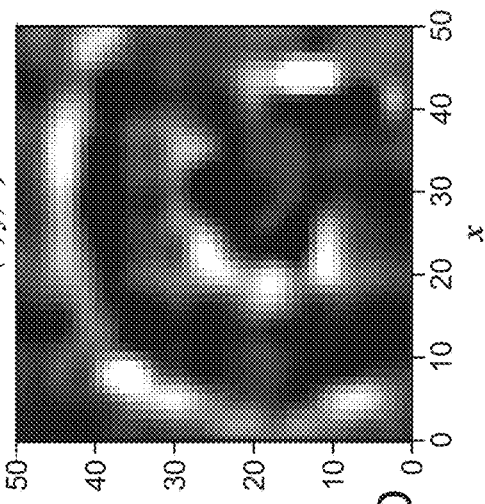
FIGS. 42A-42D illustrate examples of deconvolution, in accordance with embodiments of the present invention.
Figure 42B:
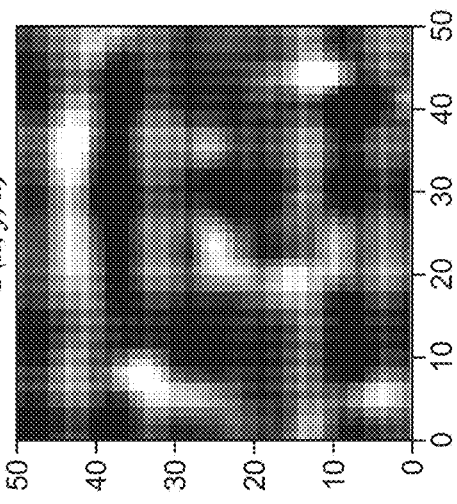
Figure 42D:
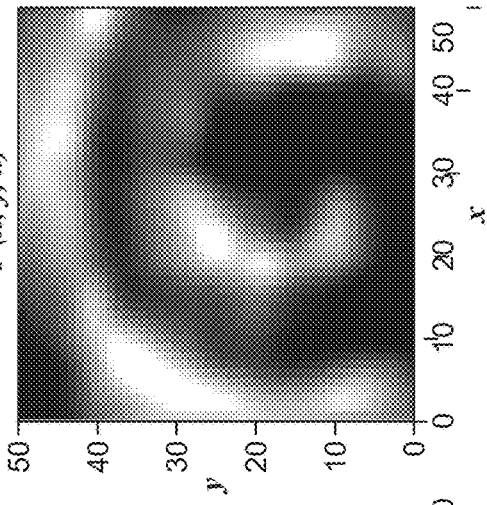
Figure 42A:
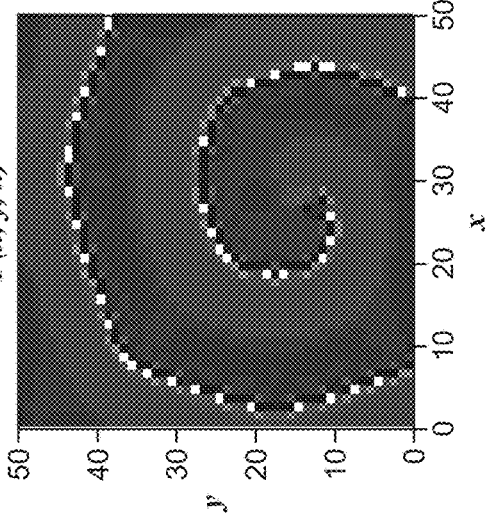
Figures 43A, 43B, 43C, 43D, 43E, 43F, 43G, 43H, 43I, 43J, 43K, 43L:
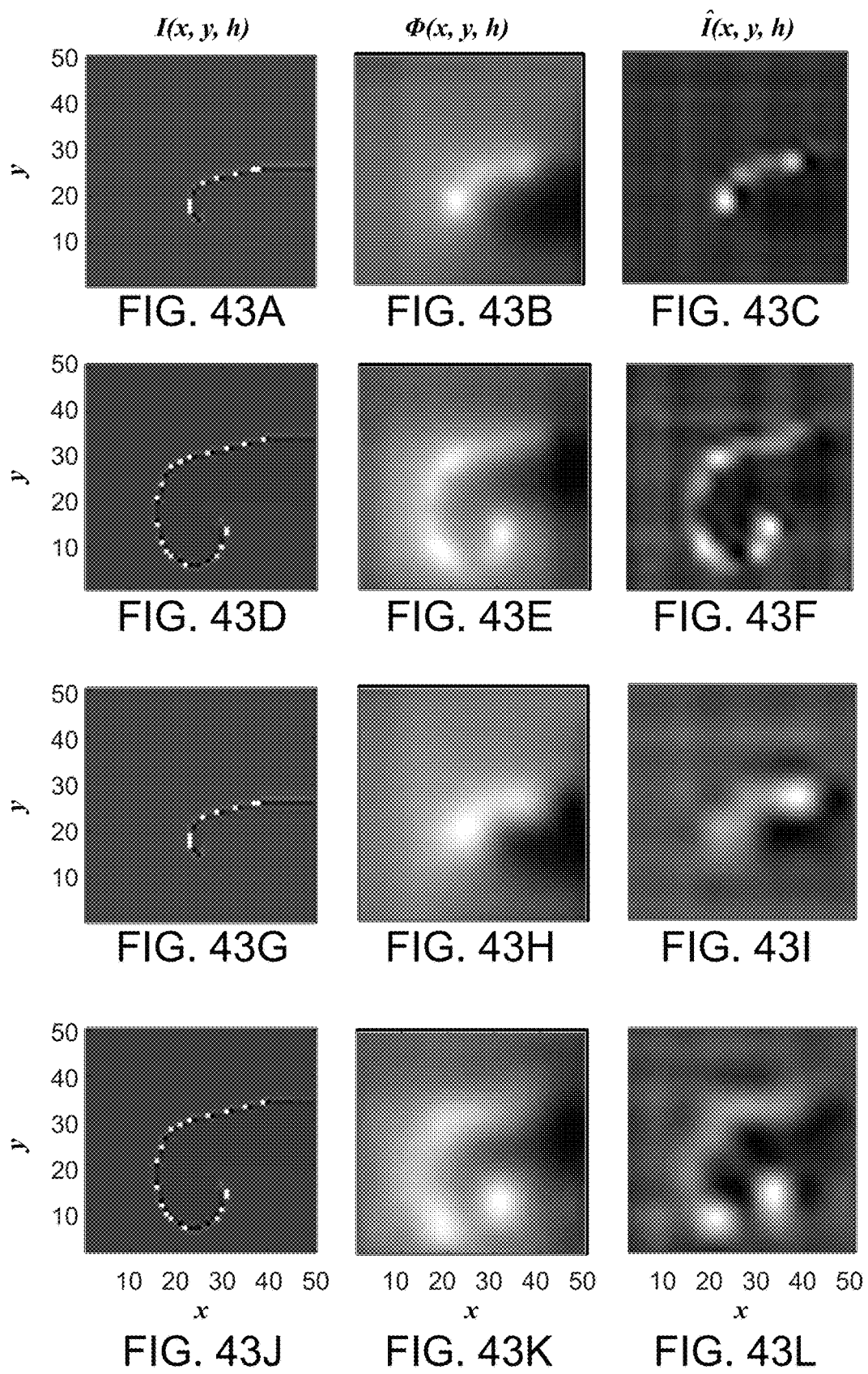
FIGS. 43A-43L illustrate maps of membrane current density, in accordance with embodiments of the present invention.

A current density field I(x, y, h) (left-hand panel) is measured at a height of 2 mm as a blurred potential field Φ(x, y, h), as shown in FIGS. 42A and 42B. Deconvolution without any form of edge extension or windowing yields a poor reconstruction of I(x, y, h) as shown in FIGS. 42C and 42D. Deconvolution after edge extension and windowing as described in the text yields a much better reconstruction. FIGS. 42A and 42D illustrates the importance of edge extension and windowing when deconvolving a truncated potential map. Without such edge processing, the deconvolved map contains high-frequency line artifacts that obscure the details of the activation pattern (FIGS. 42A and 42B). When edge processing is applied, these artifacts are effectively eliminated (FIGS. 42C and 42D).

The goal in this study was to determine the conditions (i.e. the values of n and h) under which deconvolution provides a more useful picture of tissue activation than the raw samples of Φ(x, y, h) themselves. As an objective measure of map accuracy, the mean squared residual (MSR) was calculated between the actual current density distribution, Im(x, y), and the observed potential samples as $$MSR_{obs} = \frac{\sum_{i=1}^{n^2}(I_i - \Phi_i)^2}{n^2} \qquad (16)$$

where the index i is summed over all n2 electrode locations. Similarly, the MSR between Im(x, y) and the deconvolved map at the electrode locations is $$MSR_{dec} = \frac{\sum_{i=1}^{n}\left(I_i - \hat{I}_i\right)^2}{n^2} \qquad (17)$$

The relative benefits of performing deconvolution by this measure are then indicated by the extent to which MSRobs is greater than MSRdec.

Nevertheless, much of the useful information in an activation map pertains to the details of the structural features present in the map, particular as it evolves dynamically in front of the observer, and these are difficult to quantify. In fact, when any medical imaging modality is employed to make clinical decisions, such decisions are usually made on the basis of subtle pattern recognition processes that take place in the mind of a trained observer. Accordingly, the value of deconvolution was assessed through subjective evaluation of image sequences.

FIGS. 43A-43L demonstrates the ability of deconvolution to resolve a simple rotor, showing the true current density, the observed potential field, and the deconvolved estimate of the current density at two time steps using arrays of FIGS. 43A-43F 20×20 electrodes and FIGS. 43G-43L 10×10 electrodes. Deconvolution visibly improves the estimate of the current density in both cases. These conclusions are borne out by the quantitative measures of accuracy shown in FIGS. 44A and 44B, where I^(x, y) can be seen to be improved over Φ(x, y,h) for electrode arrays greater than 3×3. Interestingly, the relative improvement in map accuracy is greater with the larger number of electrodes (FIGS. 43A-43F), showing that deconvolution becomes progressively more worthwhile as electrode density over the tissue increases. FIGS. 45A-45L illustrates a similar demonstration for a more complex activation pattern arising when a rotor begins to degenerate into multi-wavelet reentry. Here, arrays of 30×30 and 15×15 electrodes are compared. In this case, the complex details in I(x, y) are almost impossible to make out in (x, y,h), but are for the most part readily apparent in I^(x, y), Again, the quantitative measures based on MSR (FIGS. 46A and 46B) bear out the visual impressions arising from FIG. 5. That is, for most values of n, MSRdec is less than MSRobs. FIGS. 43A-43L. Maps of membrane current density (left), electrical potential (middle), and the deconvolved image (right) at two different time points in the evolution of a rotor obtained using FIGS. 43A-43F a 20×20 array of electrodes at a height of 2 above the tissue. And FIGS. 43G-43L a 10×10 array of electrodes at the same height.

Figure 44B:
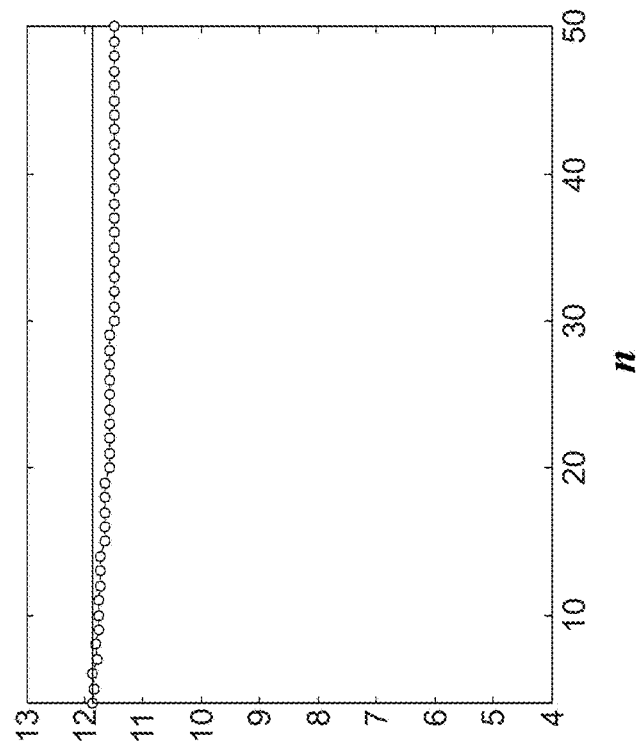
FIGS. 44A-44B illustrate graphically mean square residual for the observed and deconvolved signals relative to the true signal for the two activation pattern shown in FIGS. 43A-43L, in accordance with embodiments of the present invention.
Figure 44A:
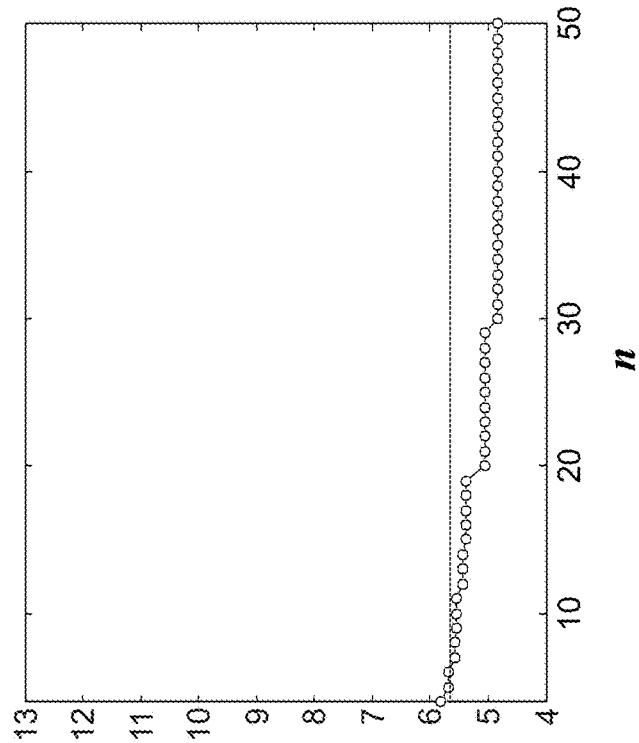
Figure 45A:
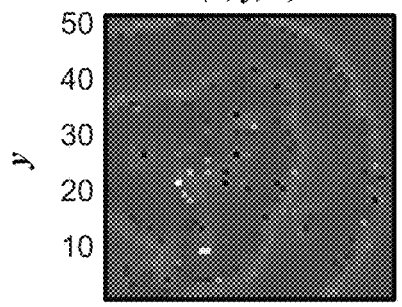
FIGS. 45A-45L illustrate true current density, observed signal, and deconvolved signal using different array electrodes, in accordance with embodiments of the present invention.
Figure 45B:
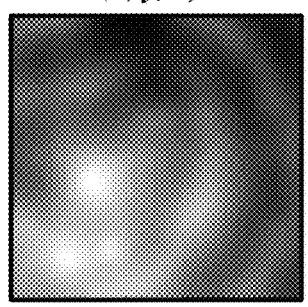
Figure 45C:
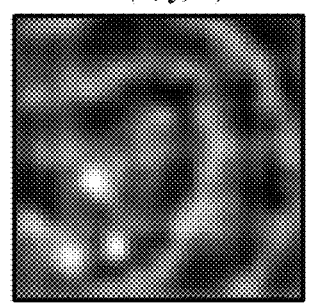
Figure 45D:
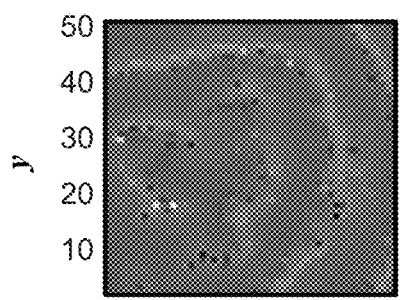
Figure 45E:
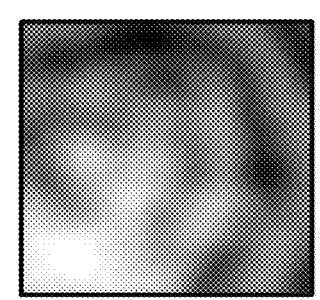
Figure 45F:
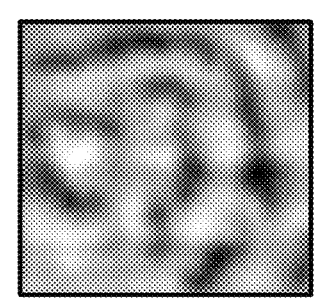
Figure 45G:
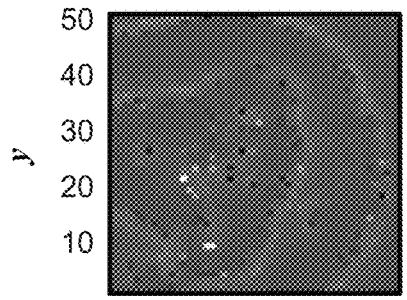
Figure 45H:
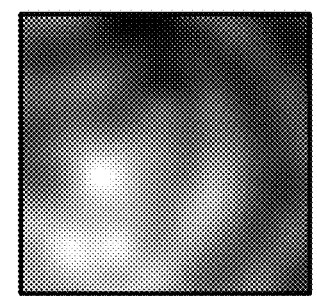
Figure 45I:
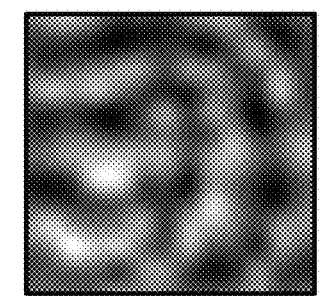
Figure 45J:
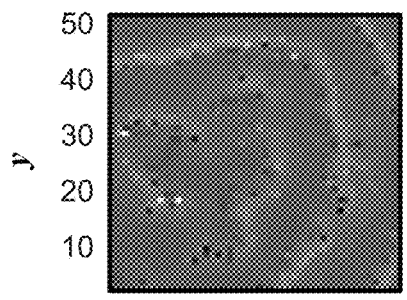
Figure 45K:
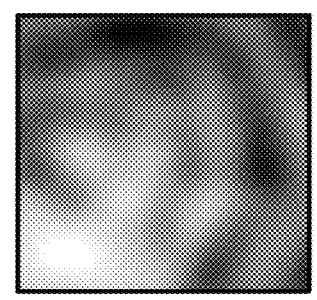
Figure 45L:
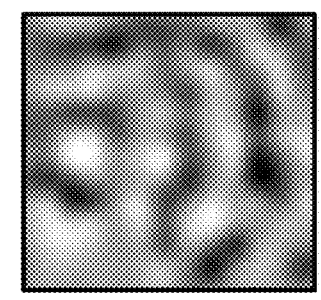
Figure 48B:
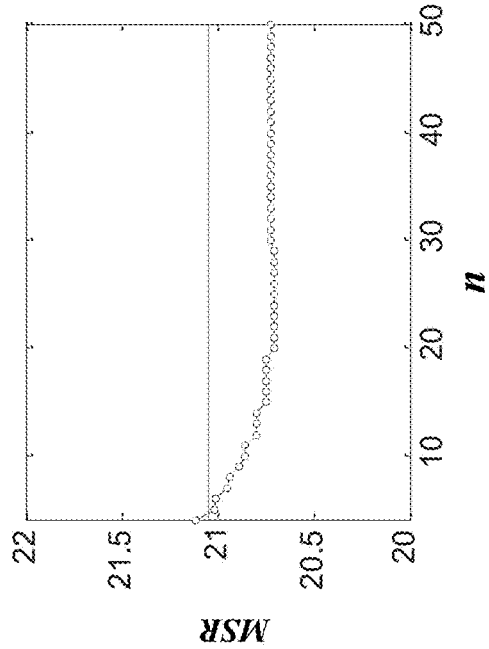
FIGS. 48A-48D graphically illustrate mean square residual for the observed and deconvolved signals relative to the true signal for the activation pattern shown in FIGS. 47A-47I.
Figure 48D:
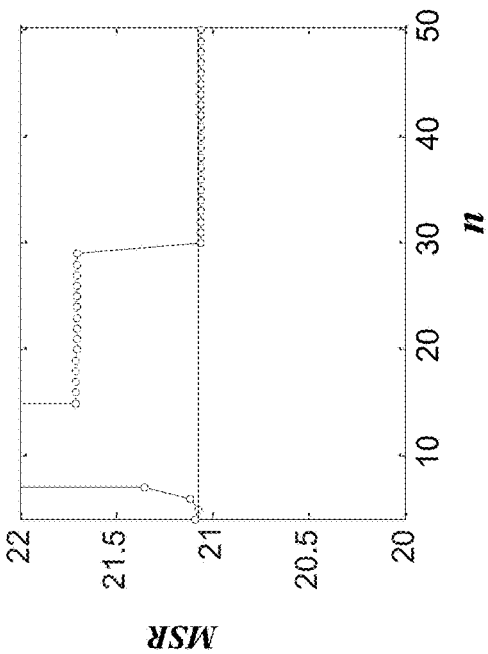
Figure 48A:
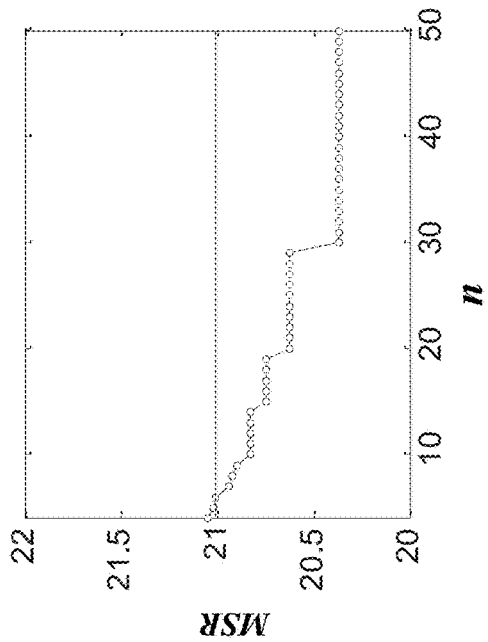
Figure 48C:
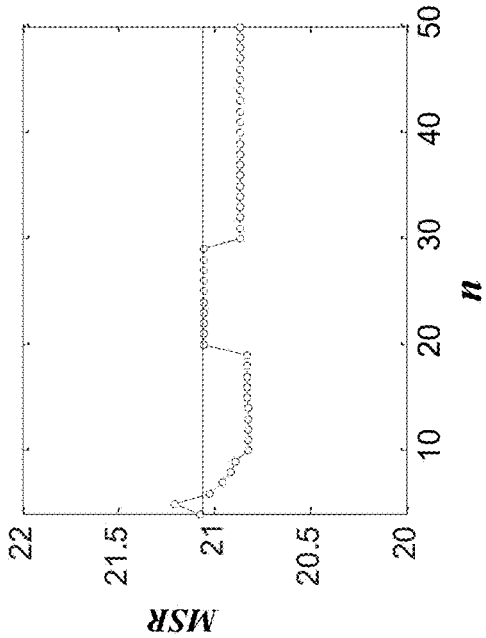

FIGS. 47A-47I illustrate the effect of increasing h upon both the observed and deconvolved signals. Importantly, as h increases from 1 to 5 the blurring in (x, y,h) relative to I(x, y) becomes rapidly worse, and even the ability of our edgeprocessing technique to ameliorate the streak artifacts in I^(x, y) becomes severely degraded (FIG. 47C). This demonstrates how important it is to place the mapping electrodes as close to the cardiac tissue as possible. Even so, the deconvolved signal improves upon the raw data at heights up to 5. However, this is not always the case. FIGS. 48A-48B illustrates that MSRobs becomes greater than MSRdec at a height of 10. Color videos of the progression of activation over time corresponding to FIGS. 43A-43L, 45A-45L and 47A-47I are available on the web site repository. FIGS. 44A and 44B. MSR for the observed and deconvolved signals relative to the true signal for the two activation patterns shown in FIGS. 43A-43L. Solid line—MSRobs, circles—MSRdec. The unit of MSR is the square of the model cell dimension. FIGS. 45A-47L. True current density, observed signal, and deconvolved signal using arrays of (a) 30×30 electrodes, and (b) 15×15 array electrodes, with h=2. The activation patterns represented here consist of two time points during the degeneration of a rotor into multi-wavelet reentry.

Figures 46A, 46B:
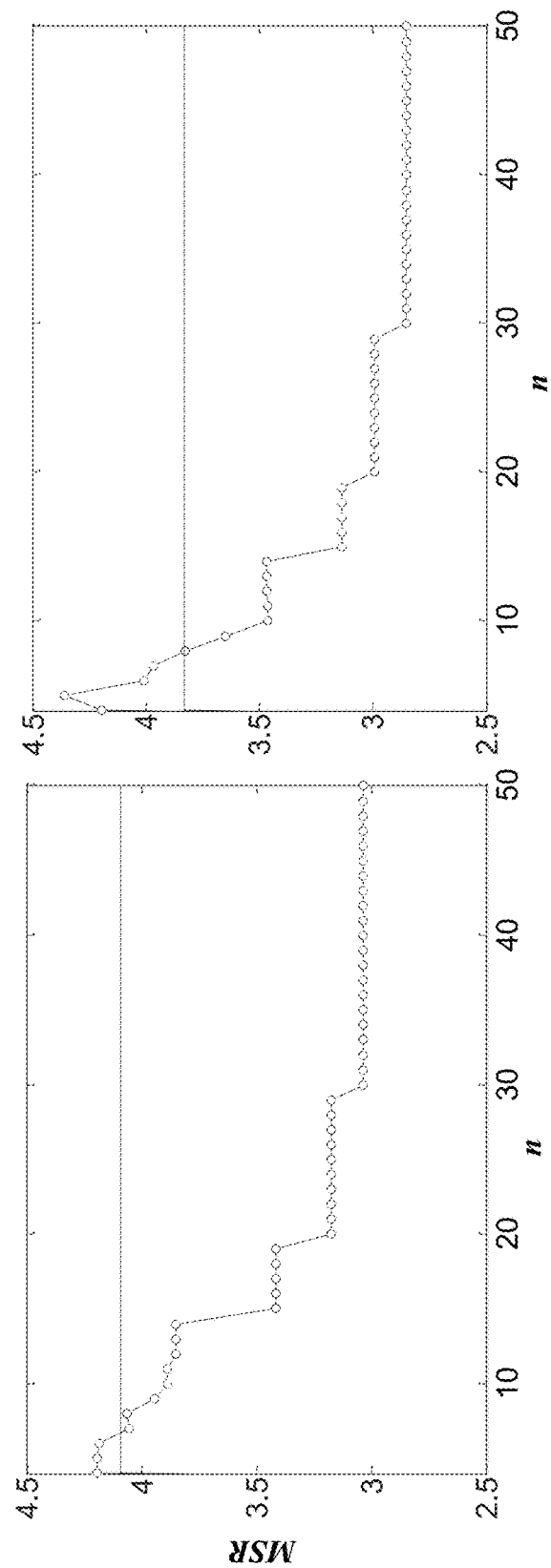
FIGS. 46A-46B graphically illustrate the mean square residual for the observes and deconvolved signals relative to the true signal for the two activation patterns shown in FIGS. 45A-45L, in accordance with embodiments of the present invention.

Although catheter ablation therapy for the treatment of atrial fibrillation has an impressive success rate, effectively curing the condition in about 75% of patients, it continues to present a major clinical challenge in the remaining 25% in whom atrial fibrillation persists [12]. These recalcitrant patients tend to have more advanced disease characterized by complex patterns of atrial activity featuring intricate dynamic structures such as meandering rotors and multi-wavelet reentry [13-15]. These patterns are often reflected in complex fractionated electrical activity seen on intra-cardiac electrograms, likely reflecting the simultaneous activity of a number of tissue regions that are close enough to the sensing electrode to contribute simultaneously to the recording [16]. Because of this complexity, and the fact that these activation patterns typically change continually, elucidating the precise nature of tissue activation by sequential mapping with a single roving electrode is not possible. Thus, electrode arrays in accordance with embodiments of the present invention that have the spatial coverage and sampling density to resolve complex dynamic patterns of tissue activation were developed. Prior art electrode arrays do not have sufficient spatial resolution to fully resolve the most complex activation patterns seen in cardiac fibrillation. Finer arrays of electrodes capable of measuring intra-cardiac potential at multiple closely-spaced sites over a localized region of tissue will need to be developed to facilitate atrial fibrillation mapping. Methods of digital signal processing can be used to enhance the spatial resolution of such arrays beyond the physical limitations imposed by electrode size and number. FIGS. 46A and 46B illustrate the MSR for the observed and deconvolved signals relative to the true signal for the two activation patterns shown in FIGS. 45A-45L. The basic resolution enhancement issue in atrial fibrillation mapping can be expressed as a problem in deconvolution. Although straightforward in principle, in practice deconvolution is fraught with a number of pitfalls related to noise and data truncation. Fortunately, there are established methods for dealing with these problems in general, although each deconvolution problem stands on its own merits in terms of the details of these methods. In the case of deconvolving maps of atrial fibrillation activity, the two major problems are sparseness of data sampling and incompleteness of spatial coverage. The first of these is readily dealt with through interpolation between the measured data samples, the success of which is dependent upon the sampling density relative to the spatial frequencies in the activation pattern being sampled. A previous study, for example, has applied this approach to the problem of distinguishing local from distant sources in electrogram recordings [8]. A potentially more insidious problem for deconvolution, however, arises when the sampled map represents only a portion of the entire activation pattern, leading to the problem of leakage contaminating the deconvolved image. There are two approaches to dealing with this problem, the most common being to multiply the sampled data by a window that has a value of unity at its center while decaying smoothly to zero at the borders of the data array [5]. The problem with this approach, however, is that it eliminates a significant amount of the data around the borders, which should be minimized given the sparseness of the original data set. The alternative approach is to extend the borders of the data array with synthetic data that proceed smoothly to zero beyond the bounds of the original data set. The disadvantage here is that the missing data must be guessed at. Therefore, a combined approach was intended to hedge against the disadvantages of either method on its own. That is, the data was extended beyond the boundaries of the original array of samples by one quarter of the width of the point spread function, and windowed the existing data in from the boundary by the same distance. Furthermore, the extended data set was differentiable at the border between the original and extended data points by matching the spatial derivatives at their intersection (FIGS. 41A-41C). This led to a major improvement in our ability to recover the original tissue activation pattern by deconvolution (FIGS. 42A-42D).

FIGS. 47A-47I illustrate the effects of electrode height on the resolution of a rotor, showing the true current density, the observed signal, and the deconvolved signal at heights of FIG. 47A 1, FIG. 47B 3, and FIG. 47C 5. The deconvolution approach was applied to simulated rotors (FIGS. 43A-43L and 47A-47I) and multi-wavelet reentry (FIGS. 45A-45L), as these typify the kinds of complex activity patterns seen in atrial fibrillation. The results indicate that deconvolution can provide a useful improvement in map resolution compared with raw electrode array recordings. The accuracy of deconvolution is substantially improved by an edge processing technique that combines windowing and edge extension. Accuracy is also determined by the number of electrodes, electrode height, and tissue spatial frequency. The present study considered the mapping electrodes to be of infinitesimal extent, whereas actual electrodes have finite width and length. The finite dimensions of an electrode cause it to measure a potential that is the average of the potentials at each point on its surface, further contributing to the blur in a recorded map. In principle, deconvolution could attend to this form of blurring as well, so the relative improvements seen with deconvolution in the present study may not be as great as would be achievable with real electrodes. FIGS. 48A-48D. MSR for the observed and deconvolved signals relative to the true signal for the activation pattern shown in FIGS. 47A-47I at heights of FIG. 47I 1, FIG. 47B 3, and FIG. 47C 5. Also shown are the MSR values for a height of 10 FIG. 47D. Solid line—MSRobs, circles—MSRdec. The electrode array characteristics required for deconvolution to improve upon unprocessed potential recordings in human atrial fibrillation depend upon the tissue spatial frequency of the atrial activity in such patients. Based upon high density mapping in humans with long standing persistent atrial fibrillation, it is likely that there can be greater than or equal to 1.5 waves across each cm of atrium [15]. In this range of spatial frequency deconvolution would improve spatial resolution for 10×10 arrays in which inter-electrode spacing is ~0.3 mm. Ultimately, of course, this will need to be tested in humans with atrial fibrillation. In the meantime, the current modeling experiments allow us to accurately compare tissue current density distributions and electrogram recordings, something that is not possible in human experiments. These numerical experiments inform us as to the kinds of electrode array characteristics that should be used when performing biologic confirmation.

The treatment of atrial fibrillation by catheter ablation is likely to be accompanied in the future by attempts to map atrial excitation with electrode arrays placed over tissue regions suspected of harboring candidate ablation sites. The relationship between the recorded patterns of electric potential and the underlying tissue membrane current fields can be expressed as a convolution involving a point spread function that depends on the height of the electrode above the tissue[3]. Numerical deconvolution thus has the potential to improve the spatial resolution of recorded activation maps. A combination of interpolation between the electrode recording sites and edge processing around the borders of the electrode array ameliorates problems due to sparseness of sampling and data truncation. Our results indicate that, when these issues are addressed, deconvolution is likely to lead to improved resolution in recorded potential maps when using electrode arrays of roughly 10×10 or greater placed within a few mm of the atrial surface when attempting to resolve activation patterns with 2-3 features spanning the recorded area.

In accordance with some embodiments of the present invention, the electrogram frequency pattern may be measured simultaneously across a tissue substrate to indicate the tissue activation frequency pattern, which indicates the circuit core density and distribution. For example, in certain embodiments, a multi-electrode array may be deployed via thoracotomy at the time of surgery, percutaneously, and/or transvenously and positioned over a region of cardiac tissue.

Figure 49:
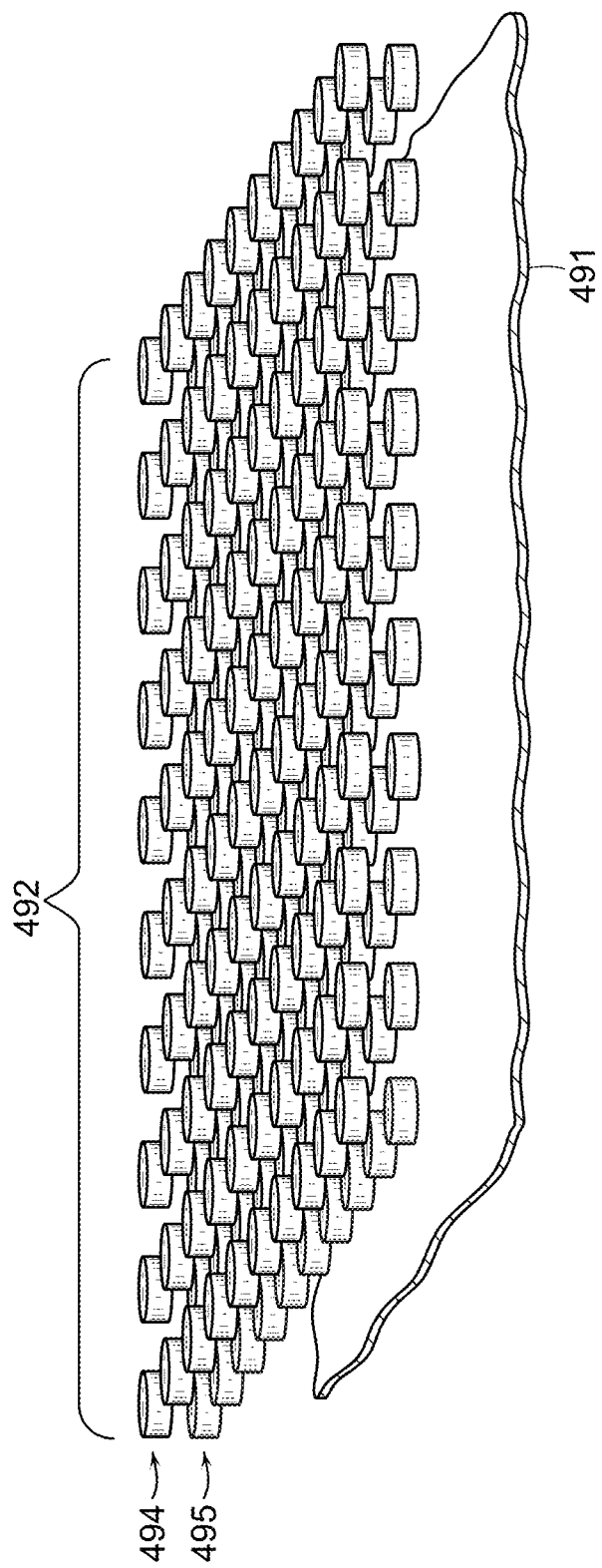
FIGS. 49 and 50 illustrate two-dimensional multi-electrode arrays, in accordance with embodiments of the present invention.

FIG. 49 illustrates a tissue substrate surface 491, over which a two-dimensional multi-electrode array 492 has been deployed in OCU configuration in accordance with some embodiments of the present invention. In this example, 100 index electrodes 493 are paired with 100 indifferent electrodes 494. Each pair of electrodes is itself in OCU configuration.

As described above, high spatial resolution at each recording site (e.g., each OCU electrode pair in a multi-electrode array) is important for electrogram signal frequencies to accurately reflect tissue activation frequencies (and hence local circuit core densities). The maximum distance between recording sites relates to the optimal distance between ablation lesions, which, in turn, relates to what extent the circuit core density will be reduced in the area around a lesion as a result of the lesion. Thus, even though high spatial resolution is important, the recording sites themselves need not be spaced extremely close together relative to the inter-electrode spacing in accordance with some embodiments of the present invention. For example, the multi-electrode array in FIG. 49 may have an inter-electrode spacing of only 0.1 mm to 3.0 mm, but the distance between each OCU electrode pair may be 5 mm to 10 mm).

Figure 50:
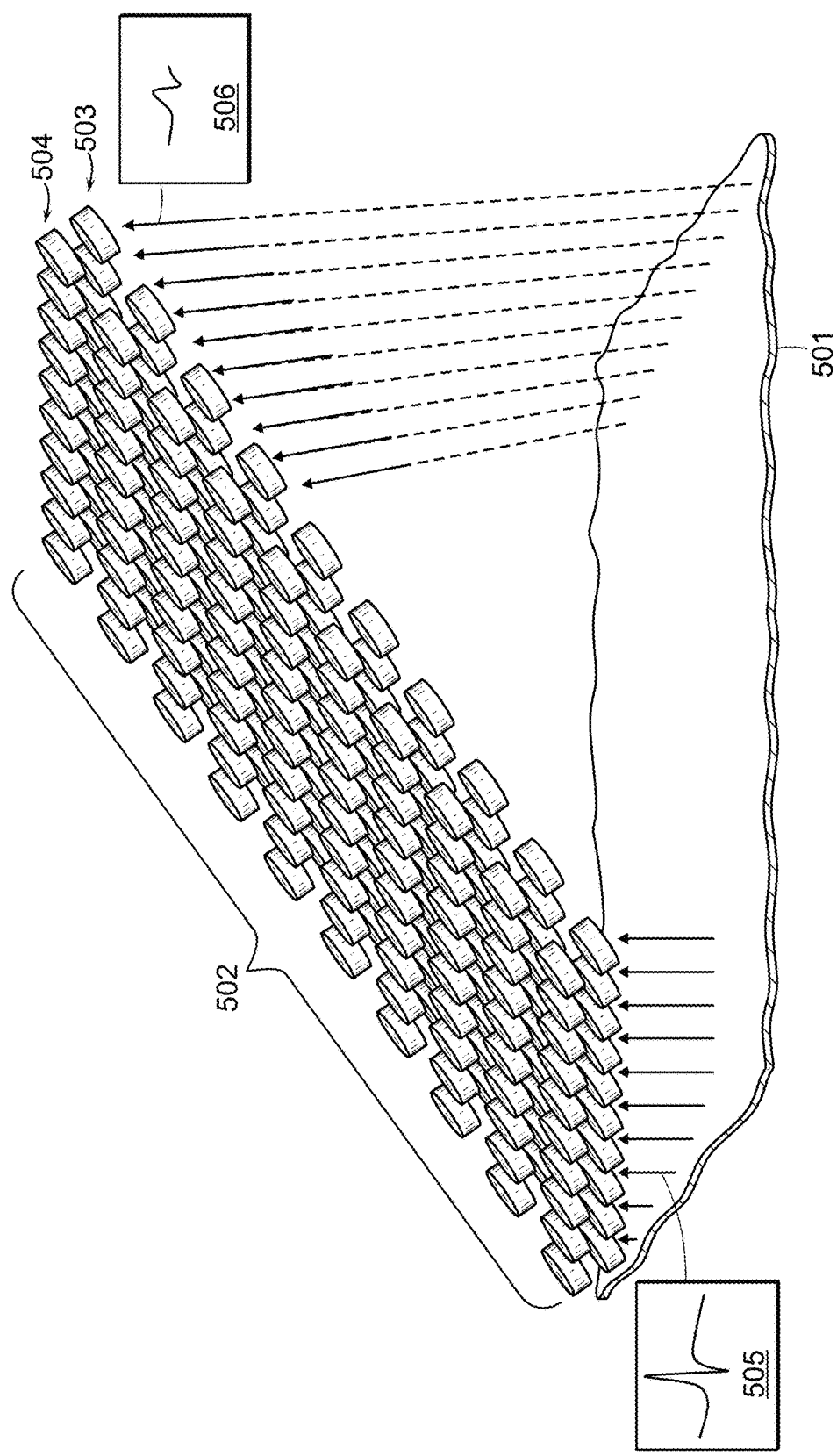

FIG. 50 illustrates a tissue substrate surface 501, over which a two-dimensional multi-electrode array 502 has been deployed in accordance with some embodiments of the present invention. As in FIG. 49, the array includes 100 OCU electrode pairs, each with one index electrode 503 and one indifferent electrode 504. However, unlike FIG. 49, the multi-electrode array 502 itself is not orthogonal to the tissue surface 501 (due to, e.g., incomplete apposition of the catheter with the tissue). Unlike a catheter with a single pair of electrodes in OCU configuration, the orientation of a multi-electrode array may be determined without seeing the tissue. Examination of the electrogram morphology may be sufficient to identify whether a multi-electrode array tilted relative to the tissue surface 501. In FIG. 50, electrogram signal 205 is more sudden with greater amplitude than electrogram 506, which is smaller and more gradual, thus indicating that the recording position for the electrogram signal 505 is closer to the tissue surface 501 than the recording position for the electrogram signal 506. Thus, by comparing the two electrograms 505-506, and without viewing the tissue (using, e.g., an imaging modality with a contrast agent), it can be deduced that the recording electrodes are not equally placed relative to the tissue surface 501.

Each electrode in a multi-electrode array records a net electric field potential, to which each cardiac cell contributes in an amount proportional to the cell's tissue current density and inversely proportional to the linear distance from the cell to the electrode. Thus, the recorded net electric field potential may be a blurred approximation of the tissue current density field, which is used to indicate tissue activation frequency and, in turn, the circuit core density and distribution.

In accordance with some embodiments of the present invention, this blurring may be treated as though the tissue current density field was convolved with a spatially decaying point spread function, which can be estimated. Thus, numerical deconvolution of the measured net electric field potential may be applied to extract information about the spatial nature of tissue activation frequency from multi-electrode recordings and thereby improve spatial resolution.

The success of deconvolution for improving spatial resolution is subject to a number of practical constraints in accordance with some embodiments of the present invention. First, only a finite number of electrodes may be simultaneously positioned inside the heart, so any resulting maps of or based on net electric field potentials inevitably are sampled versions instead of continuous versions. If a sufficient number of electrodes are present, a useful continuous approximation to the true net electric field potentials may be obtained by interpolating between the samples according to some embodiments. A sufficient number of electrodes are present when the spatial frequency of the sampling approaches the Nyquist criterion with respect to the spatial frequency content of the electric field potentials. Thus, in some embodiments, a suitable interpolation scheme (e.g., two-dimensional cubic spline interpolation or another smooth interpolation function) may be used to approximate the missing data in a map of or based on net electric field potentials.

Second, the success of deconvolution for improving spatial resolution is subject to spatial truncation. In some embodiments, even a high-density multi-electrode array may cover only a modest region of the tissue surface. Thus, only a spatially truncated version of the complete pattern of net electric field potentials may be sampled at any instant. Deconvolution following spatial truncation leads to a phenomenon known as "leakage," which can be ameliorated by either windowing or artificially extending the edges of the sampled pattern of net electric field potentials.

Figure 51A:
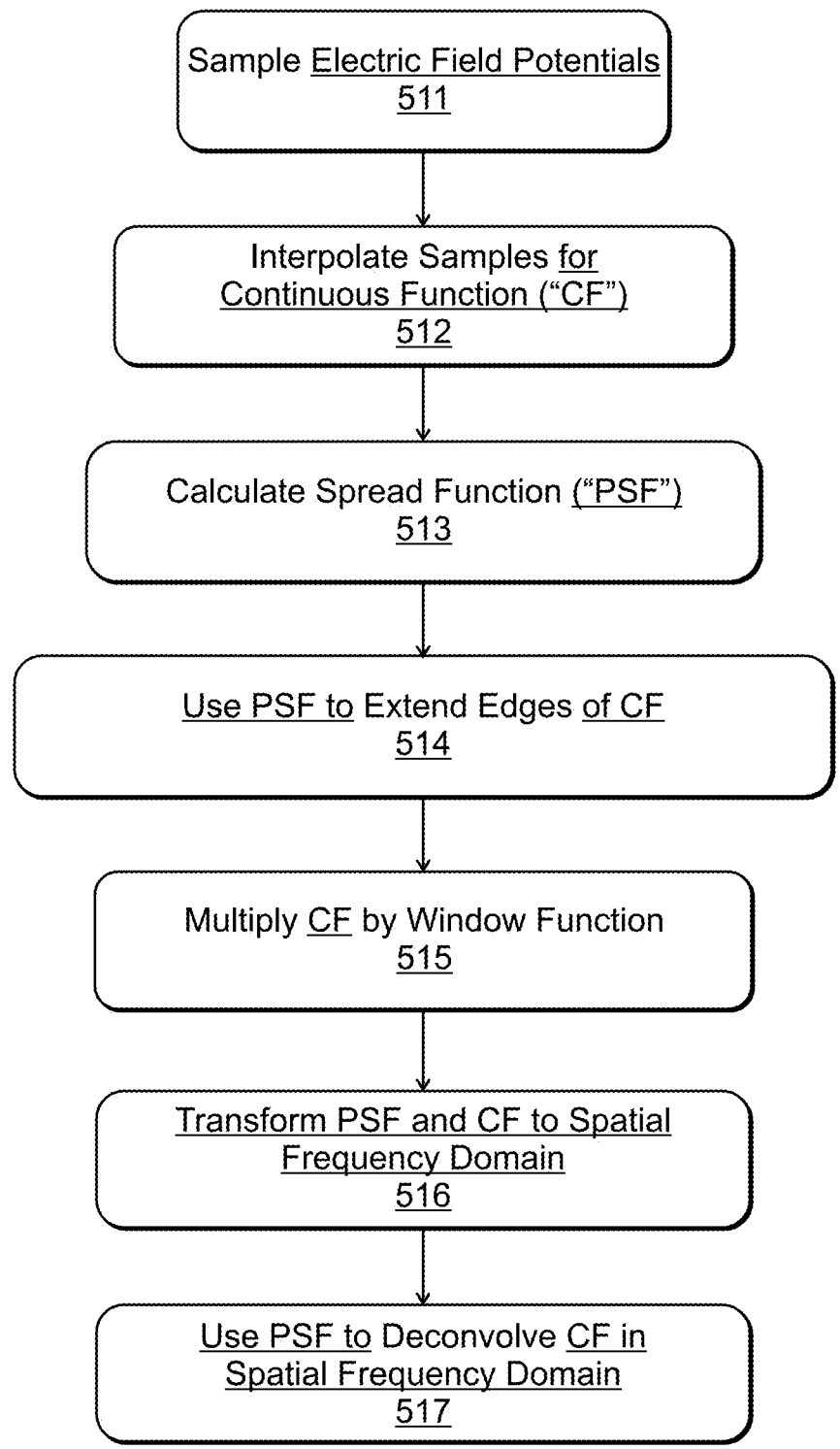
FIG. 51A is a process flowchart for improving spatial resolution using deconvolution, in accordance with embodiments of the present invention.

FIG. 51A is a process flowchart for improving spatial resolution using deconvolution in accordance with some embodiments of the present invention. In step 511, a spatially truncated intra-cardiac pattern of net electric field potentials is sampled using an m×n array of electrodes recording at height h above a tissue surface. In step 512, interpolation (e.g., two-dimensional cubic spline interpolation) is applied to the m×n sampled data points to estimate a continuous function representing the complete pattern of net electric field potentials over the region of tissue surface covered by the multi-electrode array. In step 513, a point spread function is calculated from height h.

Figure 51B:
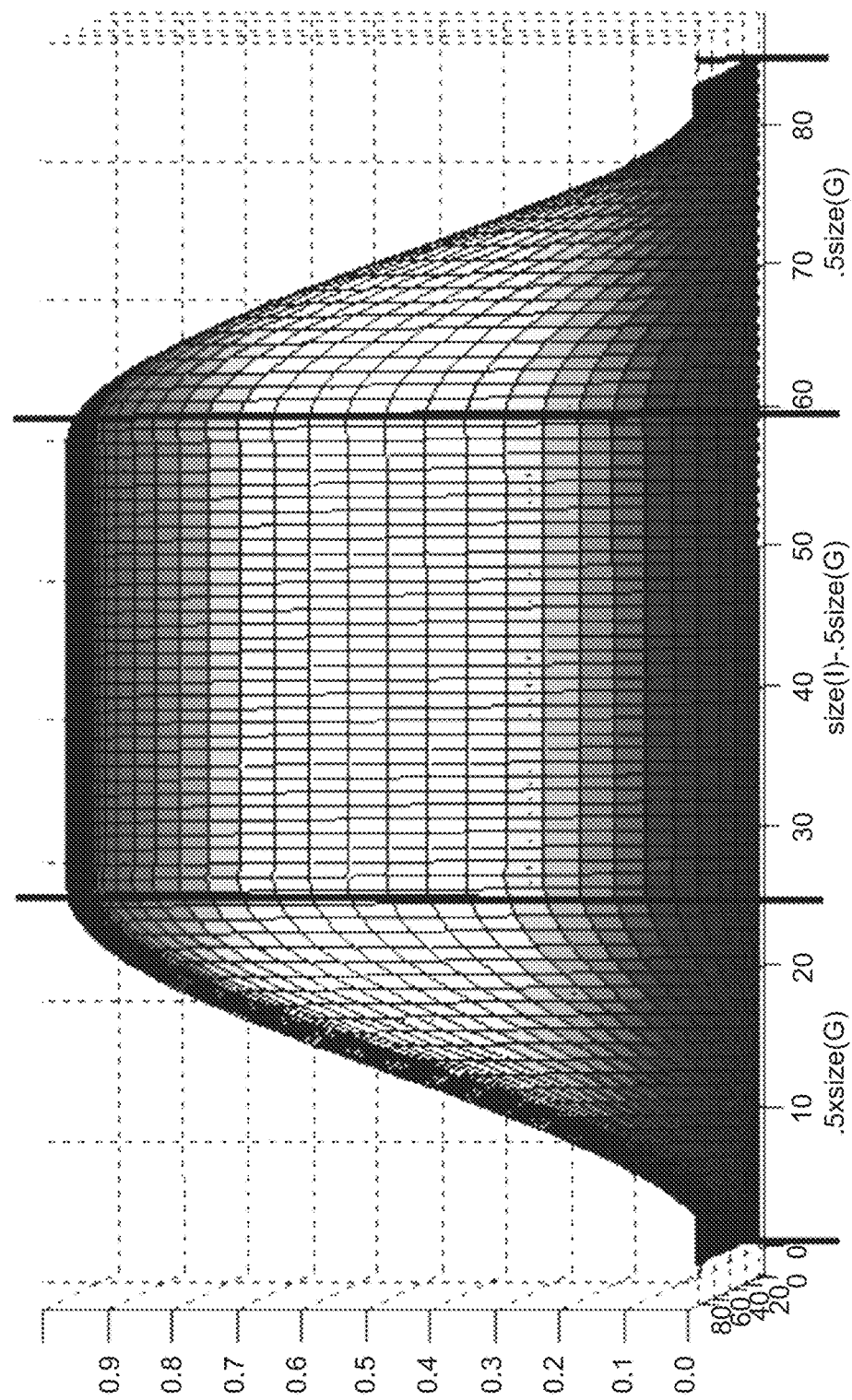
FIG. 51B illustrates an exemplary window, in accordance with embodiments of the present invention.

The truncated edges of the continuous function representing the complete net electric field potentials may be processed using a combination of edge extension and windowing in accordance with some embodiments of the present invention. In step 514, the continuous function is analytically extended beyond the boundaries of the original m×n sampled data points to a distance of half the nominal width of the point spread function. The nominal width of the point spread function is the horizontal distance from the peak of the function to the value at 10% of peak. In step 515, the extended continuous function is multiplied by a window. The window may comprise, but is not limited to, a central rectangular section of unity height. In accordance with some embodiments, the dimensions of the central section are the same as of the dimensions of the original m×n array of sampled data points less half the nominal width of the point spread function. FIG. 51B illustrates an exemplary window in accordance with some embodiments of the present invention.

In step 516, the continuous function and the point spread function are transformed to the spatial frequency domain using, for example, the fast Fourier Transform ("FFT"). In step 517, deconvolution is performed in the spatial frequency domain by dividing the transformed continuous function by the transformed point spread function. In accordance with some embodiments, a Wiener filter may be invoked and/or a small constant may be added to the denominator when dividing in the spatial frequency domain to prevent amplification of noise arising from numerical and measurement errors.

Patient-Specific Topological Maps for Tailored Treatment Strategies

As described above, a patient-specific map of a tissue substrate indicating appropriately acquired electrogram frequencies—which may indicate tissue activation frequencies and, in turn, circuit core density and distribution—informs the optimal placement of ablation lesions to treat cardiac fibrillation.

FIG. 13 is a system component diagram in accordance with some embodiments of a system for detecting and/or mapping cardiac fibrillation in a patient. The system may include, but is not limited to, a catheter subsystem 132, a processing unit 135, a memory 134, a transceiver 133 including one or more interfaces 139, a GUI 138, and/or a display 136 (each described in detail below). The system may also include, but is not limited to, an ECG/EKG subsystem 130 and/or an imaging subsystem 131 (described above).

The catheter subsystem 132 may be configured for determining patient-specific (and location-specific) tissue spatiotemporal variations, mapping one or more measurements indicative of the density and distribution of circuit cores, and/or assessing the efficacy of a treatment procedure (e.g., whether ablation lesions completely prevent conduction in both directions).

A catheter in the catheter subsystem 132 may be configured to perform one or more types of procedures according to some embodiments of the present invention. In a preferred embodiment, a catheter for mapping one or more measurements indicative of the density and distribution of circuit cores (i.e., a "mapping catheter") includes one or more pairs of recording electrodes in the OCU electrode configuration. In some embodiments, a mapping catheter includes a two-dimensional array of recording electrodes, in which the electrodes are preferably: (1) as small as possible (without incurring too great an increase in noise that results from high impedance); (2) of sufficient number so that deconvolution confers a spatial resolution advantage; and (3) oriented with an inter-electrode relationship that facilitates improved spatial resolution (i.e., the OCU configuration).

Figure 52B:
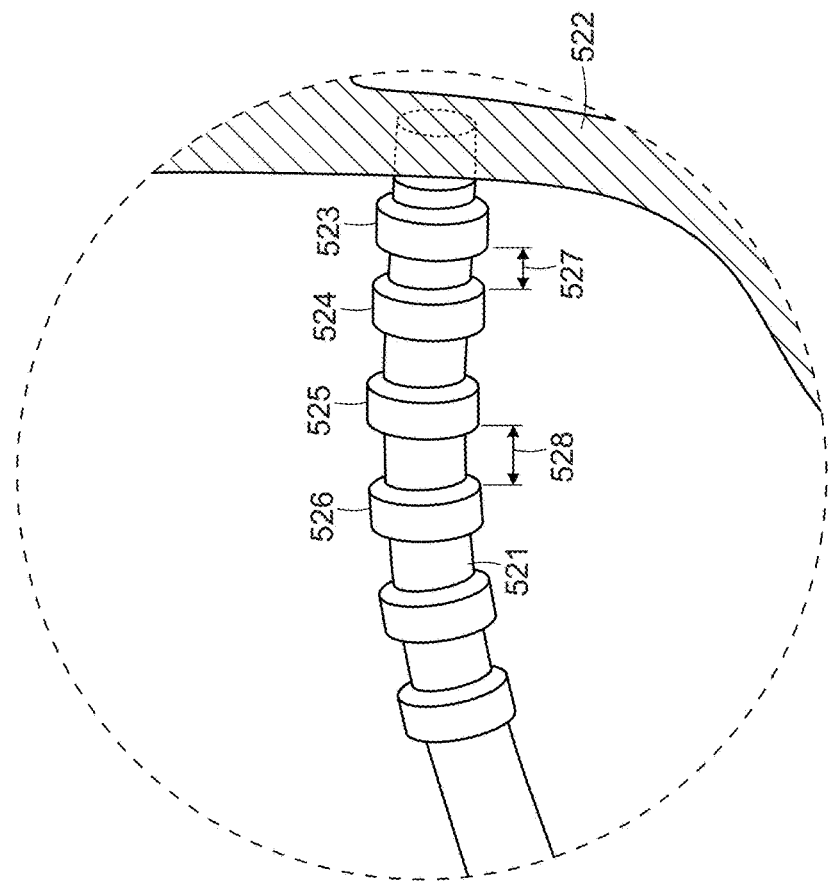
FIGS. 52A-52B illustrate a catheter with an OCU electrode configuration for identifying an optimal spatial resolution for local tissue with spatiotemporal variation, in accordance with embodiments of the present invention.
Figure 52A:
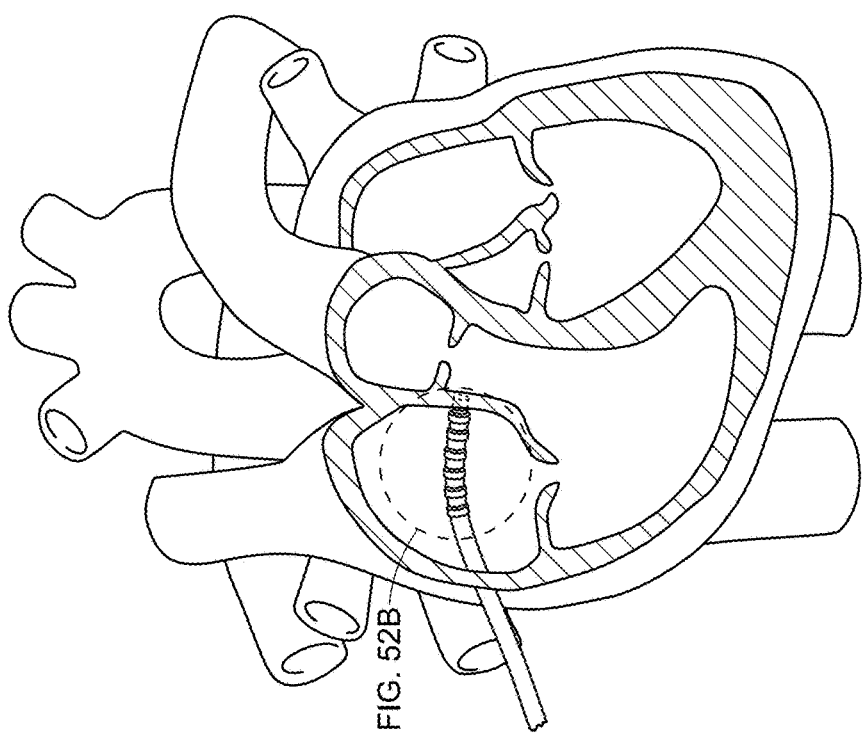

According to some embodiments of the present invention, the same or a similarly configured catheter in the catheter subsystem 132 may be used for identifying the optimal spatial resolution for local tissue with spatiotetmporal variation. For example, FIGS. 52A and 52B illustrate a similarly configured catheter with more than two electrodes on an axis orthogonal to the tissue surface.

According to some embodiments of the present invention, the same or a similarly configured catheter in the catheter subsystem 132 may be used for mapping and/or assessing the efficacy of a treatment procedure. For example, a similarly configured catheter also may be used to assess whether an ablation lesion completely prevents conduction by selecting one electrode on either side of the lesion for pacing, and then recording the tissue activation timing on the remaining electrodes to quickly identify the presence or absence of a complete conduction block. By selecting one electrode on the opposite side of the lesion for pacing, a complete bi-directional conduction block may or may not be confirmed. (by pacing from both sides of the ablation lesion one can confirm bi-directional block).

Figure 54:
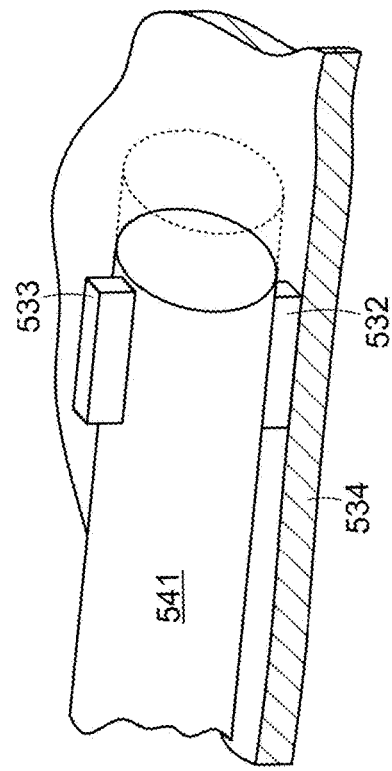
FIGS. 53 and 54 illustrate different views of a catheter configured for both mapping and treating cardiac fibrillation according to some embodiments of the present invention.
Figure 53:
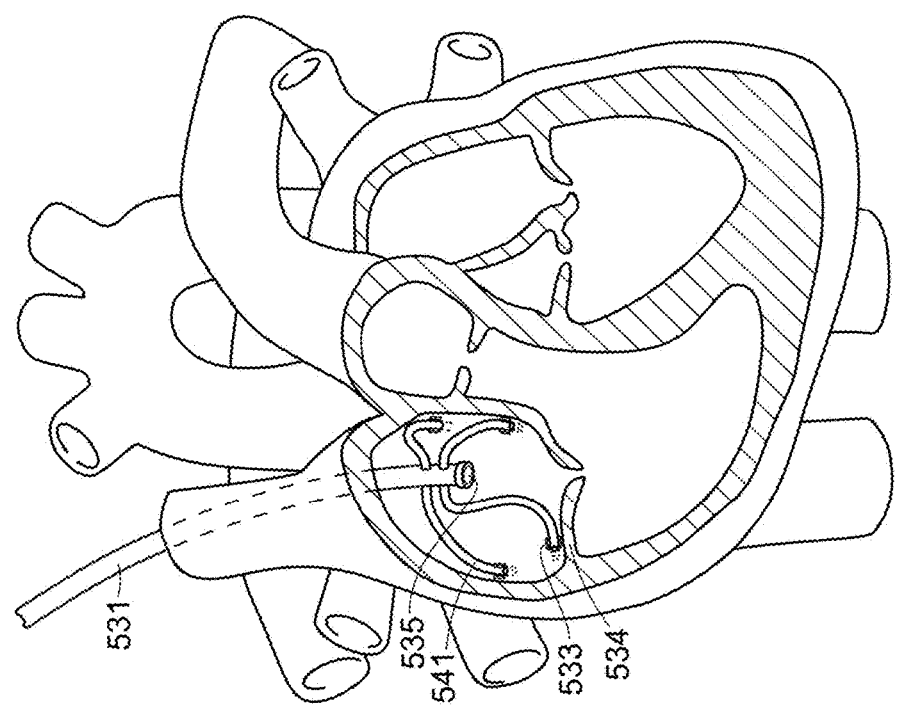

According to some embodiments of the present invention, a similarly configured catheter in the catheter subsystem 132 may be used for treating cardiac fibrillation. In some embodiments, a similarly configured catheter also may include an ablation electrode configured for creating point and/or linear ablation lesions in the heart tissue. FIGS. 53 and 54 illustrate different views of a catheter configured for both mapping, minimizing, and treating cardiac fibrillation. For example, an ablation electrode may be included on one of a multiple of catheter splines while one or more pairs of recording electrodes may be included on a separate catheter spline. Or, an ablation electrode may be included as part of a multi-electrode array, such that mapping, lesion assessment, and ablation treatment may all be performed using a single catheter. According to some embodiments of the present invention, the system for detecting and mapping fibrillation may also include one or more processing units, shown collectively in FIG. 13 as processing unit 135, that process instructions and run software that may be stored in memory. For example, processing unit 135 executes applications, which may include, but are not limited to, catheter-related applications for positioning electrodes and recording electrograms; signal processing applications for performing, for example, deconvolution processes; and topological mapping applications for identifying reentrant circuit core density and distribution in the heart. In some embodiments, the software needed for implementing a process or a database includes a high level procedural or an object-orientated language such as C, C++, C#, Java, Perl, or MATLAB®. The software may also be implemented in assembly language if desired. Processing unit 135 can be any applicable processing unit that combines a CPU, an application processing unit, and memory. Applicable processing units may include any microprocessor (single or multiple core), system on chip (SoC), microcontroller, digital signal processor (DSP), graphics processing unit (GPU), combined hardware and software logic, or any other integrated circuit capable of processing instructions.

According to some embodiments of the present invention, the system for detecting and mapping fibrillation may also include one or more memory devices, shown collectively in FIG. 13 as memory 134. Memory 134 stores the instructions for the above applications, which are executed by processing unit 135. Memory 134 also may store data relating to detecting and mapping fibrillation, such as the electrogram recordings and frequencies.

According to some embodiments of the present invention, the system for detecting and mapping fibrillation may also include one or more transceivers, shown collectively in FIG. 13 as transceiver 133. Transceiver 133 includes a transmitter and a receiver. The transmitter and the receiver may be integrated into a single chip or may be embodied in separate chips, or may be integrated with processing unit 135 and/or memory 134. Transceiver 133 may also include one or more interfaces 139, that provide an input and/or output mechanism to communicate with other devices, such as the catheter subsystem 132. As an input and/or output mechanism, interface(s) 139 may operate to receive electrogram recordings from as well as transmit instructions to the catheter subsystem 132. Interface(s) 139 can be implemented in software or hardware to send and receive signals in a variety of mediums, such as optical, copper, and wireless, and in a number of different protocols some of which may be non-transient.

According to some embodiments of the present invention, the system for detecting and mapping fibrillation may also include a GUI 138 to provide communication with an input and/or output mechanism to communicate with a user. For example, a clinician may use input/output devices to send/receive data to/from the processing unit 135 and catheter-based subsystem 132 over the GUI 508. Input devices may include, but are not limited to, a keyboard, a touch screen, a microphone, a pen device, a trackball, a touch pad, and a mouse. Meanwhile, output devices may include, but are not limited to, a display 136, a speaker, and a printer. Other input/output devices may also include, but are not limited to, a modem and interface(s) 139 of transceiver 133. The GUI 138 can operate under a number of different protocols, and the GUI interface 138 can be implemented in hardware to send and receive signals via transceiver 133 in a variety of mediums, such as optical, copper, and wireless.

Figure 55:
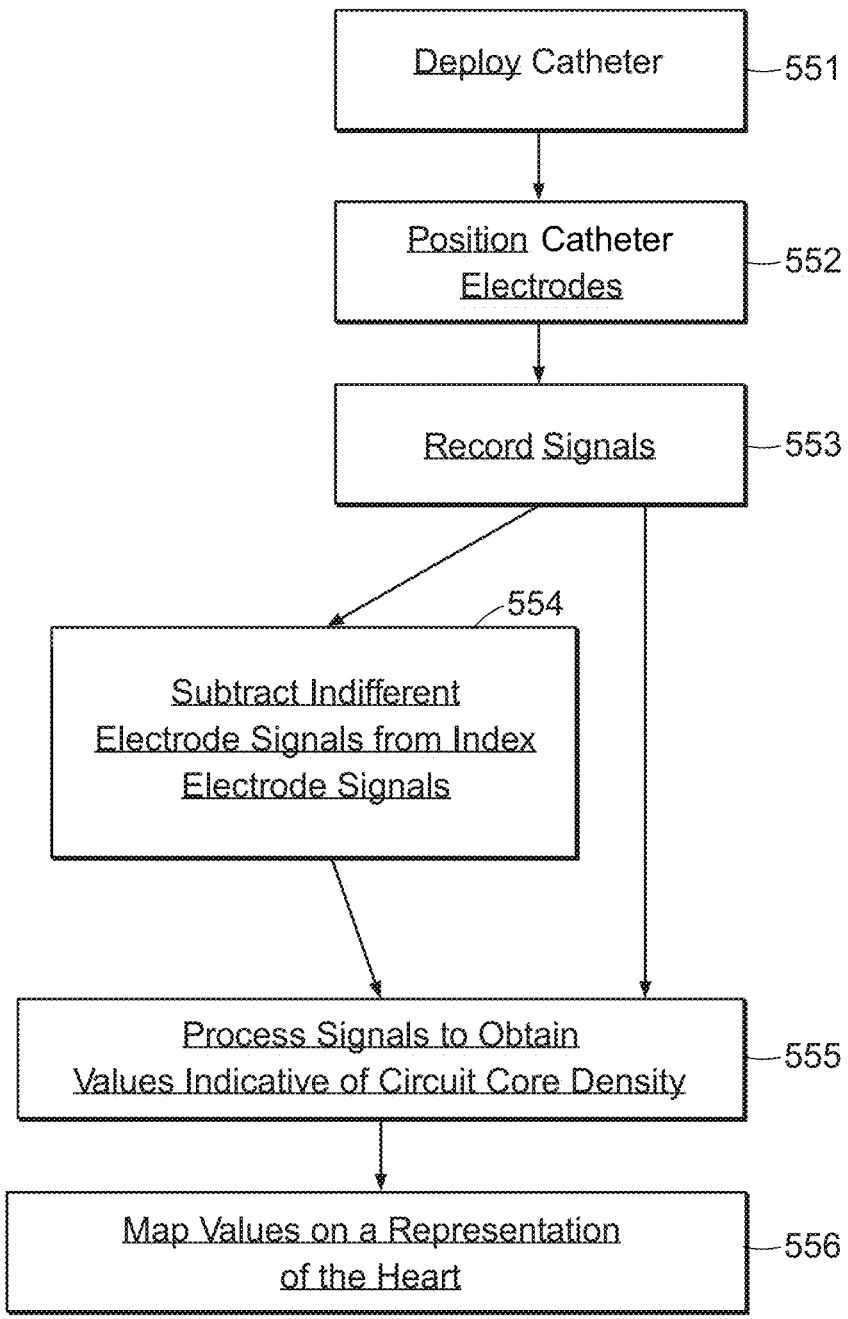
FIG. 55 is a process flowchart for assessing fibrillogenicity in a patient according to some embodiments of the present invention.

FIG. 55 is a process flowchart for detecting and mapping fibrillation in accordance with some embodiments of the present invention. In step 551, a puncture is made in a distal vessel, a guidewire is inserted, and a vascular sheath is threaded over the wire. A mapping catheter with a multi-electrode array is inserted using a guidewire and moved toward the heart. Alternatively, this insertion can be made percutaneously via the chest or via thoracotomy at the time of surgery. In step 552, the catheter is positioned so that the one or more inter-electrode axes are orthogonal to the surface of the tissue substrate. Once the mapping catheter is in position, an OCU-configured electrode pair or array may be engaged in one tissue location or region at a time so that an array of signals (e.g., net electric field potentials) may be recorded in step 553. In optional (but preferred) step 554, the signal recorded by each orthogonal indifferent electrode is subtracted from the signal recorded by its associated index electrode to acquire a new array of signals. In step 555, signal processing including, but not limited to, interpolation, edge extension and windowing, FFT, deconvolution, and/or calculation of the centroid of a signal power spectrum is performed to return values (e.g., local electrogram signal frequencies as defined by the centroid of the power spectrums) indicative of tissue activation frequencies, which are indicative of reentrant circuit core density and distribution across the tissue substrate.

In step 556, these values are mapped (e.g., in a color-coded fashion) onto a representation (e.g., a two-dimensional image or three-dimensional model) of the tissue substrate surface according to the positions of the recording electrodes, which are identified using an appropriate electrode localization technology.

Figure 56B:
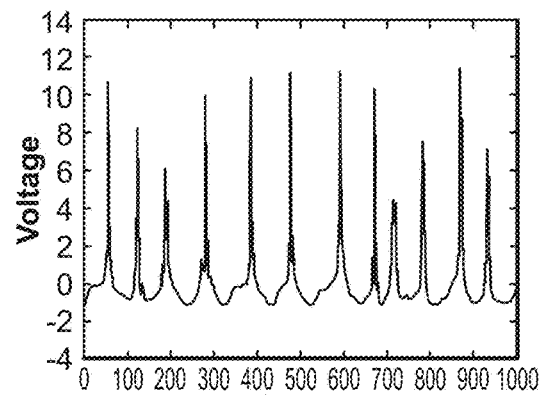
FIGS. 56A-56C illustrate the relationship between electrogram recordings and a resulting electrogram frequency map of a tissue substrate, in accordance with embodiments of the present invention.
Figure 56A:
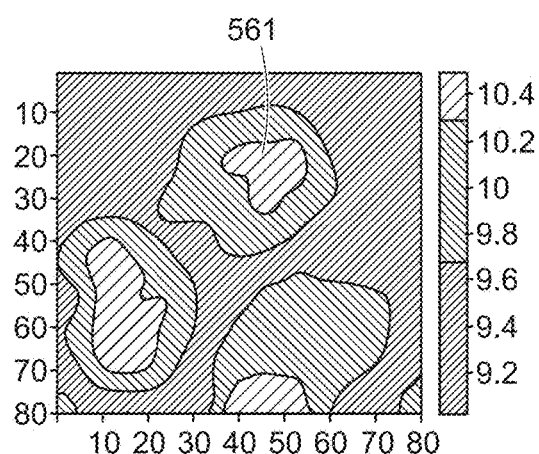
Figure 56C:
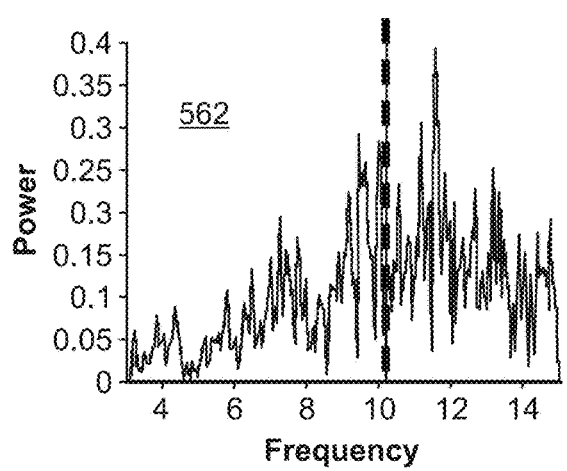

FIGS. 56A-56C illustrates the relationship between: (FIG. 56A) an OCU electrogram frequency map of a tissue substrate indicating circuit core density and distribution (using the centroids of the power spectrums); (FIG. 56B) an OCU electrogram recording for a location 1801 in the mapped tissue substrate; and (FIG. 56C) the power spectrum derived through FFT of the OCU electrogram in accordance with some embodiments of the present invention. At location 561 in the tissue substrate shown in FIG. 56A), electrogram signals of an index electrode and its associated indifferent electrode, which are in OCU configuration and located above location 561 in the tissue substrate, are recorded. The resulting OCU electrogram (i.e., the difference between the two signals) for location 561 is shown in FIG. 56B. The local electrogram frequency at location 561 is calculated by deriving the power spectrum of the FFT of the OCU electrogram. FIG. 56C is a plot of the power spectrum, on which centroid 562 has been calculated and marked. The value of the centroid 562 of the power spectrum is mapped onto a representation of the tissue substrate at the coordinates for location 561 to indicate tissue activation frequency, which is indicative of circuit core density, at location 561.

Figure 57:
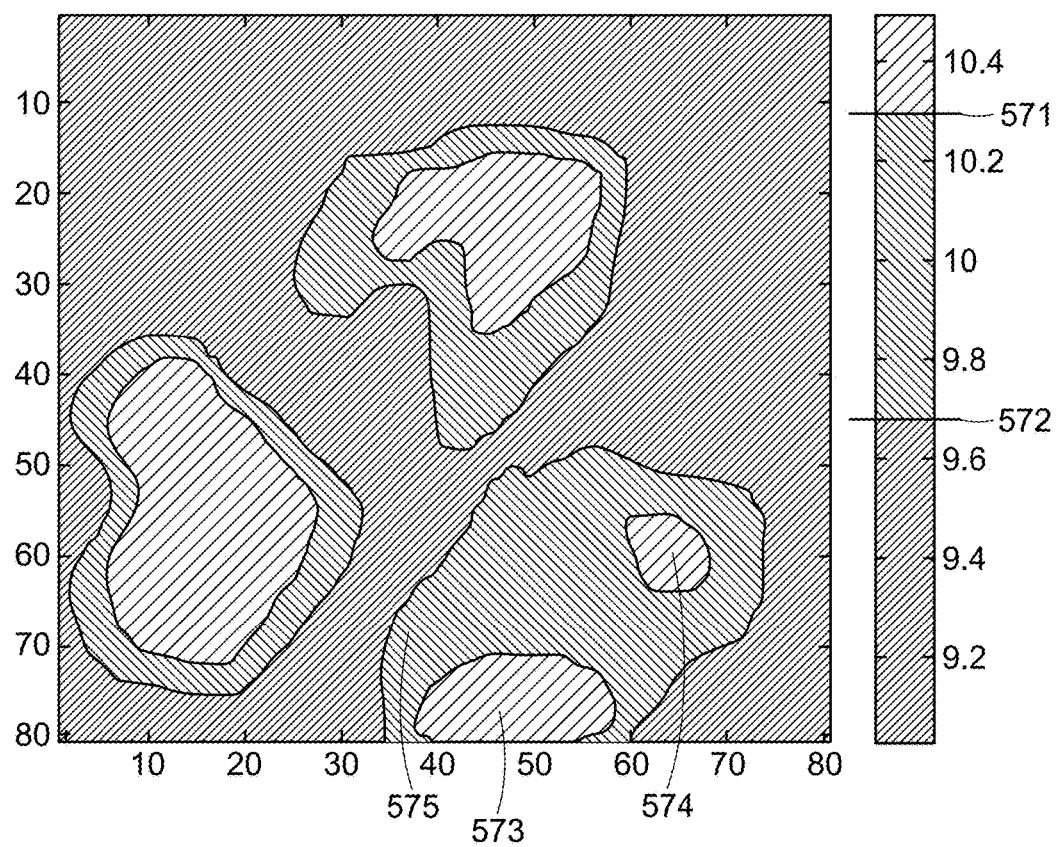
FIG. 57 illustrates the impact of selecting a threshold frequency to define the size and number of high circuit core density regions across a tissue substrate, in accordance with embodiments of the present invention.

FIG. 57 is a map of a tissue substrate indicating tissue activation frequencies, which are indicative of circuit core densities, in accordance with some embodiments of the present invention. In this example, the values on the map are the local electrogram signal frequencies as defined by the centroid of the respective power spectrums. FIG. 57 illustrates the impact of selecting a threshold frequency to define the size and number of high circuit core density regions across a tissue substrate in accordance with some embodiments of the present invention. For example, if threshold frequency 571 is selected for this tissue, four regions of high circuit core density, including region 573 and region 574, are indicated. However, if a lower threshold frequency 572 is selected, all of the regions expand and region 573 and region 574 are fused into one high circuit core density region 575.

Optimization of Lesion Distribution

The efficiency of ablation lesions can be maximized by making use of the previously identified locations of high circuit core density. Because high circuit density sites can be distributed throughout the surface of the atrial tissue in complex arrangements that vary by patient, finding a distribution of ablations that overlaps the largest number of high circuit density sites and connects to the tissue edge with the smallest total lesion length is an important optimization question.

The connection of multiple sites using the shortest possible distance is as a combinatorial optimization problem that can be solved using a number of computer-based algorithmic solutions. For a small number of sites, the problem can be solved by exact algorithms, comparing every possible permutation to find the optimal solution. The complexity of the problem rises at the rate of O(n!). Thus, as the number of sites n increases, solving the problem by exact algorithms become increasingly inefficient and impractical.

Instead, heuristics or approximation algorithms can be used to reach a solution very quickly for large numbers of sites, although the solution may not be optimal and complete. Heuristics algorithms iteratively improve a solution until search termination criteria are met, rather than exploring every permutation. Different algorithms have different methods for choosing permutations on their iterations. The termination criteria can include the number of iterations, a threshold value, the speed at which a solution is improving, or a number of iterations without improvement. Some examples of heuristics algorithms include greedy algorithm, genetic algorithm, simulated annealing, particle swarm optimization, and ant colony optimization.

In some embodiments, a genetic program, which is a specialization of genetic algorithms, is used to solve this optimization problem. The genetic program iteratively improves a solution based upon the principles of evolution and "survival of the fittest." In certain embodiments, "fitness" is characterized as a line distribution that covers the largest total circuit density with the smallest number of ablation points (i.e., shortest total lesion length). The program may also incorporate constraints such as, for example, avoidance of ablating across atrial arteries. Additional fitness criteria can be added so that the search strategy reflects current best lesion distribution characteristics. Embodiments of cardiac fibrillation detection and mapping system may use the genetic program to identify and, optionally, display the highest efficiency distribution of lesions to connect the "peaks" in the topological map representing circuit core density and distribution. This information can then be used by a clinician based upon complete consideration of the clinical context.

Figure 58:
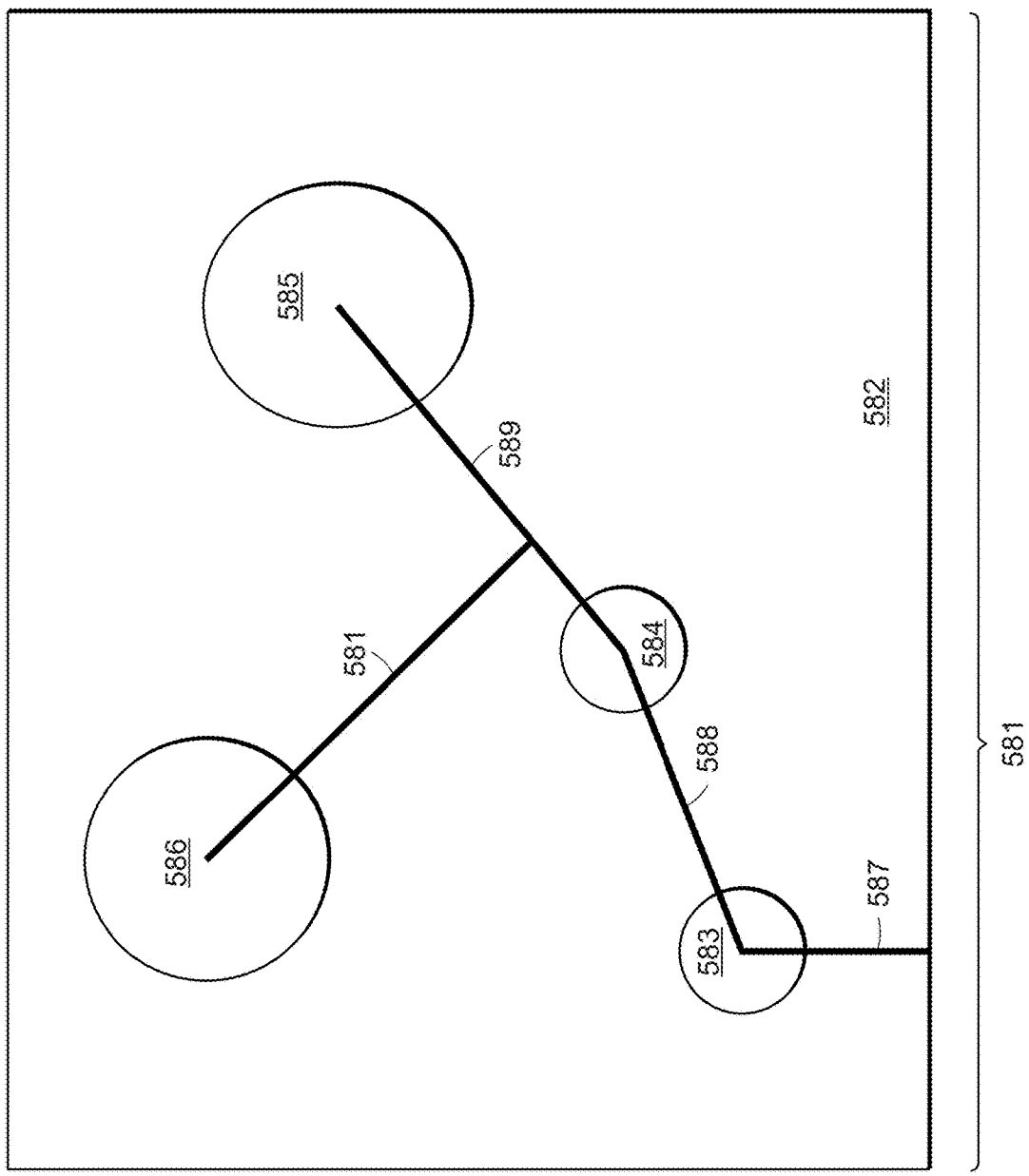
FIG. 58 illustrates a hierarchical tree-like structure provided by a genetic algorithm for optimizing lesion placement, in accordance with embodiments of the present invention.

As shown in FIG. 58, the genetic program provides a hierarchical tree-like structure to define the genotype of its solutions in accordance with some embodiments of the present invention. Embodiments of the genetic program take a unique approach in which the genotype is also the phenotype. In other words, the tree-like structure itself represents the distribution of ablation lesions. The individual elements are potential sets of ablation lesions (i.e., an ablation lesion set). Thus, an individual element is defined by the locations of its connection(s) to the tissue's boundary edge, the first branch point, subsequent branch points and each end point. The fitness of each individual element in a population is measured as the total density of the map points that that ablation lesion set overlaps.

In a series of experiments using a computational model, tissue (80×80 cells) was created with heterogeneous electrophysiologic properties. Specifically, the tissue had two different regions, each region having variability of action potential duration randomly distributed around a mean value. In the majority of the tissue, the action potential duration mean was 130 ms (with an intercellular resistance of 9 ohms). However, in one square patch of the tissue (26×26 cells), the action potential duration mean was 80 ms (with an intercellular resistance of 13 ohms).

Burst pacing (from each of 64 pacing sites) was applied during multiple simulations in each tissue region. In the presence and absence of ablation lines extending from a tissue edge, measurements were obtained of (1) the percentage of instances in which pacing resulted in successful induction of multi-wavelet reentry, and (2) the duration of each episode of multi-wavelet reentry. The location, length, and number of ablation lines were randomized over 500 iterations.

The total ablation line lengths (aggregated from the lengths of individual ablation lines in each set) were calculated and varied from 0 to 150 cells. Measurements of the average circuit density of the cells at each ablation site were obtained and used to calculate the average circuit density underneath the entire ablation line set. Of the total 500 ablation line sets, 10 sets were selected based upon their average circuit density overlap such that there was an even distribution of ablation line sets ranging from minimal to maximal circuit density overlap.

Figure 64:
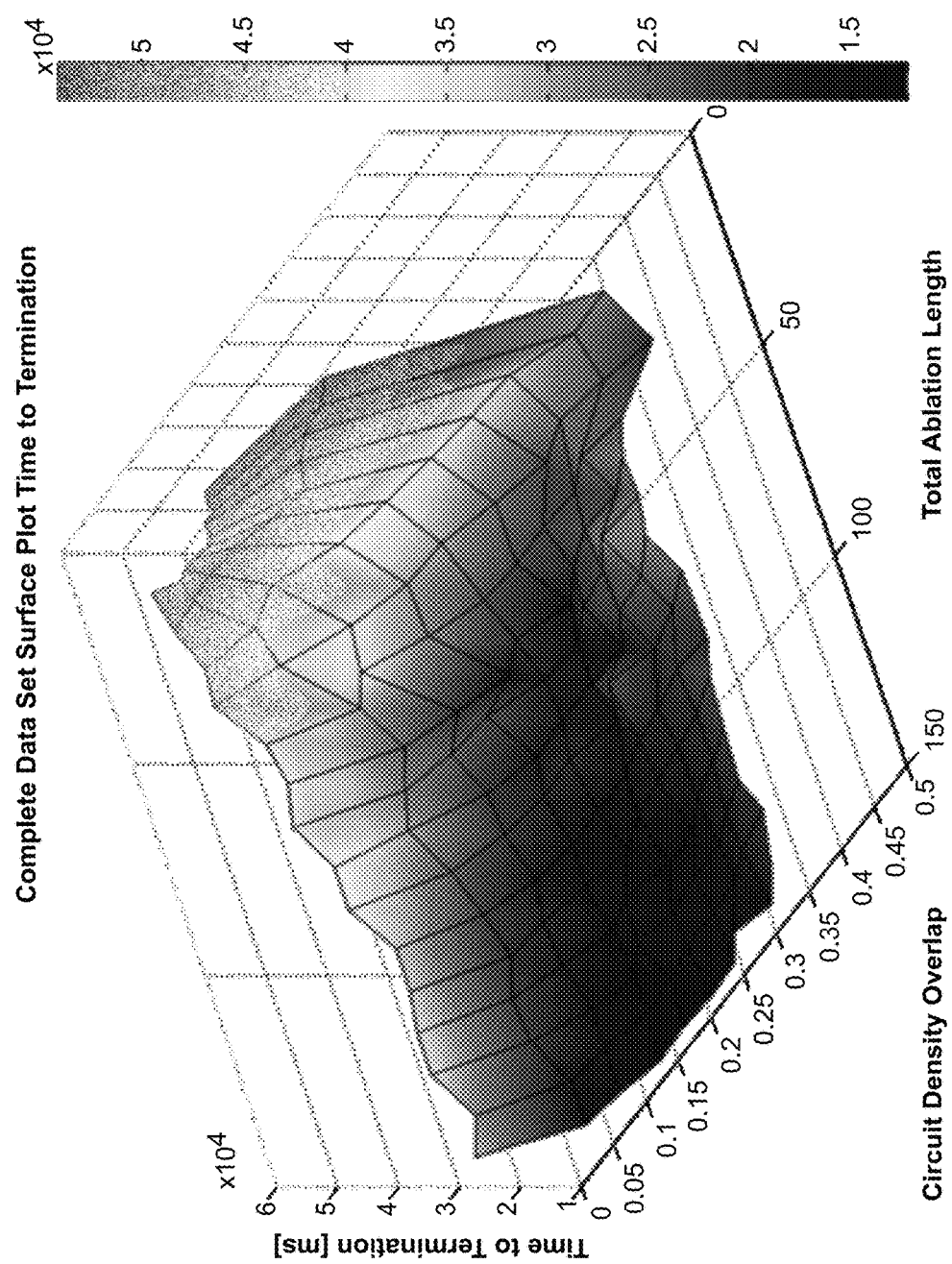
FIGS. 64-65 are two views of a three-dimensional plot of the time to termination of induced episodes of multi-wavelet reentry as a function of total ablation length and circuit density overlap according to some aspects of the present invention.
Figure 65:
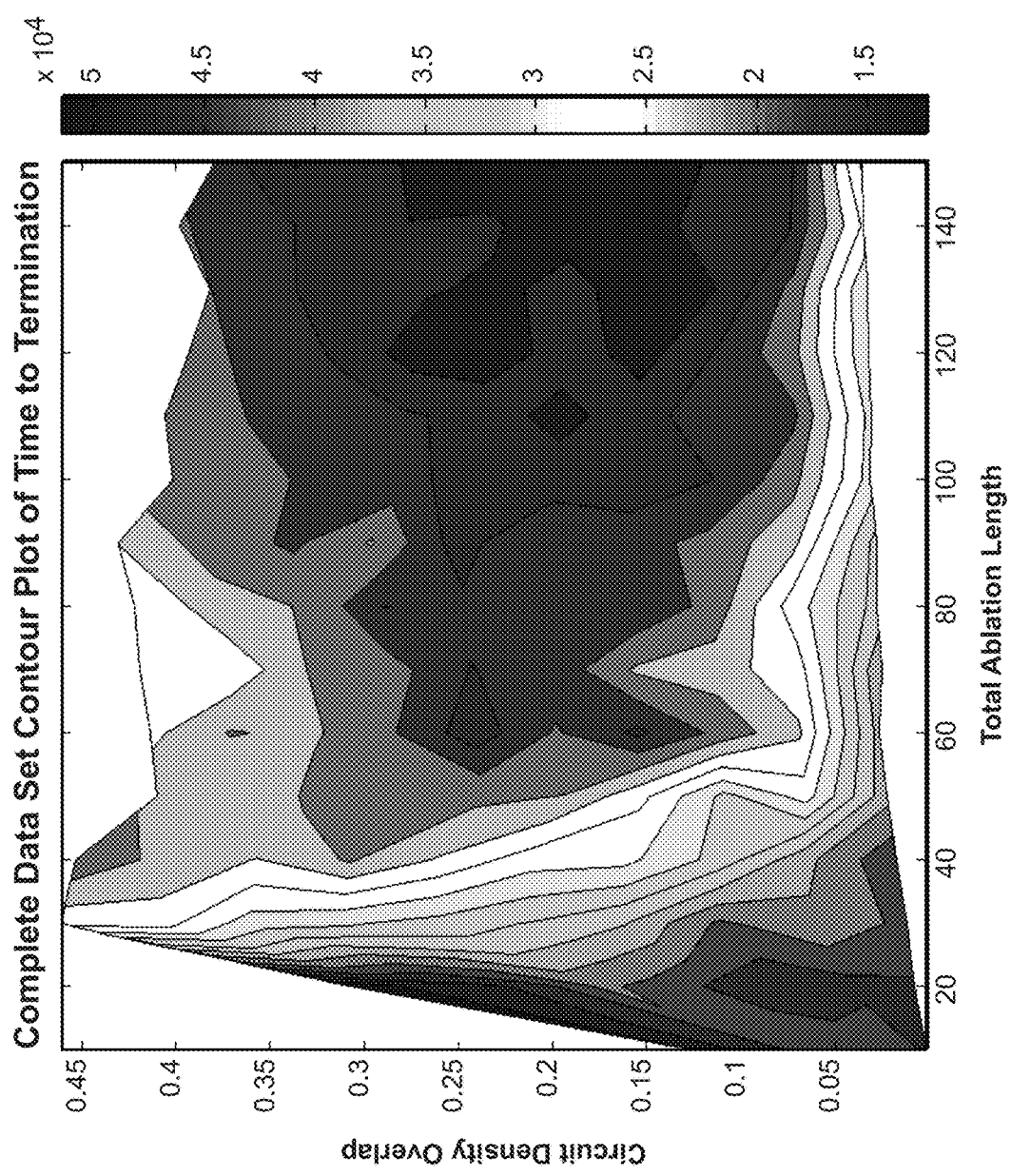

Also calculated, as a function of total ablation length and circuit density overlap, were (1) the time to termination of induced episodes of multi-wavelet reentry, and (2) the percentage of attempted inductions (pacing episodes) that successfully produced sustained multi-wavelet reentry. FIGS. 64-65 are two views of a three-dimensional plot of the time to termination of induced episodes of multi-wavelet reentry (z-axis) as a function of total ablation length (x-axis) and circuit density overlap (y-axis) in accordance with some aspects of the present invention. FIGS. 64-65 reveal that time to termination is reduced as (1) total ablation length increases and (2) circuit density overlap increases. FIGS. 64-65 also reveal that the relationship between time to termination and total ablation length is largely linear when circuit density overlap is low but distinctly non-linear when circuit density overlap is high. With high circuit density overlap (compared to low circuit density overlap), there is a marked reduction in time to termination with a smaller total ablation length. Thus, when ablation lesions are placed so as to maximize circuit density overlap, greater efficiency may be achieved (i.e., greater reduction in time to termination per amount of ablation). Also, the total ablation length reaches a point of diminishing returns in terms of the impact on time to termination. that time to termination begins to decline steeply when an ablation line extends from a tissue edge to the high circuit density patch and that the point of diminishing returns is reached when the ablation line extends through the high density patch.

Figure 66:
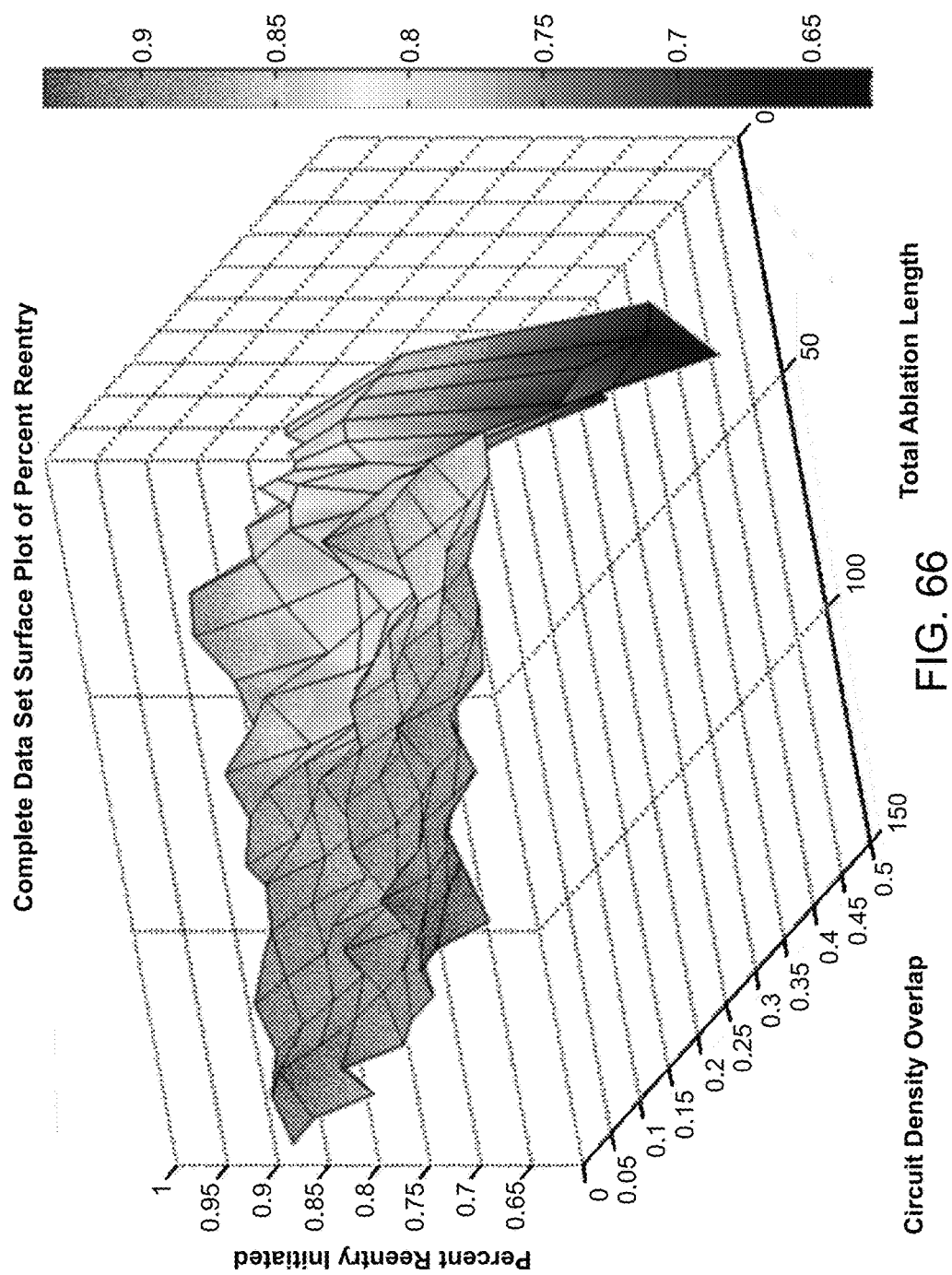
FIGS. 66-67 are two views of a three-dimensional plot of the percent inducibility (z-axis) as a function of total ablation length (x-axis) and circuit density overlap (y-axis) in accordance with some aspects of the present invention.
Figure 67:
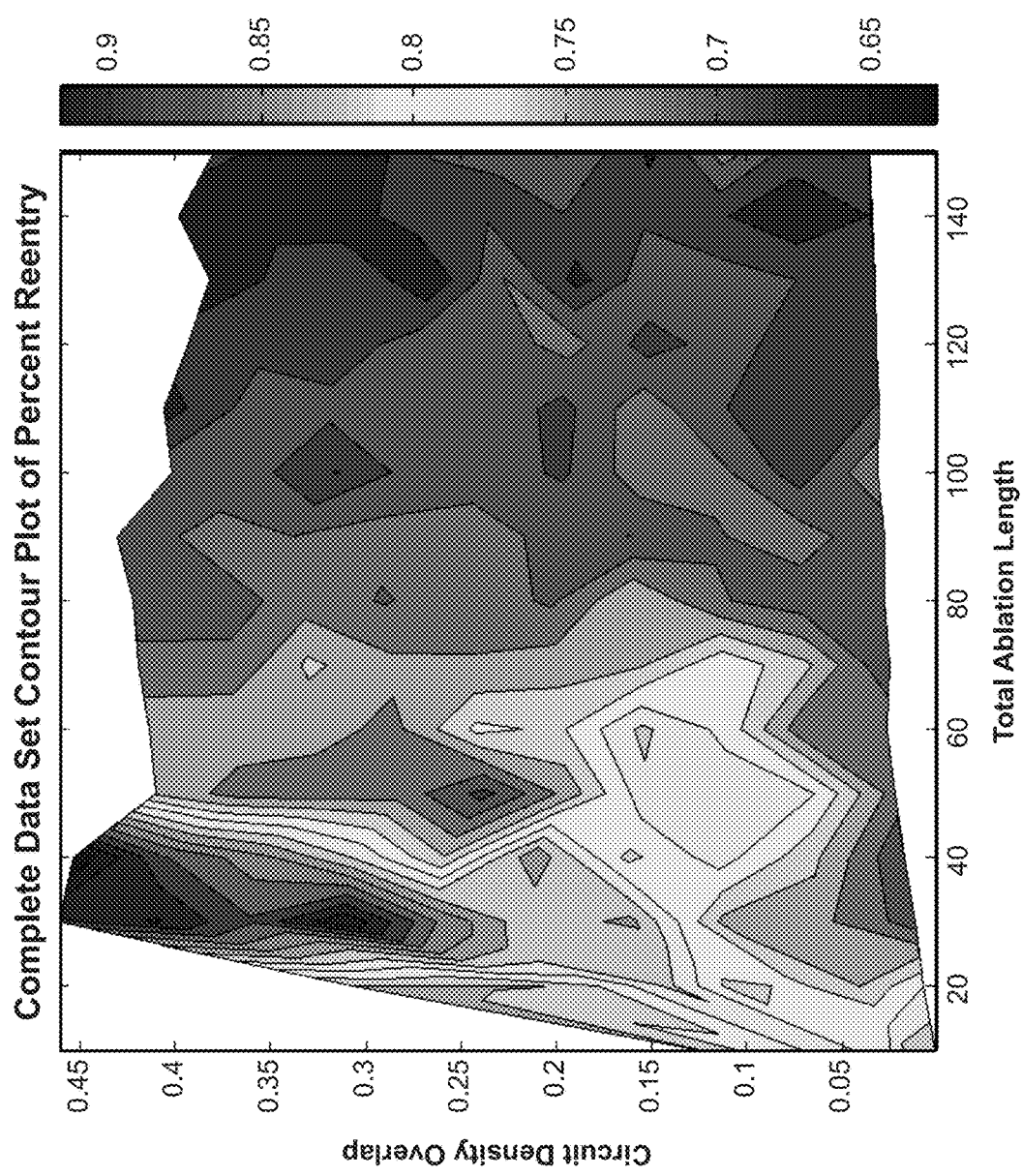
Figure 68:
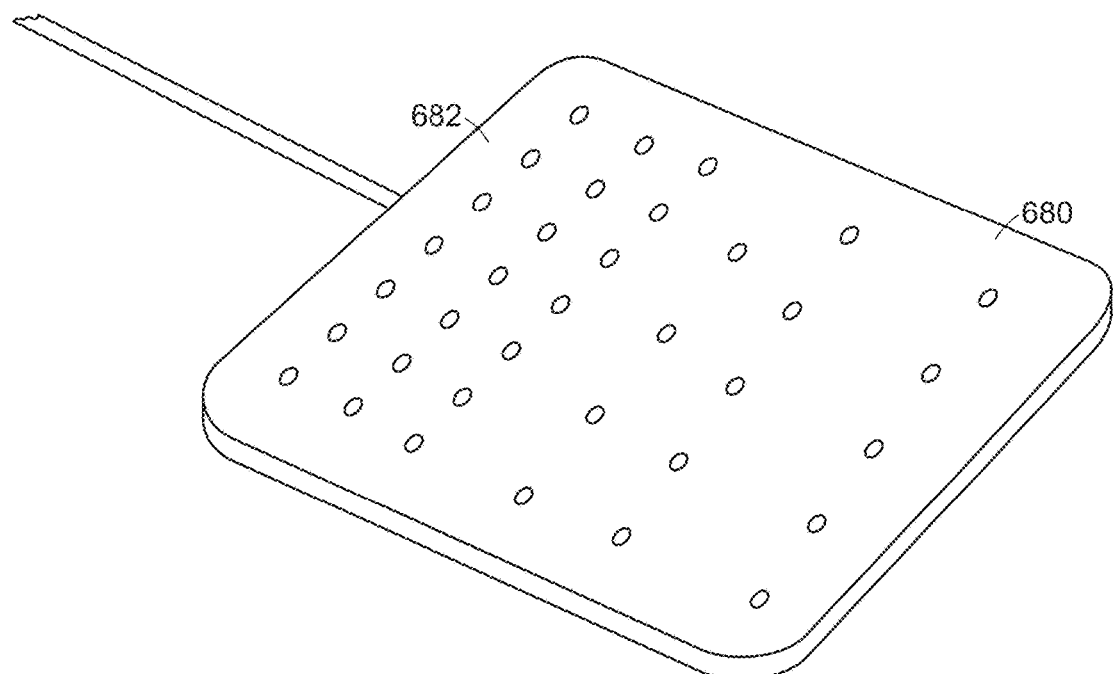
FIGS. 68, 69A-69B, and 70 illustrate catheter designs of alternative embodiments in accordance with some embodiments of the present invention.

In another series of experiments using a computational model, the distance of the high circuit density patch from the edge of the tissue was varied, as was the size of the patch. FIGS. 66-67 are two views of a three-dimensional plot of the percent inducibility (z-axis) as a function of total ablation length (x-axis) and circuit density overlap (y-axis) in accordance with some aspects of the present invention. FIGS. 66-67 reveal that (1) at low circuit density overlap, inducibility of multi-wavelet reentry steadily increases as total ablation length is increased, and (2) at high circuit density overlap, the relationship between total ablation length and inducibility is non-linear (e.g., increasing total ablation length first increases, then markedly decreases, and finally again increases inducibility).

Additional experiments demonstrated that (1) ablation lines delivered to sites of low circuit density increase inducibility, and (2) ablation lines delivered to sites of high circuit density decrease inducibility. Inducibility began to decrease once ablation lines reached the high circuit density patch and continued to decrease until the ablation line extended through the patch (the "to and through" approach). Once the ablation line extended beyond the high circuit density patch into the low circuit density regions, inducibility began to rise again.

Together, the experimental data data indicate that accurate circuit density maps allow for determination of the ideal total length and placement of ablation lesions so as to maximize the efficiency of ablation at reducing time to termination and the efficacy of ablation at minimizing inducibility of multi-wavelet reentry.

FIG. 13 is a system component diagram in accordance with some embodiments of a system for optimizing the placement of ablation lesions in a patient's heart. The system may include, but is not limited to, a processing unit 135, a memory 134, a transceiver 133 including one or more interfaces 139, a GUI 138, and/or a display 136 (each described above).

Figure 59:
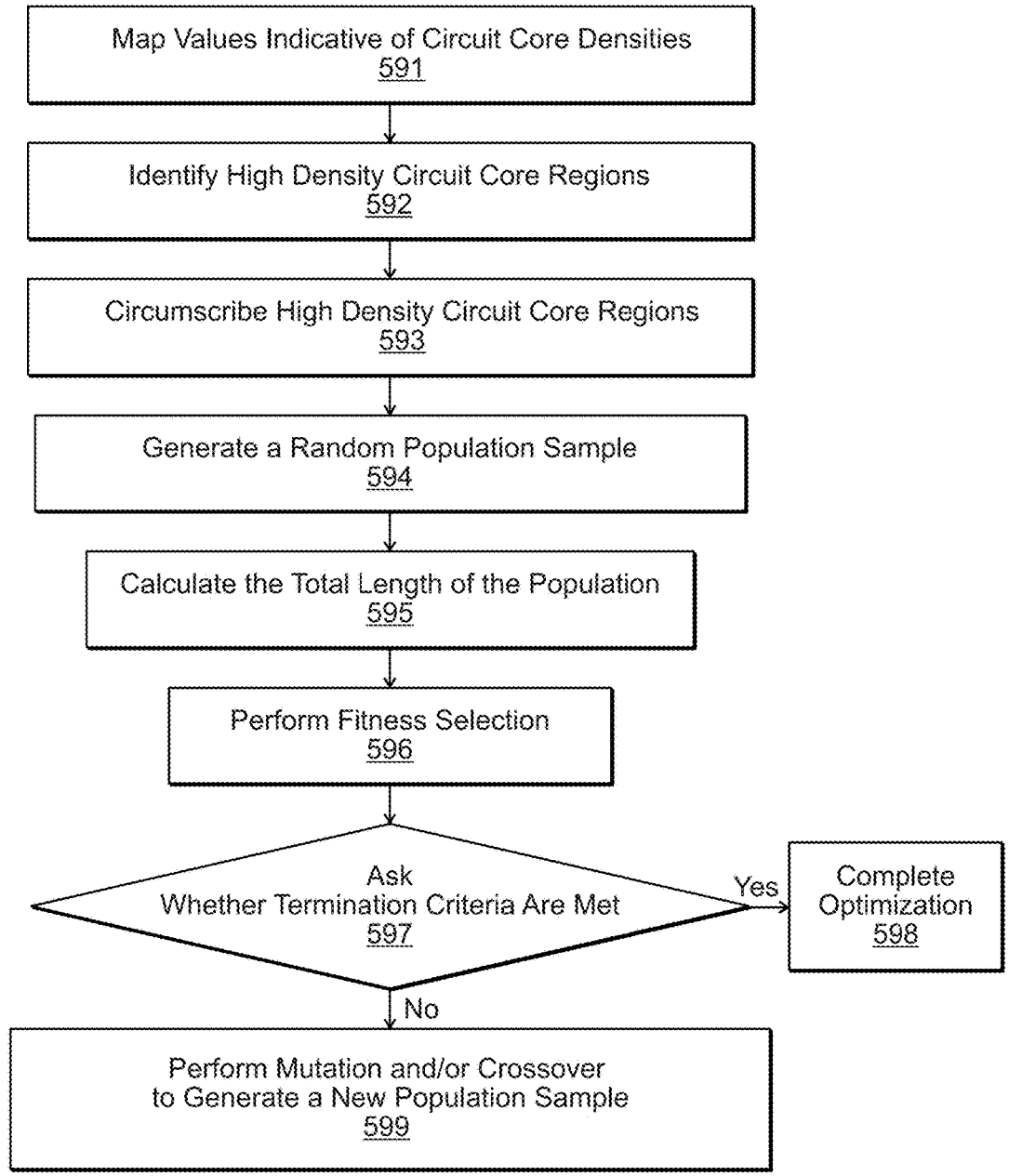
FIG. 59 is a process flowchart for applying a genetic algorithm for optimizing lesion placement to a map indicating circuit core density and distribution, in accordance with embodiments of the present invention.

FIG. 59 is a process flowchart for applying a genetic algorithm for optimizing lesion placement to a map indicating circuit core density and distribution according to some embodiments of the present invention. In step 591, one or more measurements indicating reentrant circuit core density and distribution across a tissue substrate are mapped. In step 592, a threshold (e.g., the top 20%) is selected to identify high circuit core density regions. In step 593, the high circuit core density regions are circumscribed. In step 594, a random initial ablation lesion set (i.e., a sample) is generated. The random sample may include a population of, for example, 100 potential lesions. Each potential lesion in the sample connects a high circuit core density region with a tissue boundary. The connection between a high circuit core density region and a tissue boundary may be direct or indirect. That is, a lesion line may be connected to another lesion line and/or a tissue boundary. The connection between high circuit core density regions and between a high circuit core density region and a tissue boundary may be linear, curvilinear, or some other shape, as long as the connections are continuous. In step 595, total length of the proposed ablation lesions is optimized, which can be used for the fitness selection in step 596. During the fitness selection, elements with the highest fitness are chosen. For example, two elements in the sample could be chosen. The number of elements to be selected is based on an optimization parameter. The chosen elements based on the fitness selection are used to produce the next generation in step 599, while the other individual elements are discarded. In step 597, the computer algorithm decides if termination criteria is met. If the termination criteria is met, the optimization is complete as shown in step 598. Otherwise, in step 599, a new generation of individual elements is created through mutation and crossover from the "parents." Mutation changes one or more elements of the solution but leaves other elements, thus creating a slight variation. Crossover derives a new solution based on parts of two or more parents. For example, a first half of the solution comes from one parent and a second half comes from another parent. Then the process returns to step 592: fitness calculation. The fitness of each individual element in this new generation is calculated so that the fittest may be chosen. The process is repeated and the fitness of the solution evolves to maximize the total density of the map points covered while minimizing the extent of ablation.

However, as a solution evolves, its effectiveness does not improve linearly with its efficiency. There is a point of diminishing return for ablation lesion concentration within the high circuit density region. After this point it is advantageous to distribute any additional lesions in the remaining tissue based on an ideal inter-ablation-line distance.

Assessment of Fibriollogenicity

FIG. 13 is a system component diagram in accordance with some embodiments of a system for assessing fibrillogenicity in a patient. The system may include a catheter subsystem 132, a processing unit 135, a memory 134, a transceiver 133 including one or more interfaces 139, a GUI 138, and/or a display 136 (each described above). The system may also include, but is not limited to, an ECG/EKG subsystem 130 and/or an imaging subsystem 131 (also described above).

Figure 60:
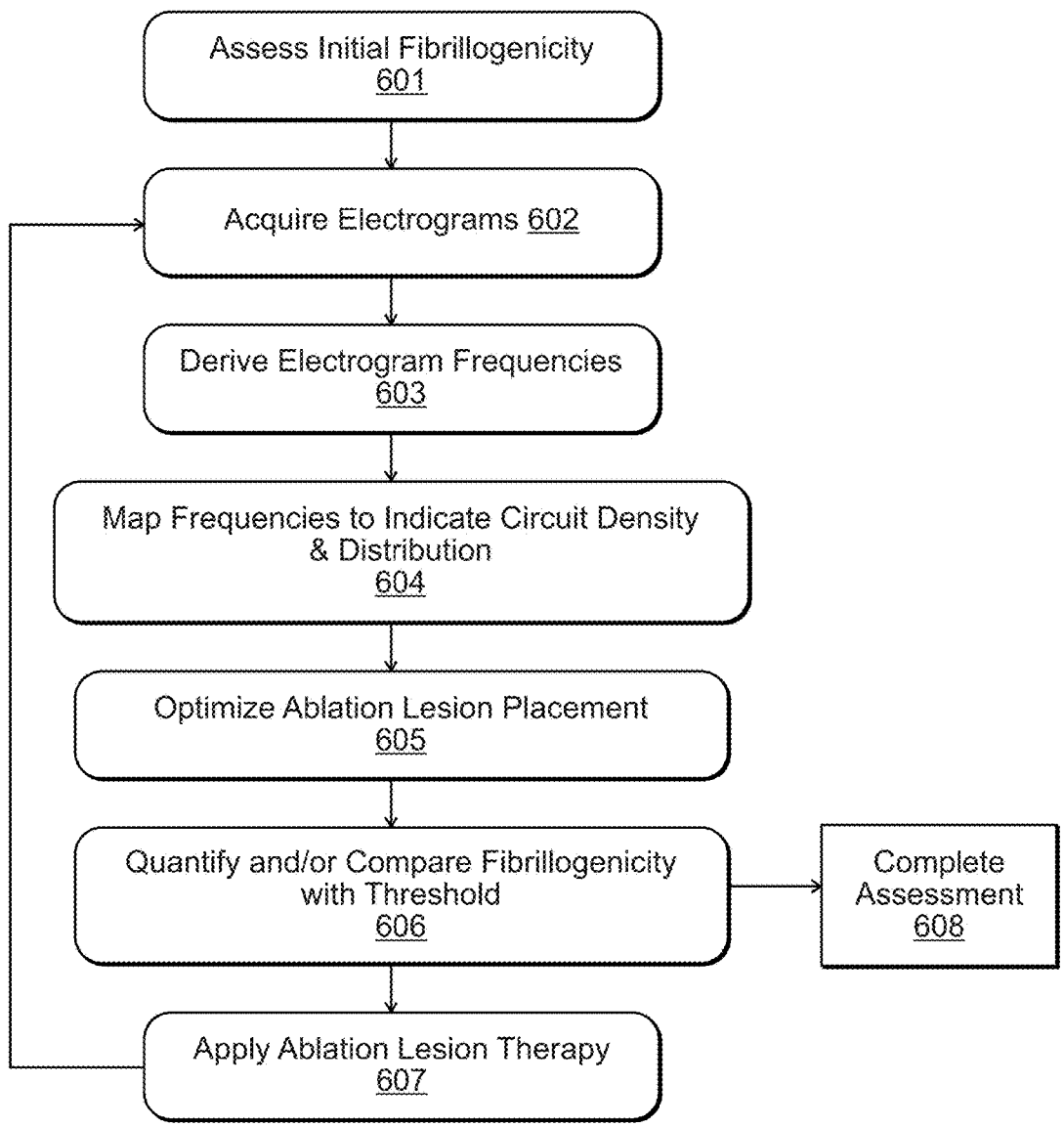
FIG. 60 is a process flowchart for assessing fibrillogenicity in a patient, in accordance with embodiments of the present invention.

FIG. 60 is a process flowchart for quantifying and/or assessing fibrillogenicity in a patient in accordance with some embodiments of the present invention. In step 601, initial fibrillogenicity is assessed. In step 602, electrograms are acquired, from which electrogram frequencies are derived in step 603. In step 604, the frequencies indicative of circuit density and distribution are mapped. The process then includes step 605, in which ablation lesion placement is optimized. In step 606, fibrillogenicity is quantified and compared with a predetermined threshold. In step 607, ablation lesion therapy is applied, and the process iterates back to step 602, wherein new electrograms are acquired. The process is completed in 608, once the measure of fibrillogencity meets is below the predetermined threshold.

Feedback-Driven Ablation Treatment

After introducing an ablation lesion, clinicians may determine if additional lesions should be placed. This determination can be made by measuring the tissue activation frequency following an ablation. If the tissue activation frequency becomes lower than a threshold frequency, then the process of ablation treatment ends. However, if the tissue activation frequency is higher than a predetermined threshold frequency, clinicians may add more lesions.

Figure 62:
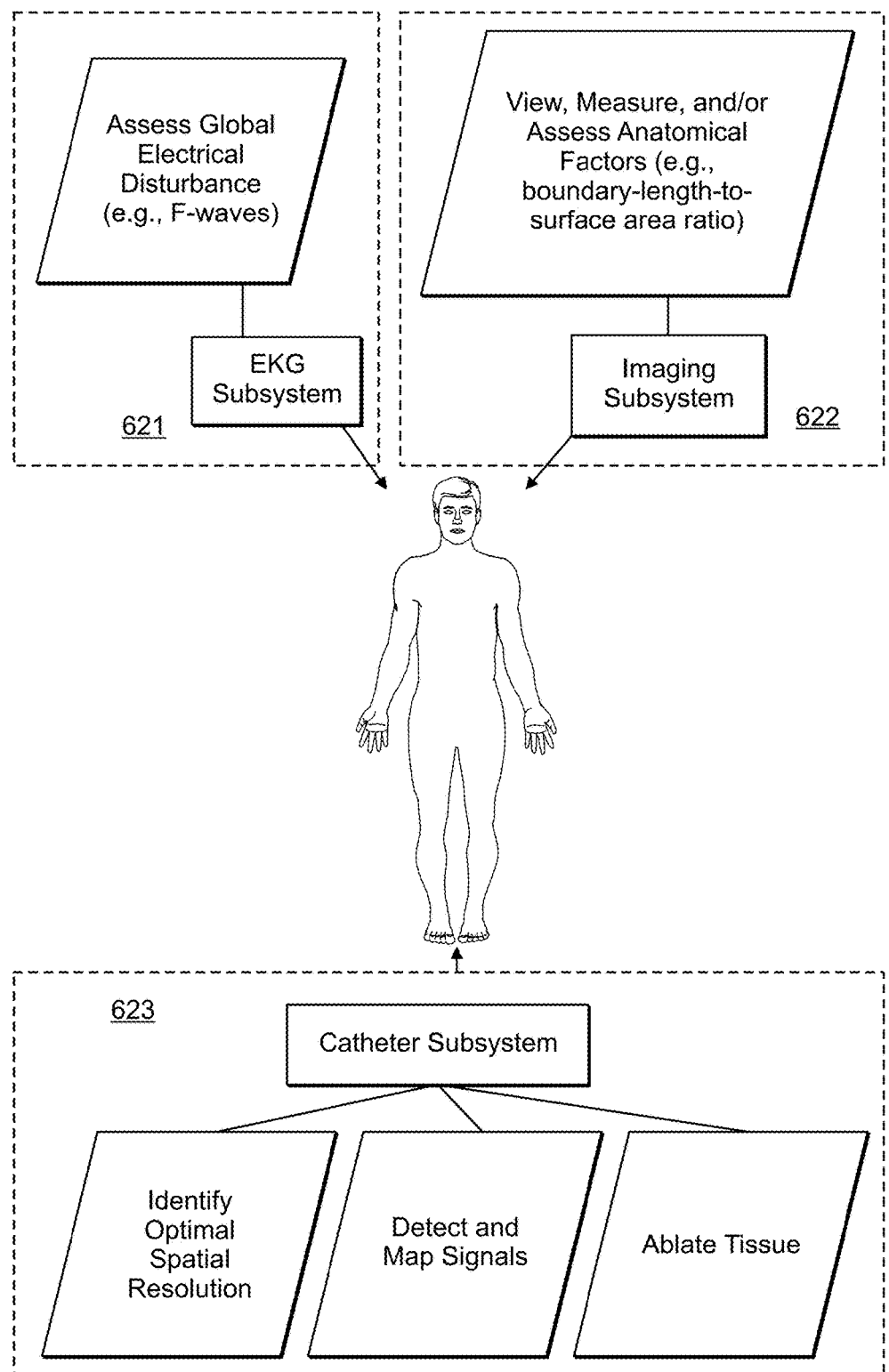
FIG. 62 is a system diagram, in accordance with embodiments of the present invention.

FIG. 13 is a system component diagram in accordance with some embodiments of a system for iteratively treating cardiac fibrillation in a patient. The system may include a catheter subsystem 132, a processing unit 135, a memory 134, a transceiver 133 including one or more interfaces 139, a GUI 138, and/or a display 136 (each described above). The system may also include, but is not limited to, an ECG/EKG subsystem 130 and/or an imaging subsystem 131 (also described above). FIG. 62 is a system diagram, in accordance with embodiments of the present invention. FIG. 62 describes the EKG subsystem 621, imaging subsytem 622, and catheter subsystem 623, as detailed above.

Figure 61:
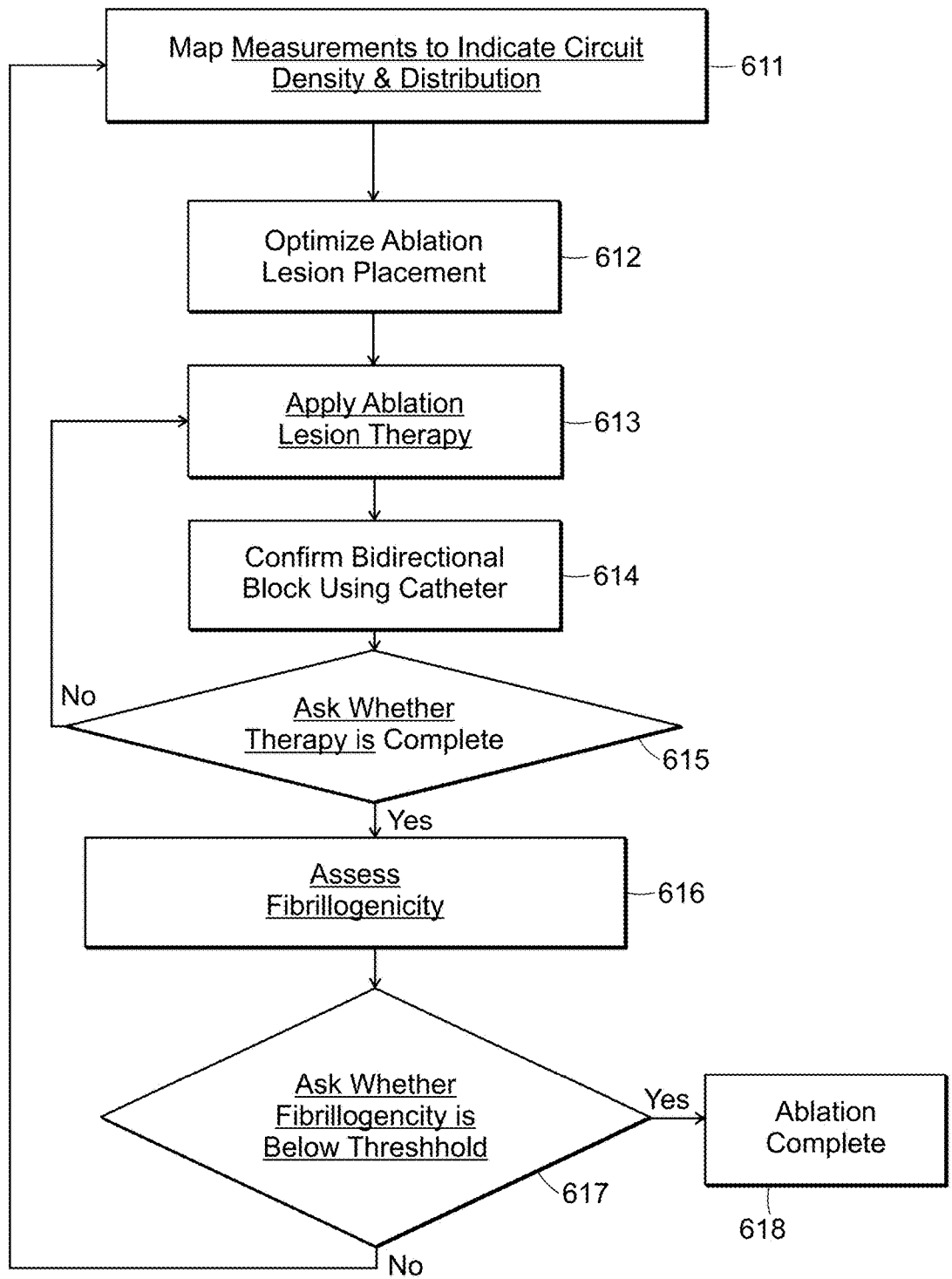
FIG. 61 is a process flowchart for treating cardiac fibrillation in a patient using iterative feedback, in accordance with embodiments of the present invention.

FIG. 61 is a process flowchart for treating cardiac fibrillation in a patient using iterative feedback in accordance with some embodiments of the present invention. In step 611, one or more measurements indicative of circuit core density and distribution are mapped. After finding the regions with higher circuit density from the map, an optimization method is applied to find the optimal distribution of ablation lesions in step 612. The optimization may be based on the regions with, for example, the top 30% of the highest circuit core density sites. In step 613, the atria of a patient are ablated based on this optimal distribution. In step 614, clinicians use a catheter, preferably a mapping catheter in accordance with the systems of the present invention, to ascertain the presence or absence of bidirectional block across ablation lesions. In step 615, a determination is made as to whether the ablation lesions are or are not complete as performed (i.e. is further ablation required to achieve bidirectional block?). If bidirectional block is not complete, the process goes back to step 613 and additional ablation is added. If bidirectional block is complete, then F-wave cycle length is checked in step 616. In step 617, a determination is made as to whether the F-wave cycle length is greater than, for example, 180 milliseconds. If the F-wave cycle length is greater than 180 milliseconds, ablation therapy is complete. Otherwise, if the F-wave cycle length is less than 180 milliseconds, the entire process repeats beginning at step 611.

Ablation lesions may be produced via tissue heating or cooling. Such energies include radiofrequency, high frequency and/or focused ultrasound, laser, microwave or cryotechnologies. The only requirement is that tissue be irreversibly damaged such that recovery of conduction cannot occur.

As will be apparent to one of ordinary skill in the art from a reading of this disclosure, the present disclosure can be embodied in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. The scope of the present invention is as set forth in the appended claims and equivalents thereof, rather than being limited to the examples contained in the foregoing description.

The invention claimed is:

1. A catheter system, comprising:
    a catheter optimized for mapping cardiac fibrillation in a patient, the catheter comprising
        an array of at least one stacked electrode pair, each electrode pair including a first electrode and a second electrode,
        each electrode pair configured to be orthogonal to a surface of a cardiac tissue substrate
        wherein the electrodes in each electrode pair have a size, shape, and inter-electrode spacing optimized for high spatial resolution,
        each first electrode configured to be in contact with the surface to record a first signal, and
        each second electrode configured to be separated from the first electrode and the surface by a distance which enables the second electrode to record a second signal;
    the catheter being configured to obtain one or more measurements including at least one measure indicative of local tissue activation frequency from at least one first signal and at least one second signal of the at least one stacked electrode pair in response to electrical activity in the cardiac tissue substrate indicative of a number of electrical circuit cores and distribution of the electrical circuit cores for a duration across the cardiac tissue substrate in the patient's heart; and
    a processor in communication with the catheter and configured to process the one or more measurements from the at least one first signal and the at least one second signal of the at least one stacked electrode pair in response to electrical activity in the cardiac tissue substrate indicative of the number of electrical circuit cores and the distribution of the electrical circuit cores for the duration across the cardiac tissue substrate in the patient's heart, and generate a map of the number of electrical circuit cores and the distribution of the electrical circuit cores onto a representation of the patient's heart.

2. The system of claim 1, wherein the system is further configured such that the one or more measurements are used to determine whether an ablation procedure at least one of minimized or treated the cardiac fibrillation.

3. The system of claim 1, wherein the system is further configured such that the one or more measurements include at least one measure of electrogram signal frequency.

4. The system of claim 3, wherein the system is further configured such that the accuracy of the at least one measure of electrogram signal frequency is a function of a ratio between spatial resolution and spatiotemporal variation of the cardiac tissue substrate.

5. The system of claim 1, further configured to optimize a number of locations across the cardiac tissue substrate in the patient's heart to which the array must be moved in order to acquire a sufficient number of measurements to indicate the number of electrical circuit cores and the distribution of the electrical circuit cores for the duration across the cardiac tissue substrate in the patient's heart.

6. The system of claim 1, the catheter further comprising at least one ablation electrode for applying ablation lesion therapy to at least one of minimize or treat the cardiac fibrillation.

7. A catheter system optimized for aligning electrodes normal to a surface of a cardiac tissue substrate in a patient, comprising:
    an elongated conduit with a proximal end and a distal end; and
    a flexible member with a proximal end and a distal end, disposed in the elongated conduit, configured to expand and conform to the surface when unsheathed from the distal end of the elongated conduit, and comprising an array of at least one stacked electrode pair, each electrode pair including a first electrode and a second electrode and each electrode pair configured to be orthogonal to the surface, wherein the electrodes in each electrode pair have a size, shape, and interelectrode spacing, optimized for high spatial resolution, each first electrode disposed on a first side of the flexible member to be configured to be in contact with the surface to record a first signal, and each second electrode disposed on a second side of the flexible member to be configured to be separated from the first electrode of its electrode pair and the surface by a thickness of the flexible member that allows the second electrode to record a second signal;

the catheter being configured to obtain one or more measurements including at least one measure indicative of local tissue activation frequency from at least one first signal and at least one second signal of the at least one stacked electrode pair in response to electrical activity in the cardiac tissue substrate indicative of a number of electrical circuit cores and distribution of the electrical circuit cores for a duration across the cardiac tissue substrate in the patient's heart; and a processor in communication with the catheter configured to process the one or more measurements from the at least one first signal and at least one second signal of the at least one stacked electrode pair in response to electrical activity in the cardiac tissue substrate indicative of the number of electrical circuit cores and the distribution of the electrical circuit cores for the duration across the cardiac tissue substrate in the patient's heart, and generate a map of the number of electrical circuit cores and the distribution of the electrical circuit cores onto a representation of the patient's heart.

8. The catheter system of claim 7, wherein the flexible member is at least one of a sheet or a balloon.

9. The catheter system of claim 7, wherein the proximal end of the flexible member is tapered to facilitate resheathing the flexible member in the distal end of the elongated conduit.

10. The catheter system of claim 7, wherein the flexible member comprises a distensible material configured to vary recording site density without substantially changing a thickness of the flexible member.

11. A catheter system optimized for mapping cardiac fibrillation in a patient, comprising:
an array of electrodes, at least one electrode having a size; and shape, optimized for high spatial resolution, each electrode configured to be in contact with a surface to record an electrogram signal, the catheter being configured to obtain a first set of two or more sequential measurements from a first tissue location and a second set of two or more sequential measurements from a second tissue location including at least one measure indicative of tissue activation frequency from at least one electrogram signal in response to electrical activity in a cardiac tissue substrate at the first and second tissue locations indicative of a number of electrical circuit cores and distribution of the electrical circuit cores for a duration across the cardiac tissue substrate in the patient's heart; and a processor in communication with the catheter configured to process the first and second sets of two or more measurements from the at least one electrogram signal in response to electrical activity in the first and second tissue locations of the cardiac tissue substrate indicative of the number of electrical circuit cores and the distribution of the electrical circuit cores for the duration across the cardiac tissue substrate in the patient's heart, and generate a map of the number of electrical circuit cores and the distribution of the electrical circuit cores onto a representation of the patient's heart.

12. The catheter system of claim 11, wherein the catheter is further configured such that the first and second sets of two or more measurements are used to determine whether an ablation procedure at least one of minimized or treated the cardiac fibrillation.

13. The catheter system of claim 11, wherein the first and second sets of two or more measurements include at least one measure of electrogram signal frequency.

14. The catheter system of claim 13, wherein accuracy of the at least one measure of electrogram signal frequency is a function of a ratio between spatial resolution and spatiotemporal variation of the cardiac tissue substrate.

15. The catheter system of claim 14, wherein the optimal spatial resolution is selected by varying deconvolution at the one or more locations of the cardiac tissue substrate.

16. The catheter system of claim 11, further configured to optimize a number of locations across the cardiac tissue substrate in the patient's heart to which the array must be moved in order to acquire a sufficient number of measurements to indicate the number of electrical circuit cores and the distribution of the electrical circuit cores for the duration across the cardiac tissue substrate in the patient's heart.

17. The catheter system of claim 11, further comprising at least one ablation electrode for applying ablation lesion therapy to at least one of minimize or treat the cardiac fibrillation.

18. A catheter system optimized for aligning electrodes normal to a surface of a cardiac tissue substrate in a patient, comprising:
an elongated conduit with a proximal end and a distal end; and a flexible member with a proximal end and a distal end, disposed in the elongated conduit, configured to expand and conform to the surface when unsheathed from the distal end of the elongated conduit, and comprising an array of electrodes, at least one electrode having a size and shape optimized for high spatial resolution, each electrode configured to be in contact with the surface to record an electrogram signal;

the catheter being configured to obtain one or more measurements including a first set of two or more at least one measure sequential measurements from a first tissue location and a second set of two or more sequential measurements from a second tissue location indicative of tissue activation frequency from at least one electrogram signal in response to electrical activity in the cardiac tissue substrate at the first and second tissue locations indicative of a number of electrical circuit cores and distribution of the electrical circuit cores for a duration across the cardiac tissue substrate in the patient's heart; and a processor in communication with the catheter configured to process the first and second sets of two or more measurements from the at least one electrogram signal in response to electrical activity in the cardiac tissue substrate indicative of the number of electrical circuit cores and the distribution of the electrical circuit cores for the duration across the first and second tissue locations of the cardiac tissue substrate in the patient's heart, and generate a map of the number of electrical circuit cores and the distribution of the electrical circuit cores onto a representation of the patient's heart.

19. The catheter system of claim 18, wherein the flexible member is at least one of a sheet or a balloon.

20. The catheter system of claim 18, wherein the proximal end of the flexible member is tapered to facilitate resheathing the flexible member in the distal end of the elongated conduit.

21. The catheter system of claim 18, wherein the flexible member comprises a distensible material configured to vary recording site density without substantially changing a thickness of the flexible member.

* * * * *